(12) United States Patent
Berkower et al.

(10) Patent No.: US 9,566,329 B2
(45) Date of Patent: Feb. 14, 2017

(54) LIVE, ATTENUATED RUBELLA VECTOR TO EXPRESS VACCINE ANTIGENS

(71) Applicant: **

(56) References Cited

OTHER PUBLICATIONS

Tzeng et al., "Functional Replacement of a Domain in the Rubella Virus P150 Replicase Protein by the Virus Capsid Protein," *Journal of Virology*, vol. 83, No. 8, pp. 3549-3555, Apr. 1, 2009.

Virnik et al., "Enhanced expression of HIV and SIV vaccine antigens in the structural gene region of live attenuated rubella viral vectors and their incorporation into virions," *Vaccine*, vol. 31, No. 17, pp. 2119-2125, Apr. 1, 2013.

Virnik et al., "Live attenuated rubella viral vectors stably express HIV and SIV vaccine antigens while reaching high titers," *Vaccine*, vol. 30, No. 37, pp. 5453-5458, Aug. 1, 2012.

\* cited by examiner

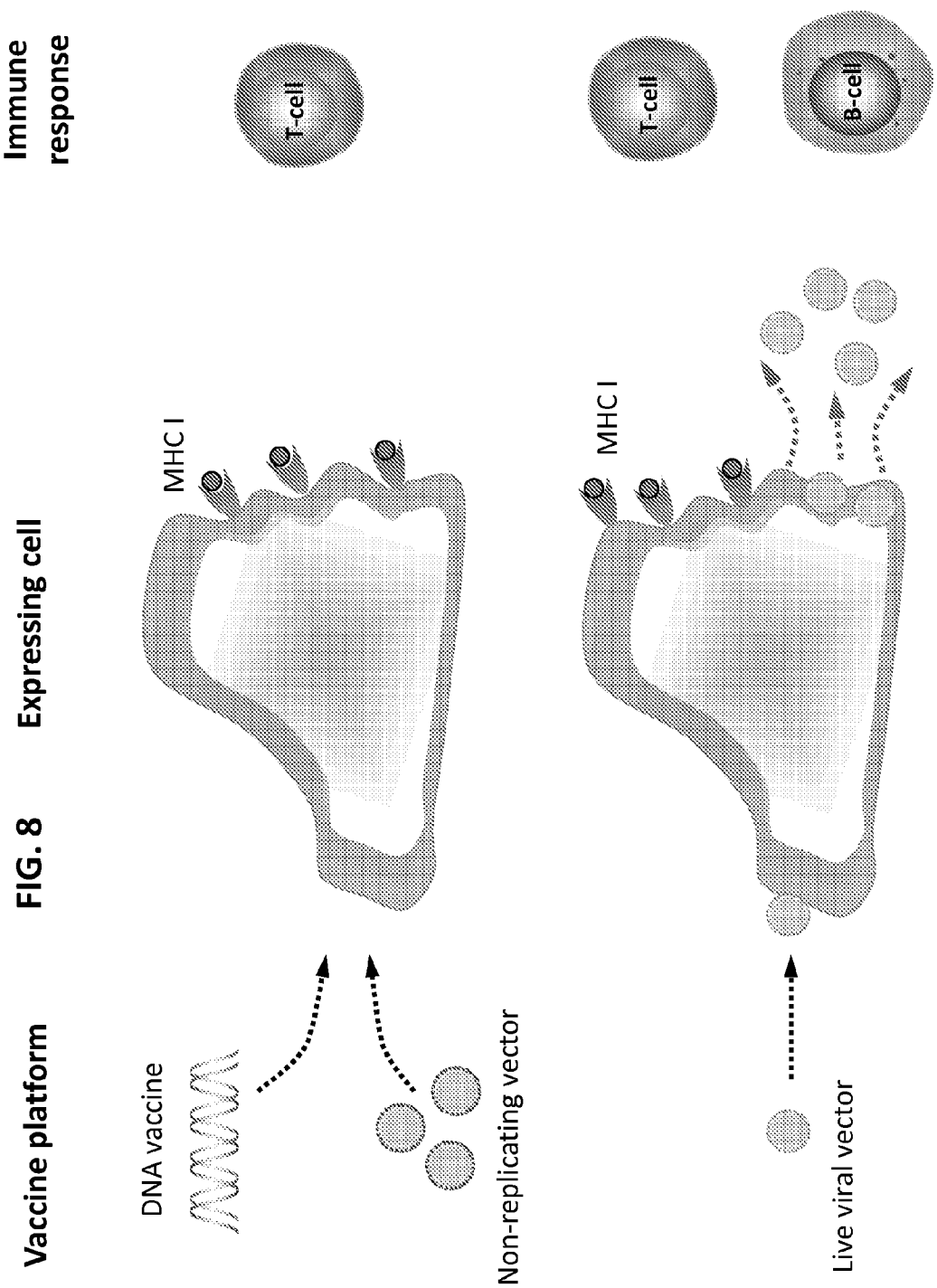

FIG. 9A Inserts at the Not I site
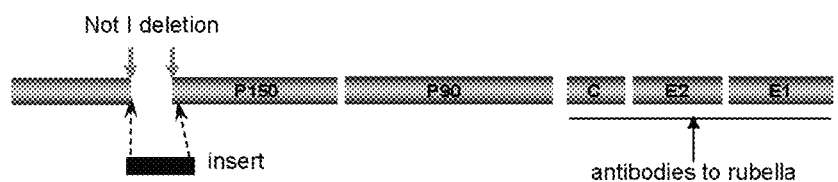
FIG. 9B Inserts at the structural site
HIV-1 gp41 inserts
FIG. 9C
| | | Inserts at the Not I site | | Replication |
|---|---|---|---|---|
| MPER$_F$ | —[2F5]— | | 70 bp | + |
| MPER$_E$ | —[4E10]— | | 60 bp | +/− |
| MPER | —[2F5]—[4E10]— | | 111 bp | − |
| | | Inserts at the structural site | | |
| MPER$_F$-E2TM | —[2F5]—[E2TM]—[E1SP]— | | 222 bp | + |
| MPER$_F$-E1TM | —[2F5]—[E1TM]—[E1SP]— | | 234 bp | + |
| MPER-HIVTM | —[2F5]—[4E10]—[HIVTM]—[E1SP]— | | 258 bp | + |
SIV Gag inserts at the Not I site
FIG. 9D
| | KP11 | GY9 | TE15 | CM9 | ME11 | | |
|---|---|---|---|---|---|---|---|
| T cell epitopes in SIV

FIG. 10

Inserts at the Not I site

| Insert/Vector name | Amino Acid Sequence of the inserts |
|---|---|
| MPER$_F$ | QEKNEKELL<u>ELDKWASL</u>WN  SEQ ID NO: 128<br>          2F5 |
| MPER$_E$ | WN<u>WFDITNWLWYIRL</u>  SEQ ID NO: 129<br>    4E10 |
| MPER | QENEKELL<u>ELDKWASL</u>WN<u>WFDITNWLWYIRLFI</u>  SEQ ID NO: 130<br>       2F5         4E10 |
| sGag1 | REGSQ<u>KILSVLAPLVPT</u><u>GSENLKSL</u>YNTVSVIWSIHAED  SEQ ID NO: 82<br>       A         B |
| sGag2 | FQALSEG<u>CTPYDINQM</u>LNCVGDHQAA<u>MQIIRDIINEE</u>A  SEQ ID NO: 83<br>        D                          E |
| sGag2L | LPLSPRTLNAWVKLIEEKKFGAEVVPGFQALSEG<u>CTPYDINQM</u>LNCVGDHQAA<br>                                                            D<br><u>MQIIRDIINEE</u>A  SEQ ID NO: 84<br>    E |
| sGag2L-A | LPLSPRTLNAWVKLIEEKKFGAEVVPGFQALSEG<u>CTPYDINQM</u>LNCVGDHQAA<br><u>MQIIRDIINEE</u>ATRSQ<u>KILSVLAPLVPT</u>  SEQ ID NO: 85<br>    E               A |
| sGag2L-B | LPLSPRTLNAWVKLIEEKKFGAEVVPGFQALSEG<u>CTPYDINQM</u>LNCVGDHQAA<br><u>MQIIRDIINEE</u>ATRT<u>GSENLKSL</u>YNT  SEQ ID NO: 86<br>    E             B |
| sGag2L-C | LPLSPRTLNAWVKLIEEKKFGAEVVPGFQALSEG<u>CTPYDINQM</u>LNCVGDHQAA<br><u>MQIIRDIINEE</u>ATRH<u>TEEAKQIVQRHLVVETGTT</u>  SEQ ID NO: 87<br>    E             C |
| BC-sGag2 | VPT<u>GSENLKSL</u>YNTVTRVKH<u>TEEAKQIVQRHLVVETGTT</u>SDAFQALSEG<u>CTPYD</u><br>      B               C                                  D<br><u>INQM</u>LNCVGDHQAA<u>MQIIRDIINEE</u>A  SEQ ID NO: 88<br>                      E |

Inserts at the structural site

| | |
|---|---|
| MPER$_F$-E2TM | GEEPRQEKNEKELL<u>ELDKWASL</u>WNWFDM<u>HTLAAFVLLVPWVLIFMVCRRTCR</u><br>                2F5                                              E2TM<br>RRG<u>AAAALTAVVLQGYNPPAYG</u>  SEQ ID NO: 126<br>      E1SP |
| MPER$_F$-E1TM | GEEPRQEKNEKELL<u>ELDKWASL</u>WNWFDM<u>HWWQLTLGATCALPLAGLLACCA</u><br>                  2F5                                              E1TM<br>RRTCRRR<u>GAAAALTAVVLQGYNPPAYG</u>  SEQ ID NO: 127<br>          E1SP |
| MPER-HIVTM | GEEPRQEKNEKELL<u>ELDKWASL</u>WN<u>WFDITNWLWYIRL</u><u>FIMIVGGLIGLRIVFAVL</u><br>                2F5          4E10           HIV-1 gp41 TM<br><u>SIVCRRTCRRR</u><u>GAAAALTAVVLQGYNPPAYG</u>  SEQ ID NO: 131<br>               E1SP |

Anti-rubella Abs

2F5 anti-MPER$_F$ mAb

Deletion at the Not I site and insertion at the structural site

Insertion at the structural site but no deletion

FIG. 16 Vectors grow to high titer for in vivo studies

| Titers of rubella vectors carrying different inserts | |
|---|---|
| Vector | Titer (pfu/ml) |
| *A. Not I site:* | |
| pBR-dNotI-$MPER_F$ | $3.1\times10^6$ |
| pBR-dNotI-BCsGag2 | $2.5\times10^5$ |
| *B. Structural site:* | |
| pBR-dNotI-E2-MPER-HIVTM-E1 | $1.3\times10^6$ |
| pBR-dNotI-E2-BCsGag2-E2TM-E1 | $2.7\times10^5$ |
| *C. Structural site, no deletions:* | |
| pBR-E2-MPER-HIVTM-E1 | $5.8\times10^5$ |
| pBR-E2-BCsGag2-E2TM-E1 | $2.3\times10^5$ |

FIG. 17

Rhesus Macaque response to rubella vectors

| Insert location | vector dose |
| --- | --- |
| Structural site with deletion | 1° and 2° |
| Not I site with deletion | 3° |
| Structural site no deletion | 4° |

FIG. 19

Group 3 Antibodies to the sGag Insert

- CL49
- CL67
- DCVV
- CL6A empty rubella
- J6L prebleed

FIG. 20A

Amino acid sequences of SIV Gag inserts expressed at the structural site.

| Insert/ Vector name | Amino Acid Sequence of the inserts |
|---|---|
| sGag-E2TM (aa 41-211; SEQ ID NO: 132) | LDRFGLAESLLENKEGCQKILSVLAPLVPTGSENLKSLYNTVCVIWCIHAEEKVK HTEEAKQIVQRHLVVETGTTETMPKTSRPTAPSSGRGGNYPVQQIGGNYVHLP LSPRTLNAWVKLIEEKKFGAEVVPGFQALSEGCTPYDINQMLNCVGDHQAAMQ IIRDIINEEASLDMHTLAAFVLLVPWVLIFMVCRRTCRRRGAAAALTAVVLQGYNP PAYG (A, B, C, D, E, E2TM, E1SP) |
| sGag-E2TM (aa 135-271; SEQ ID NO: 133) | YPVQQIGGNYVHLPLSPRTLNAWVKLIEEKKFGAEVVPGFQALSEGCTPYDINQ MLNCVGDHQAAMQIIRDIINEEAADWDLQHPQPAPQQGQLREPSGSDIAGTTS SVDEQIQWMYRQQNPIPVGNIYRRWIQLGLMHTLAAFVLLVPWVLIFMVCRRTC RRRGAAAALTAVVLQGYNPPAYG (D, E, F, G, E2TM, E1SP) |
| fullp28-sGag-E2TM (SEQ ID NO: 134) | YPVQQIGGNYVHLPLSPRTLNAWVKLIEEKKFGAEVVPGFQALSEGCTPYDINQ MLNCVGDHQAAMQIIRDIINEEAADWDLQHPQPAPQQGQLREPSGSDIAGTTS SVDEQIQWMYRQQNPIPVGNIYRRWIQLGLQKCVRMYNPTNILDVKQGPKEPF QSYVDRFYKSLRAEQTDAAVKNWMTQTLLIQNANPDCKLVLKGLGVNPTLEEM LTACQGVGGPGQKARLMHTLAAFVLLVPWVLIFMVCRRTCRRRGAAAALTAVV LQGYNPPAYG (D, E, F, G, E2TM, E1SP) |

FIG. 20B

| | |
|---|---|
| fullp28plus-<br>sGag-E2TM<br>(SEQ ID NO: 135) | YPVQQIGGNYVHLPLSPRTLNAWVKLIEEKKFGAEVVPGFQALSEG<u>CTPYDINQ</u><br>                                                                                                                          D<br><u>MLNCVGDHQAAMQIIRDIINEE</u>AADWDLQHPQPAPQQGQLREPSGSDIAGTT<u>S</u><br>              E<br><u>SVDEQIQWMYRQQNPIPVGNI</u>YRRWIQLGLQKCVRMYNPTNILDVKQGPKEPF<br>          F                  G<br>QSYVDRFYKSLRAEQTDAAVKNWMTQTLLIQNANPDCKLVLKGLGVNPTLEEM<br>LTACQGVGGPGQKARLMAEALKEA<u>LAPVPIPFAAA</u>QQRGPRKPIM<u>HTLAAFVLL</u><br>                                  H       I                             E2TM<br><u>VPWVLIFMVCRRTCRRRGAAAALTAVVLQGYNPPAYG</u><br>                               E1SP |

Underlined sequences show T cell epitopes in SIV Gag and membrane-spanning domains in SIV Gag inserts expressed at the structural site.

FIG. 21A

MPER-HIVTM-E1 and E2-MPER-HIVTM fusion proteins (partially cleavable by signal peptidase)

| | |
|---|---|
| MPER-HIVTM-E1<br><br>Seq ID No: 77 | GEEPRQEKNEKELL<u>ELDKWASLWNWFDITNWLWYIR</u><u>LFIMIVGGLIGLRIVFAVL</u><br>              2F5          4E10              HIV-1 gp41 TM<br><u>SIVCRRTCRRR</u><u>GAAAALTAVVLQGYNPPAYG</u>EEAFTYLCTAPGCATQAPVPV<br>          E1SP                   gpE1<br>RLAGVRFESKIVDGGCFAPWDLEATGACICEIPTDVSCESLGAWVPAAPC<br><br>ARIWNGTQPACTFWAVNAYSSGCYAQLASYFNPGGSYYKQYHPTACEVEP<br><br>APCHSDAACWGPPTDIVMSVFALASYVQHPHKTVRVKFHTETRTVWQLSV<br><br>AGVSCNVTTEHPFCNTPHGQLEVQVPPDPGDLVEYIMNYTGNQQSRWGL<br><br>GSPNCHGPDWASPVCQRHSPDCSRLVGATPERPRLRLVDADDPLLRTAPG<br><br>PGEVWVTPVIGSQARKCGLHIRAGPYGHATVEMPEWIHAHTTSDPWHPG<br><br>PLGLKFKTVRPVALPRTLAPPRNVRVTGCYQCGTPALVEGLAPGGGNCHL<br><br>TVNCEDLG AVPPGKFVTAALLNTPPPYQVSCGGESDRATARVIDPAAQS<br><br>FTGVVYGTHTPAVSETRQTWAEWAAAHWWQLTLGAICALPLAGLLACCAK<br><br>CLYYLRGAIAPR |

FIG. 21B

| | |
|---|---|
| MPER-HIVTM-<br>E1SPL1<br><br>Seq ID No: 78 | GEEPRQEKNEKEL<u>LELDKWASLW</u>N<u>WFDI</u>TNWLWYIR<u>LFIMIVGGLIGLRIVFAVL</u><br>               2F5            4E10                  HIV-1 gp41 TM<br>SIVCRRTCRRR<u>GAAAALTAVVLQGYNPPALG</u>EEAFTYLCTAPGCATQAPVPV<br>          E1SP                   gpE1 →<br>RLAGVRFESKTVDGGCFAPWDLEATGACICEIPTDVSCEGLGAWVPAAPC<br><br>ARIWNGTQRACTFWAVNAYSSGGYAQLASYFNPGCSYYKQYHPTACEVEP<br><br>AFGHSDAACWGFPTDTVMSVFALASYVQHPHKTVRVKFHTETRTVWQLSV<br><br>AGVSCNVTTEHPFCNTPHGQLEVQVFPDFGDLVEYIMNYTGNQQSRW GL<br><br>GSPNCHGPDWASPVCQRHSPDCSRLVGATPERPRLRLVDADDPLLRTAPG<br><br>PGEVWVTPVICSQARKCCLHIRAGPYCHATVEMPEWIHAHTTSDPWHPPG<br><br>PLGLKFKTVRFVALPRTLAPPRNVRVTGCYQCGTPALVEGLAPGGGNCHL<br><br>TVNGEDLG AVPPGKFVTAALLNTPPPYQVSCGGESDRATARVIDPAAQS<br><br>FTGVVYSTHTTAVSETRQTWAEWAAAHWWQLTLGAICALPLAGLLACCAK<br><br>CLYYLRGAIAPR |

FIG. 21C

MPER-HIVTM-
E1SPL3

Seq ID No: 79

GEEPRQEKNEKELLELDKWASLWNWFDITNWLWYIRLFIMIVGGLIGLRIVFAVL
                  2F5          4E10                      HIV-1 gp41 TM

SIVCRRTCRRRGAAAALTAVVLQGYNPPLYGEEAFTYLCTAPGCATQAPVPV
           E1SP                  gpE1

RLAGVRFESKIVDGGCFAPWDLEATGACICEIPTDVSCEGLGAWVPAAPC

ARIWNGTQRACTFWAVNAYSSGGYAQLASYFNPGGSYYKQYHPTACEVEP

AFGHSDAACWGFPTDTVMSVFALASYVQHPHKTVRVKFHTETRTVWQLSV

AGVSCNVTTEHPFCNTPHGQLEVQVPPDPGDLVEYIMNYTGNQQSRW GL

GSPNCHGPDWASPVCQRHSPDCSRLVGATPERPRLRLVDADDPLLRTAPG

PGEVWVTPVIGSQARKCGLHIRAGPYGHATVEMPEWIHAHTSDPWHPPG

PLGLKFKTVRPVALPRTLAPPRNVRVTGCYQCGTPALVEGLAPGGGNCHL

TVNGEDLG AVPPGKFVTAALLNTPPPYQVSCGGESDRATARVIDPAAQS

FTGVVYGTHTTAVSETRQTWAEWAAAHWWQLTLGAICALPLAGLLACCAK

CLYYLRGAIAPR

FIG. 21D

| | |
|---|---|
| MPER-HIVTM- | GEEPRQEKNEKELL<u>ELDKWASLWN</u><u>WFDITNWLWY</u>IR<u>LFIMIVGGLIGLRIVFAVL</u> |
| |                           2F5            4E10                    HIV-1 gp41 TM |
| E1SPLV64 | <u>SIV</u>CRRTCRRR<u>GAAAALTAVVLQGYNLVAYG</u>EEAFTYLCTAPGCATQAPVPV |
| |                   E1SP                   gpE1 ▶ |
| Seq ID No: 80 | RLAGVRFESKIVDGGCFAPWDLEATGACICEIPTDVSCEGLGAWVPAAPC |
| | ARIWNGTQRACTFWAVNAYSSGGYAQLASYFNPGSSYYKQYHPTACEVEP |
| | AFCHSDAACWGFPTDTVMSVFALASYVQHPHKTVRVKFHTETRTVWQLSV |
| | AGVSCNVTTEHPFCNTPHGQLEVQVPPDFGDLVEYIMNYTGNQQSRW GL |
| | GSPNCHGPDWASPVCQRHSPDCSRLVGATPERPRLRLVDADDFLLRTAPG |
| | PGEVWVTPVIGSQARKCGLHTRAGPYGHATVEMPEWIHAHTTSDPWHPPG |
| | PLGLKFKTVRPVALPRTLAPPRNVRVTGCYQCGTPALVEGLAPGGGNCHL |
| | TVNGEDLG AVPPGKFVTAALLNTPPPYQVSCGGESDRATARVIDPAAQS |
| | FTGVVYGTHTTAVSETRQTWAENAAAHWWQLTLGAICALPLAGLLACCAK |
| | QLYYLRGAIAPR |

Underlined sequences show the core epitopes for broadly neutralizing antibodies 2F5 and 4E10, T cell epitopes in SIV Gag and membrane-spanning domains expressed at the structural site.

FIG. 21E

| | |
|---|---|
| E2-MPER-HIVTM | GLQPRADMAAPPTLPQPPRAHGQHYGHHHHQLPFLGHDGHHGGTLRVGQHY <br> *gpE2* <br> RNASDVLPGHWLQGGWGCYNLSDWHQGTHVCHTKHMDFWCVEHARPPPAT |
| Seq ID No:136 | PTPLTTAANSTTAATPATAPAPCHAGLNDSCGGFLSGCGPMRLRHGADTRCG <br><br> RLICGLSTTAQYPPTRFGCAMRWGLPPWELVVLTARPEDGWTCRGVPAHPGA <br><br> RCPELVSPMGRATCSPASALWLATANALSLDHALAAFVLLVPWVLIFMVCRRAC <br><br> RRRGAAAALTAVVLQGYNPPAYGEEPRQEKNEKELLELDKWASLWNWFDITN <br> *gpE2*                                    2F5       4E10 <br> WLWYIRLFIMIVGGLIGLR

FIG. 22

An MPER construct incorporating the gp41 trimerization domain (N and C domains) before MPER. This will increase MPER valency and size.

| N-C-MPER-HIVTM Seq ID No: 137 | PRNNLLRAIEAQQHM

FIG. 23

Amino acid sequences of HIV Gag inserts expressed at the structural site.

| Insert/Vector name | Amino Acid Sequence of the inserts |
|---|---|
| HIV Gag-E2TM (aa 41-211) (SEQ ID NO: 138) | LERFAVNPSLLETSEGCRQILGQLQSSLQTGSEELKSLYNTVATLYCVH QRIEVKDTKEALDKIEEEQNKSKKKAQQAAADTGNSSQVSQNYPIVQNI QGQMVHQAISPRTLNAWVKVVEEKAFSPEVIPMFSALSEGATPQDLNT MLNTVGGHQAAMQMLKETINEEAAEWDM<u>HTLAAFVLLVPWVLIFMVCR RTCRRR</u><u>GAAAALTAVVLQGYNPPAYG</u> |
| HIV Gag-E2TM (aa 135-271) (SEQ ID NO: 139) | YPIVQNIQGQMVHQAISPRTLNAWVKVVEEKAFSPEVIPMFSALSEGAT PQDLNTMLNTVGGHQAAMQMLKETINEEAAEWDRLHPVQAGPVAPGQ MREPRGSDIAGTTSTLQEQIGWMTNNPPIPVGEIYKRWIILGLM<u>HTLAAF VLLVPWVLIFMVCRRTCRRR</u><u>GAAAALTAVVLQGYNPPAYG</u> |
| HIV Gag p24-E2TM (SEQ ID NO. 140) | YPIVQNIQGQMVHQAISPRTLNAWVKVVEEKAFSPEVIPMFSALSEGAT PQDLNTMLNTVGGHQAAMQMLKETINEEAAEWDRLHPVQAGPVAPGQ MREPRGSDIAGTTSTLQEQIGWMTNNPPIPVGEIYKRWIILGLQKCVRM YNPTNILDVKQGPKEPFQSYVDRFYKSLRAEQTDAAVKNWMTQTLLIQN ANPDCKLVLKGLGVNPTLEEMLTACQGVGGPGQKARLM<u>HTLAAFVLLV PWVLIFMVCRRTCRRR</u><u>GAAAALTAVVLQGYNPPAYG</u> |

Underlined sequences correspond to the E2TM and E1 signal peptidase sites

FIG. 25  Rubella expression of MPER and SIV Gag at the structural site

Immune response to the SIV Gag insert.
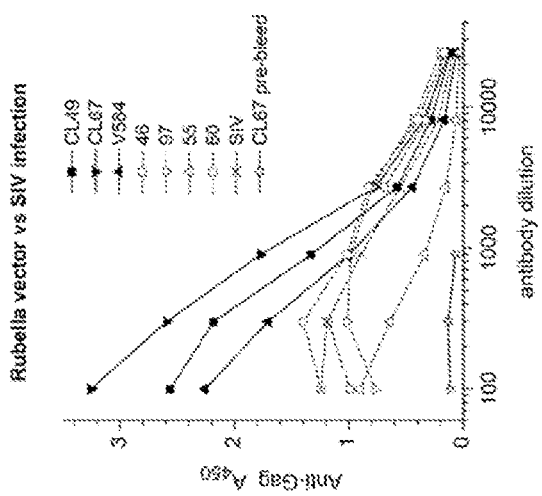
FIG. 26A
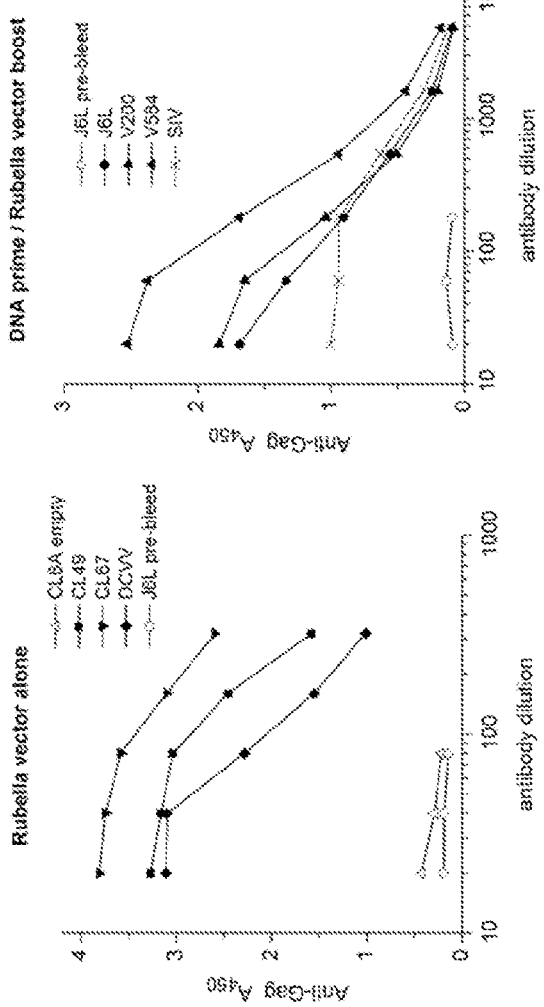
FIG. 26B
FIG. 26C

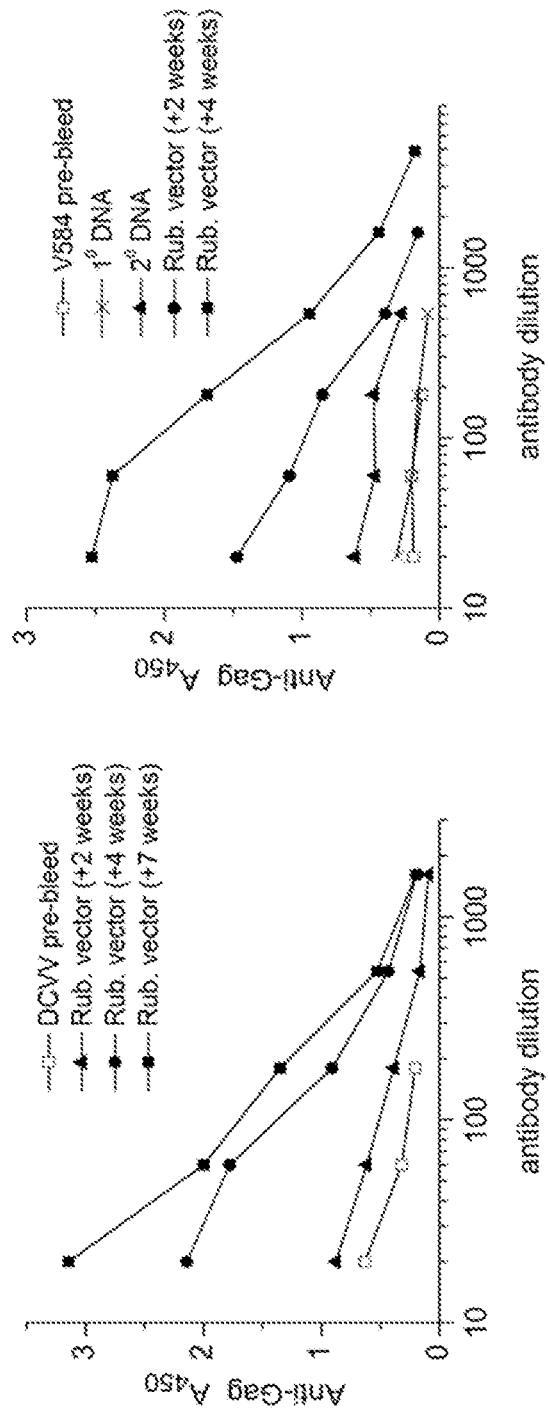

Persistence of antibodies elicited in group 3.
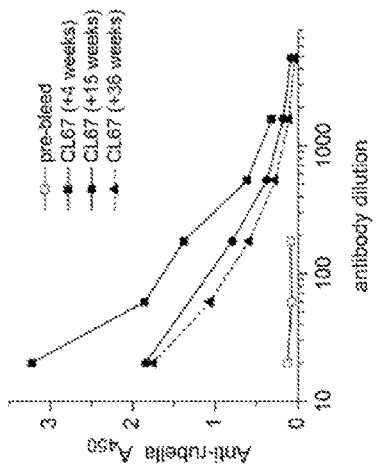
FIG. 28A
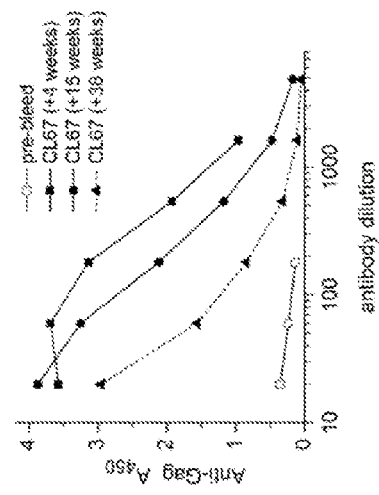
FIG. 28B
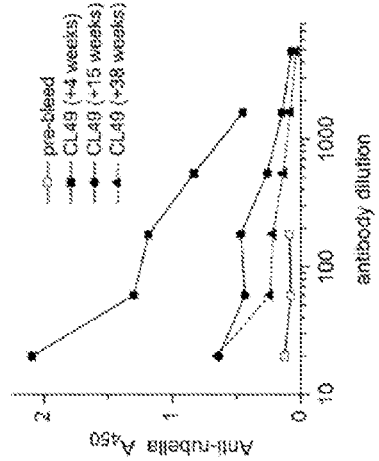
FIG. 28C
FIG. 28D
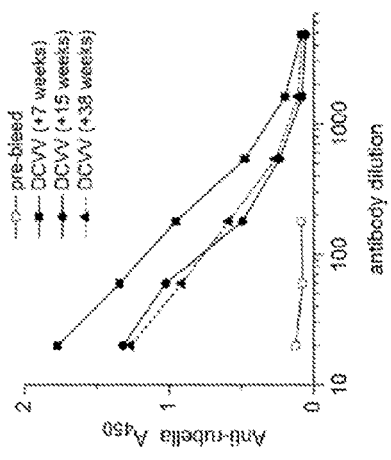
FIG. 28E
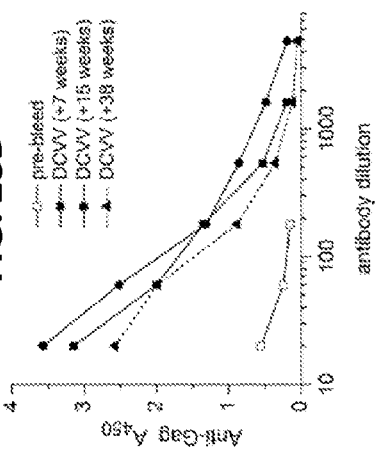
FIG. 28F Anti-Gag response to a live vector boost.

Immune response to the MPER insert

FIG. 32

Rubella expression of large Gag antigens

SGAG → 　　　　　　　　　　　　　← p55

Anti-p28 mAb (2F12)

1 pBRA3226-E2-SGAG(41-363)-E2TM-E1 (P3) passed by cells
2 pBRA3226-E2-SGAG(41-363)-E2TM-E1 (P6) passed by virus
3 pBRA3226-E2-SGAG(41-363)-E2TM-E1 (P6) passed by cells
4 pBRA3226-E2-SGAG(41-391)-E2TM-E1 (P3) passed by cells
5 pBRA3226-E2-SGAG(41-391)-E2TM-E1 (P6) passed by virus
6 pBRA3226-E2-SGAG(41-391)-E2TM-E1 (P6) passed by cells
7 pBRobo3226-dNot1-zsGreen
8 Positive control P55

FIG. 34

Rubella expression of novel gp120 constructs

Anti-gp120 mAb (2G12)

1 pBRA3226-E2-CC2(79-506)dV1V2V3C-G4S-E2TM-E1
2 pBRA3226-E2-CC2(88-506)dV1V2V3C-G4S-E2TM-E1
3 pBRA3226-E2-CC2(88-484)dV1V2V3C-G4S-E2TM-E1
4 pBRA3226-E2-CC2(93-506)dV1V2V3C-G4S-E2TM-E1
5 pBRA3226-E2-CC2(93-484)dV1V2V3C-G4S-E2TM-E1
6 pBRA3226-E2-CC2(79-215-SIGG-252-506)-G4S-E2TM-E1
7 pBRobo3226-dNotI-zsGreen
8 gp120 recomb.

LIVE, ATTENUATED RUBELLA VECTOR TO EXPRESS VACCINE ANTIGENS

CROSS REFERENCE TO RELATED APPLICATIONS

This is the U.S. National Stage of International Application No. PCT/US2013/035634, filed Apr. 8, 2013, which was published in English under PCT Article 21(2), which in turn claims the benefit of U.S. Provisional Application No. 61/621,394, filed Apr. 6, 2012, and 61/642,333, filed May 3, 2012, each of which is incorporated herein by reference in its entirety.

FIELD

This disclosure relates to the field of viral vectors, specifically to a live, attenuated rubella viral vector platform capable of expressing a heterologous antigen, and the use of this platform to induce an immune response.

BACKGROUND

The worldwide spread of human immunodeficiency virus/acquired immunodeficiency syndrome (HIV/AIDS) has created an urgent need for HIV immunogens that can elicit broad protection against infection. Natural HIV infection in man and SIV infection in monkeys often elicit a strong antibody-mediated (B cell) and T cell-mediated immune response. A number of viral antigens targeted by broadly reactive neutralizing antibodies and antigen specific T cells have been identified. The challenge is to develop vaccines with sufficient potency to stimulate an effective immune response to these important viral antigens. Live viral vectors can enhance both T cell and B cell responses by presenting antigens in the most immunogenic way, in the context of an acute infection.

Weak immunogenicity of vaccine antigens is one of the main problems in vaccine development. Several approaches have been tried to improve presentation and enhance immunogenicity of these antigens, including DNA vaccines, non-replicating vectors and live viral vectors (FIG. 8). DNA vaccines have been used to immunize or to prime for immunization. They have the advantage of flexibility and safety, but often lack potency when used alone. By expressing vaccine antigens in the cytoplasm, DNA vaccines may favor endogenous antigen processing and presentation pathways, leading to induction of MHC class I restricted T cells. Similarly, non-replicating viral vectors deliver antigens directly into cytoplasmic pathways needed to elicit a strong T cell response. These vaccine platforms usually require a high immunizing dose, as antigen expression is limited by vector dose. Live viral vectors can immunize at the lowest dose of any vector, sufficient to initiate infection; they immunize as they replicate. Some vectors set up a chronic infection, while others persist for only a few weeks.

Some of the most successful vaccines, such as oral polio virus and measles, mumps, and rubella virus vaccine, consist of live attenuated viruses. These are given at very low doses, so the vaccine strain must grow in the host to produce sufficient viral antigens to elicit an immune response. By simulating a viral infection, they can elicit innate and adaptive immune responses, resulting in antigen-specific T cells and antibody-producing B cells. Through a process of attenuation, the vaccine strains have retained the growth and immunogenicity of wild type virus while losing its pathogenicity and virulence. However, for many pathogenic viruses, such as HIV, SIV, RSV and/or hepatitis, it has not been possible to produce a live attenuated vaccine. Thus, additional approaches for creating vaccines for pathogenic viruses are needed.

SUMMARY

Disclosed herein is a live attenuated rubella viral vector platform capable of stably expressing a heterologous antigen, such as a vaccine antigen (e.g., an HIV antigen (for example, an envelope glycoprotein antigen, such as, a gp41 or a gp120), a Gag antigen (such as an HIV or SIV Gag antigen), hepatitis B surface antigen (HBsAg), or an RSV antigen and the use of this platform to induce an immune response. The inventors utilized the rubella vaccine strain RA27/3 as a viral vector because of its safety and immunogenicity. Its safety has been demonstrated in millions of children around the world. If the rubella vector losses its insert, it reverts to the vaccine strain. At the same time, it is immunogenic and elicits both humoral and mucosal immunity. The inventors surprisingly found that rubella viral vector can accommodate foreign inserts at either of two sites, in the nonstructural region or between two structural genes. Each site was found to be controlled by a different viral promoter, resulting in expression of the insert as an early or late antigen of rubella. At the nonstructural site the insert was expressed as a fusion protein, while at the structural site it was expressed with the structural polyprotein and cleaved to a mature protein. The mature protein was incorporated into virions and co-sedimented with viral particles in sucrose density gradients. The vectors stably expressed the insert, while replicating for at least eight to ten passages in culture.

One advantage of rubella vectors for vaccine research is their ability to infect rhesus macaques. This animal model allows the testing of vector replication and immunogenicity in vivo. Rhesus macaques are also the animal of choice for SIV and SHIV challenge studies; thus, the immune response can be evaluated for durability and protection against SIV or SHIV challenge. Production of rubella vectors is efficient, as they grow to high titer in cell culture, yet they immunize at a low dose. Their one limitation, eliciting antibodies to the vector, is overcome by combining a live rubella vector with another vaccine delivery platform in a prime and boost strategy.

The disclosed vectors are of interest to vaccine researchers as they reprogram the rubella vaccine strain to present new vaccine antigens. In the developed world, where virtually all rubella infections are caused by design (vaccination), the disclosed rubella vectors can be used to immunize against two or more infectious agents instead of one. In the third world, where rubella vaccine is not currently used, there is a window of opportunity for the vector to be given prior to the age of natural rubella infection, which ranges from two to six years old in most countries. It is contemplated that the disclosed vectors can be used against a variety of infectious diseases, including HIV, SIV, RSV and hepatitis.

In some embodiments, an isolated rubella viral vector includes a rubella non-structural protein open reading frame (ORF) without an in-frame deletion, a rubella structural protein ORF, and a heterologous antigenic insert. In some examples, the heterologous antigenic insert is positioned within the rubella structural protein ORF. In other examples, the heterologous antigenic insert is positioned in between the genes encoding structural proteins E2 and E1. In some examples, the heterologous antigenic insert is positioned between the genes encoding structural protein capsid and E2. In some examples, the antigenic insert comprises an amino acid sequence set forth as SEQ ID NO: 126, 127, 128, 129, 130, 131, 132, 133, 134, 135, 136, 137, 138, 140, 141, 142, 143, 144, 145, 146, 147, 148, 149, 150, 151, 152, 153, 154, 155, 156, 158, 159, 160, 161, or 162.

Exemplary antigenic inserts can include cytotoxic T lymphocyte (CTL) epitopes, HIV envelope protein epitopes, RSV antigen and HBsAg inserts. For example, an antigenic insert can include a CTL epitope of HIV or SIV Gag, an epitope of HIV gp41, including a membrane proximal region (MPER or MPR) or an epitope of HIV gp120. The antigenic insert can include repeats of any one of the disclosed antigenic epitopes, such as one to ten copies of one or more of the disclosed antigenic envelope or CTL epitopes.

In some examples, an antigenic insert is a wildtype or variant of a CTL epitope of a Gag polypeptide or a fragment thereof. In some examples, the antigenic peptide includes one or more major CTL epitopes of Gag, and can be from about 8 to about 350 amino acids in length, such from about 10 to about 280 amino acids in length, such as 20 to about 270 amino acids in length, such as from about 40 to about 250 amino acids in length, including 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 57, 60, 63, 65, 67, 70, 73, 75, 77, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 231, 232, 233, 234, 235, 236, 237, 238, 239, 240, 245, 250, 255, 260, 265, 270, 275, 280, 285, 290, 295, 300, 305, 310, 315, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349 or 350. In some examples, an antigenic insert includes one or more CTL epitopes, such as one or more CTL HIV or SIV epitopes, including those set forth as SEQ ID NOs: 77, 78, 79, 80, 92, 93, 94, 95, 96, 97, 98, 99, 100, 101, and 102. In some examples, an antigenic insert includes one or more antigenic polypeptide fragments of Gag, such as one or more antigenic polypeptides with an amino acid sequence provided by SEQ ID NOs: 82-88, 90, 91, 132, 133, 134, 135, 138, 139, 140, 141 or 142.

In some examples, an antigenic insert is a wildtype or variant gp41 polypeptide or a fragment thereof. In some examples, a gp41 antigenic insert can include (a) an antigenic polypeptide fragment of gp41 and (b) a transmembrane spanning region of gp41. For example, the gp41 antigenic insert includes (a) an antigenic polypeptide fragment, such as an antigenic polypeptide fragment with the amino acid sequence set forth in SEQ ID NO:1 (in which wherein $X_1$, $X_2$ and $X_3$ are any amino acid) and the polypeptide is between 8 and 400 amino acids in length, such as between 10 and 300 amino acids in length, such as from about 12 to about 250, such as from about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, or 145 amino acids; and (b) a transmembrane spanning gp41 region, such as a transmembrane spanning gp41 region with the amino acid sequence set forth in SEQ ID NO: 25 (in which $X_4$, $X_5$, and $X_6$ are any hydrophobic amino acid) and is between 22 and 40 amino acids in length, such as about 23 and 38 amino acids in length, including 24, 25, 26, 27, 28, 29, 30, 31, 32, 33, 34, 35, 36, 37, 38 amino acids. In certain examples, an antigenic insert includes an antigenic polypeptide fragment of gp41 with an amino acid sequence provided by SEQ ID NOs: 1-22, 30, 81 or 89 and a transmembrane region of gp41 with an amino acid sequence provided by SEQ ID NOs: 25-28.

In some examples, an antigenic insert is a wildtype or variant gp120 polypeptide. In an example, a wildtype gp120 polypeptide has an amino acid provided by SEQ ID NO: 63 or a fragment thereof. In other examples, a variant gp120 polypeptide includes a gp120 polypeptide in which at least 8 consecutive residues of the fourth conserved loop (C4) between residues 419 and 434 of gp120 according HXB2 numbering of SEQ ID NO: 63 are deleted. This deletion within the β20-21 loop of the gp120 polypeptide exposes the CD4 binding site thereby providing improved antibody binding and antibody induction. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 63 have been deleted.

In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63). In other embodiments, variant gp120 polypeptides include combinations of the amino and carboxyl ends between residues 419 and 434.

In some embodiments, a variant gp120 polypeptide does not include a variant in which residues 419-428 of SEQ ID NO: 63 are deleted. In other embodiments, a variant gp120 polypeptide does not include a variant in which residues 437-452 of SEQ ID NO: 63 are deleted. In certain examples, an antigenic insert includes an amino acid sequence set forth by SEQ ID NOs: 63, 66, 67, 69, 71, 73 or 74.

In some embodiments, an isolated rubella viral vector comprises an antigenic insert comprising an amino acid sequence set forth as SEQ ID NO: 126, 127, 131-156 or 158-162.

In some embodiments, an isolated rubella viral vector comprises an antigenic insert consisting of an amino acid sequence set forth as SEQ ID NO: 126, 127, 131-156 or 158-162.

In some embodiments, a disclosed isolated rubella viral vector comprises an antigenic insert comprising a Gag antigenic insert, comprising the amino acid sequence as set forth by SEQ ID NO: 141, SEQ ID NO. 142, SEQ ID NO: 82 or SEQ ID NO: 83.

In some embodiments, a disclosed isolated rubella viral vector comprises an antigenic insert comprising the amino acid sequence set forth as one of SEQ ID NOs: 143-155; SEQ ID NO. 156; SEQ ID NOs: 158-162; or SEQ ID NOs: 84-91.

In some embodiments, a disclosed isolated rubella viral vector comprises an antigenic insert consisting of the amino acid sequence set forth as one of SEQ ID NOs: 143-155; SEQ ID NO. 156; SEQ ID NOs: 158-162; or SEQ ID NOs: 84-91.

Viral-like particles including any of the disclosed isolated viral vector constructs are provided herein. Compositions comprising the viral-like particles are also provided.

The disclosed isolated viral vectors can be used to induce an immune response, such as a protective immune response, when introduced into a subject. The provided rubella viral vector platforms can also be used in assays to diagnose a viral infection, such as an HIV infection, an SIV infection, RSV infection or hepatitis. Thus, methods are provided for inhibiting a viral infection, such as an HIV infection in a subject, for inducing an immune response to HIV in a subject, and for diagnosing HIV infection in a subject. The disclosed viral vector platforms can also be used for measuring host range, testing sensitivity to neutralizing antibodies, or screening antiviral drugs. In one example, methods of screening antiviral drugs including methods of identifying protease inhibitors are disclosed.

The foregoing and other features of the disclosure will become more apparent from the following detailed description, which proceeds with reference to the accompanying sequence listing and figures.

BRIEF DESCRIPTION OF SEQUENCES

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date.

SEQ ID NO: 1 is a consensus amino acid sequence for the membrane proximal region (MPR) of gp41 of HIV-1. An X represents specific amino acids where alterations can be tolerated.

SEQ ID NO: 2 is a consensus amino acid sequence based on each clade consensus sequence of the MPR region from HIV-1.

SEQ ID NO: 3 is the ancestral amino acid sequence of the MPER region from HIV-1 clade M. This sequence is also the consensus amino acid sequence of the MPR region from HIV-1 clade AG.

SEQ ID NO: 4 is the consensus amino acid sequence of the MPER region from HIV-1 clade A1. This sequence is also the ancestral amino acid sequence of the MPER region from HIV-1 clade A1.

SEQ ID NO: 5 is the consensus amino acid sequence of the MPER region from HIV-1 clade A2.

SEQ ID NO: 6 is the consensus amino acid sequence of the MPER region from HIV-1 clade B. This sequence is also the ancestral amino acid sequence of the MPER region from HIV-1 clade B.

SEQ ID NO: 7 is the consensus amino acid sequence of the MPER region from HIV-1 clade C.

SEQ ID NO: 8 is the ancestral amino acid sequence of the MPER region from HIV-1 clade C.

SEQ ID NO: 9 is the consensus amino acid sequence of the MPER region from HIV-1 clade D.

SEQ ID NO: 10 is the consensus amino acid sequence of the MPER region from HIV-1 clade F1.

SEQ ID NO: 11 is the consensus amino acid sequence of the MPER region from HIV-1 clade F2.

SEQ ID NO: 12 is the consensus amino acid sequence of the MPER region from HIV-1 clade G.

SEQ ID NO: 13 is the consensus amino acid sequence of the MPER region from HIV-1 clade H.

SEQ ID NO: 14 is the consensus amino acid sequence of the MPER region from HIV-1 clade AE.

SEQ ID NO: 15 is the consensus amino acid sequence of the MPER region from HIV-1 clade AB.

SEQ ID NO: 16 is the consensus amino acid sequence of the MPER region from HIV-1 clade 04CPX.

SEQ ID NO: 17 is the consensus amino acid sequence of the MPER region from HIV-1 clade 06CPX.

SEQ ID NO: 18 is the consensus amino acid sequence of the MPER region from HIV-1 clade 08BC.

SEQ ID NO: 19 is the consensus amino acid sequence of the MPER region from HIV-1 clade 10CD.

SEQ ID NO: 20 is the consensus amino acid sequence of the MPER region from HIV-1 clade 11CPX.

SEQ ID NO: 21 is the consensus amino acid sequence of the MPER region from HIV-1 clade 12BF.

SEQ ID NO: 22 is the consensus amino acid sequence of the MPER region from HIV-1 clade 14BG.

SEQ ID NOs: 23-24 are oligonucleotide primers used to amplify a rubella sequence flanking a zGFP insert.

SEQ ID NO: 25 is a consensus amino acid sequence for the transmembrane region of gp41. An X represents any hydrophobic amino acid.

SEQ ID NOs: 26-28 are amino acid sequences for a transmembrane spanning region of gp41.

SEQ ID NO: 29 is an amino acid sequence for a disclosed isolated immunogen in which the first transmembrane domain of hepatitis B surface antigen is replaced with the MPER and transmembrane domain of gp41.

SEQ ID NO: 30 is an exemplary MPER region from HIV-1 amino acid sequence.

SEQ ID NO: 31 is an exemplary wildtype amino acid sequence of HBsAg.

SEQ ID NO: 32 is an example of a nucleotide sequence for a T helper cell epitope.

SEQ ID NO: 33 is an example of an amino acid sequence for a T helper cell epitope.

SEQ ID NO: 34 is the CAAX amino acid sequence, where C is cystein, A is an aliphatic amino acid and X is any amino acid.

SEQ ID NO: 35 is the core amino acid sequence of the 2F5 epitope.

SEQ ID NO: 36 is the core amino acid sequence of the 4E10 epitope.

SEQ ID NO: 37 is the linker sequence GPGP.

SEQ ID NO: 38 (ggagctcgtcgacagcaa) is a forward primer for amplification of the HBsAg.

SEQ ID NO: 39 (gctctagacccgatgtacaccca) is a reverse primer for amplification of the HBsAg.

SEQ ID NO: 40 (gctctagaaacgagcaggagctgctg) is a forward primer for amplification of MPER.

SEQ ID NO: 41 (cgcggatcctcaccccttgatgtaccacagccactt) is a reverse primer for amplification of MPER.

SEQ ID NO: 42 (cgcggatcctcaatggtgatggtgatggtgggg) is a reverse primer for amplification of MPER-Foldon.

SEQ ID NO: 43 (gctctagagccgtggagcggtacctg) is a forward primer for amplification of C-heptad.

SEQ ID NO: 44 (ctcggatcctcaaatcatgatgaaaatcttgat) is a reverse primer for amplification of MPER-Tm5.

SEQ ID NO: 45 (ctcggatcctcacaccaggccaccaacaat) is a reverse primer for amplification of MPER-Tm10.

SEQ ID NO: 46 (ctcggatcctcacaccagcctcaggcccac) is a reverse primer for amplification of MPER-Tm15.

SEQ ID NO: 47 (ctcggatcctcaggcgggcgc) is a reverse primer for amplification of MPER-Tm23.

SEQ ID NO: 48 (ccctgcaagacctgcaccaccaccggtcagggcaactccaagttcccc) is a forward primer for amplification of the MPER region with AgeI.

SEQ ID NO: 49 (ggggaacttggagttgccctgaccggtggtggtgcaggtcttgcaggg) is a reverse primer for amplification of the MPER region with AgeI.

SEQ ID NO: 50 (ggcaccggtaacgagcaggagctgctg) is a forward primer for amplification of the MPER region with AgeI.

SEQ ID NO: 51 (ggcaccggtccccttgatgtaccacagccactt) is a reverse primer for amplification of the MPER region with AgeI.

SEQ ID NO: 52 (agcgaattcaacgagcaggagctgctg) is a forward primer for amplification of the MPER region with HBsAg (MPER SAG or MPER-N-term).

SEQ ID NO: 53 (cgcggatcctcacccgatgtacaccca) is a reverse primer for amplification of the MPER region with HBsAg (MPER SAG or MPER-N-term).

SEQ ID NO: 54 (caggaagccggaggtgatgaacccccttgatgtaccacagc cactt) is a forward primer for amplification of SAGMPER-R1 (HBsAg at the N-terminus of MPER).

SEQ ID NO: 55 (aagtggctgtggtacatcaaggggttcatcacctccggcttcctg) is a reverse primer for amplification of SAGMPER-R1 (HBsAg at the N-terminus of MPER).

SEQ ID NO: 56 is an nucleic acid sequence which encodes the Gag antigenic insert with an amino acid sequence set forth as SEQ ID NO: 103

SEQ ID NO: 57 (MKTIIALSYIFCLVFAQDLPGNDNNSEFNEKELLELDKWASL WNWFDITNWLWYIRLFIMIVGGLIGLRIVFAVLSIPQSLDSWWTSLNFLGGSPVCLGQNSQS PTSNHSPTSCPPICPGYRWMCLRRFIIFLFILLLCIFLLVLLDYQGMLPVCPLIPGSTTTSTGP CKTCTTPAQGNSKFPSCCCTKPTDGNCTCIPINEKELLELDKWASLWNWFDITNWLWYIRL FIMIVGGLIGLRIVFAVLSIVVGLSPTVWLSAIWMMWYWGPSLYSIVSPFIPLLPIFFCLWVY IG) is an amino acid sequence for a disclosed isolated immunogen in which the first and third transmembrane domains of hepatitis B surface antigen are each replaced with the MPER and transmembrane domain of gp41.

SEQ ID NO: 58 is a nucleic acid sequence for a disclosed isolated immunogen in which the third transmembrane domains of HBsAg is replaced with the MPER and transmembrane domain of gp41.

SEQ ID NO: 59 is an amino acid sequence for a disclosed isolated immunogen in which the third transmembrane domain of hepatitis B surface antigen is replaced with the MPER and transmembrane domain of gp41.

SEQ ID NO: 60 (NEKELLELDKWASLW) is an amino acid sequence of the MPER region in the TM32 or TM32F constructs.

SEQ ID NO: 61 (NEKELLELDKWASLWNWFDITNWLW) is an amino acid sequence of the MPER region in the TM34 construct.

SEQ ID NO: 62 (MKTIIALSYIFCLVFAQDLPGNDNNSEFNEKELLELDKWASLW NWFDITNWLWYIRLFIMIVGGLIGLRIVFAVLSIPQSLDSWWTSLNFLGGSPVCLGQNSQSP TSNHSPTSCPPICPGYRWMCLRRFIIFLFILLLCIFLLVLLDYQGMLPVCPLIPGSTTTSTGPC KTCTTPAQGNSKFPSCCCTKPTDGNCTCISINEKELLELDKWASLWNWFDITNWLWSSLW AIKYLWEWASVRFSWLSLLVPFVQWFVGLSPTVWLSAIWMMWYWGPSLYSIVSPFIPLLPI FFCLWVYIG) is an amino acid sequence of a disclosed variant HbsAg construct (TM16+34) in which the first domain is replaced with a MPER and transmembrane domain of gp41 and an additional MPER is inserted between a second and third domain in the variant HBsAg.

SEQ ID NO: 63 is an amino acid sequence of a variant gp120 with a V1V2 deleted gp120.

SEQ ID NO: 64 (MKTIIALSYIFCLVFAQDLPGNDNNSEFNEKELLELDKWASL WNWFDITNWLWYIRLFIMIVGGLIGLRIVFAVLSIPQSLDSWWTSLNFLGGSPVCLGQNSQS PTSNHSPTSCPPICPGYRWMCLRRFIIFLFILLLCIFLLVLLDYQGMLPVCPLIPGSTTTSTGPC KTCTTPAQGNSKFPSCCCTKPTDGNCTCISINEKELLELDKWASLWAINEKELLELDKWAS LWAINEKELLELDKWASLWAINEKELLELDKWASLWAIKYLWEWASVRFSWLSLLVPFV QWFVGLSPTVWLSAIWMMWYWGPSLYSIVSPFIPLLPIFFCLWVYIG) is an amino acid sequence of a disclosed variant HbsAg construct (TM16+32F) in which the first domain is replaced with a MPER and transmembrane domain of gp41 and four additional MPERs are inserted between a second and third domain in the variant HBsAg.

SEQ ID NO: 65 (MKTIIALSYIFCLVFAQDLPGNDNNSEFITSGFLGPLLVLQAGF FLLTRILTIPQ SLDSWWTSLNFLGGSPVCLGQN SQSPTSNHSPTSCPPICPGYRWMCLRRFIIF LFILLLCLIFLLVLLDYQGMLPVCPLIPGSTTTSTGPCKTCTTPAQGNSKFPSCCCTKPTDGN CTCISINEKELLELDKWASLWAINEKELLELDKWASLWAINEKELLELDKWASLWAINEKE LLELDKWASLWAIKYLWEWASVRFSWLSLLVPFVQWFVGLSPTVWLSAIWMMWYWGPS LYSIVSPFIPLLPIFFCLWVYIG) is an amino acid sequence of a disclosed variant HbsAg construct (32F) in which four MPERs are inserted between a second and third domain in the variant HBsAg.

SEQ ID NO: 66 is an amino acid sequence for a variant gp120 with a V1V2 deletion with a beta 20-21 loop deletion.

SEQ ID NO: 67 is an amino acid sequence for a variant gp120 from HIV isolate JR-FL.

SEQ ID NO: 68 is a nucleic acid sequence for a variant gp120 from HW isolate JR-FL.

SEQ ID NO: 69 is an amino acid sequence for a variant gp120 from HW isolate AD8.

SEQ ID NO: 70 is a nucleic acid sequence for a variant gp120 from HIV isolate AD8.

SEQ ID NO: 71 is an amino acid sequence for a variant gp120 from HIV isolate BaL.

SEQ ID NO: 72 is a nucleic acid sequence for a variant gp120 from HIV isolate BaL.

SEQ ID NO: 73 is an amino acid sequence for a variant gp120 from HIV isolate IIIB SEQ ID NO: 74 is a nucleic acid sequence for a variant gp120 from HIV isolate IIB.

SEQ ID NOS: 75-76 are oligonucleotide primers used to amplify *Zoanthus* sp. green fluorescent protein (zGFP).

SEQ ID NOS: 77-80 are amino acid sequences of disclosed variant rubella constructs in which one MPER is inserted into the structural open reading frame of the rubella construct.

SEQ ID NO: 81 is an amino acid sequence of MPER$_f$ which contains the epitope recognized by neutralizing monoclonal antibody 2F5.

SEQ ID NOS: 82-88 are amino acid sequences of Gag antigenic inserts.

SEQ ID NO: 89 is an amino acid sequence of MPER$_e$ which contains the epitope recognized by neutralizing monoclonal antibody 4E1.

SEQ ID NOs: 90-91 are amino acid sequences of Gag antigenic inserts.

SEQ ID NOs: 92-96 are amino acid sequences of CTL epitopes of SIV Gag.

SEQ ID NOs: 97-102 are amino acid sequences of CTL epitopes of HIV Gag.

SEQ ID NO: 103 is an amino acid sequence of a Gag antigenic insert.

SEQ ID NOs: 104-125 are oligonucleotide primer sequences.

SEQ ID NOs: 126-127 are amino acid sequences of $MPER_F$ inserts.

SEQ ID NO: 128 is an amino acid sequence of $MPER_F$ insert.

SEQ ID NO: 129 is an amino acid sequence of $MPER_E$ insert.

SEQ ID NO: 130 is an amino acid sequence of MPER insert.

SEQ ID NO: 131 is an amino acid sequence of MPER-HIVTM insert.

SEQ ID NO: 132 is an amino acid sequence of an SW Gag insert (sGag-E2TM amino acids 41-211) expressed at the structural site.

SEQ ID NO: 133 is an amino acid sequence of an SW Gag insert (SGag-E2TM, amino acids 135-271) expressed at the structural site.

SEQ ID NO: 134 is an amino acid sequence of an SW Gag insert (full p28-sGag-E2TM) expressed at the structural site.

SEQ ID NO: 135 is an amino acid sequence of an SW Gag insert (full p28 plus-sGag-E2TM) expressed at the structural site.

SEQ ID NOS: 136 is an amino acid sequence of a disclosed variant rubella constructs in which one MPER is inserted into the structural open reading frame of the rubella construct.

SEQ ID NO: 137 is an amino acid sequence of an MPER construct incorporating the gp41 trimerization domain (N and C domains) before MPER, such arrangement can increase MPER valency and size.

SEQ ID NOs: 138-140 are amino acid sequences of HIV Gag inserts expressed at the rubella structural site.

SEQ ID NOs: 141-162 are sequences of inserts expressed at the rubella structural site.

The Sequence Listing is submitted as an ASCII text file in the form of the file named Sequence.txt, which was created on Apr. 8, 2013, and is 196,048 bytes, which is incorporated by reference herein.

BRIEF DESCRIPTION OF THE DRAWINGS

FIG. 8 is a schematic illustrating different vaccine platforms. DNA vaccines, non-replicating vectors, and live viral vectors are under development as vaccine platforms for viral antigens. Due to transient expression and limited antigen production, DNA vaccines and non-replicating vectors favor T cell immunity. In contrast, a replicating viral vector, while immunizing at the lowest dose of any vector, produces exponentially increasing amounts of antigen to stimulate stronger T cell and B cell responses. Live rubella vectors combine the safety of a licensed vaccine with the targeted antigenicity of a vector. The disclosed live rubella vectors provide a vaccine platform that can be used alone or in combination with the other platforms in a prime and boost strategy.

FIGS. 9A-9D illustrate a deletion/insertion strategy for producing rubella vectors and composition of foreign gene inserts. FIG. 9A. Permissive deletion between two Not I restriction sites in nonstructural protein P150 made room for insertion of foreign genes at the same site. Vector replication was detected with anti-rubella antibodies directed primarily to the structural proteins C and E1. FIG. 9B. Deletion at the Not I site was combined with insertions in the structural region between envelope glycoproteins E2 and E1. FIG. 9C. HIV-1 gp41 inserts contained one or two epitopes of the membrane-proximal external region (MPER) targeted by broadly neutralizing antibodies 2F5 and 4E10. Alternatively, inserts at the structural site included the transmembrane domain from rubella proteins E1 (E1TM), E2 (E2TM) or HIV-1 gp41 (HIVTM), as well as the E1 signal peptide sequence (E1SP) for proper processing and potential anchoring in the viral envelope. As indicated, four MPER vectors replicated strongly for at least seven passages. Vectors containing $MPER_E$ or full length MPER inserts at the Not I site, replicated poorly or not at all, respectively. FIG. 9D. SIV Gag amino acids 41 to 211 contain five T cell epitopes denoted by letters A through E. In constructs denoted by an asterisk (*) one epitope at a time was added to the carboxyl end of sGag2L to produce sGag2L-A, -B, or -C. All vectors were grown for several passages, and the largest construct BC-sGag2 was grown for at least eight passages.

FIG. 10 provides amino acid sequences of the HIV-1 MPER- and SIV Gag-derived inserts expressed at the Not I and structural sites. Underlined sequences show the core epitopes for broadly neutralizing antibodies 2F5 and 4E10, T cell epitopes in SIV Gag, or membrane-spanning domains in MPER inserts expressed at the structural site.

FIG. 13A is a schematic representation of processing of the native structural polyprotein and one with MPER-derived inserts. In unmodified rubella (upper panel), the structural proteins are separated by transmembrane domains that provide a signal peptide for the next protein. Signal peptidase cleaves the polyprotein at two sites (arrows) to release three mature proteins: capsid, E2 and E1. In rubella vectors with an MPER insert (FIG. 13A, lower panel), the MPER insert is followed by an additional transmembrane domain and signal peptide. Cleavage at three sites would produce the same three rubella structural proteins plus MPER with membrane spanning domains at a size of 8.5 to 10 kDa. Incomplete cleavage before or after MPER gave additional bands corresponding to E2-MPER-HIVTM (50 to 57 kDa) or MPER-HIVTM-E1 (66 to 68 kDa). E2SP and E1SP denote the E2 and E1 signal peptides, respectively. E2TM, E1TM, and HIVTM denote the E2, E1, and HIV transmembrane domains, respectively. The membrane spanning domains anchor rubella structural proteins in the viral envelope. FIGS. 13B-13C show results achieved with these vectors.

FIG. 14A illustrates a permissive deletion between two Not I restriction sites in nonstructural protein p150 and an insertion of foreign genes at the structural site between E1 and E2.

FIG. 16 is a table illustrating titers of rubella vectors carrying exemplary inserts.

FIG. 17 is a graph illustrating disclosed rubella vectors are infectious in vivo and immunize subjects, such as macaques, efficiently.

FIG. 19 is graph illustrating the antibody response to the BCsGag-2 insert.

FIGS. 20A and 20B is a table illustrating amino acid sequences of exemplary SIV Gag inserts (SEQ ID NOs: 132-135).

FIGS. 21A-21E is a table illustrating amino acid sequences of MPER-HIVTM-E1 or E2-MPER-HIVTM fusion proteins (SEQ ID NOs: 77-80 and 136).

FIG. 22 is a table illustrating the amino acid sequence of an MPER construct incorporating the gp41 trimerization domain (N and C domains) before MPER (SEQ ID NO: 137).

FIG. 23 is a table illustrating amino acid sequences of HIV Gag inserts expressed at the rubella structural site (SEQ ID NOs: 138-140).

FIG. 25 is a digital image of Western blots of rubella expression of MPER or BCsGag2 antigens. MPER expression is shown over time: it is optimal between day 5 and 10 of infection. On the right, BCsGag2 is detected in lane 1 by polyclonal antibodies to SW Gag obtained from a macaque immunized with a rubella vector expressing Gag.

FIGS. 26A-26C are graphs illustrating the immune response to the SIV Gag insert expressed by rubella vectors. FIG. 26A illustrates sera from three macaques that received rubella-Gag 4 to 7 weeks earlier. FIG. 26B illustrates sera from three macaques that received three doses of DNA vaccine, followed by rubella-Gag 4 weeks earlier. Both groups developed high tittered antibodies to Gag. FIG. 26C compares three of these sera with five sera from SW infected macaques. In each case, the antibody titers elicited by rubella-Gag vectors were greater than or equal to SIV infection.

FIGS. 27A and 27B are graphs illustrating the antibody response to a single dose of Rubella-Gag vectors. Antibodies rose steadily between 2 and 4 to 7 weeks after immunization with the live vectors.

FIGS. 28A-28F are graphs illustrating persistence of antibodies elicited by rubella vectors. All three animals in group 3 were followed over 9 months following their dose of live rubella-Gag vectors. The decline in anti-Gag titers was compared to the decline in anti-rubella antibodies at the same time points. Both antibodies fell at nearly the same rate, indicating that anti-Gag antibodies may be long-lived in these animals.

Figure 29A:
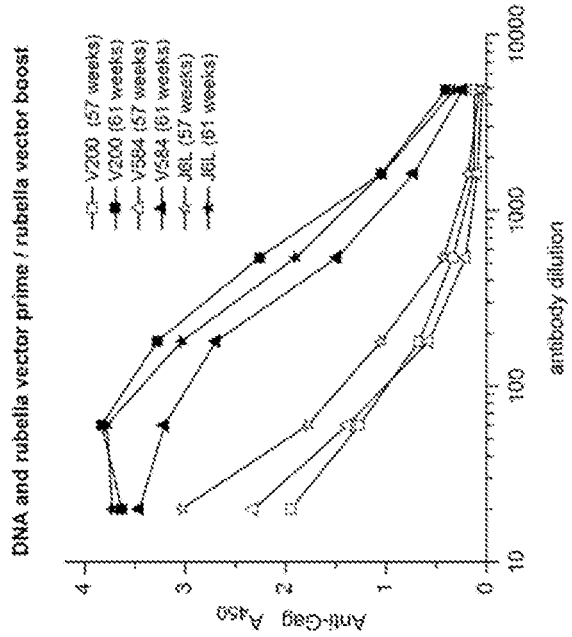
Figure 29B:
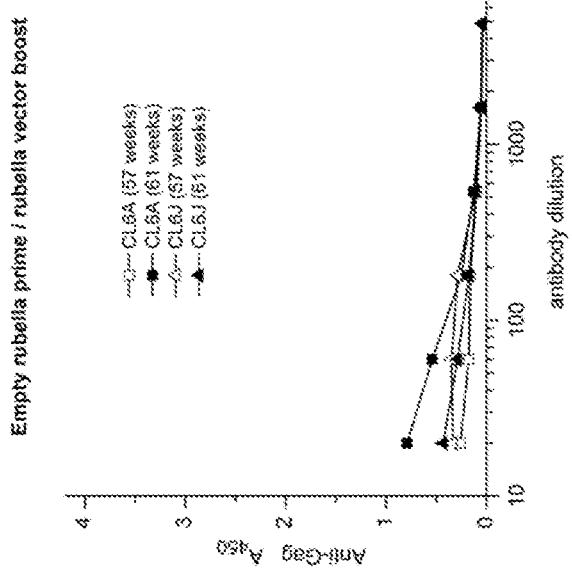

FIGS. 29A and 29B are graphs illustrating the immune response to a live rubella-Gag vector boost. Group 1 (right panel) and group 4 (left panel) macaques were rested for 6 to 9 months after their first dose and then re-immunized with rubella vectors expressing SIV Gag antigens. Group 4 macaques were unable to respond, but the group 1 macaques responded strongly. Boosting indicates that the initial vaccination with rubella-Gag had successfully induced memory B cells specific for the Gag insert.

Figure 30:
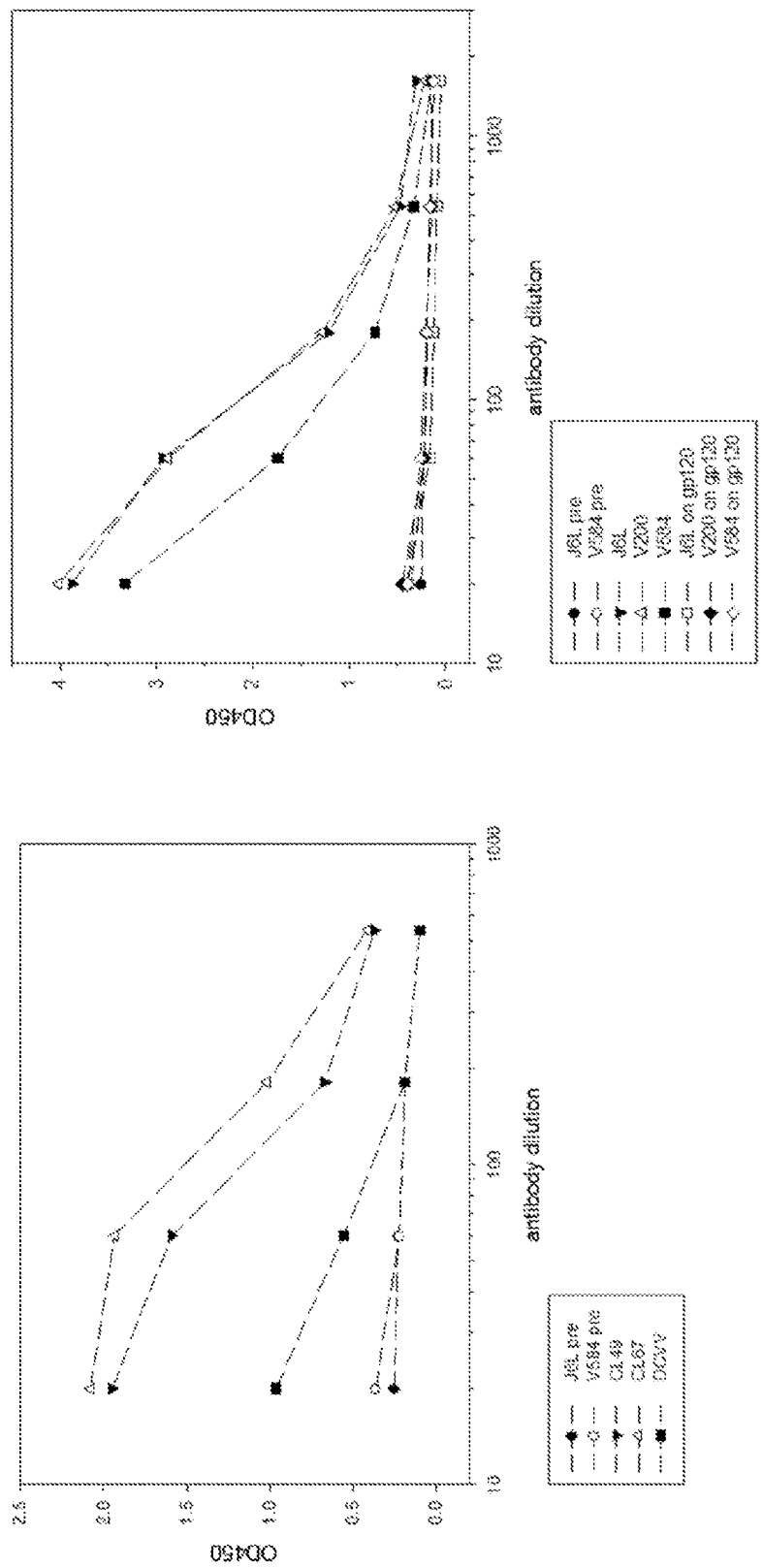

FIG. 30 is a set of graphs illustrating the immune response to the MPER insert expressed by rubella vectors. Macaques in groups 1 and 3 were exposed to two rubella vectors concurrently, one expressing HIV MPER and the other expressing SIV Gag. As shown above (FIGS. 26A and 27B), all six macaques made antibodies to the Gag insert. In addition, this figure shows that five out of six macaques developed strong antibody titers to MPER. These results indicate that immunization with two rubella vectors at the same time results in antibodies to both vaccine inserts.

Figure 31:
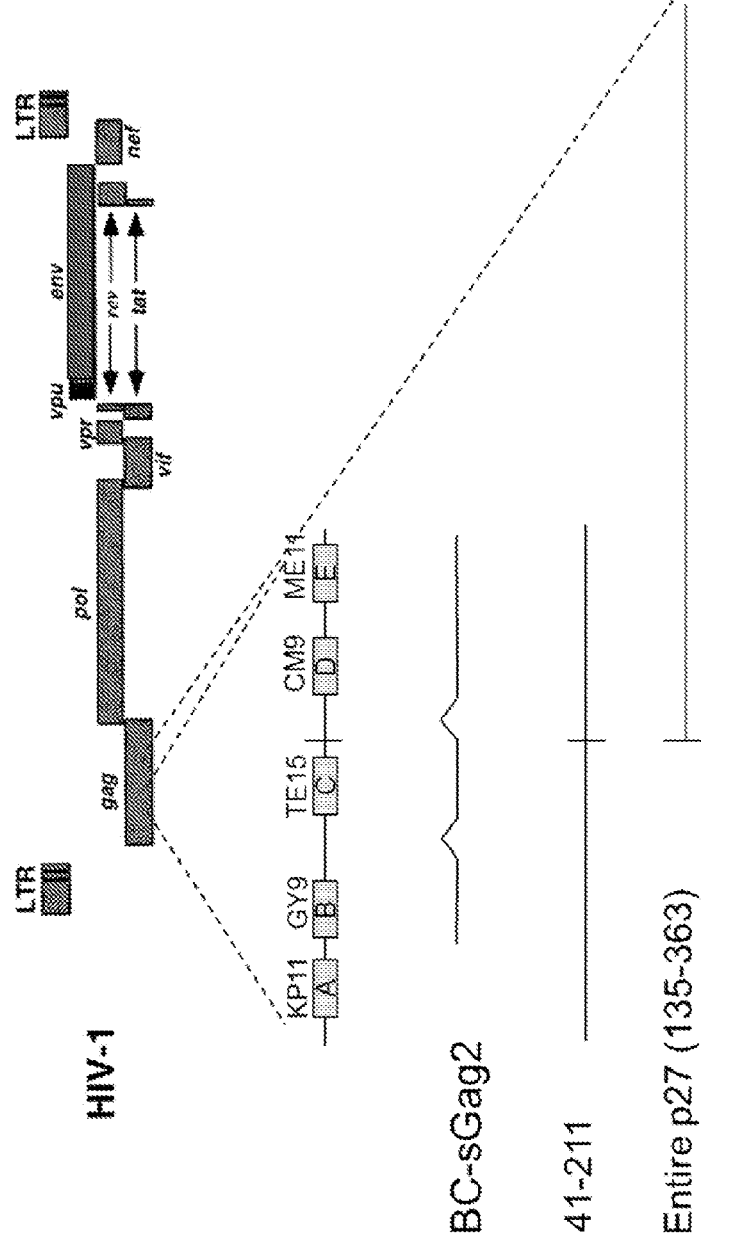

FIG. 31 is a schematic illustrating the position of various larger Gag antigens. The size of Gag inserts that were expressed in the structural site of rubella expanded from 85 amino acids (BCsGag2) to 170 amino acids (Gag 41-211) to 322 amino acids (Gag 41-363) and even to 350 amino acids (Gag 41-391) (see FIG. 32). The last two constructs include the entire p27 Gag protein, with or without p2.

FIG. 32 is a digital image illustrating the expression of large Gag antigens was demonstrated by western blot, using monoclonal antibody 2F12. Lanes 1 to 3 show the expression of Gag protein 41-363 by rubella vectors at passages P3 and P6. Lanes 4 to 7 show expression of Gag 41-391 at passages P3 to P6. Lane 8 is a positive control of recombinant p57 Gag protein. The sequences of these constructs are provided in the Table 8, part A, large Gag inserts. Known epitopes for T cell recognition including Class I restricted epitopes are shown and are known targets of CTLs. Class II restricted epitopes are also shown.

Figure 33:
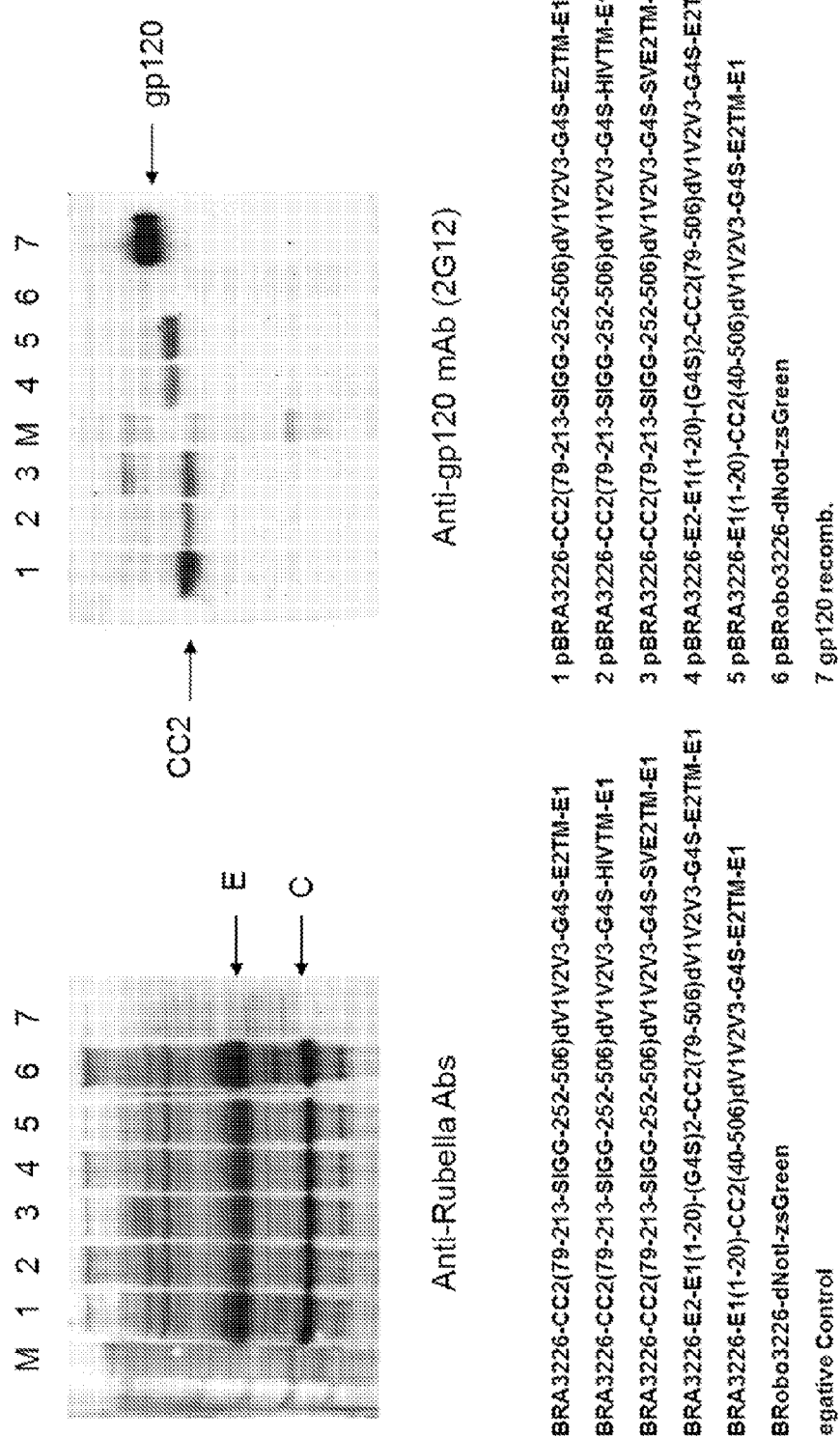

FIG. 33 is a set of digital images illustrating growth and expression of rubella vectors with gp120 inserts. Vector growth was detected by western blot with anti-rubella antibodies (left panel). Expression of rubella proteins capsid and E1 indicate vector growth. These vectors also expressed gp120 constructs with internal deletions, lanes 1-3, or with amino acids 1-20 of rubella E1 protein attached at the amino end of gp120. Antigen expression was detected by western blot, using monoclonal antibody 2G12. These inserts are listed in Table 8, part C, HIV gp120 inserts.

FIG. 34 is a digital image of a western blot illustrating expression of additional gp120 inserts, as detected by western blot with monoclonal antibody 2G12. These gp120 constructs were truncated at the amino end (amino acid (aa) 79, 88 or 93) or at the carboxyl end (aa 484 or 506). The sequences of these inserts are given in Table 8, part C, HIV gp120 inserts.

DETAILED DESCRIPTION OF SEVERAL EMBODIMENTS

I. Introduction

Many of the most successful vaccines are based on live attenuated vaccine strains of pathogens. As they replicate, they expose the host to exponentially increasing amounts of viral antigens, while presenting the antigens in the most immunogenic way, in the context of an acute infection. They combine innate and adaptive immunity to elicit antigen specific T cells and neutralizing antibodies. In the past, these strains were derived from virulent viruses by repeated passage under selective conditions, until virulence genes were mutated or lost, while retaining the ability to replicate and elicit an immune response in the host.

Human immunodeficiency virus (HIV) infection often elicits a strong immune response, including T cell immunity and neutralizing antibodies. Similarly, prior infection with nef deleted simian immunodeficiency virus (SIV) can protect animals against a subsequent challenge. However, it seems unlikely that HIV virus could be attenuated sufficiently for vaccine use. In part, this is due to the retroviral life cycle, with its obligatory integration into host DNA. It is also due to the high rate of mutation, with the risk of reversion to wild type. In addition, no virulence genes have been identified that could be mutated or deleted to produce a reliably attenuated vaccine strain.

Instead of classical attenuation, the inventors have developed live attenuated rubella viral vectors to combine the safety and immunogenicity of the vector with the antigenicity of the HIV and SIV protein inserts. Previous vectors have included DNA viruses, such as vaccinia virus and modified vaccinia Ankara, adenovirus and cytomegalovirus (CMV). They also have included RNA viruses, such as Venezuelan equine encephalomyelitis replicons, attenuated vesicular stomatitis virus, and yellow fever vaccine. Some vectors are defective and replicate poorly or not at all in vivo, while others grow freely. Rubella virus has a number of desirable properties for a live vector. The live attenuated rubella vaccine strain is immunogenic in humans at a dose of just 5,000 PFU. The RA27/3 vaccine strain is a licensed product, and its safety record has been established in millions of children around the world. It is immunogenic: one dose protects for life (against rubella infection), and it elicits mucosal as well as systemic immunity. It has no DNA intermediate, cannot integrate into host DNA, and does not persist after the acute infection. A full length, infectious cDNA clone is available, both for wild type rubella and for the RA27/3 vaccine strain, making it possible to manipulate rubella genetically. Rubella readily infects rhesus macaques. These are the animal model of choice for demonstrating protection against SIV or simian-human immunodeficiency virus (SHIV) challenge.

Despite these desirable properties, the use of rubella virus for a live vector has been unsuccessful because of the inability to maintain stable expression of foreign genes in a live rubella vector. Moreover, it has remained unclear which foreign genes could be inserted, where to insert them, and how large an insert could be accommodated in viral RNA and packaged into virions. For example, if the insert exceeded the size limit, selective pressure resulted in an unstable construct with loss of gene expression.

Disclosed herein is a rubella viral vector construct that is capable of expressing foreign genes at a high level without interfering with expression of essential rubella genes and packaging of live virus. This vector construct maintains stable expression of foreign genes for multiple passages. Thus, the inventors have created a new way to use rubella vaccine as a viral vector to express an additional protein antigen of a second virus. In this way, the safety and immunogenicity of a rubella vaccine can be combined with the antigenicity of another virus.

For example, previous vectors, with up to 1000 fold less potency, have been tested for immunization with HIV antigens, and they all failed to protect against HIV infection. The vector constructs disclosed herein are believed to be capable of actually immunizing against this pathogen. Further, unlike previous vectors, the safety and immunogenicity of a live attenuated rubella vaccine has been demonstrated in tens of millions of children throughout the world. Vaccine potency is based on the fact that this is a replicating vector that simulates infection. One dose protects for life against rubella. The vaccine induces mucosal as well as systemic immunity. Each of these properties would be desirable in a vaccine against HIV or other pathogens, such as SIV, RSV or hepatitis.

At the same time, a disclosed vector construct can also be the lowest cost vector for virtually any viral pathogen, since the immunizing dose is so low that one ml of culture fluid can make up to 1,000 doses of vaccine. The market could be more than 100 million doses per year. Moreover, in the United States, the disclosed vector construct can be used to generate a rubella vaccine that could be substituted for the current rubella vaccine, at almost zero cost, and used to immunize against rubella plus the inserted antigen. Without vaccination, the average age of becoming seropositive to rubella is about 9 years old in many parts of the world. Thus, it could be given to 1-2 year olds with a boost at 9 years old, with a high likelihood of success in immunizing against rubella as well as the foreign antigen (such as HBsAg or HIV, SIV or RSV antigen).

II. Abbreviations and Terms aa: amino acid
AIDS: acquired immune deficiency syndrome
bp: base pair
CTL: cytotoxic T lymphocyte
ELISA: enzyme linked immunosorbent assay
Gag: group-specific antigen
GFP: green fluorescent protein
Gp41: glycoprotein 41
Gp120: glycoprotein 120
HBsAg: hepatitis B surface antigen
HIV: human immunodeficiency virus
MHC: major histocompatibility complex
MPER or MPR: membrane proximal region
MW molecular weight
ORF: open reading frame
PCR: polymerase chain reaction
TM: transmembrane
VLP: viral like particle Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

Amplification: Of a nucleic acid molecule (e.g., a DNA or RNA molecule) refers to use of a technique that increases the number of copies of a nucleic acid molecule in a specimen. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No.

6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, that is, molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complimentarity determining region (CDR); and (vi) a F(ab')$_2$ fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, *Current Protocols in Immunology* Wiley/Greene, NY, 1991; and Harlow and Lane, *Antibodies: A Laboratory Manual* Cold Spring Harbor Press, NY, 1989; Stites et al., (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y. 1986; and Kohler and Milstein, *Nature* 256: 495-497, 1975. Other suitable techniques for antibody preparation include selection of libraries of recombinant antibodies in phage or similar vectors. See, Huse et al., *Science* 246: 1275-1281, 1989; and Ward et al., *Nature* 341: 544-546, 1989. "Specific" monoclonal and polyclonal antibodies and antisera (or antiserum) will usually bind with a $K_D$ of at least about 0.1 µM, preferably at least about 0.01 µM or better, and most typically and preferably, 0.001 µM or better.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), *Antibody Engineering, 2$^{nd}$ Edition* Freeman and Company, NY, 1995; McCafferty et al., *Antibody Engineering, A Practical Approach*, IRL at Oxford Press, Oxford, England, 1996, and Paul *Antibody Engineering Protocols* Humana Press, Towata, N.J., 1995.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term is used interchangeably with the term "immunogen." The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. Methods of determining spatial conformation of epitopes include, for example, x-ray crystallography and multi-dimensional nuclear magnetic resonance spectroscopy. The term "antigen" denotes both subunit antigens, (for example, antigens which are separate and discrete from a whole organism with which the antigen is associated in nature), as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "antigen," when referring to a protein, includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

Antigen Delivery Platform or Epitope Mounting Platform: In the context of the present disclosure, the terms "antigen delivery platform" and "epitope mounting platform" refer to a macromolecular complex including one or more antigenic epitopes. Delivery of an antigen (including one or more epitopes) in the context of an epitope mounting platform enhances, increases, ameliorates or otherwise improves a desired antigen-specific immune response to the antigenic epitope(s). The molecular constituents of the antigen delivery platform may be antigenically neutral or may be immunologically active, that is, capable of generating a specific immune response. Nonetheless, the term antigen delivery platform is utilized to indicate that a desired immune response is generated against a selected antigen that is a component of the macromolecular complex other than the platform polypeptide to which the antigen is attached. Accordingly, the epitope mounting platform is useful for delivering a wide variety of antigenic epitopes, including antigenic epitopes of pathogenic organisms such as bacteria and viruses. The antigen delivery platform of the present disclosure is particularly useful for the delivery of complex peptide or polypeptide antigens, which may include one or many distinct epitopes.

Antigenic polypeptide fragment: A polypeptide that is antigenic. In an example, an antigenic polypeptide fragment includes an HIV antigenic polypeptide fragment, such as a Gag, gp41 or gp120 antigenic polypeptide fragment or a HBsAg antigenic polypeptide fragment.

Conservative variants: "Conservative" amino acid substitutions are those substitutions that do not substantially affect or decrease a desired activity of a protein or polypeptide. For example, in the context of the present disclosure, a conservative amino acid substitution does not substantially alter or decrease the immunogenicity of an antigenic epitope. Similarly, a conservative amino acid substitution does not substantially affect the structure or, for example, the stability of a protein or polypeptide. Specific, non-limiting examples of a conservative substitution include the following examples:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity or substantially alter a structure, such as a secondary or tertiary structure, of a protein or polypeptide.

cDNA (complementary DNA): A piece of DNA lacking internal, non-coding segments (introns) and regulatory sequences that determine transcription. cDNA is typically synthesized in the laboratory by reverse transcription from messenger RNA extracted from cells.

Cytotoxic T lymphocyte (CTL): A type of lymphocyte (white blood cell) that is involved in the immune defenses of the body. Cytotoxic T cells are capable of inducing the death of inducing the death of infected somatic or tumor cells. They are also capable of killing cells infected with viruses (or other pathogens) or are otherwise damaged or dysfunctional. Most CTLs express T-cell receptors that can recognize a specific antigenic peptide bound to Class I MHC molecules.

Deletion: Removal or loss of a sequence of nucleic or amino acids. In one example, a deletion is an "in-frame deletion" (a deletion of a number of base pairs that is a multiple of three and thus constitutes a codon, and therefore does not disrupt the triplet reading frame.)

Diagnostic: Identifying the presence or nature of a pathologic condition, such as, but not limited to a condition induced by a viral or other pathogen. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (or for example, the probability of severity) of a pathologic condition, such as a symptom induced by a viral infection or other pathogenic organism, or resulting indirectly from such an infection.

Epitope: An antigenic determinant. These are particular chemical groups or peptide sequences on a molecule that are antigenic, that is, that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8-10 amino acids in a unique spatial conformation. Methods of determining spatial conformation of epitopes include, for example, x-ray crystallography and multi-dimensional nuclear magnetic resonance spectroscopy. See, e.g., "Epitope Mapping Protocols" in *Methods in Molecular Biology*, Vol. 66, Glenn E. Morris, Ed (1996). In some embodiments, an epitope binds an MHC molecule, e.g., an HLA molecule or a DR molecule. In some embodiments, an epitope is a cytotoxic T lymphocyte (CTL) epitope, such as a CTL epitope of Gag.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

Glycoprotein 41 (gp41): An HIV-1 envelope glycoprotein that mediates receptor binding and HIV entry into a cell. Gp41 includes a membrane proximal region (MPR or MPER) and a transmembrane spanning domain. Gp41 is immunogenic and induces a variety of neutralizing antibodies, such as neutralizing antibodies directed to 2F5, 4E10 and Z13. These three gp41 neutralizing antibodies recognize the MPER of the HW-1 gp41 glycoprotein.

Gp41 antigenic insert: A peptide fragment that includes a MPER of gp41 and a transmembrane spanning region of gp41. In an example, the MPER (also referred to as the antigenic polypeptide fragment) of gp41 includes the amino acid sequence of SEQ ID NO: 1 and a transmembrane spanning region of gp41 including the amino acid sequence set forth as SEQ ID NO: 25

($X_4$FIMIVGGL$X_5$GLRIVFTX$_6$LSIV, $X_1$, $X_2$ and $X_3$ are any amino acid and $X_4$, $X_5$, and $X_6$ are any hydrophobic amino acid). For example, the antigenic polypeptide fragment of gp41 is between 16 and 150 amino acids in length (such as 28 and 150 amino acids in length) and the transmembrane spanning region of gp41 is between 22 and 40 amino acids in length and wherein the transmembrane spanning region of gp41 is C-terminal to the antigenic polypeptide fragment of gp41.

Glycoprotein 120 (gp120): An envelope protein from Human Immunodeficiency Virus (HIV). The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (such as CCR5).

Mature gp120 wildtype polypeptides have about 500 amino acids in the primary sequence. Gp120 is heavily N-glycosylated (approximately 20 to 25 sites) giving rise to an apparent molecular weight of 120 kD. Exemplary sequence of wt gp160 polypeptides are shown on GEN-BANK®, for example accession numbers AAB05604 and AAD12142 incorporated herein by reference in their entirety as available on Oct. 16, 2009.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core comprises 25 beta strands, 5 alpha helices, and 10 defined loop segments. The 10 defined loop segments include five conserved regions (C1-C5) and five regions of high variability (V1-V5).

Gp120 polypeptides also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants, for example deletions, such as loop deletions, insertions or point mutation in any combination), genetic alleles, fusions proteins of gp120, or combinations thereof.

The numbering used in gp120 polypeptides disclosed herein is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex. which is incorporated by reference herein in its entirety.

As used herein, a variant gp120 polypeptide is a gp120 polypeptide in which one or more amino acids have been altered (e.g., deleted or substituted). In one example, a variant gp120 polypeptide is a gp120 polypeptide in which at least 8 consecutive residues, such as 9, 10, 11 or 12 consecutive residues, of the fourth conserved loop (C4) between residues 419 and 434 of gp120 of SEQ ID NO: 63 has been deleted. In a particular example, a variant gp120 polypeptide includes a gp120 polypeptide in which residues 424-432 are deleted. Additional variant gp120 polypeptides include deletions of INMWQKVGK (residues 424-432 of SEQ ID NO:63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), IINMWQKVGK (residues 423-432 of SEQ ID NO: 63). In other embodiments, variant gp120 polypeptides include combinations of the amino and carboxyl ends between residues 419 and 434.

Any of the disclosed variant gp120 polypeptide including deletions in C4 can also include a deletion in the V1V2 loop region (with an amino acid sequence set forth in SEQ ID NO: 63); see SR Pollard and DC Wiley, *EMBO J.* 11:585-91, 1992 which is hereby incorporated by reference in its entirety.

In some examples, an antigenic insert includes a gp120 polypeptide with an amino acid sequence set forth by SEQ ID NOs: 152, 153, 154, 155, 156, 158, 159 or 160.

Group-specific antigen (Gag): A gene which encodes core structural proteins of HIV or SIV. In particular, Gag contains approximately 1500 nucleotides and encodes four separate proteins (capsid protein (p24), matrix protein (p17), nucleocapsid (p9) and p6) which form the building blocks for the viral core. Gag forms a spherical shell underlying the membrane of an immature viral particle. After proteolytic maturation of Gag, the capsid (CA) domain of Gag reforms into a conical shell enclosing the RNA genome. This mature shell contains 1,000-1,500 CA proteins assembled into a hexameric lattice with a spacing of 10 nm. Exemplary nucleic acid and amino acid sequences are known to those of skill in the art including the amino acid sequences provided for Gag herein.

Hepatitis B Surface Antigen (HBsAg): HBsAg is composed of 3 polypeptides, preS1, preS2 and S that are produced from alternative translation start sites. The surface proteins have many functions, including attachment and penetration of the virus into hepatocytes at the beginning of the infection process. The surface antigen is a principal component of the hepatitis B envelope. HBsAg has four membrane spanning domains. Exemplary nucleic acid and amino acid sequences are known to those of skill in the art and are shown on GENBANK®, for example accession numbers NM_001166119, NM_001130714, NM_001130713, NM_016269, BAF48754, BAF48753, BAF48752, BAF48751, AAA35977, AAA35976, AAA35975, AAA35974 and AAA35973 all of which are incorporated herein by reference in their entirety as available on Oct. 16, 2009.

As used herein, a variant HBsAg can include natural variants or recombinant variants such as a HBsAg that includes a MPER from gp41. In a particular example, a variant HBsAg includes a MPER and a membrane spanning domain from gp41.

Heterologous antigenic insert: An insert with an antigenic sequence that is not normally (in the wild-type sequence) found adjacent to a second sequence. In one embodiment, the antigenic insert is from a different genetic source, such as a virus or organism, than the second sequence. In one particular example, the antigenic insert is an HIV envelope protein or an HIV Gag protein. For example, the heterologous antigenic insert is a MPER of the HIV-1 gp41 glycoprotein. In other examples, the heterologous antigenic insert is not a rubella structural protein, such as a capsid.

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A virus, known to cause AIDS, which includes HIV-1 and HIV-2. HIV-1 is composed of two copies of single-stranded RNA enclosed by a conical capsid including the viral protein p24, typical of lentiviruses. The capsid is surrounded by a plasma membrane of host-cell origin.

The RNA genome has at least three genes, gag, pol, and env, which contain information needed to make the structural proteins for new virus particles. The envelope protein of HIV-1 is made up of a glycoprotein called gp160. The mature, virion associated envelope protein is a trimeric molecule composed of three gp120 and three gp41 subunits held together by weak noncovalent interactions. This structure is highly flexible and undergoes substantial conformational changes upon gp120 binding with CD4 and chemokine coreceptors, which leads to exposure of the fusion peptides of gp41 that insert into the target cell membrane and mediate viral entry. Following oligomerization in the endoplasmic reticulum, the gp160 precursor protein is cleaved by cellular proteases and is transported to the cell surface. During the course of HIV-1 infection, the gp120 and gp41 subunits are shed from virions and virus-infected cells due to the noncovalent interactions between gp120 and gp41 and between gp41 subunits.

The HIV-1 envelope glycoproteins (gp120-gp41), which mediate receptor binding and entry, are major targets for neutralizing antibodies. Although the envelope glycoproteins are immunogenic and induce a variety of antibodies, the neutralizing antibodies that are induced are strain-specific, and the majority of the immune response is diverted to non-neutralizing determinants. Broadly neutralizing monoclonal antibodies have been isolated only rarely from natural HIV infection. For example, only three gp41-directed neutralizing antibodies (2F5, 4E10 and Z13) and a few gp120-directed neutralizing antibodies have been identified to date.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. For purposes of the present invention, a "humoral immune response" refers to an immune response mediated by antibody molecules, while a "cellular immune response" is one mediated by T-lymphocytes and/or other white blood cells. A "protective immune response" is an immune response that inhibits a detrimental function or activity (such as a detrimental effect of a pathogenic organism such as a virus), reduces infection by a pathogenic organism (such as, a virus), or decreases symptoms that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo.

An immunogenic composition can induce a B cell response. The ability of a particular antigen to stimulate a B cell response can be measured by determining if antibodies are present that bind the antigen. In one example, neurtralizing antibodies are produced.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surface of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al. (1993) *J. Immunol.* 151: 4189-4199; Doe et al. (1994) *Eur. J. Immunol.* 24:2369-2376. Recent methods of measuring cell-mediated immune response include measurement of intracellular cytokines or cytokine secretion by T-cell populations, or by measurement of epitope specific T-cells (for example, by the tetramer technique) (reviewed by McMichael and O'Callaghan (1998) *J. Exp. Med.* 187(9)1367-1371; Mcheyzer-Williams et al. (1996) *Immunol. Rev.* 150:5-21; Lalvani et al. (1997) *J. Exp. Med.* 186:859-865).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or gamma-delta T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

Immunogenic composition: A composition comprising at least one epitope of a virus, or other pathogenic organism, that induces a measurable CTL response, or induces a measurable B cell response (for example, production of antibodies that specifically bind the epitope). It further refers to isolated nucleic acids encoding an immunogenic epitope of virus or other pathogen that can be used to express the epitope (and thus be used to elicit an immune response against this polypeptide or a related polypeptide expressed by the pathogen). For in vitro use, the immunogenic composition may consist of the isolated nucleic acid, protein or peptide. For in vivo use, the immunogenic composition will typically include the nucleic acid, protein or peptide in pharmaceutically acceptable carriers or excipients, and/or other agents, for example, stabilizers. An immunogenic polypeptide (such as an antigenic polypeptide), or nucleic acid encoding the polypeptide, can be readily tested for its ability to induce a CTL or antibody response by art-recognized assays.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

Inhibiting an infection: Inhibiting infection by a pathogen such as a virus, such as a lentivirus, or other virus, refers to inhibiting the full development of a disease either by avoiding initial infection or inhibiting development of the disease process once it is initiated. For example, inhibiting a viral infection refers to lessening symptoms resulting from infection by the virus, such as preventing the development of symptoms in a person who is known to have been exposed to the virus, or to lessening virus number or infectivity of a virus in a subject exposed to the virus.

Isolated: An "isolated" biological component (such as a nucleic acid or protein or organelle) has been substantially separated or purified away from other biological components in the cell of the organism in which the component naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, affinity tags, enzymatic linkages, and radioactive isotopes. An affinity tag is a peptide or polypeptide sequence capable of specifically binding to a specified substrate, for example, an organic, non-organic or enzymatic substrate or cofactor. A polypeptide including a peptide or polypeptide affinity tag can typically be recovered, for example, purified or isolated, by means of the specific interaction between the affinity tag and its substrate. An exemplary affinity tag is a poly-histidine (e.g., six-histidine) affinity tag which can specifically bind to non-organic metals such as nickel and/or cobalt. Additional affinity tags are well known in the art.

Linking peptide: A linking peptide (or linker sequence) is an amino acid sequence that covalently links two polypeptide domains. Linking peptides can be included between a polypeptide and an antigenic epitope to provide rotational freedom to the linked polypeptide domains and thereby to promote proper domain folding. Linking peptides, which are generally between 2 and 25 amino acids in length, are well known in the art and include, but are not limited to the amino acid sequences glycine-proline-glycine-proline (GPGP) (SEQ ID NO: 37) and glycine-glycine-serine (GGS), as well as the glycine(4)-serine spacer described by Chaudhary et al., *Nature* 339:394-397, 1989. In some cases multiple repeats of a linking peptide are present.

Lymphocytes: A type of white blood cell that is involved in the immune defenses of the body. There are two main types of lymphocytes: B cells and T cells. "T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

Membrane proximal region (MPER) of gp41: A region that is immediately N-terminal of the transmembrane region of gp41. The MPER is also known and referred to herein as the MPER (Membrane proximal external region). The MPER is highly hydrophobic (50% of residues are hydrophobic) and is highly conserved across many HIV clades (Zwick, M. B., et al., *J Virol*, 75 (22): p. 10892-905, 2001). The conserved MPER of HIV-1 gp41 is a target of two broadly neutralizing human monoclonal antibodies, 2F5 and 4E10. The core of the 2F5 epitope has been shown to be ELDKWAS (SEQ ID NO: 35). With this epitope, the residues D, K, and W were found to be involved in recognition by 2F5. The core of the 4E10 epitope, NWFDIT (SEQ ID NO: 36), maps just C-terminal to the 2F5 epitope on the gp41 ectodomain.

Oligonucleotide: A linear polynucleotide sequence of up to about 100 nucleotide bases in length.

Open reading frame ("ORF"): A series of nucleotide triplets (codons) coding for amino acids without any internal termination codons. These sequences are usually translatable into a polypeptide (peptide or protein). In one example, an open reading frame is a rubella non-structural protein open reading frame, such as one coding amino acids that include two NotI restriction enzyme sites. In other examples, an open reading frame is a rubella structural protein open reading frame.

Operatively linked: A first nucleic acid sequence is operatively linked with a second nucleic acid sequence when the first nucleic acid sequence is placed in a functional relationship with the second nucleic acid sequence. For instance, a promoter is operatively linked to a coding sequence if the promoter affects the transcription or expression of the coding sequence. Generally, operatively linked DNA sequences are contiguous and, where necessary to join two protein-coding regions, in the same reading frame, for example, two polypeptide domains or components of a fusion protein.

Pharmaceutically acceptable carriers and/or pharmaceutically acceptable excipients: The pharmaceutically acceptable carriers or excipients of use are conventional. *Remingtons: The Science and Practice of Pharmacy*, University of the Sciences in Philadelphia, Lippincott Williams & Wilkins, Philadelphia, Pa., 21st Edition (2005), describes compositions and formulations suitable for pharmaceutical delivery of the constructs disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition used to achieve a desired effect in a subject. For instance, this can be the amount of the composition necessary to inhibit viral (or other pathogen) replication or to prevent or measurably alter outward symptoms of viral (or other pathogenic) infection. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (for example, glycosylation or phosphorylation), such as a protein or a fragment or subsequence of a protein. The term "peptide" is typically used to refer to a chain of amino acids of between 3 and 30 amino acids in length. For example an immunologically relevant peptide may be between about 7 and about 25 amino acids in length, e.g., between about 8 and about 10 amino acids.

In the context of the present disclosure, a polypeptide can be a fusion protein comprising a plurality of constituent polypeptide (or peptide) elements. Typically, the constituents of the fusion protein are genetically distinct, that is, they originate from distinct genetic elements, such as genetic elements of different organisms or from different genetic elements (genomic components) or from different locations on a single genetic element, or in a different relationship than found in their natural environment. Nonetheless, in the context of a fusion protein the distinct elements are translated as a single polypeptide. The term monomeric fusion protein (or monomeric fusion protein subunit) is used synonymously with such a single fusion protein polypeptide to clarify reference to a single constituent subunit where the translated fusion proteins assume a multimeric tertiary structure.

Probes and primers: A probe comprises an isolated nucleic acid attached to a detectable label or reporter molecule. Primers are short nucleic acids, preferably DNA oligonucleotides, for example, a nucleotide sequence of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only about 15 nucleotides. Thus, in order to obtain greater specificity, probes and primers may be selected that comprise 20, 25, 30, 35, 40, 50 or more consecutive nucleotides.

Promoter: A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (for example, metallothionein promoter) or from mammalian viruses (for example, the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Purified: The term "purified" does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques.

Respiratory syncytial virus (RSV): A virus which is a leading cause of acute upper and lower respiratory tract infection in adults, young children and infants. Serological evidence indicates that in the western world approximately 95% of all children have been infected with RSV by the age of two and 100% of children have been exposed by the time they reach adulthood. In most cases the RSV infections will only cause minor upper respiratory illness with symptoms resembling that of the common cold. However, severe infection with the virus may result in bronchiolitis or pneumonia which may result in hospitalization or death. In a given year, around 91,000 infants are hospitalized with RSV infection in the United States. Infants who have been born prematurely or have a pre-existing lung disease are a high risk of severe infection and complications. These infections are responsible for 40 to 50% of hospitalizations for pediatric bronchiolitis and 25% of hospitalizations for pediatric pneumonia. Since the immune response to RSV infection is not protective, RSV infections reoccur throughout adulthood. In adults and older children, RSV infection has been associated with upper respiratory infection, tracheobronchitis, and otitis media. However, RSV in the institutionalized elderly can be more serious and is characterized by severe pneumonia and mortality rates of up to 20 and 78%, respectively. Adults with a previous history of heart or lung conditions are at a high risk for RSV infection. The infection has been linked to exacerbation of patients with chronic obstructive pulmonary disease. Significant mortality has been observed in immunocompromised patients, particularly those undergoing bone marrow transplantation.

RSV is a member of the order Mononegaviraies, which includes the non-segmented negative strand RNA viruses in the Families Paramyxoviridae, Rhandoviridae and Filoviridae. RSV of humans (often also termed RSV or HRSV) is a member of the Pneumovirus genus of the sub-family Pneumovirinae within the Family Paramyxoviridae. Based on genetic and antigenic variations in the structural proteins, RSV is classified into two subgroups, A and B (Mufson, M. et al., *J. Gen. Virol.* 66:2111-2124). Other members of the Pneumovirus genus include viruses such as bovine RSV (BRSV), ovine RSV (ORSV) and pneumonia virus of mice (PVM) amongst others. The sub-family Pneumovirinae also includes the genus *Metapneumovirus* which contains the human pathogen human *metapneumovirus* (hMPV).

hMPV causes respiratory illness ranging from mild upper respiratory symptoms to severe lower respiratory disease such as bronchiolitis and pneumonia. Depending on the patient population sampled, between 5 and 15% of respiratory infections in young children may be attributable to hMPV infection. hMPV is also associated with 12 to 50% of otitis media in children. In the Netherlands, 55% of tested individuals were seropositive for hMPV by age 2, and almost all individuals 5 years and older were seropositive.

In addition to the genome features described above, Family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbors, can also result in the formation of fused multinucleate cells known as syncytia in some cases. The fusion process is believed to be glycoprotein mediated and is a feature shared with diverse enveloped viruses in other taxonomic groups. In the case of the Parctmyxoviridae viruses of all genera characteristically express a fusion glycoprotein (F) which mediates membrane fusion.

Rubella: A small, quasi-spherical, enveloped, nonsegmented, plus-strand RNA virus that is a member of the *rubivirus* genus of the togavirus family (Togaviridae). Molecular biology of rubella virus is summarized by Frey, T. K. in *Adv. Virus Res.* 44:69-160 (1994) which is hereby incorporated by reference in its entirety. The rubella virion (virus particle) includes a single-stranded RNA encapsidated in an icosahedral nucleocapsid surrounded by a lipid envelope. This virion has at least two RdRp nonstructural proteins (nsP150 and nsP90) and three structural proteins (Capsid (C), E2 and E1). Multiple copies of a viral protein, designated the C protein (molecular weight (MW)=32,000-38,000 daltons), make up the nucleocapsid. Two types of viral glycoprotein, designated E1 and E2 (MW=53,000-58,000 daltons and 42,000-48,000 daltons, respectively), are embedded in the envelope. The E2 glycoprotein has been further subdivided into two subgroups, designated E2a and E2b, by their ability to migrate differently when resolved by polyacrylamide gel electrophoresis. E1 is the viral hemagglutinin. Neutralizing epitopes have been found on both E1 and E2. In one example, MPER and other HIV antigenic determinants are linked to E2 and E1 to elicit similar neutralizing antibodies against HIV.

The rubella genome consists of RNA of positive polarity that is roughly 10,000 nucleotides long and is capped and polyadenylated. In infected cells, three viral RNA species are synthesized: the genomic RNA, which also is the mRNA for translation of the nonstructural proteins (whose function is in viral RNA synthesis) from a long open reading frame (ORF) at the 5' end of the genome; a complementary genome-length RNA of minus polarity which is the template for synthesis of plus-strand RNA species; and a subgenomic (SG) RNA which is initiated internally and contains the sequences of the 3'-terminal one-third of the genome (3327 nucleotides) and serves as the mRNA for the translation of the structural proteins. The structural proteins are proteolytically processed from a polyprotein precursor during translation. The order of these proteins in the polyprotein is NH2-C-E2-E1-COOH.

Sequence identity: The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. However, the converse is not necessarily true, and polypeptides with low sequence identity at the amino acid level can nonetheless have highly similar tertiary and quaternary structures.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^+$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993. and Ausubel et al. *Short Protocols in Molecular Biology*, 4$^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

For example, a specific example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Subject: Living multi-cellular vertebrate organisms, a category that includes both human and veterinary subjects, including human and non-human mammals.

Therapeutically active polypeptide: An agent, such as an epitope of a virus or other pathogen that causes induction of an immune response, as measured by clinical response (for example increase in a population of immune cells, increased cytolytic activity against the epitope). Therapeutically active molecules can also be made from nucleic acids. Examples of a nucleic acid based therapeutically active molecule is a nucleic acid sequence that encodes an epitope of a protein of a virus or other pathogen, wherein the nucleic acid sequence is operatively linked to a control element such as a promoter.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., prevention, inhibition, or reduction in a virus, such as inhibition or reduction of viral infection or replication). In one example, a desired response is to inhibit or reduce HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of a composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 μg-10 mg per 70 kg body weight if administered intravenously.

Transformed or Transfected: A transformed cell is a cell into which a nucleic acid molecule has been introduced by molecular biology techniques. As used herein, the term introduction or transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transmembrane spanning region or membrane spanning domain of gp41: A region or domain of gp41 that is immediately C-terminal to the membrane proximal region of gp41. An example of a transmembrane spanning region is provided in SEQ ID NO: 25.

Treating a disease: "Treatment" refers to a therapeutic intervention that ameliorates a sign or symptom of a disease or other pathological condition, such as an infection, for example a sign or symptom of HIV. Treatment can also induce remission or cure of a condition, such as elimination of detectable HIV infected cells. In particular examples, treatment includes preventing a disease, for example by inhibiting the full development of a disease, such as HIV, by inhibiting HIV replication or infection or the development of AIDS. Prevention of a disease does not require a total absence of disease. For example, a decrease of at least 50% can be sufficient.

Vaccine: A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV). HIV-1 is a retrovirus that causes immunosuppression in humans (HIV disease), and leads to a disease complex known as AIDS. "HIV infection" refers to the process in which HIV enters macrophages and CD4+ T cells by the adsorption of glycoproteins on its surface to receptors on the target cell followed by fusion of the viral envelope with the cell membrane and the release of the HIV capsid into the cell. "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

Virus-like particle or VLP: A nonreplicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

III. Overview of Several Embodiments

Rubella vectors expressing a variety of antigens, such as SIV, HIV, RSV or hepatitis antigens are demonstrated herein to be useful for evaluating new immunogens and for developing prime and boost strategies for eliciting protective immunity.

The inventors have discovered that rubella virus can be adapted for protein expression by making a permissive deletion in the nonstructural p150 gene (Not I deletion), to make room for the insert or by inserting positioning an insert in between two structural proteins within the rubella virus without making a deletion in the nonstructural p150 gene. The resulting rubella vectors replicate with kinetics similar to wild type virus, while stably expressing a reporter gene coding for *Zoanthus* sp. green fluorescent protein (zGFP) for at least 12 passages in cell culture. The inventors also report herein live rubella vectors expressing heterologous antigens, such as HIV and SIV vaccine antigens. These vectors express the HIV membrane-proximal external region (MPER) or SIV Gag antigens at either of two insertion sites: the Not I site or an insertion site in the structural gene region. The foreign antigens are controlled by early or late rubella promoters, depending on the insertion site. At the structural insertion site, HIV MPER was highly expressed as part of the structural polyprotein, processed to a free protein, and incorporated into virions. The vectors are based on rubella vaccine strain RA27/3 and grow to high titers in vitro. These vectors provide an ideal vaccine platform for testing vector replication and immunogenicity in vivo, as well as protection against SW or SHIV challenge.

In some embodiments, an isolated rubella viral vector construct includes a rubella non-structural protein ORF with an in-frame deletion, a rubella structural protein ORF, and a heterologous antigenic insert. In one example, the in-frame deletion within the rubella non-structural protein ORF is an in-frame deletion between two NotI restriction enzyme sites. In some examples, the heterologous antigenic insert is positioned within the rubella non-structural protein ORF. In other examples, the heterologous antigenic insert is positioned within the rubella structural protein ORF.

In some embodiments, an isolated rubella viral vector includes a rubella non-structural protein open reading frame (ORF) without an in-frame deletion, a rubella structural protein ORF, and a heterologous antigenic insert. In some examples, the heterologous antigenic insert is positioned within the rubella structural protein ORF. In other examples, the heterologous antigenic insert is positioned in between the genes encoding structural proteins E2 and E1.

In some examples, the antigenic insert comprises an amino acid sequence set forth as SEQ ID NO: 126, 127, 128, 129, 130, 131, 132, 133, 134, 135, 136, 138, 139, 140, 141, 142, 143, 144, 145, 146, 147, 148, 149, 150, 151, 152, 153, 154, 155, 156, 158, 159, 160, 161 or 162.

Exemplary antigenic inserts include an HIV antigenic insert (such as a Gag antigenic insert, a gp41 antigenic insert or a gp120 antigenic insert) or a hepatitis B antigenic insert. In some examples, a Gag antigenic insert includes an antigenic polypeptide fragment with an amino acid sequence provided by SEQ ID NOs: 82, 83, 84, 85, 86, 87, 88, 90, 91, 132, 133, 134, 135, 138, 139, 140, 141, or 142. In some examples, a gp41 antigenic insert includes an antigenic polypeptide fragment of gp41 with an amino acid sequence provided by SEQ ID NOs: 1-22, 30, 81 or 89 and a transmembrane region of gp41 with an amino acid sequence provided by SEQ ID NOs: 25-28. In certain examples, a gp120 antigenic insert includes an amino acid sequence set forth by SEQ ID NOs: 63, 66, 67, 69, 71, 73, 74, 152, 153, 154, 155, 156, 158, 159 or 160. For example, the gp120 antigenic insert includes a variant gp120 polypeptide comprising a deletion of at least 8 consecutive residues of the fourth conserved loop (C4) between residues 423 and 433 of SEQ ID NO: 63. In some examples, an antigenic insert includes one or more CTL epitopes, such as one or more CTL HIV or SIV epitopes, including those set forth as SEQ ID NOs: 77, 78, 79, 80, 92, 93, 94, 95, 96, 97, 98, 99, 100, 101, and 102.

Viral-like particles including the isolated viral vector construct are provided herein. Compositions comprising the viral-like particles are also provided.

Also disclosed are methods of using the disclosed isolated viral vectors to induce an immune response, such as a protective immune response, when introduced into a subject or to diagnose an HIV infection. For example, methods are provided for inhibiting HIV infection in a subject, for inducing an immune response to HIV in a subject, and for diagnosing HIV infection in a subject. Also disclosed are methods for measuring host range, testing sensitivity to neutralizing antibodies, or screening antiviral drugs, such as protease inhibitors.

A. Rubella Viral Vector Constructs

Disclosed herein are rubella viral vector constructs. In one example, an isolated rubella viral vector construct is disclosed that includes a rubella non-structural ORF with an in-frame deletion, a rubella structural protein ORF, and a heterologous antigenic insert. In some examples, an isolated rubella viral vector includes a sub genomic promoter. For example, the sub genomic promoter can control the expression of the structural proteins.

In one example, an in-frame deletion is within the rubella non-structural protein ORF. For example, the in-frame deletion is within nsP150. In one particular example, the in-frame deletion is an in-frame deletion between two NotI restriction enzyme sites located in nsP150, such as between base pairs (bp) 1685 and 2192. For example, the heterologous antigenic insert can be positioned within the rubella non-structural protein ORF. For example, the heterologous antigenic insert is positioned into nsP150, such as into the site of the Not I deletion (see FIG. 1A).

In other examples, the heterologous antigenic insert is positioned at either end of the three rubella structural proteins, capsid (C), E2 and E1 in a rubella viral construct that does not include a deletion, such as a Not I deletion, in the non-structural protein ORF.

In some embodiments of this example, the heterologous antigenic insert is positioned in between the genes encoding structural proteins C, E2 and E1. For example, the heterologous antigenic insert is positioned in between the genes encoding structural protein E2 and E1.

In some examples, the antigenic insert comprises an amino acid sequence set forth as SEQ ID NO: 77, 78, 79, 80, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 160, 161 or 162.

In one example, the heterologous antigenic insert sequence is expressed at the carboxyl end of rubella capsid protein without a deletion being made, such as an in-frame deletion within nsP150, in the non-structural protein ORF. For example, the heterologous antigenic insert sequence is expressed at the amino end of envelope protein E2 and no deletion is present, such as an in-frame deletion within nsP150, in the non-structural protein ORF. In another exemplary construct, the heterologous antigenic insert is expressed at the carboxyl end of E2 and no deletion is present, such as an in-frame deletion within nsP150, in the non-structural protein ORF. In another example, the heterologous antigenic insert sequence is expressed at the amino end of envelope protein E1.

In some examples, the MPER sequence is expressed at the carboxyl end of rubella capsid protein. In other examples, the MPER sequence is expressed at the amino end of envelope protein E2. In another exemplary construct, MPER is expressed at the carboxyl end of E2. In another example, the MPER sequence is expressed at the amino end of envelope protein E1.

In additional examples, a deletion is made within the P150 of the rubella construct, such as in the middle in a size comparable to the Not I deletion to allow for the insertion and expression of genes coding for heterologous antigens, such as one or more HIV envelope protein. In one particular example, a deletion comparable to the Not I deletion is present in the middle of the P150 of the rubella vaccine strain RA27/3. Various heterologous antigens, including any of those described herein are inserted into either the non-structural ORF or structural ORF in this strain known to be safe and immunogenic in humans.

For use, the disclosed vector constructs are chemically introduced into susceptible culture cells, for example, E. coli, for amplification and production of large amounts of the cDNA clone by methods known to those of ordinary skill in the art, including chemical introduction. In one particular example, the purified infectious clone is digested with an restriction endonuclease such as EcoRI (New England Biolabs, Beverly, Mass.) for linearization at the termination of the rubella virus cDNA sequences. The linearized plasmid is then transcribed in vitro with an RNA polymerase such as SP6 RNA polymerase, which results in production of RNA transcripts. The resulting RNA transcripts are used to transfect the cells by transfection procedures known to those skilled in the art. The cells, in turn, will produce both the native structural proteins of the rubella virus and the protein encoded by the foreign gene (such as HIV antigens, SIV antigens or HBsAgs). The replication of the RNA sequences and the expression of the encoded protein by the cells may be monitored by various means known to the ones skilled in the art. In some examples, the cells will further produce recombinant virus particles which, in turn, may be used to infect cells or organisms.

The recombinant virus particles can be recovered in quantity using any purification process known to those of skill in the art, such as a nickel (NTA-agarose) affinity chromatography purification procedure. These particles can be combined with a pharmaceutically acceptable carrier to provide a safe, effective vaccine, such as a HIV, SIV, RSV or Hepatitis B vaccine. The carrier can be oil, water, saline, phosphate buffer, polyethylene glycol, glycerine, propylene glycol, and combinations thereof, or other vehicles routinely used by the pharmaceutical industry for these purposes (as described in detail below). The vaccine is usually provided in lyophilized form and therefore is free of preservatives.

The disclosed recombinant virus particles can also be used to identify antibodies, such as antibodies within a subject. The immunogenic compositions of this disclosure can be employed to generate antibodies that recognize the antigens disclosed herein and the antigen from which the disclosed antigen was derived. The methods include administering to a subject an immunogenic composition including a disclosed antigen or administering to the subject a polynucleotide encoding a disclosed antigen to generate antibodies that recognize the disclosed antigen. The subject employed in this embodiment is one typically employed for antibody production. Mammals, such as, rodents, rabbits, goats, sheep, etc., are preferred.

The antibodies generated can be either polyclonal or monoclonal antibodies. Polyclonal antibodies are raised by injecting (for example subcutaneous or intramuscular injection) antigenic polypeptides into a suitable animal (for example, a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

i. Wildtype and Variant Gp41 Antigenic Inserts

In some examples, isolated rubella viral vectors disclosed herein include an antigenic insert that is a wildtype or variant gp41 polypeptide. In an example, an antigenic insert is a wildtype gp41 polypeptide or a fragment thereof. Exemplary sequence of wildtype gp41 polypeptides are shown on GENBANK®, for example accession number CAD23678 incorporated herein by reference in its entirety as available on Oct. 15, 2009. In other examples, a gp41 antigenic insert can include (a) an antigenic polypeptide fragment of gp41 and (b) a transmembrane spanning region of gp41.

In an example, the gp41 antigenic insert includes (a) an antigenic polypeptide fragment, such as an antigenic polypeptide fragment with the amino acid sequence set forth in SEQ ID NO:1 and is between 8 and 400 amino acids in length, including 10 and 300 amino acids in length, such as from about 10 to about 150, such as about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, 141, 142, 143, 144 or 145 amino acids; and (b) a transmembrane spanning gp41 region, such as a transmembrane spanning gp41 region with the amino acid sequence set forth in SEQ ID NO: 25 (in which wherein $X_1$, $X_2$ and $X_3$ are any amino acid; and $X_4$, $X_5$, and $X_6$ are any hydrophobic amino acid) and is between 22 and 40 amino acids in length, such as about 23 and 38 amino acids in length, including 24, 25, 26, 27, 28, 29, 30, 31, 32, 33, 34, 35, 36, 37, 38 amino acids.

In one example, the antigenic polypeptide includes the amino acid sequence of NEX$_1$X$_2$LLX$_3$LDKWASLWN (SEQ ID NO: 1). In this sequence, $X_1$, $X_2$ and $X_3$ are any amino acid. The antigenic epitope can include repeats of this sequence, such as one to five copies of SEQ ID NO: 1. As noted above, the antigenic peptide includes one or more antigenic epitopes, such as one or more envelope proteins of HIV-1, and, including SEQ ID NO: 1, can be from about 10 to about 200 amino acids in length, such as from about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, 141, 142, 143, 144 or 145 amino acids.

In several examples, the antigenic polypeptide includes one or more of the amino acid sequences set forth below:

a) (NEQELLALDKWASLWNWFDITNWLWYIK); SEQ ID NO: 2 b) (NEQDLLALDKWASLWNWFDITNWLWYIK); SEQ ID NO: 3 c) (NEQDLLALDKWANLWNWFDISNWLWYIK); SEQ ID NO: 4 d) (NEQDLLALDKWANLWNWFNITNWLWYIR); SEQ ID NO: 5 e) (NEQELLELDKWASLWNWFDITNWLWYIK); SEQ ID NO: 6 f) (NEKDLLALDSWKNLWNWFDITNWLWYIK); SEQ ID NO: 7 g) (NEQDLLALDSWENLWNWFDITNWLWYIK); SEQ ID NO: 8 h) (NEQELLELDKWASLWNWFSITQWLWYIK); SEQ ID NO: 9 i) (NEQELLALDKWASLWNWFDISNWLWYIK); SEQ ID NO: 10 j) (NEQDLLALDKWDNLWSWFTITNWLWYIK); SEQ ID NO: 11 k) (NEQDLLALDKWASLWNWFDITKWLWYIK); SEQ ID NO: 12 l) (NEQDLLALDKWASLWNWFSITNWLWYIK); SEQ ID NO: 13 m) (NEKDLLELDKWASLWNWFDITNWLWYIK); SEQ ID NO: 14 n) (NEQEILALDKWASLWNWFDISKWLWYIK); SEQ ID NO: 15 o) (NEQDLLALDKWANLWNWFNISNWLWYIK); SEQ ID NO: 16 p) (NEQDLLALDKWASLWSWFDISNWLWYIK); SEQ ID NO: 17 q) (NEKDLLALDSWKNLWSWFDITNWLWYIK); SEQ ID NO: 18 r) (NEQELLQLDKWASLWNWFSITNWLWYIK); SEQ ID NO: 19 s) (NEQDLLALDKWASLWNWFDISNWLWYIK); SEQ ID NO: 20 t) (NEQELLALDKWASLWNWFDISNWLWYIR); SEQ ID NO: 21 u) (NEQELLELDKWASLWNWFNITNWLWYIK); SEQ ID NO: 22 v) (PSAQEKNEKELLELDKWASLWN); SEQ ID NO: 30 w) (QEKNEKELLELDKWASLWNWFDITNWLWYIRLFI); SEQ ID NO: 81 or x) (PSWNWFDITNWLWYIRLDA). SEQ ID NO: 89

In some examples, the antigenic polypeptide can include one of the amino acid sequences set forth as SEQ ID NOs: 2-22, 30, 81, 89, 126-131, 136 or 137. A single copy of one of SEQ ID NOs: 2-22, 30, 81, 89 or 137 can be included as the antigenic polypeptide. Alternatively, multiple copies of one of SEQ ID NOs: 2-22, 30, 81, 89, 126-131, 136 or 137 can be included as the antigenic polypeptide. Thus, one, two, three, four or five copies of one of the amino acid sequences set forth as SEQ ID NOs: 2-22, 30, 81, 89, 126-131, 136 or 137 can be included as the antigenic polypeptide.

In additional embodiments, more than one of these sequences can be included in the antigenic polypeptide.

Thus, in several examples, two, three, four or five of the amino acid sequences set forth as SEQ ID NOs: 2-22, 30, 81, 89, 126-131, 136 or 137 can be included as the antigenic polypeptide in tandem. Each amino acid sequence included in the antigenic polypeptide can be present only a single time, or can be repeated.

In some embodiments, the transmembrane spanning gp41 region includes the amino acid sequence set forth in SEQ ID NO: 25. In this sequence, $X_1$, $X_2$ and $X_3$ are any amino acid and $X_4$, $X_5$, and $X_6$ are any hydrophobic amino acid and the transmembrane spanning gp41 region is between 22 and 40 amino acids in length, such as 23, 24, 25, 26, 27, 28, 29, 30, 31, 32, 33, 34, 35, 36, 37, 38, 39 or 40 amino acids. In several examples, the antigenic polypeptide includes one or more of the amino acid sequences set forth below:

a) (IFIMIVGGLIGLRIVFTVLSIV) SEQ ID NO: 26 b) (LFIMIVGGLIGLRIVFTALSIV); SEQ ID NO: 27 or c) (IFIMIVGGLVGLRIVFTALSIV) SEQ ID NO: 28

A gp41 polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the bound molecule which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as HBsAg and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

ii. Wildtype and Variant Gp120 Antigenic Inserts

In some examples, isolated rubella viral vectors disclosed herein include an antigenic insert that is a wildtype or variant gp120 polypeptide. In an example, a wildtype gp120 polypeptide has an amino acid provided by SEQ ID NO: 63 or a fragment thereof. In other examples, a variant gp120 polypeptide includes a gp120 polypeptide in which at least 8 consecutive residues of the fourth conserved loop (C4) between residues 419 and 434 of gp120 according HXB2 numbering of SEQ ID NO: 63 are deleted. This deletion within the β20-21 loop of the gp120 polypeptide exposes the CD4 binding site thereby providing improved antibody binding and antibody induction. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 63 have been deleted.

In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63). In other embodiments, variant gp120 polypeptides include combinations of the amino and carboxyl ends between residues 419 and 434.

In some embodiments, a variant gp120 polypeptide does not include a variant in which residues 419-428 of SEQ ID NO: 63 are deleted. In other embodiments, a variant gp120 polypeptide does not include a variant in which residues 437-452 of SEQ ID NO: 63 are deleted.

Any of the disclosed variant gp120 polypeptide including deletions in C4 can also include a deletion in the V1V2 loop region (spanning from amino acids 125 to 205 of wild-type gp120, such as demonstrated in SEQ ID NO: 63); see SR Pollard and DC Wiley, *EMBO J.* 11:585-91, 1992 which is hereby incorporated by reference in its entirety.

The gp120 polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

Exemplary sequences for the amino acid sequence for full-length gp120 can be found on Genbank, EMBL and SwissProt websites. Exemplary non-limiting sequence information can be found for example, as SwissProt Accession No. P04578, (includes gp41 and gp120, initial entry Aug. 13, 1987, last modified on Jul. 15, 1999) and Genbank Accession No. AAF69493 (Oct. 2, 2000, gp120), all of which are incorporated herein by reference.

In other embodiments, the antigenic insert is a fusion protein. For example, fusion proteins are provided including a first and second polypeptide moiety in which one of the protein moieties includes a variant gp120 polypeptide such as a variant gp120 polypeptide with an amino acid sequence in which INMWQKVGK (residues 424-432 of SEQ ID NO:63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63) has been deleted. The other moiety is a heterologous protein such as a carrier protein and/or an immunogenic protein. Such fusions also are useful to evoke an immune response against gp120. In certain embodiments the gp120 polypeptides disclosed herein are covalent or non-covalent addition of toll like receptor (TLR) ligands or dendritic cell or B cell targeting moieties to produce self-adjuvanting proteins (e.g., IL-21).

In certain embodiments, a variant gp120 includes a V1V2 deletion without a beta 20-21 loop deletion with an amino acid sequence as set forth as:

(SEQ ID NO: 63)
VPVWREATTTLFCASDAKAYDTEVHNVWATHACVPTDPNPQEVVLGNVT

ENFNMWKNNMVDQMHEDIISLWDESLKPCVKLTPLSVQACPKVSFQPIP

-continued

```
IHYCVPAGFAMLKCNNKTFNGSGPCTNVSTVQCTHGIRPVVSTQLLLNG

SLAEEDIVIRSENFTDNAKTIIVQLNESVVINCTRPNNNTRRRLSIGPG

RAFYARRNIIGDIRQAHCNISRAKWNNTLQQIVIKLREKFRNKTIAFNQ

SSGGDPEIVMHSFNCGGEFFYCNTAQLFNSTWNVTGGTNGTEGNDIITL

QCRIKQIINMWQKVGKAMYAPPITGQIRCSSNITGLLLTRDGGNSTETE

TEIFRPGGGDMRDNWRSELYKYKVVRIEPIGVAPTRAKR.
```

In some embodiments, a variant gp120 includes a V1V2 deletion with a beta 20-21 loop deletion with an amino acid sequence as set forth as:

```
                                        (SEQ ID NO: 66)
VPVWREATTTLFCASDAKAYDTEVHNVWATHACVPTDPNPQEVVLGNVTE

NFNMWKNNMVDQMHEDIISLWDESLKPCVKLTPLSVQACPKVSFQPIPIH
```

```
YCVPAGFAMLKCNNKTFNGSGPCTNVSTVQCTHGIRPVVSTQLLLNGSLA

EEDIVIRSENFTDNAKTIIVQLNESVVINCTRPNNNTRRRLSIGPGRAFY

ARRNIIGDIRQAHCNISRAKWNNTLQQIVIKLREKFRNKTIAFNQSSGGD

PEIVMHSFNCGGEFFYCNTAQLFNSTWNVTGGTNGTEGNDIITLQCRIKQ

LAMYAPPITGQIRCSSNITGLLLTRDGGNSTETETEIFRPGGGDMRDNWR

SELYKYKVVRIEPIGVAPTRAKR.
```

Sequences for deletion to generate gp120 variant with an amino acid sequence set forth in SEQ ID NO: 66 are shown in bold.

In other embodiments, a variant gp120 from a HIV isolate JRFL includes an amino acid sequence as set forth in SEQ ID NO: 67 and nucleic acid sequence set forth in SEQ ID NO: 68:

```
                                        (SEQ ID NO: 67)
IIHTVPPSGADPGPKRAEFKGLRRQQKQGIILLLTMKTIIALSYILCLVLAQKLPGNDNNSEFITSGFLGPLLVLQAGFFLLTRILTIPQSL
DSWWTSLNFLGGSPVCLGQNSQSPTSNHSPTSCPPICPGYRMCLRRFIIFLFLLLLCLIFLLVLLDYQGMLPVCPLIPGSTTTSTGPCKTC
TTPAQGNSKFPSCCCTKPTDGNCTCIPIPSSWAFAKYLWEWASVRFSWLSLLVPFVQWFVGLSPTVWLSAIWMMWYWGPSLYSIVSPFIPL
LPIFFCLWVYIGVPVWKEATTTLFCASDAKAYDTEVHNVWATHACVPTDPNPQEVVLENVTEHFNMWKNNMVEQMQEDIISLWDQSLKPCV
KLTPLQACPKISFEPIPIHYCAPAGFAILKCNDKTFNGKGPCKNVSTVQCTHGIRPVVSTQLLLNGSLAEEEVVIRSDNFTNNAKTIIVQL
KESVEINCTRPNNNTRKSIHIGPGRAFYTTGEIIGDIRQAHCNISRAKWNDTLKQIVIKLREQPENKTIVFNHSSGGDPEIVMHSFNCGGE
FFYCNSTQLFNSTWNNNTEGSNNTEGNTITLPCRIKQLAMYAPPIRGQIRCSSNITGLLLTRDGGINENGTEIFRPGGGDMRDNWRSELYK
YKVVKIEPLGVAPTKAKR*LVAAAFESR.
```

```
                                        (SEQ ID NO: 68)
ggattattcataccgtcccaccatcgggcgcggatcccggtccgaagcgcgcggaattcaaaggcctacgtcgacagcaaaagcagggat
aattctattaaccatgaagactatcattgctttgagctacattttatgtctggttctcgctcaaaaacttcccggaaatgacaacaacagc
gaattcatcacctccggcttcctgggcccctgctggtgctgcaggccggcttcttcctgctgacccgcatcctgaccatccccagtccc
tggactcctggtggacctccctgaacttcctgggcggctcccccgtgtgcctgggccagaactcccagtcccccacctccaaccactccc
cacctcctgccccccatctgccccggctaccgctggatgtgcctgcgccgcttcatcatcttcctgttcatcctgctgctgtgcctgatc
ttcctgctggtgctgctggactaccagggcatgctgcccgtgtgcccctgatcccggctccaccaccacctccaccggccctgcaaga
cctgcaccacccccgcccagggcaactccaagttccctcctgctgctgcaccaagcccaccgacggcaactgcacctgcatcccatcc
ctcctcctgggccttcgccaagtacctgtgggagtgggcctccgtgcgcttctcctggctgtccctgctggtgcccttcgtgcagtggttc
gtgggcctgtcccccaccgtgtggctgtccgccatctggatgatgtggtactgggcccctccctgtactccatcgtgtcccccttcatcc
ccctgctgcccatcttcttctgcctgtgggtgtacatcggggtacctgtgtggaaagaagcaaccaccactctattttgtgcatcagatgc
taaagcatatgatacagagggtacataattgtttgggccacacatgcctgtgtacccacagacccaaccccacaagaagtagtattggaaat
gtaacagaacatttttaacatgtggaaaaataacatggtagaacagatgcaggaggatataatcagttttatgggatcaaagcctaaagccat
gtgtaaaattaaccccactccaggcctgtccaaagatatcctttgagccaattcccatacattattgtgccccggctggttttgcgattct
aaagtgtaatgataagacgttcaatgaaaaggaccatgtaaaaatgtcagcacagtacaatgtacacatgaattaggccagtagtatca
actcaactgctgctaaatggcagtctagcagaagagggtagtaattagatctgacaatttcacgaacaatgctaaaaccataatagtac
agctgaaagaatctgtagaaattaattgtacaagacccaacaacaataacaagaaaaagtatacatataggaccaggggagagcattttatac
tacaggagaaataataggagatataagacaagcacattgtaacattagtagagcaaatggaatgacacttaaaacagatagttataaaa
ttaagagaacaatttgagaataaaacaatagtctttaatcactcctcaggaggggacccagaaattgtaatgcacagttttaattgtggag
gagaattttctactgtaattcaacacaactgttaatagtacttggaataataatactgaagggtcaaataacactgaaggaaatactat
cacactcccatgcagaataaaacagctagcaatgtatgccctcccatcagaggacaaattagtgtcatcaaatattacagggctgcta
ttaacaagagatggtggtattaatgagaatgggaccgagatcttcagacctggaggaggagatatgagggacaattggaagtgaattat
ataaatataaagtagtaaaaattgaaccattaggagtagcacccaccaaggcaaagagatgactagtcgcggccgctttcgaatctaga
```

In other embodiments, a variant gp120 from a HIV isolate AD8 includes an amino acid sequence as set forth in SEQ ID NO: 69 or nucleic acid sequence set forth in SEQ ID NO: 70:

```
                                        (SEQ ID NO: 69)
IIHTVPPSGADPGPKRAEFKGLRRQQKQGIILLLTMKTIIALSYILCLVLAQKLPGNDNNSEFITSGFLGPLLVLQAGFFLLTRILTIPQSL
DSWWTSLNFLGGSPVCLGQNSQSPTSNHSPTSCPPICPGYRWMCLRRFIIFLFLILLLCLIFLLVLLDYQGMLPVCPLIPGSTTTSTGPCKT
CTTPAQGNSKFPSCCCTKPTDGNCTCIPIPSSWAFAKYLWEWASVRFSWLSLLVPFVQWFVGLSPTVWLSAIWMMWYWGPSLYSIVSPFIP
LLPIFFCLWVYIGVPVWKEATTTLFCASDAKAYDTEVHNVWATHACVPTDPNPQEVELENVTENFNMWKNNMVEQMHEDIISLWDQSLKPC
VKLTPLQACPKVSFEPIPIHYCTPAGFAILKCKDKKFNGTGPCKNVSTVQCTHGIRPVVSTQLLLNGSLAEEEVVIRSSNFTDNAKNIIVQ
LKESVEINCTRPNNNTRKSIHIGPGRAFYTTGEIIGDIRQAHCNISRTKWNNTLNQIATKLKEQFGNNKTIVFNQSSGGDPEIVMHSFNCG
GEFFYCNSTQLFNSTWNFNGTWNLTQSNGTEGNDITITLPCRIKQLAMYAPPIRGQIRCSSNITGLILTRDGGNNHNNDTETFRPGGGDMRD
NWRSELYKYKVVKIEPLGVAPTKAKR*LV.
```

```
                                        (SEQ ID NO: 70)
ggattattcataccgtcccaccatcgggcgcggatcccggtccgaagcgcgcggaattcaaaggcctacgtcgacagcaaaagcagggat
aattctattaaccatgaagactatcattgctttgagctacattttatgtctggttctcgctcaaaaacttcccggaaatgacaacaacagc
gaattcatcacctccggcttcctgggcccctgctggtgctgcaggccggcttcttcctgctgacccgcatcctgaccatccccagtccc
tggactcctggtggacctccctgaacttcctgggcggctcccccgtgtgcctgggccagaactcccagtcccccacctccaaccactccc
```

-continued

```
cacctcctgcccccccatctgccccggctaccgctggatgtgcctgcgccgcttcatcatcttcctgttcatcctgctgctgtgcctgatc
ttcctgctggtgctgctggactaccagggcatgctgcccgtgtgcccctgatcccggctccaccaccacctccaccggccctgcaaga
cctgcaccaccccgcccagggcaactccaagttccctcctgctgctgcaccaagccaccgacggcaactgcacctgcatccccatccc
ctcctcctgggccttcgccaagtacctgtgggagtgggcctccgtgcgcttctcctggctgtccctgctggtgccttcgtgcagtggttc
gtgggcctgtccccaccgtgtggctgtccgccatctggatgatgtggtactgggggcccctcctgtactccatcgtgtccccttcatcc
ccctgctgccatcttcttctgctgtgggtgtacatcggggtacctgtgtggaaagaagcaaccaccactctattttgtgcatcagatgc
taaagcatatgatacagaggtacataatgtttgggccacacatgcctgtgtacccacagaccccaacccacaagaagtagtattggaaaat
gtgacagaaaattttaacatgtggaaaaataacatggtagaacagatgcatgaggatataatcagtttatgggatcaaagcctaaagccat
gtgtaaaattaaccccactccaggcctgtccaaaggtatcctttgagccaattcccatacattattgtaccccggctggttttgcgattct
aaagtgtaaagacaagaagttcaatggaacagggccatgtaaaaatgtcagcacagtacaatgtacacatggaattaggccagtagtgtca
actcaactgctgttaaatggcagtctagcagaagaagaggtagtaattagatctagtaatttcacagacaatgcaaaaaacataatagtac
agttgaaagaatctgtagaaattaattgtacaagacccaacaacaatacaaggaaaagtatacatataggaccaggaagagcattttatac
aacaggagaaataataggagatataagacaagcacattgcaacattagtagaacaaaatggaataacactttaaatcaaatagctacaaaa
ttaaaagaacaatttgggaataataaaacaatagtctttaatcaatcctcaggaggggacccagaaattgtacgcacagttttaattgtg
gaggggaatttttctactgtaattcaacacaactgtttaatagtacttggaattttaatggtacttggaatttaacacaatcgaatggtac
tgaaggaaatgacactatcacactcccatgtagaataaaacagctagcaatgtatgcccctcccatcagaggacaaattagatgctcatca
aatattacagggctaatattaacaagagatggtggaaataaccacaataatgataccgagacctttagacctggaggaggagatatgaggg
acaattggagaagtgaattatataaatataaagtagtaaaaattgaaccattaggagtagcacccaccaaggcaaaaagatgactagtc.
```

In other embodiments, a variant gp120 from a HIV isolate BaL includes an amino acid sequence as set forth in SEQ ID NO: 71 or a nucleic acid sequence as set forth in SEQ ID NO: 72:

(SEQ ID NO: 71)
```
IIHTVPPSGADPGPKRAEFKGLRRQQKQGIILLTMKTIIALSYILCLVLAQKLPGNDNNSEFITSGFLGPLLVLQAGFFLLTRILTIPQSL
DSWWTSLNFLGGSPVCLGQNSQSPTSNHSPTSCPPICPGYRWMCLRRFIIFLFILLLCLIFLLVLLDYQGMLPVCPLIPGSTTTSTGPCKT
CTTPAQGNSKFPSCCCTKPTDGNCTCIPIPSSWAFAKYLWEWASVRFSWLSLLVPFVQWFVGLSPTVWLSAIWMMWYWGPSLYSIVSPFIP
LLPIFFCLWVYIGVPVWKEATTTLFCASDAKAYDTEVHNVWATHACVPTDPNPQEVELENVTENFNMWKNNMVEQMHEDIISLWDQSLKPC
VKLTPLQACPKISFEPIPIHYCAPAGFAILKCKDKKFNGKGPCSNVSTVQCTHGIRPVVSTQLLLNGSLAEEEVVIRSENFADNAKTIIVQ
LNESVEINCTRPNNNTRKSIHIGPGRALYTTGEIIGDIRQAHCNLSRAKWNDTLNKIVIKLREQFGNKTIVFKHSSGGDPEIVTHSFNCGG
EFFYCNSTQLFNSTWNVTEESNNTVENNTITLPCRIKQLAMYAPPIRGQIRCSSNITGLLLTRDGGPEDNKTEVFRPGGGDMRDNWRSELY
KYKVVKIEPLGVAPTKAKR*LVAAAFESR.
```

(SEQ ID NO: 72)
```
ggattattcataccgtcccaccatcgggcgcggatcccggtccgaagcgcgcggaattcaaaggcctacgtcgacagcaaaagcaggggat
aattctattaaccatgaagactatcattgctttgagctacattttatgtctggttctcgctcaaaaacttcccggaaatgacaacaacagc
gaattcatcacctccggcttcctgggcccctgctggtgctgcaggccggcttcttcctgctgaccgcatcctgaccatccccagtccc
tggactcctggtggacctccctgaacttcctgggcggctccccgtgtgcctggtcagaactcccagtccccccacctccaaccactccc
cacctcctgcccccccatctgccccggctaccgctggatgtgcctgcgccgcttcatcatcttcctgttcatcctgctgctgtgcctgatc
ttcctgctggtgctgctggactaccagggcatgctgcccgtgtgcccctgatcccggctccaccaccacctccaccggccctgcaaga
cctgcaccaccccgcccagggcaactccaagttccctcctgctgctgcaccaagccaccgacggcaactgcacctgcatccccatccc
ctcctcctgggccttcgccaagtacctgtgggagtgggcctccgtgcgcttctcctggctgtccctgctggtgccttcgtgcagtggttc
gtgggcctgtccccaccgtgtggctgtccgccatctggatgatgtggtactgggggcccctcctgtactccatcgtgtccccttcatcc
ccctgctgccatcttcttctgctgtgggtgtacatcggggtacctgtgtggaaagaagcaaccaccactctattttgtgcatcagatgc
taaagcatatgatacagaggtacataatgtttgggccacacatgcctgtgtacccacagaccccaacccacaagaagtagaattggaaaat
gtgacagaaaattttaacatgtggaaaaataacatggtagaacagatgcatgaggatataatcagtttatgggatcaaagcctaaagccat
gtgtaaaattaactccactccaggcctgtccaaagatatcctttgagccaattcccatacattattgtgccccggctggttttgcgattct
aaagtgtaaagataagaagttcaatggaaaaggaccatgttcaaatgtcagcacagtacaatgtacacatgggattaggccagtagtatca
actcaactgctgttaaatggcagtctagcagaagaagaggtagtaattagatccgaaaatttcgcggacaatgctaaaaccataatagtac
agctgaatgaatctgtagaaattaattgtacaagacccaacaacaatacaagaaaaagtatacatataggaccaggcagagcattatatac
aacaggagaaataataggagatataagacaagcacattgtaaccttagtagacaaaatggaatgacactttaaataagatagttatataaa
ttaagagaacaatttgggaataaaacaatagtctttaagcattcctcaggaggggacccagaaattgtgacgcacagttttaattgtggag
gggaattttctactgtaattcaacacaactgtttaatagtacttggaatgttactgaagagtcaaataacactgtagaaaataacacaat
cacactcccatgcagaataaaacagctagcaatgtatgccctcccatcagaggacaaattagatgttcatcaaatattacagggctgcta
ttaacaagagatggtggtccagaggacaacaagaccgaggtcttcagacctggaggaggagatatgagggacaattggagaagtgaattat
ataaatataaagtagtaaaaattgaaccattaggagtagcacccaccaaggcaaagagatgactagtcgcggccgctttcgaatctaga.
```

In other embodiments, a variant gp120 from a HIV isolate IIIB includes an amino acid sequence as set forth in SEQ ID NO: 73 or a nucleic acid sequence as set forth in SEQ ID NO: 74:

(SEQ ID NO: 73)
```
IIHTVPPSGADPGPKRAEFKGLRRQQKQGIILLTMKTIIALSYILCLVLAQKLPGNDNNSEFITSGFLGPLLVLQAGFFLLTRILTIPQSL
DSWWTSLNFLGGSPVCLGQNSQSPTSNHSPTSCPPICPGYRWMCLRRFIIFLFILLLCLIFLLVLLDYQGMLPVCPLIPGSTTTSTGPCKT
CTTPAQGNSKFPSCCCTKPTDGNCTCIPIPSSWAFAKYLWEWASVRFSWLSLLVPFVQWFVGLSPTVWLSAIWMMWYWGPSLYSIVSPFIP
LLPIFFCLWVYIGVPVWKEATTTLFCASDAKAYDTEVHNVWATHACVPTDPNPQEVVLNVTENFNMWKNDMVEQMHEDIISLWDQSLKPC
VKLTPLSVQACPKVSFEPIPIHYCAPAGFAILKCNNKTFNGTGPCTNVSTVQCTHGIRPVVSTQLLLNGSLAEEEVVIRSVNFTDNAKTII
VQLNTSVEINCTRPSVNFTDNAKTIIVQLNTSVEINCTRPMRQAHCNISRAKWNNTLKQIASKLREQFGNNKTIIFKQSSGGDPEIVTHSF
NCGGEFFYCNSTQLFNSTWFNSTWSTEGSNNTEGSDTITLPCRIKQSIAMYAPPISGQIRCSSNITGLLLTRDGGNSNNESEIFRPGGGDM
RDNWRSELYKYKVVKIEPLGVAPTKAKR.
```

(SEQ ID NO: 74)
```
ggattattcataccgtcccaccatcgggcgcggatcccggtccgaagcgcgcggaattcaaaggcctacgtcgacagcaaaagcaggggat
aattctattaaccatgaagactatcattgctttgagctacattttatgtctggttctcgctcaaaaacttcccggaaatgacaacaacagc
```

-continued
```
gaattcatcacctccggcttcctgggccccctgctggtgctgcaggccggcttcttcctgctgacccgcatcctgaccatccccagtccc
tggactcctggtggacctccctgaacttcctgggcggctccccgtgtgcctgggcagaactcccagtcccccacctccaaccactcccc
cacctcctgcccccccatctgcccccggctaccgctggatgtgcctgcgccgcttcatcatcttcctgttcatcctgctgctgtgcctgatc
ttcctgctggtgctgctggactaccagggcatgctgcccgtgtgcccctgatcccggctccaccaccacctccaccggcccctgcaaga
cctgcaccaccccgccagggcaactccaagttcccctcctgctgctgccaagcccaccgacggcaactgcacctgcatccccatccc
ctcctcctgggccttcgccaagtacctgtgggagtgggcctccgtgcgcttctcctggctgtccctgtgccttcgtgcagtggttc
gtgggcctgtccccaccgtgtggctgtccgccatctggatgatgtggtactggggccctccctgtactccatcgtgtcccccttcatcc
ccctgctgcccatcttcttctgcctgtgggtgtacatcggggtacctgtgtggaaggaagcaaccaccactctattttgtgcatcagatgc
taaagcatatgatacagaggtacataatgtttgggccacacatgcctgtgtacccacagaccccaacccacaagaagtagtattggtaaat
gtgacagaaaattttaacatgtggaaaaatgacatggtagaacagatgcatgaggatataatcagttttatgggatcaaagcctaaagccat
gtgtaaaattaaccccactctcggtccaggcctgtccaaaggtatccttttgagccaattcccatacattattgtgccccggctggttttgc
gattctaaaatgtaataataagacgttcaatggaacaggaccatgtacaaatgtcagcacagtacaatgtacacatggaattaggcagta
gtatcaactcaactgctgttaaatggcagtctagcagaagaagaggtagtaattagatctgtcaatttcacggacaatgctaaaaccataa
tagtacagctgaacacatctgtagaaattaattgtacaagaccctctgtcaatttcacggacaatgctaaaaccataatagtacagctgaa
cacatctgtagaaattaattgtacaagacccatgagacaagcacattgtaacattagtagagcaaaatgaataacactttaaaacagata
gctagcaaattaagagaacaatttggaaataataaaacaataatctttaagcaatcctcaggaggggacccagaaattgtaacgcacagtt
ttaattgtggagggaattttctactgtaattcaacacaactgtttaatagtacttggtttaatagtacttggagtactgaagggtcaaa
taacactgaaggaagtgacacaatcaccctcccatgcagaataaaacaatgcaatgtatgccccctcccatcagtggacaaattaga
tgttcatcaaatattacagggctgctattaacaagagatggtggtaatagcaacaatgagtccgagatcttcagacctggaggaggagata
tgagggacaattggagaagtgaattatataaatataaagtagtaaaaattgaaccattaggagtagcacccaccaaggcaaagagataa.
```

A gp120 polypeptide can be covalently linked to a carrier, which is an immunogenic macromolecule to which an antigenic molecule can be bound. When bound to a carrier, the bound polypeptide becom

TABLE 1

CTL epitope sequence table for SIV-Gag epitopes.

| Name | MCH Class I or Class II | Gag Epitope | Residues | Location | Sequence | SEQ ID NO: |
|------|------|------|------|------|------|------|
| D | A01 | CM9 | 181-189 | p27 gag | CTPYDINQM | 92 |
| B | A02 | GY9 | 71-79 | P17MA | GSENLKSLY | 93 |
| A | DP$_{B1-06}$ | KP11 | 59-70 | P17 MA | KILSVLAPLVP | 94 |
| C | DR$_{B-W606}$ | TE15/KT15 | 97-111 | | TEEAKQIVQRHLVVET | 95 |
| E | DR$_{B1-0306}$ | ME11 | 200-210 | p27 gag | MQIIRDIINEE | 96 |

TABLE 2

CTL epitope sequence table for HIV-Gag epitopes.

| Epitope | Protein | HXB2 location | Subtype | SEQ ID NO: |
|------|------|------|------|------|
| TRANSPTRR | Gag_Pol_TF | 21-29 | B | 97 |
| NSPTRREL | Gag_Pol_TF | 24-31 | B | 98 |
| PTRRELQVW | Gag_Pol_TF | 26-34 | B | 99 |
| PTSRELQVW | Gag_Pol_TF | 26-34 | A1 | 100 |
| AGAERQGTL | Gag_Pol_TF | 44-52 | C | 101 |
| FSFPQITLW | Gag_Pol_TF | 54-6 | B | 102 |

In some examples, an antigenic polypeptide includes one or more of CTL epitopes of Gag, such as one or more of the epitopes listed in Table 1 or 2 or provided in present FIGS., including FIGS. 20 and 23. In some examples, an antigenic polypeptide includes one or more of the amino acid sequences set forth by any one of SEQ ID NOs: 82-102, 132, 133, 134, 135, 138, 139, 140, 141, 142, 143, 144, 145, 146, 147, 148, 149, 150, 151, 152, 153, 154, 155, 156, 158, 159, 160, 161 or 162. The antigenic epitope can include repeats of any one of these sequences, such as at least two repeats, such as between two to ten copies, such as three to five copies, such as one, two, three, four, five, six, seven, eight, nine or ten copies of SEQ ID NOs: 82-102, 132, 133, 134, 135, 138, 139, 140, 141, 142, 143, 144, 145, 146, 147, 148, 149, 150, 151, 152, 153, 154, 155, 156, 158, 159, 160, 161 or 162 or combinations thereof.

In some examples, an antigenic polypeptide includes the amino acid sequence FQALSEGCTPYDINQMLNCVGD-HQAAMQIIRDIINEEA (SEQ ID NO: 83) or REG-SQKILSVLAPLVPTGSENLKSLYNTVSVIWSIHAED (SEQ ID NO: 82). For example, the isolated rubella viral vector includes a Gag antigenic insert including the amino acids FQALSEGCTPYDINQMLNCVGDHQAAMQIIR-DIINEEA (SEQ ID NO: 83). In some examples, the Gag antigenic insert includes the amino acids LPLSPRTL-NAWVKLIEEKKFGAEVVPG (residues 1 to 27 of SEQ ID NO: 84). In additional examples, the Gag antigenic insert includes the amino acids SQKILSVLAPL (residues 4-14 of SEQ ID NO: 82). In some examples, the antigenic insert includes a Gag antigenic insert, comprising the amino acids GSENLKSLYNT (residues 4-14 of SEQ ID NO: 88).

The antigenic epitope can include repeats of any one of these sequences, such as at least two repeats, such as between two to ten copies, such as three to five copies, such as one, two, three, four, five, six, seven, eight, nine or ten copies of SEQ ID NOs: 82-88 or combinations thereof (e.g., one or more copies of FQALSEGCTPYDINQMLNCVGDHQAAMQIIRDIINEEA (SEQ ID NO: 83); LPLSPRTLNAWVKLIEEKKFGAEVVPG (residues 1 to 27 of SEQ ID NO: 84). SQKILSVLAPL (residues 4-14 of SEQ ID NO: 82); or GSENLKSLYNT (residues 4-14 of SEQ ID NO: 88)).

In several examples, the antigenic polypeptide includes one or more of the amino acid sequences set forth below:

(SEQ ID NO: 82)
REGSQKILSVLAPLVPTGSENLKSLYNTVSVIWSIHAED;

(SEQ ID NO: 83)
FQALSEGCTPYDINQMLNCVGDHQAAMQIIRDIINEEA;

(SEQ ID NO: 84)
LPLSPRTLNAWVKLIEEKKFGAEVVPGFQALSEGCTPYDINQMLNC
VGDHQAAMQIIRDIINEEA;

(SEQ ID NO: 85)
LPLSPRTLNAWVKLIEEKKFGAEVVPGFQALSEGCTPYDINQMLNC
VGDHQAAMQIIRDIINEEATRSQKILSVLAPLVPT;

(SEQ ID NO: 86)
LPLSPRTLNAWVKLIEEKKFGAEVVPGFQALSEGCTPYDINQMLNC
VGDHQAAMQIIRDIINEEATRTGSENLKSLYNT;

(SEQ ID NO: 87)
LPLSPRTLNAWVKLIEEKKFGAEVVPGFQALSEGCTPYDINQMLNC
VGDHQAAMQIIRDIINEEATRHTEEAKQIVQRHLVVETGTT;

(SEQ ID NO: 88)
VPTGSENLKSLYNTVTRVKHTEEAKQIVQRHLVVETGTTSDAFQAL
SEGCTPYDINQMLNCVGDHQAAMQIIRDIINEEA;

(SEQ ID NO: 90)
LDRFGLAESLLENKEGSQKILSVLAPLVPTGSENLKSLYNTVTRVK
HTEEAKQIVQRHLVVETGTTETSDAFQALSEGCTPYDINQMLNCVG
DHQAAMQIIRDIINEEA;
or (SEQ ID NO: 91)
LDRFGLAESLLENKEGSQKILSVLAPLVPTGSENLKSLYNTVTRVK
HTEEAKQIVQRHLVVETGTTETRLPLSPRTLNAWVKLIEEKKFGAE
VVPGFQALSEGCTPYDINQMLNCVGDHQAAMQIIRDIINEEA.

The antigenic polypeptide can include one of the amino acid sequences set forth as SEQ ID NOs: 82-88, 90 and 91. A single copy of one of SEQ ID NOs: 82-88, 90 and 91 can be included as the antigenic polypeptide. Alternatively, multiple copies of one of SEQ ID NOs: 82-88, 90 and 91 can be included as the antigenic polypeptide. Thus, one, two, three, four, five, six, seven, eight, nine or more copies of one of the amino acid sequences set forth as SEQ ID NOs: 82-88, 90 and 91 can be included as the antigenic polypeptide.

In additional embodiments, more than one of these sequences can be included in the antigenic polypeptide. Thus, in several examples, two, three, four or five of the amino acid sequences set forth as SEQ ID NOs: 82-88, 90 and 91, can be included as the antigenic polypeptide in tandem. Each amino acid sequence included in the antigenic polypeptide can be present only a single time, or can be repeated.

In some examples, an antigenic polypeptide includes an amino acid sequence set forth as

```
                                        (SEQ ID NO: 103)
LDRFGLAESLLENKEGCQKILSVLAPLVPTGSENLKSLYNTVCVIVVCIH

AEEKVKHTEEAKQIVQRHLVVETGTTETMPKTSRPTAPSSGRGGNYPVQQ

IGGNYVHLPLSPRTLNAWVKLIEEKKFGAEVVPGFQALSEGCTPYDINQM

LNCVGDHQAAMQIIRDIINEEA
``` and is encoded by a nucleic acid sequence set forth as

```
                                         (SEQ ID NO: 56)
ATTAGATAGATTTGGATTAGCAGAAAGCCTGTTGGAGAACAAAGAAGGAT

AATACTTTCGGTCTTAGCTCCATTAGTGCCAACAGGCTCAGAAAATTTAA

AAAGCCTTTATAATACTGTCTGCGTCATCTGGTGCATTCACGCAGGTCAA

AAAAGAGAAAGTGAAACACACTGAGGAAGCAAAACAGATAGTGCAGAGAC

ACCTAGTGGTGGAAACAGGAACAACAGAAACTATGCCAAAAACAAGTAGA

CCAACAGCACCATCTAGCGGCAGAGGAGGAAATTACCCAGTACAACAAAT

AGGTGGTAACTATGTCCACCTGCCATTAAGCCCGAGAACATTAAATGCCT

GGGTAAAATTGATAGAGGAAAAGAAATTTGGAGCAGAAGTAGTGCCAGGA

TTTCAGGCACTGTCAGAAGGTTGCACCCCCTATGACATTAATCAGATGTT

AAATTGTGTGGGAGACCATCAAGCGGCTATGCAGATTATCAGAGATATTA

TAAACGAGGAGGCTG.
```

An antigenic insert of a CTL epitope of a Gag polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the bound molecule which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as HBsAg and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

iv. Wildtype and Variant HBsAgs

In an example, a disclosed isolated rubella viral vector includes a wildtype or variant HBsAg. Suitable amino acid sequences for HBsAg are known in the art, and are disclosed, for example, in PCT Publication No. WO 2002/079217, which is incorporated herein by reference. Additional sequences for hepatitis B surface antigen can be found, for example, in PCT Publication No. 2004/113369 and PCT Publication No. WO 2004/09849. An exemplary HBsAg amino acid sequence, and the sequence of a nucleic acid encoding HBsAg, is shown in Berkower et al., *Virology* 321: 74-86, 2004, which is incorporated herein by reference in its entirety. An amino acid sequence of an exemplary HBsAg is set forth as follows:

```
                                        (SEQ ID NO: 31)
EFITSGFLGPLLVLQAGFFLLTRILTIPQSLDSWWTSLNFLGGSPVCLG

QNSQSPTSNHSPTSCPPICPGYRWMCLRRFIIFLFILLLCLIFLLVLLD

YQGMLPVCPLIPGSTTTSTGPCKTCTTPAQGNSKFPSCCCTKPTDGNCT

CISIPSSWAFAKYLWEWASVRFSWLSLLVPFVQWFVGLSPTVWLSAIWM

MWYWGPSLYSIVSPFIPLLPIFFCLWVYIG.
```

Naturally occurring variants of HBsAg are found in other hepadnaviruses and also self assemble. These include: woodchuck hepatitis, ground squirrel hepatitis and duck hepatitis virus variants. Any of these naturally occurring HBsAg variants can be included within the disclosed constructs.

By itself, HBsAg assembles into approximately 22 nm virus-like particles. When expressed together with an HIV-1 antigenic epitope, the HBsAg fusion proteins assemble spontaneously and efficiently into virus-like particles (see Berkower et al., *Virology* 321: 75-86, 2004, which is incorporated herein by reference). Without being bound by theory, the multimeric form expresses the one or more antigenic epitopes at the lipid-water interface. These epitopes can be used to induce an immune response, such as to induce the production of neutralizing antibodies.

The preparation of HBsAg is well documented. See, for example, Harford et al. (1983) *Develop. Biol. Standard* 54:125; Greg et al. (1987) *Biotechnology* 5:479; EP-A-0 226 846; and EP-A-0 299 108.

Fragments and variants of HBsAgs as disclosed herein are fragments and variants that retain the ability to spontaneously assemble into virus-like particles. By "fragment" of an HBsAg is intended a portion of a nucleotide sequence encoding a HBsAg, or a portion of the amino acid sequence of the protein. By "homologue" or "variant" is intended a nucleotide or amino acid sequence sufficiently identical to the reference nucleotide or amino acid sequence, respectively.

It is recognized that the gene or cDNA encoding a polypeptide can be considerably mutated without materially altering one or more the polypeptide's functions. The genetic code is well known to be degenerate, and thus different codons encode the same amino acids. Even where an amino acid substitution is introduced, the mutation can be conservative and have no material impact on the essential functions of a protein (see Stryer, *Biochemistry* 4th Ed., W. Freeman & Co., New York, N.Y., 1995). Part of a polypeptide chain can be deleted without impairing or eliminating all of its functions. Sequence variants of a protein, such as a 5' or 3' variant, can retain the full function of an entire protein. Moreover, insertions or additions can be made in the polypeptide chain for example, adding epitope tags, without impairing or eliminating its functions (Ausubel et al., *Current Protocols in Molecular Biology*, Greene Publ. Assoc. and Wiley-Intersciences, 1998). Specific substitutions include replacing one or more transmembrane spanning domains of HBsAg with a gp41 transmembrane spanning domain, such as replacing the first domain and/or third domain of HBsAg with a gp41 transmembrane spanning domain. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquitination, labeling, such as with radionucleides, and various enzymatic modifications, as will be readily appreciated by those well skilled in the art. A variety of methods for labeling polypeptides and labels useful for such purposes is well known in the art, and includes radioactive isotopes such as $^{125}$I or $^3$H, ligands that bind to or are bound by labeled specific binding partners (such as antibodies), fluorophores, chemiluminescent agents, enzymes, and antiligands or crosslinkers to produce dimers or multimers.

Functional fragments and variants of HBsAg include those fragments and variants that are encoded by nucleotide sequences that retain the ability to spontaneously assemble into virus-like particles. Functional fragments and variants can be of varying length. For example, a fragment may consist of 10 or more, 25 or more, 50 or more, 75 or more, 100 or more, or 200 or more amino acid residues of a HBsAg amino acid sequence.

A functional fragment or variant of HBsAg is defined herein as a polypeptide that is capable of spontaneously assembling into virus-like particles and/or self-aggregating into stable multimers. This includes, for example, any polypeptide six or more amino acid residues in length that is capable of spontaneously assembling into virus-like particles. Methods to assay for virus-like particle formation are well known in the art (see, for example, Berkower et al. (2004) *Virology* 321:75-86, herein incorporated by reference in its entirety).

"Homologues" or "variants" of a HBsAg are encoded by a nucleotide sequence sufficiently identical to a nucleotide sequence of hepatitis B surface antigen, examples of which are described above. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, for example using the NCBI Blast 2.0 gapped BLAST set to default parameters. Alignment may also be performed manually by inspection. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). In one embodiment, the HBsAg protein is at least about 85%, at least about 90%, at least about 95%, at least about 96%, at least about 97%, at least about 98%, at least about 99% identical to the polypeptide set forth as SEQ ID NO: 31.

One or more conservative amino acid modifications can be made in the HBsAg amino acid sequence, whether an addition, deletion or modification, that does not substantially alter the 3-dimensional structure of the polypeptide. For example, a conservative amino acid substitution does not affect the ability of the HBsAg polypeptide to self-aggregate into stable multimers. HBsAg proteins having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type HBsAg protein can also be included in the fusion proteins described herein. The deletion may be a terminal deletion, or an internal deletion, so long as the deletion does not substantially affect the structure or aggregation of the fusion protein.

In certain embodiments, a variant HBsAg can include a linker sequence. This peptide is a short amino acid sequence providing a flexible linker that permits attachment of an antigenic polypeptide, such as an HIV antigen (such as a gp41 or gp120 polypeptide), without disruption of the structure, aggregation (multimerization) or activity of the self-aggregating polypeptide component. Typically, a linear linking peptide consists of between two and 25 amino acids. Usually, the linear linking peptide is between two and 15 amino acids in length. In one example, the linker polypeptide is two to three amino acids in length, such as a serine and an arginine, or two serine residues and an arginine residue, or two arginine residues and a serine residue.

In other examples, the linear linking peptide can be a short sequence of alternating glycines and prolines, such as the amino acid sequence glycine-proline-glycine-proline. A linking peptide can also consist of one or more repeats of the sequence glycine-glycine-serine. Alternatively, the linear linking peptide can be somewhat longer, such as the glycine (4)-serine spacer described by Chaudhary et al., *Nature* 339:394-397, 1989.

Directly or indirectly adjacent to the remaining end of the linear linking peptide (that is, the end of the linear linking peptide not attached to the self-aggregating polypeptide component of the fusion protein) is a polypeptide sequence including at least one antigenic epitope of HIV-1, such as an epitope of gp41, such as at least one antigenic epitope of the membrane proximal region. The antigenic polypeptide can be a short peptide sequence including a single epitope. For example the antigenic polypeptide can be a sequence of amino acids as short as eight or nine amino acids, sufficient in length to provide an antigenic epitope in the context of presentation by a cellular antigen presenting complex, such as the major histocompatibility complex (MHC). The antigenic polypeptide can also be of sufficient in length to induce antibodies, such as neutralizing antibodies. Larger peptides, in excess of 10 amino acids, 20 amino acids or 30 amino acids are also suitable antigenic polypeptides, as are much larger polypeptides provided that the antigenic polypeptide does not disrupt the structure or aggregation of the HBsAg polypeptide component.

In some examples, the variant HBsAg includes one or more epitopes of the envelope protein of HIV-1 or major CTLs of HIV or SIV Gag, and is about 20 to about 200 amino acids in length, such as about 25 to about 150 amino acids in length, such as about 25 to about 100 amino acids in length. In several additional examples, the antigenic polypeptide includes one or more antigenic epitopes of HIV-1 gp41, such as the membrane proximal region (MPER) of gp41.

Exemplary sequences for HIV-1, as well as the amino acid sequence for full-length gp41 and gp120 and CTLs of Gag can be found on Genbank, EMBL and SwissProt websites.

Exemplary non-limiting sequence information can be found for example, as SwissProt Accession No. P04578, (includes gp41 and gp120, initial entry Aug. 13, 1987, last modified on Jul. 15, 1999); Genbank Accession No. HIVHXB2CG (full length HIV-1, including RNA sequence and encoded proteins, Oct. 21, 2002); Genbank Accession No. CAD23678 (gp41, Apr. 15, 2005); Genbank Accession No. CAA65369 (Apr. 18, 2005); all of which are incorporated herein by reference. Similar information is available for HIV-2.

Suitable Env proteins are known in the art and include, for example, gp160, gp120, gp41, and gp140. Any clade of HIV is appropriate for antigen selection, including HIV clades A, B, C, and the like. HIV Gag, Pol, Nef and/or Env proteins from HIV clades A, B, C, as well as nucleic acid sequences encoding such proteins and methods for the manipulation and insertion of such nucleic acid sequences into vectors, are known (see, for example, HIV Sequence Compendium, Division of AIDS, National Institute of Allergy and Infectious Diseases, 2003, HIV Sequence Database (on the world wide web at hiv-web.lanl.gov/content/hiv-db/main-page.html), Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Association. Exemplary Env polypeptides, for example, corresponding to clades A, B and C are represented by the sequences of Genbank® Accession Nos. U08794, K03455 and AF286227, respectively.

Variant HBsAgs can form a self-aggregating multimeric spherical or rod-shaped structure upon expression in a host cell. Similarly, the variant HBsAgs can assemble spontaneously (self-aggregate) when placed in suspension in a solution of physiological pH (for example, a pH of about 7.0 to 7.6). Thus, in the present disclosure, wherever a single or monomeric variant HBsAg is disclosed, polymeric forms are also considered to be described.

In some embodiments, an isolated rubella viral vector includes a variant HBsAg with one or more transmembrane domains of the HBsAg replaced with a gp41 antigenic insert. The gp41 antigenic insert can include (a) an antigenic polypeptide fragment of gp41 and (b) a transmembrane spanning region of gp41. In an example, the gp41 antigenic insert includes (a) an antigenic polypeptide fragment, such as an antigenic polypeptide fragment with the amino acid sequence set forth in SEQ ID NO:1 and is between 28 and 350 amino acids in length and (b) a transmembrane spanning gp41 region, such as a transmembrane spanning gp41 region with the amino acid sequence set forth in SEQ ID NO: 25 (in which wherein $X_1$, $X_2$ and $X_3$ are any amino acid; and $X_4$, $X_5$, and $X_6$ are any hydrophobic amino acid) and is between 22 and 40 amino acids in length.

In one example, the antigenic polypeptide includes the amino acid sequence of NEX$_1$X$_2$LLX$_3$LDKWASLWN (SEQ ID NO: 1). In this sequence, $X_1$, $X_2$ and $X_3$ are any amino acid. The antigenic epitope can include repeats of this sequence, such as one to five copies of SEQ ID NO: 1. As noted above, the antigenic peptide includes one or more epitopes of the envelope protein of HIV-1, and, including SEQ ID NO: 1, about 10 to about 300 amino acids in length, such as from about 16 to about 160 amino acids, such as from about 28 to about 150 amino acids in length, such as from about 28 to about 140 amino acids in length.

In several examples, the antigenic polypeptide includes one or more of the amino acid sequences set forth in SEQ ID NOs: 2-22, 30, 81-102, 126-156 and 158-162. A single copy of one of SEQ ID NOs: 2-22, 30, 81-102, 126-156 and 158-162 can be included as the antigenic polypeptide. Alternatively, multiple copies of one of SEQ ID NOs: 2-22, 30, 81 or 89 can be included as the antigenic polypeptide. Thus, one, two, three, four or five copies of one of the amino acid sequences set forth as SEQ ID NOs: 2-22, 30, 81 or 89 can be included as the antigenic polypeptide.

In additional embodiments, more than one of these sequences can be included in the antigenic polypeptide. Thus, in several examples, two, three, four or five of the amino acid sequences set forth as SEQ ID NOs: 2-22, 30, 81 and 89 can be included as the antigenic polypeptide in tandem. Each amino acid sequence included in the antigenic polypeptide can be present only a single time, or can be repeated.

The HBsAg variants can include one or more transmembrane spanning domains that include one of the amino acid sequences set forth as SEQ ID NOs: 26-28. A single gp41 transmembrane can be included in the variant HBsAg. Alternatively, multiple gp41 transmembrane domains with amino acid sequences set forth as SEQ ID NOs: 26-28 can be included within the variant HBsAg. Thus, one, two, three, four or five gp41 transmembrane domains with one of the amino acid sequences set forth as SEQ ID NOs: 26-28 can be included in the variant HBsAg.

In one particular embodiment, an isolated rubella viral construct includes a variant HBsAg in which the first transmembrane spanning domain of the HBsAg is replaced by a gp41 antigenic insert. For example, the gp41 antigenic insert replaces at least the first 29 amino acid residues of SEQ ID NO:20, for example amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In a particular example, an isolated construct includes a variant HBsAg in which the first transmembrane spanning domain of the HBsAg is replaced by a gp41 antigenic insert that has the amino acid sequence set forth as SEQ ID NO: 29.

In another particular embodiment, an isolated construct includes a variant HBsAg in which the third transmembrane spanning domain of the HBsAg is replaced by a gp41 antigenic insert. For example, the gp41 antigenic insert replaces at least 29 amino acids residues of SEQ ID NO: 31, for example amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a particular example, an isolated construct includes a variant HBsAg in which the third transmembrane spanning domain of the HBsAg is replaced by a gp41 antigenic insert has the amino acid sequence set forth as SEQ ID NO: 59.

In an even more particular embodiment, an isolated rubella viral construct includes a variant HBsAg in which more than one transmembrane spanning domains of HBsAg have been replaced with an antigenic insert. In one example, an isolated construct includes a variant HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, an isolated construct including a variant HBsAg in which the third transmembrane spanning domain of the HBsAg is replaced by a gp41 antigenic insert has the amino acid sequence set forth as:

(SEQ ID NO: 59)
MKTIIALSYIFCLVFAQDLPGNDNNSEFITSGFLGPLLVLQAGFFLLTR

ILTIPQSLDSWWTSLNFLGGSPVCLGQNSQSPTSNHSPTSCPPICPGYR

WMCLRRFIIFLFILLLCLIFLLVLLDYQGMLPVCPLIPGSTTTSTGPCK

TCTTPAQGNSKFPSCCCTKPTDGNCTCININEKELLELDKWASLWNWFD

ITNWLWYIRLFIMIVGGLIGLRIVFAVLSIVVGLSPTVWLSAIWMMWYW

GPSLYSIVSPFIPLLPIFFCLWVYIG.

In one example of an isolated construct, in which the first transmembrane domain of HBsAg is replaced with the MPER and transmembrane domain of gp41 has the amino acid sequence set forth as:

(SEQ ID NO: 29)
MKTIIALSYIFCLVFAQDLPGNDNNSEFNEKELLELDKWASLWNWFDIT

NWLWYIRLFIMIVGGLIGLRIVFAVLSIPQSLDSWWTSLNFLGGSPVCL

GQNSQSPTSNHSPTSCPPICPGYRWMCLRRFIIFLFILLLCLIFLLVLL

DYQGMLPVCPLIPGSTTTSTGPCKTCTTPAQGNSKFPSCCCTKPTDGNC

TCIPIPSSWAFAKYLWEWASVRFSWLSLLVPFVQWFVGLSPTVWLSAIW

MMWYWGPSLYSIVSPFIPLLPIFFCLWVYIG.

In one example of the isolated construct, the third transmembrane domain of HBsAg is replaced with the MPER and transmembrane domain of gp41 has the amino acid sequence set forth as:

(SEQ ID NO: 59)
MKTIIALSYIFCLVFAQDLPGNDNNSEFITSGFLGPLLVLQAGFFLLTR

ILTIPQSLDSWWTSLNFLGGSPVCLGQNSQSPTSNHSPTSCPPICPGYR

WMCLRRFIIFLFILLLCLIFLLVLLDYQGMLPVCPLIPGSTTTSTGPCK

TCTTPAQGNSKFPSCCCTKPTDGNCTCININEKELLELDKWASLWNWFD

ITNWLWYIRLFIMIVGGLIGLRIVFAVLSIVVGLSPTVWLSAIWMMWYW

GPSLYSIVSPFIPLLPIFFCLWVYIG.

In an example, an isolated construct is provided in which the first transmembrane domain and third domain of HBsAG is each replaced with the MPER and transmembrane domain of gp41 and has the amino acid sequence set forth as:

(SEQ ID NO: 58)
MKTIIALSYIFCLVFAQDLPGNDNNSEFNEKELLELDKWASLWNWFDIT

NWLWYIRLFIMIVGGLIGLRIVFAVLSIPQSLDSWWTSLNFLGGSPVCL

GQNSQSPTSNHSPTSCPPICPGYRWMCLRRFIIFLFILLLCLIFLLVLL

DYQGMLPVCPLIPGSTTTSTGPCKTCTTPAQGNSKFPSCCCTKPTDGNC

TCIPINEKELLELDKWASLWNWFDITNWLWYIRLFIMIVGGLIGLRIVF

AVLSIVVGLSPTVWLSAIWMMWYWGPSLYSIVSPFIPLLPIFFCLWVYIG.

In one example, an isolated construct is provided in which the first transmembrane domain of HBsAg is replaced with the MPER and transmembrane domain of gp41 and an additional MPER is inserted just proximal to the third membrane spanning domain of HBsAg. In another example, an isolated construct is provided in which multiple MPERs are inserted within the HBsAg, such as two, three, four or more MPERs are inserted just proximal to the third membrane spanning domain of HBsAg. In yet another example, an isolated construct is provided in which a MPER and transmembrane domain of gp41 is inserted following the fourth HBsAg membrane spanning domain.

The variant HBsAg can optionally include additional elements, such as a leader sequence or a suitable T cell epitope. Generally, a T cell epitope is about eight to about ten amino acids in length, such as about nine amino acid in length, and binds major histocompatibility complex (MHC), such as HLA 2, for example, HLA 2.2. Examples of suitable T cell epitopes include, but are not limited to, ASLWNWF-NITNWLWY (SEQ ID NO: 32) and IKLFIMIVGGLVGLR (SEQ ID NO: 33).

The variant HBsAg may also include a CAAX (SEQ ID NO: 34) sequence, for isoprenyl addition in vivo. In this sequence, C is cysteine, A is an aliphatic amino acid and X is any amino acid. The X residue determines which isoprenoid will be added to the cysteine. When X is a methionine or serine, the farnesyl-transferase transfers a farnesyl, and when X is a leucine or isoleucine, the geranygeranyl-transferase I transfers a geranylgeranyl group. In general, aliphatic amino acids have protein side chains containing only carbon or hydrogen atoms. Aliphatic amino acids include proline (P), glycine (G), alanine (A), valine (V), leucine (L), and isoleucine (I), presented in order from less hydrophobic to more hydrophobic. Although methionine has a sulphur atom in its side-chain, it is largely non-reactive, meaning that methionine effectively substitutes well with the true aliphatic amino acids.

B. Therapeutic Methods and Pharmaceutical Compositions

The disclosed isolated rubella viral vector constructs including antigenic inserts, such as HIV polypeptides (e.g., Gag, gp41 or gp120), RSV polypeptides or HBsAgs polypeptides (natural and recombinant) described herein can be used to produce pharmaceutical compositions, including compositions suitable for prophylactic and/or therapeutic administration. These compositions can be used to induce an immune response to HIV, SIV, RSV or Hepatitis B, such as a protective immune response. However, the compositions can also be used in various assays, such as in assays designed to detect an HIV-1 or Hepatitis B infection.

The disclosed isolated rubella viral constructs including can be administered to a subject in order to generate an immune response to HIV-1, SIV or Hepatitis B. In one example, the immune response is a protective immune response. Thus, the constructs disclosed herein can be used in a vaccine, such as a vaccine to inhibit subsequent infection with HIV, SIV or Hepatitis B. In some examples the disclosed constructs are administered as a virus like particle.

A therapeutically effective amount of a rubella viral construct, a virus-like particle including this construct, or a composition including the construct or virus-like particle can be administered to a subject to prevent, inhibit or to treat a condition, symptom or disease, such as AIDS. As such, the constructs can be administered as vaccines to prophylactically or therapeutically induce or enhance an immune response. For example, the pharmaceutical compositions described herein can be administered to stimulate a protective immune response against HIV, such as a HIV-1, SIV or Hepatitis B. In some examples, a disclosed composition is administered to a subject either alone or in combination with other HIV, SIV or Hepatitis B therapeutic agents. A single administration can be utilized to prevent or treat an HIV or Hepatitis B infection, or multiple sequential administrations can be performed.

In exemplary applications, compositions are administered to a subject infected with HIV or Hepatitis B, or likely to be exposed to an infection, in an amount sufficient to raise an immune response to HIV or Hepatitis B. Administration induces a sufficient immune response to reduce viral load, to prevent or lessen a later infection with the virus, or to reduce a sign or a symptom of HIV or Hepatitis B infection. Amounts effective for this use will depend upon various clinical parameters, including the general state of the subject's health, and the robustness of the subject's immune system, amongst other factors. A therapeutically effective amount of the compound is that which provides either subjective relief of one or more symptom(s) of HIV or Hepatitis B infection, an objectively identifiable improvement as noted by the clinician or other qualified observer, a decrease in viral load, an increase in lymphocyte count, such as an increase in CD4 cells, or inhibition of development of symptoms associated with infection. In one particular example, the administration of the composition will result in in vivo protein expression of the proteins encoded by the open reading frames contained in the expression vector construct. For example, the administration of the composition will result in the induction of immunity against the viruses whose proteins are encoded by the open reading frames.

The compositions can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated.

In some examples, the compositions are administered in a formulation including a carrier or excipient. A wide variety of suitable excipients are known in the art, including physiological phosphate buffered saline (PBS), and the like. Optionally, the formulation can include additional components, such as aluminum hydroxylphophosulfate, alum, diphtheria $CRM_{197}$, or liposomes. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts may also be used to produce an immune response.

In a specific example, the composition is administered as a vaccine subcutaneously at a concentration range from 102 to 104 $TCID_{50}$/person (TCID is an abbreviation for tissue culture infectious doses). For example, the vaccine is provided to the physician in a lyophilized form, reconstituted in an appropriate solvent such as deionized water or saline, and administered as a single injection.

In one embodiment, the construct is mixed with two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977; and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

An adjuvant can be included in the composition. In one example, the adjuvant is a water-in-oil emulsion in which antigen solution is emulsified in mineral oil (such as Freund's incomplete adjuvant or montanide-ISA). In one embodiment, the adjuvant is a mixture of stabilizing detergents, micelle-forming agent, and oil available under the name PROVAX® (IDEC Pharmaceuticals, San Diego, Calif.). Other examples of suitable adjuvants are listed in the terms section of this specification.

Actual methods for preparing administrable compositions will be known or apparent to those skilled in the art and are described in more detail in such publications as *Remington: The Science and Practice of Pharmacy*, University of the Sciences in Philadelphia, Lippincott Williams & Wilkins, Philadelphia, Pa., 21st Edition (2005). The compositions can be administered, either systemically or locally, for therapeutic treatments, such as to treat an HIV infection. In therapeutic applications, a therapeutically effective amount of the composition is administered to a subject infected with HIV, such as, but not limited to, a subject exhibiting signs or symptoms of AIDS. Single or multiple administrations of the compositions can be administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of the HIV infection without producing unacceptable toxicity to the subject.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa. (1995). Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342 (1994); Tice & Tabibi, *Treatise on Controlled Drug Delivery*, A. Kydonieus, ed., Marcel Dekker, Inc. New York, N.Y., pp. 315-339 (1992)). In one example, virus like particles are in the range of 10-30 nm.

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

C. Immunodiagnostic Reagents and Kits

In addition to the therapeutic methods provided above, any of the disclosed rubella viral constructs herein can be utilized to produce antigen specific immunodiagnostic reagents, for example, for serosurveillance. Immunodiagnostic reagents can be designed from any of the constructs including antigenic polypeptides described herein. For example, the presence of serum antibodies to HIV, SIV, RSV or Hepatitis B can be monitored using the isolated immunogens disclosed herein, such as to detect an HIV, SIV, RSV or Hepatitis B infection. Generally, the method includes contacting a sample from a subject, such as, but not limited to a blood, serum, plasma, urine or sputum sample from the subject with one or more of the variant molecules disclosed herein and detecting binding of antibodies in the sample to the variant molecule. For example, the method can include contacting a sample from a subject, such as, but not limited to a blood, serum, plasma, urine or sputum sample from the subject with one or more of the constructs disclosed herein and detecting binding of antibodies in the sample to the antigenic insert. The binding can be detected by any means known to one of skill in the art, including the use of labeled secondary antibodies that specifically bind the antibodies from the sample. Labels include radiolabels, enzymatic labels, and fluorescent labels.

Any such immunodiagnostic reagents can be provided as components of a kit. Optionally, such a kit includes additional components including packaging, instructions and various other reagents, such as buffers, substrates, antibodies or ligands, such as control antibodies or ligands, and detection reagents.

Methods are further provided for a diagnostic assay to monitor a particular disease and/or to monitor the response of the subject to immunization by a particular vaccine, such as HIV, SIV, RSV or Hepatitis B vaccine. In one example, a diagnostic assay is to monitor an HIV-1 induced disease in a subject and/or to monitor the response of the subject to immunization by an HIV vaccine. By "HIV-1 induced disease" is intended any disease caused, directly or indirectly, by HIV. An example of an HIV-1 induced disease is acquired autoimmunodeficiency syndrome (AIDS). The method includes contacting a disclosed construct with a sample of bodily fluid from the subject, and detecting binding of antibodies in the sample to the disclosed antigens. In addition, the detection of the HIV-1 binding antibody also allows the response of the subject to immunization by a HIV vaccine to be monitored. In still other embodiments, the titer of the HIV-1 binding antibodies is determined. The binding can be detected by any means known to one of skill in the art, including the use of labeled secondary antibodies that specifically bind the antibodies from the sample. Labels include radiolabels, enzymatic labels, and fluorescent labels. In other embodiments, a disclosed construct is used to isolate antibodies present in a subject or biological sample obtained from a subject.

The provided isolated viral vectors can also be used in screening antiviral drugs. In one example, methods of screening antiviral drugs including methods of identifying protease inhibitors are disclosed. Viral inhibitory peptides correspond to the sequence of a protease target site for rubella. Inhibitory peptides contain synthetic amino acids, such as dehydro-alanine, on either side of the expected cleavage site. When these groups are attacked by the active site cysteine of the protease, they react with it and form a covalent bond. This attaches irreversibly to the free SH-group of the active site of the enzyme and results in non-competitive inhibition of the protease.

In one particular example, a method of identifying protease inhibitors is provided that utilizes a disclosed rubella-GFP construct to detect the effect of protease inhibition. Typically, in the absence of a protease inhibitor, GFP is expressed well by days 3 to 7 of infection. However, when an inhibitory peptide is added, the virus fails to cleave its nonstructural protein precursor into two fragments: P150 and active RNA polymerase. Without this cleavage, no RNA transcription can occur, either of the negative strand template RNA, or of the positive strand RNA coding for the nonstructural and structural proteins. In particular, protease inhibition prevents expression of GFP linked to P150, as manifested by a loss of green fluorescence. Therefore, a protease inhibitor is identified by detecting a decrease or inhibition of GFP expression or a decrease or inhibition in expression of one or more of the rubella nonstructural and structural proteins, such as a 10%, 20%, 30% 40%, 50%, 60%, 70%, 80%, 90% or more reduction in expression. In one particular example, a method of identifying a protease inhibitor includes contacting a cell expressing one or more of the disclosed rubella-GFP viral constructs with one or more test agents and with an amount of an agent capable of inhibiting protease activity. Expression of GFP or one or more of the rubella nonstructural and/or structural proteins is subsequently measured, whereby a decrease in expression of one or more of this proteins indicates that the agent is a protease inhibitor.

Besides reducing GFP expression, protease inhibitors disrupt the localization of P150-GFP to viral replicating centers in the cytoplasm. P150-GFP preserves the normal functions of P150 and localizes correctly to sites of viral RNA synthesis as noted by P150-GFP localizing to these centers as intensely fluorescent dots in the cytoplasm. When protease is inhibited, even partially, this is detected as a reduction in replicating centers. It is believed that rubella will be just as sensitive to protease inhibitors as is HIV as both viruses work by similar mechanisms. Additionally, other alphaviruses, such as VEE, have a similar requirement for protease activation of RNA replication, and their inhibitory peptides can be designed similarly, based on the known targets for viral protease.

The disclosure is illustrated by the following non-limiting Examples.

EXAMPLES

Example 1

Materials and Methods

This example describes the materials and methods used in Example 2.

Construction of Rubella Expression Plasmids and Mutant Viruses.

A full length, infectious cDNA clone coding for wild type rubella of the Therien strain (GenBank accession M15240), called Robo 302, was kindly provided by Dr. Teryl Frey of Georgia State University (Pugachev et. al., *J. Virol.* 71, 562-568, 1999). For the generation of pRubΔNot 1, Robo 302 was digested with Not I and re-ligated, resulting in deletion of a 507 bp fragment from the non-structural region (bp 3661-4168 of the plasmid), without disruption of the reading frame. For the generation of pRubΔNot 1-GFP, a 3807 bp Hind III-Sca 1 fragment from pRubΔNot 1 was cloned into pBR322, resulting in plasmid pBR322-3818ΔNot1.

This construct contained a single Not I site. *Zoanthus* sp. green fluorescent protein (zGFP) was PCR-amplified from pZsGreen1-C1 (Cat. No. 632447, Clontech Laboratories, Inc. Mountain View, Calif.) using upstream primer 5' CGGCGGCCGCACCGGTCGCCACCATGGCCCAGTC-CAAGCACGGCCTGACC-3' (SEQ ID NO: 75) and downstream primer 5'-TGGCGGCCGCTCTAGATCCGGTG-GATCCCGGGCCCGCGGTACCGTCG-3' (SEQ ID NO: 76) and the resulting 804 bp product was digested with Not I and ligated into the Not 1 site of pBR322-3818 ΔNot 1 in frame with the non structural sequence, generating pBR322-3818ΔNot1-GFP. A 4096 bp Bsu36 I-Sca 1 restriction fragment from pBR322-3818ΔNot1-GFP, comprising GFP cloned into the Not I deletion in Rub non-structural coding sequences, was cloned into corresponding sites of Robo302 to generate pRub-ΔNot1-GFP.

Vero Cell Culture.

African Green monkey kidney (Vero) cells were maintained in DMEM containing L-Glutamine, penicillin/streptomycin (MediaTech, Inc. Herndon Va.) and 10% fetal bovine serum at 37° C. and 5% $CO_2$ in a humidified incubator. All microscopy was carried out using an inverted Nikon Diaphot microscope equipped for fluorescence detection and digital image capture.

Generation of Capped, Infectious Rubella Virus RNA and Cell Transfection.

In each of the pRub plasmids, the viral genome is located downstream of an SP6 promoter. The plasmids were linearized by digestion with Spe I and transcribed using the RiboMAX Large scale RNA Production System (Promega Corp., Madison Wis.). The transcription reaction contained 1× SP6 transcription buffer, 0.8U RNAsin, 5 mM rATP, 5 mM rCTP, 5 mM rUTP, 1 mM rGTP, 2 mM Ribo m7G(5') ppp(5')G cap analog, 5-10 μg linear ds-DNA template and 1 μL of SP6 RNA polymerase. The reaction mixture was incubated at 37° C. for 3 hours, followed by another hour in the presence of 1 μl of RNAse-free DNAse. Capped infectious rubella RNA was transfected into Vero cells as follows. The RNA was combined with 1 mL of OptiMEM, while 14 μL of DMRIEC lipid reagent (Invitrogen Corporation Carlsbad, Calif.) was added to 1 mL of OptiMEM. The two mixtures were combined and mixed gently. Cells were seeded 12-18 hours before and were washed twice with OptiMEM before being overlaid with the transfection mixture and incubated for 6-12 hours at 37° C. and 5% $CO_2$ in a humidified incubator.

Western Blot Analyses.

Rubella structural proteins were detected by western blot. Vero cell lysates in RIPA buffer were sonicated for 30 seconds and then electrophoresed on a denaturing Nupage 4-12% acrylamide Bis-Tris gel (Invitrogen Corporation, Carlsbad, Calif.). Proteins were transferred to 0.2 μm Nitrocellulose filters followed by blocking for 30 min in TBS with 3% bovine serum albumin at room temperature on a rocking platform. Primary antibody binding was performed with polyclonal goat anti-rubella antibodies at a 1:400 dilution (Fitzgerald Industries International, Inc. Concord, Mass. Cat#20-RG04) in TBS with 0.2% Tween, 0.3% BSA at 4° C. overnight on a rocking platform. Blots were washed 3 times with 10 ml TBS with 0.2% Tween for 10 minutes each on an orbital shaker. Horseradish peroxidase-conjugated rabbit anti-goat IgG at a dilution of 1:5000 (Santa Cruz Biotechnology, Santa Cruz, Calif.) was added in TBS with 0.2% Tween for 40 minutes at room temperature on a rocking platform, followed by the same washing procedure as above. Proteins were visualized by enhanced chemiluminescence (Amersham Biosciences, Buckinghamshire, England) and autoradiography.

Analysis of the zGFP Insert in Viral RNA.

Viral RNA was extracted by treating infected cells or pelleted virus with TRIzol (Invitrogen Corporation, Carlsbad, Calif.) and purified according to the manufacturer's instructions. Reverse transcription was performed using a SuperScript III kit (Invitrogen Corporation, Carlsbad, Calif.) and random hexamers. The cDNA was PCR amplified using an Advantage-GC PCR kit (Clonetech Laboratories, Mountain View, Calif.) and primers specific for rubella sequences flanking the insert. The 5' primer Robo-55 was 5'-CCATTAAGCGGTTCCTCGGTAGC (SEQ ID NO: 23), and the 3' primer was 5'-GAGTGCCGCGAGCGTCCGAGTGC (SEQ ID NO: 24), resulting in a product of 1.2 Kb. Amplified cDNA was analyzed by gel electrophoresis, purified using a Qiagen kit, and sequenced using the same PCR primers. To analyze zGFP function, the amplified cDNA was cloned into *E. coli* and each colony was examined for fluorescence. The cDNA was PCR amplified using a puReTaq Ready-To-Go PCR kit (GE Healthcare) and 5' primers containing an NcoI restriction site and 3' primers containing an EcoRI restriction site. The purified PCR products and a pZsGreen plasmid (Clontech Laboratories, Mountain View, Calif.) were cleaved using NcoI and EcoRI restriction endonucleases (NEB), gel purified, and ligated together to produce a functional zGFP plasmid. The products were transformed into competent DH5-α cells (Invitrogen Corporation, Carlsbad, Calif.), plated overnight in LB/Amp medium containing 100 uM IPTG, and visualized in an inverted fluorescent Nikon Diaphot microscope. Fifty five to 76 colonies per passage were analyzed for green fluorescence. Representative colonies of either type were grown in LB/Amp medium, and the plasmid was isolated (Qiagen Mini-prep kit) and sequenced (FDA core facility).

Example 2

Stable Expression of GFP Insert in a Rubella Vector

This example illustrates that a foreign gene, zGFP, can be inserted into the Not I site in the nonstructural gene nsP150 of a rubella vector, resulting in an infectious rubella hybrid that expresses the foreign protein for many generations. Although this example utilizes the foreign gene zGFP, it is contemplated that other foreign genes such as HIV antigens, SIV antigens, RSV antigens or HBsAgs can also be incorporated in a similar manner.

Figure 1A:
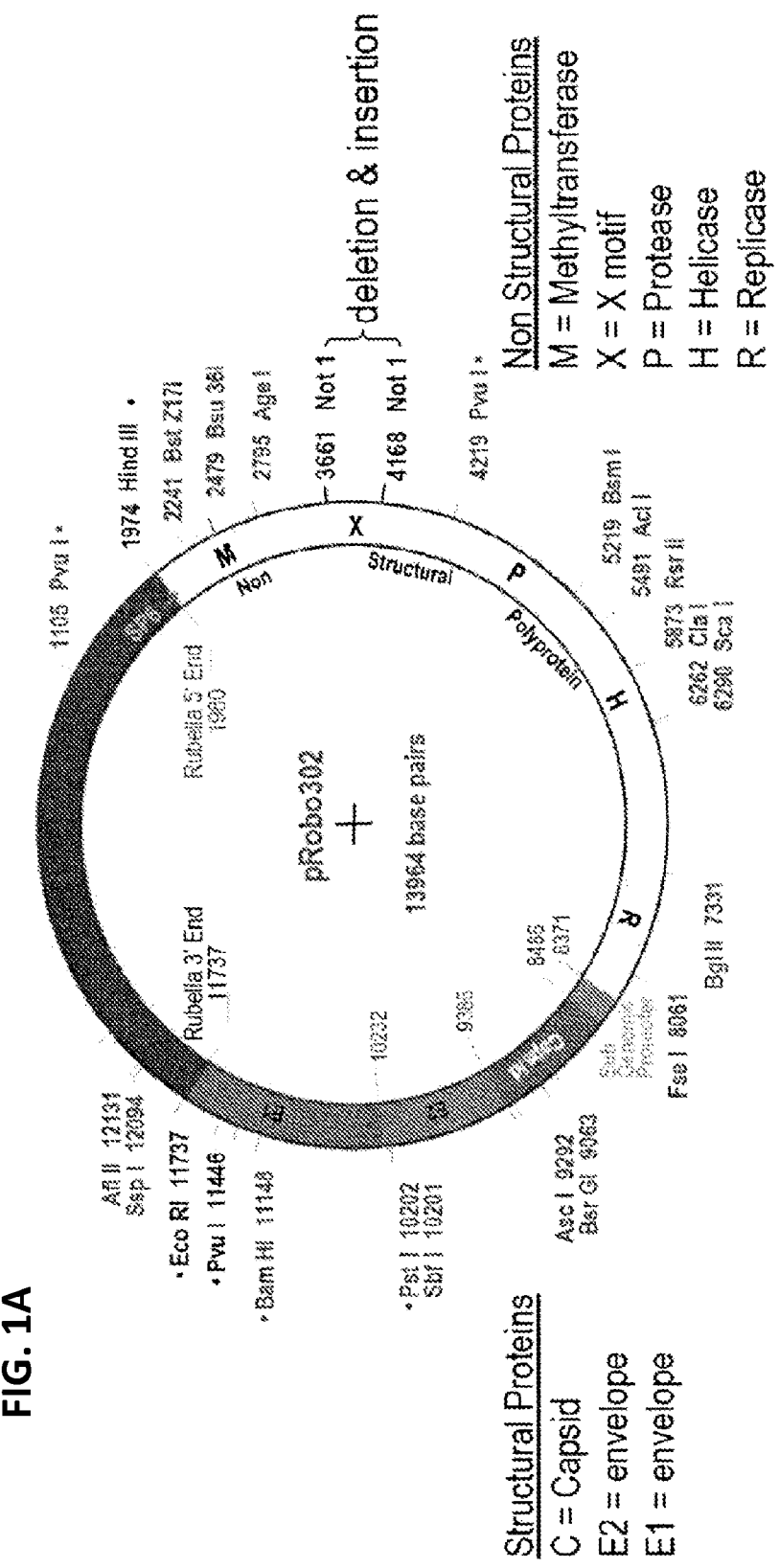
FIG. 1A is a restriction map of a rubella cDNA plasmid in which the two Not I sites are shown and the deletion between such sites becomes the site of zGFP insertion.
Figure 1B:
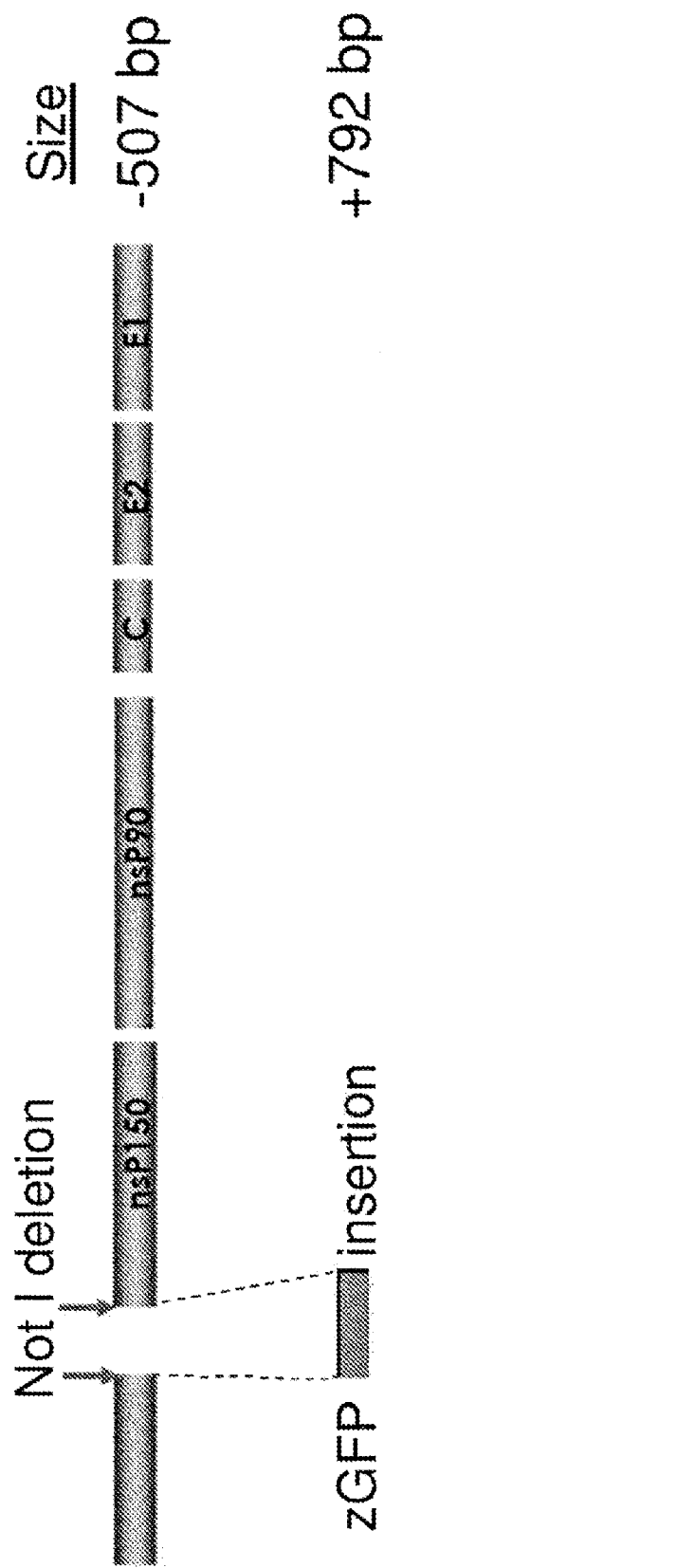
FIG. 1B is a schematic drawing of the expressed nonstructural proteins nsP150 and nsP90 and the structural proteins C, E2 and E1. The zGFP insert is expressed as part of the nsP150 polyprotein.

FIG. 1A provides an illustration of the pRobo 302 plasmid coding for full length, infectious rubella virus. Rubella nonstructural proteins (nsPs) are expressed as a polyprotein precursor, which is cleaved to produce nsP150 and nsP90. The structural proteins, capsid, E2 and E1, are expressed from a subgenomic promoter and cleaved to produce proteins that assemble into mature virions. Two Not I restriction sites are located in nsP150 at by 1685 and 2192 (FIG. 1B).

Figure 2:
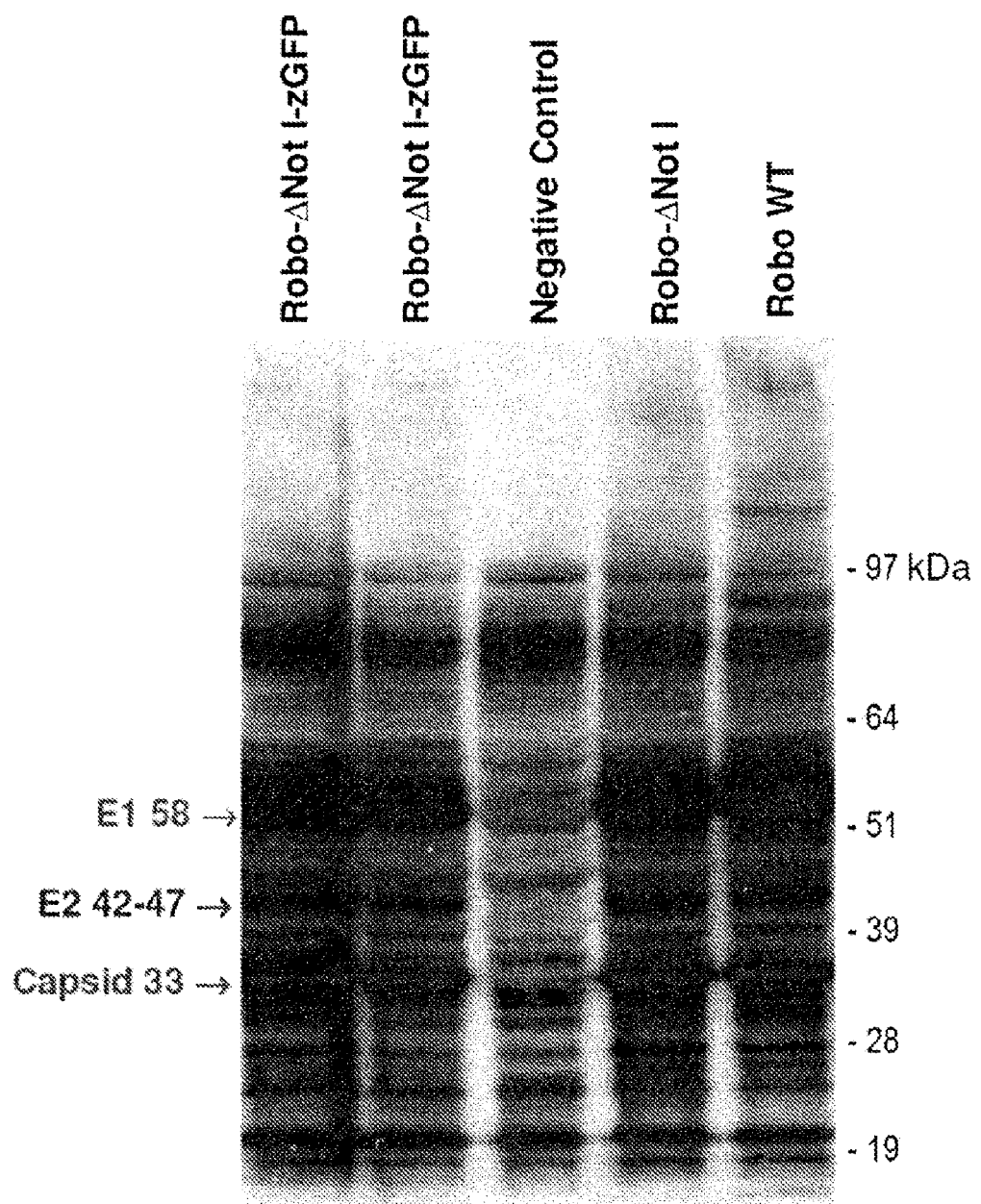
FIG. 2 is a digital image of a Western blot illustrating expression of rubella genes in Not I deletion/insertion mutants. Each full length rubella cDNA was transcribed, capped, and transfected into Vero cells. Expression of rubella structural proteins was detected by western blot of the $P_0$ cell lysates on day 12. Wild type rubella expressed Capsid 33, E1 and E2 proteins (lane 5) at the same level as Not I deleted rubella (lane 4). Two clones with zGFP inserted at the Not I site expressed normal levels of rubella proteins (lanes 1 and 2).

To determine if a deletion of 507 bp between two Not I restriction sites was permissive for subgenomic transcription and viral replication, each full length rubella cDNA was transcribed, capped, and transfected into Vero cells as described above. Expression of rubella structural proteins was detected by western blot of the $P_0$ cell lysates on day 12. Wild type rubella expressed capsid, E2 and E1 proteins (FIG. 2, lane 5) at the same level as Not I deleted rubella (FIG. 2, lane 4).

Normal expression of the structural proteins indicated that viral RNA polymerase made negative strand template RNA, followed by plus strand subgenomic RNA coding for the structural proteins. The deletion was located in a region of unknown function, and created a potential space for insertion of a foreign gene without interfering with essential viral functions. The reporter gene zGFP was inserted into the site of the Not I deletion. This added 792 bp of DNA, for a net increase of 285 bp, and preserved the open reading frame. Vero cells were transfected with capped viral RNA, and viral supernatants were transferred onto fresh cultures. The rubella-GFP hybrid virus expressed normal levels of rubella structural proteins, as shown by western blot (FIG. 2, lanes 1 and 2 showing two independent clones). zGFP expression was detected as fluorescence of infected Vero cells. The initial transfection with infectious RNA resulted in multiple foci of bright fluorescence. The supernatants of these cultures contained infectious virus that produced bright fluorescent foci on Vero cells.

Stability of GFP expression was tested during serial passage of culture supernatants on Vero cells. GFP expression was manifested by multiple bright fluorescent foci that appeared by day 4 and spread throughout the culture by day 7 to 10. Each intermediate passage showed GFP expression, and there was no fluorescence from an uninfected control run in parallel.

Genetic stability of zGFP was examined by recovering viral RNA from culture supernatants or infected cells after passages 5, 6, 10, and 11 and generating cDNA by RT-PCR of the insert. The overall GFP sequence was unchanged at passages 5 and 6, but showed a deletion of 27 bp at passages 10 and 11. This finding contrasted with fluorescence observed at later passages and suggested the possibility of a mixed population of wild type viruses giving fluorescence and mutants giving the observed sequence. To test this, the cDNAs were cloned into E. coli and individual colonies were examined for GFP expression. At passage 5, 76% of colonies (42 out of 55) were fluorescent, but by passages 10 and 11 only 5% of colonies (5 out of 100) expressed functional GFP.

Several clones of each phenotype were sequenced. At passage 5, four non-fluorescing clones constituted a swarm of different mutants. Two clones had point mutations Leu 46 to Pro or Phe 83 to Ser, while two others had deletions of 9 or 54 bp coding for amino acids Ile 79-Asp 81 or Lys 39-Phe 56. The deletion mutant that predominated at later passages was not detected at this passage. By passage 11, all five non-fluorescing clones had deletions ranging from 9 to 27 bp. Three had the predominant 27 bp deletion coding for amino acids Phe 83-Tyr 91 that was identical to the bulk culture. Two others had deletions coding for Asp 78-Val 80 or Thr 73-Asp 81. In contrast, two fluorescent clones at passage 11 showed the full wild type zGFP sequence. The loss of 9, 27, or 54 bp suggests persistent selective pressure to reduce the size of the zGFP insert. However, the emergence after 10 passages of a predominant clone with a 27 bp deletion that preserves the reading frame suggests that zGFP may achieve stability at a size of about 765 bp.

Figure 3:
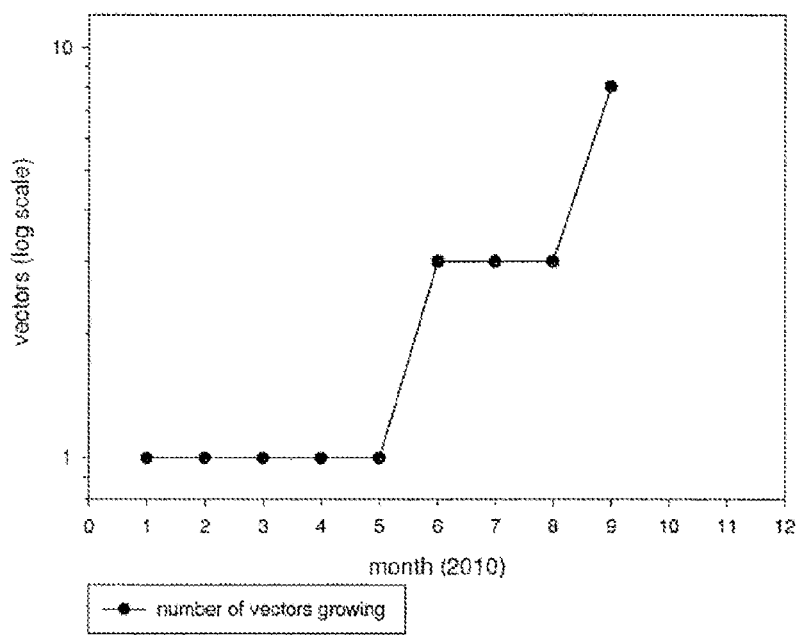
FIG. 3 is a graph of a time course illustrating rubella vector growth over a number of months.

Rubella-GFP allowed the host range and sensitivity to interferon to be examined. FIG. 3 shows that infection was limited to Vero cells, as the virus did not grow well or at all on fibroblasts, osteocytes, epithelial cells, or a glioma. This finding may be due to cells that do not support infection lacking receptors for rubella. Alternatively, since rubella replication proceeds via a double stranded RNA intermediate that strongly elicits interferon, the growth pattern may reflect the inability of Vero cells to produce interferon, while the other cells resist infection by producing interferon.

These studies support the notion that rubella can be a vector for delivering vaccine antigens, since it can express genes as large as most viral antigens, while growing to high enough titers for vaccine production and immunization. For example, the current insert size of 792 bp (or 765 bp after deletion) is larger than hepatitis B surface antigen (680 bp) and most HIV antigens, including p24 (660 bp) and the gp41 ectodomain (570 bp). In addition, rubella hybrids can achieve sufficiently high titers for efficient vaccine production. After four passages on Vero cells, the titer reached $4 \times 10^6$ fluorescent foci per ml. Live attenuated rubella is one of the most efficient vaccines, with a recommended human dose of 5,000 PFU (Plotkin et al., Rubella Vaccine. In: Plotkin, S. A., and Orenstein W. A. (Eds.), Vaccines, $4^{th}$ ed. Saunders, Philadelphia, pp. 707-7432004), so this culture supernatant could provide 800 doses per ml.

Example 3

Treatment or Prevention of HIV in a Human Subject

This example describes a particular method that can be used to prevent or treat HIV in a human subject by administration of one or more compositions that includes an effective amount of any of the disclosed isolated immunogens. Although particular methods, dosages, and modes of administrations are provided, one skilled in the art will appreciate that variations can be made without substantially affecting the treatment.

Based upon the teaching disclosed herein, a virus, such as HIV, such as HIV type 1, can be prevented and/or treated by administering a therapeutically effective amount of a composition that includes a viral-like particle produced by an isolated rubella viral vector with an HIV antigenic insert to prevent, reduce or eliminate HIV infection, replication or a combination thereof. The method can include screening subjects to determine if they are HIV sero-positive, for example infected with HIV-1. Subjects having HIV infection are selected. In one example, subjects having increased levels of HIV antibodies in their blood (as detected with an enzyme-linked immunosorbent assay, Western blot, immunofluorescence assay, or nucleic acid testing, including viral RNA or proviral DNA amplification methods) are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the compositions including an isolated rubella viral vector with an HIV antigenic insert (as described herein). In another example, a clinical trial would include half of the subjects following the established protocol for treatment of HIV (such as a highly active antiretroviral therapy). The other half would receive a composition including the isolated rubella viral vector with an HIV antigenic insert.

In another example, a population of subjects at high risk of HIV infection would be screened for rubella antibodies. The seronegative subjects would be randomized to receive conventional rubella vaccine without an insert or the rubella vectors with HIV inserts. The subjects would be observed over time for protection against rubella or HIV. If the vectors elicit protective immunity to HIV, the number of HIV infections in the rubella control group would greatly exceed the number in the rubella vector group. The cohort size and risk per year would be large enough to produce at least 30 infections in the control group. Under these conditions, a reduction of 50% or greater would be statistically significant protection.

Screening Subjects

In particular examples, the subject is first screened to determine if they are infected with HIV. Examples of methods that can be used to screen for HIV infection include a combination of measuring a subject's CD4+ T cell count and the level of HIV in serum blood levels or determine whether a subject is sero-positive for HIV antibodies.

In some examples, HIV testing consists of initial screening with an enzyme-linked immunosorbent assay (ELISA) to detect antibodies to HW, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive and occasionally provide an indeterminate Western blot result, which may be either an incomplete antibody response to HIV in an infected subject, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is also indicative that the subject has HIV and is a candidate for receiving the therapeutic compositions disclosed herein. Moreover, detection of a CD4+ T cell count below 350 per microliter, such as 200 cells per microliter, suggests that the subject is likely to have HIV. However, lack of HIV antibodies could indicate that the subject is not infected and is a candidate for HIV prevention by the rubella vector treatment.

Pre-screening is not required prior to administration of the therapeutic compositions disclosed herein.

Pre-Treatment of Subjects

In particular examples, the subject is treated prior to administration of a therapeutic composition that includes one or more of the disclosed viral constructs. However, such pre-treatment is not always required, and can be determined by a skilled clinician. For example, the subject can be treated with an established protocol for treatment of HIV (such as a highly active antiretroviral therapy).

Administration of Therapeutic Compositions

Following subject selection, a therapeutic effective dose of the composition including one or more of the disclosed rubella viral constructs including an HIV antigen is administered to the subject (such as an adult human or a newborn infant either at risk for contracting HIV or known to be infected with HIV). Administration induces a sufficient immune response to reduce viral load, to prevent or lessen a later infection with the virus, or to reduce a sign or a symptom of HIV infection. Additional agents, such as anti-viral agents, can also be administered to the subject simultaneously or prior to or following administration of the disclosed compositions. Administration can be achieved by any method known in the art, such as oral administration, intranasal administration, inhalation, intravenous, intramuscular, intraperitoneal, or subcutaneous.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, therapeutic compositions that include rubella viral vector constructs including an HIV antigenic insert, such as a Gag, gp41 or gp120 antigenic insert are administered intramuscularly to a human. As such, these compositions may be formulated with an inert diluent or with a pharmaceutically acceptable carrier.

In one specific example, a composition including an isolated rubella viral vector with an HIV antigenic insert is administered intravenously from 0.1 pg to about 100 mg per kg per day. In an example, the composition is administered continuously. Administration of the therapeutic compositions can be taken long term (for example over a period of months or years). In another example, the composition is administered at 50 μg per kg given twice a week for 2 to 3 weeks. In another example, the composition is administered at a dose of 1 pg to 10 ng and given at 0, 1, and 6 months to achieve a maximum immune response. It may also be given at escalating doses of 1 to 10 pg for the first dose, 100 pg to 1 ng for the second dose, and 10 ng to 100 ng for the third dose. This will allow immunity to the carrier virus to be overcome and to boost immunity to the heterologous antigen, including MPER.

Assessment

Following the administration of one or more therapies, subjects having HIV (for example, HIV-1 or HIV-2) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HW or CD4+ T cell levels evaluated.

For uninfected subjects, HIV antibodies and neutralizing antibodies elicited by the vectors can have provide protection against subsequent HIV infection, particularly if the overall level of antibodies, or the level of neutralizing antibodies, exceeds some protective level.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 4

Method of Monitoring Serum Antibodies to HIV or Hepatitis B

This example illustrates the methods of monitoring serum antibodies to HIV or Hepatitis B.

Based upon the teachings disclosed herein, the presence of serum antibodies to HIV or Hepatitis B can be monitored using the isolated rubella viral vector construct platforms disclosed herein, such as to detect an HIV or Hepatitis B infection. Generally, the method includes contacting a sample from a subject, such as, but not limited to a blood, serum, plasma, urine or sputum sample from the subject with one or more of the disclosed compositions including one or more rubella viral vector constructs with an HIV or Hepatitis B antigenic insert and detecting binding of antibodies in the sample to the one or more constructs. The binding can be detected by any means known to one of skill in the art, including the use of labeled secondary antibodies that specifically bind the antibodies from the sample. Labels include radiolabels, enzymatic labels, and fluorescent labels.

Example 5

Binding of HIVIgG and Human Sera from HIV-1 Positive Patients to Disclosed Rubella Viral Vector Constructs Based upon the teaching herein, the utility of a rubella viral vector construct with an HIV antigenic insert to identify sera that contain neutralizing antibodies against the HIV antigenic insert included with the rubella viral vector construct can be determined by screening a set of weakly and broadly neutralizing human HIV-1 positive sera and HW-IgG for binding to one or more of the disclosed constructs or virus like particles that include one or more disclosed viral constructs. Human sera from HIV-1 positive patients and antibodies specific for HIV antigens can be serially diluted and analyzed for binding to HIV antigens and particles containing such polypeptides in ELISA format.

Example 6

Immunization of Subjects Against HIV or of Animals Against SIV or SHIV

Based upon the teaching herein, subjects are immunized with a dose of 1 pg to 100 ng and given at 0, 1, and 6 months of the disclosed rubella viral vector including one or more HIV antigens or virus-like particles containing the disclosed vector including one or more of such antigens by intramuscular route. Sera from the subject is analyzed for binding to one or more of the HIV antibodies by ELISA.

In addition, the sera can be checked for their neutralizing ability in a viral neutralization assay using luciferase-based HIV entry assay. If the neutralizing titers are high enough, the subject is challenged with SHIV virus bearing the same envelope glycoproteins as HIV. Alternatively, SIV antigens can be incorporated into the disclosed viral vector, monkeys can be immunized with rubella-SIV, and challenged with virulent SIV strains. In one particular example, the subject is a rhesus monkey.

Example 7

Stable Expression of SIV and HIV Antigens in a Rubella Vector

This example illustrates that SW and HIV antigens can be inserted into the Not I site of a rubella vector, resulting in an infectious rubella hybrid that expresses the foreign protein for multiple generations.

In a first set of studies, full length RNA coding for the rubella vector plus the insert was transcribed, capped, and the vector genes were transfected into Vero cells (passage 0) as described previously in Example 1. Growth of vector with the insert was then determined by measuring rubella proteins by Western blot analysis. Alternatively, expression of the insert gene product was determined by Western blot using antibodies specific for the insert. For example, this could be the Gag genes of SIV or the MPER antigen of HIV.

In a second set of studies, Vero cells were transfected as in the original method with rubella viral constructs containing SIV or HIV sequences inserted at the Not I site. These cells were called passage P0. After 7 days, virus and cells were transferred together as a cell suspension. The suspension was made by scraping a quarter of the cell monolayer, and then diluting the cell suspension to 2 ml, followed by transferring 0.1 to 0.2 ml directly onto a new monolayer of Vero cells to make passage P1. This procedure was repeated for multiple passages.

Figure 4:
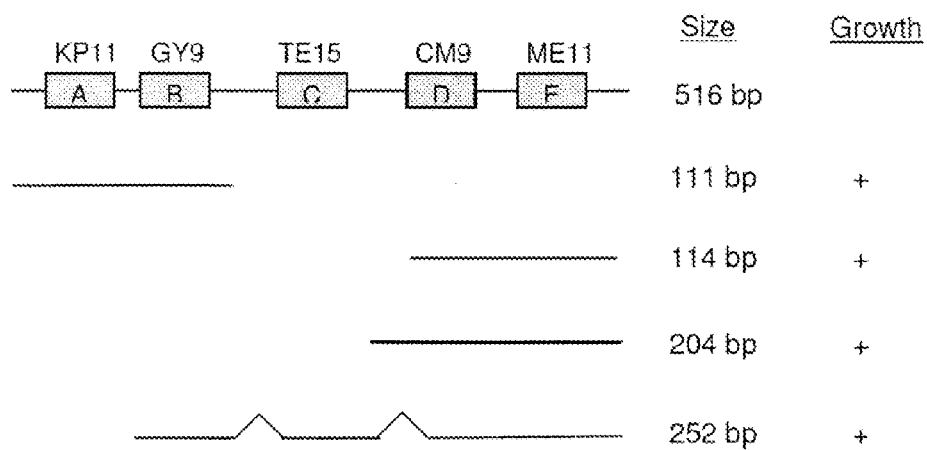
FIG. 4 is a schematic illustrating the arrangement of various Gag epitopes expressed in a rubella vector.
Figure 7:
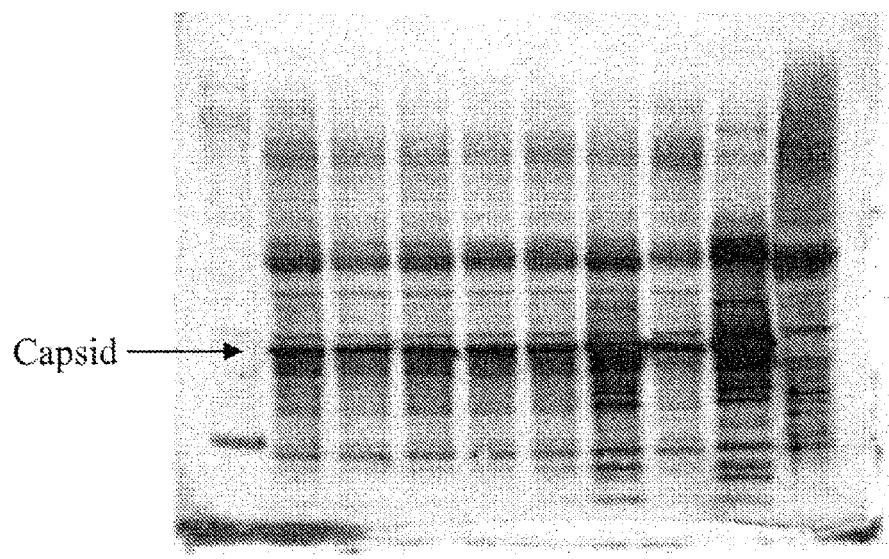
FIG. 7 is a digital image of a western blot illustrating growth of seven rubella-sGag vectors at passage 2, as detected with antibodies to rubella capsid.

FIG. 3 illustrates the number of vectors expressed within cells that were able to grow over a period of months by using the second rubella viral cell culture method. FIG. 4 illustrates the size and position of various Gag epitopes expressed in live rubella vectors. Table 3 provides the amino acid sequences, insert name and size of inserts which were expressed in live rubella vectors. Western blot analyses presented in FIGS. 7-9 illustrate successful vector growth and expression of rubella proteins when the vector includes various Gag and MPER epitopes with both cell culture methods.

TABLE 3

SIV Gag and HIV MPER sequences expressed in live rubella vectors

| Insert name | Bp Insert | Amino acid sequence | SEQ ID NO. |
|---|---|---|---|
| SGAG1-1 | 111 | REGSQKILSVLAPLVPTGSENLKSLYNTVSVIWSIHAED | 82 |
| SGAG2 | 114 | FQALSEGCTPYDINQMLNCVGDHQAAMQIIRDIINEEA | 83 |
| SGAG2L | 204 | LPLSPRTLNAWVKLIEEKKFGAEVVPGFQALSEGCTPYDINQMLNC VGDHQAAMQIIRDIINEEA | 84 |
| SGAG2L-A | 249 | LPLSPRTLNAWVKLIEEKKFGAEVVPGFQALSEGCTPYDINQMLNC VGDHQAAMQIIRDIINEEATRSQKILSVLAPLVPT | 85 |
| SGAG2L-B | 243 | LPLSPRTLNAWVKLIEEKKFGAEVVPGFQALSEGCTPYDINQMLNC VGDHQAAMQIIRDIINEEATRTGSENLKSLYNT | 86 |
| SGAG2L-C | 267 | LPLSPRTLNAWVKLIEEKKFGAEVVPGFQALSEGCTPYDINQMLNC VGDHQAAMQIIRDIINEEATRHTEEAKQIVQRHLVVETGTT | 87 |
| BC-SGAG2 | 252 | VPTGSENLKSLYNTVTRVKHTEEAKQIVQRHLVVETGTTSDAFQAL SEGCTPYDINQMLNCVGDHQAAMQIIRDIINEEA | 88 |
| MPER-E | | PSWNWFDITNWLWYIRLDA | 89 |
| MPER-F | 70 | PSAQEKNEKELLELDKWASLWN | 30 |
| ABC-SGAG2 | 335 | LDRFGLAESLLENKEGSQKILSVLAPLVPTGSENLKSLYNTVTRVK HTEEAKQIVQRHLVVETGTTETSDAFQALSEGCTPYDINQMLNCVG DHQAAMQIIRDIINEEA | 90 |
| ABC-SGAG2L | 411 | LDRFGLAESLLENKEGSQKILSVLAPLVPTGSENLKSLYNTVTRVK HTEEAKQIVQRHLVVETGTTETRLPLSPRTLNAWVKLIEEKKFGAE VVPGFQALSEGCTPYDINQMLNCVGDHQAAMQIIRDIINEEA | 91 |

Figure 5:
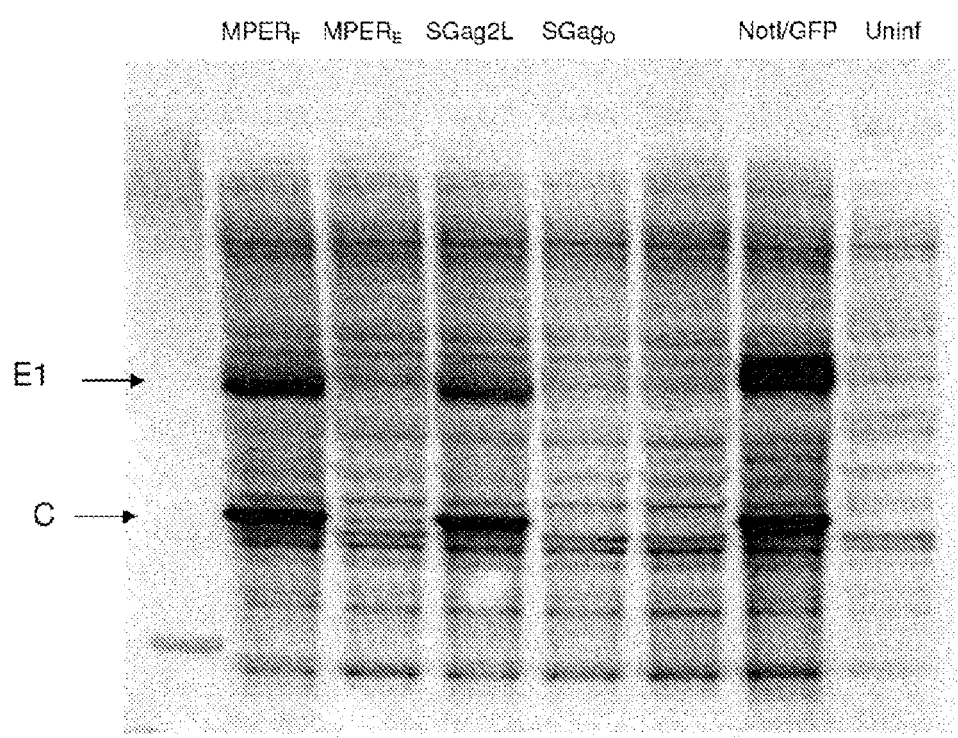
FIG. 5 is a digital image illustrating growth of two rubella vectors and rubella-GFP control as detected by western blot of rubella proteins E1 and C.

For example, FIG. 5 illustrates growth of two rubella vectors (made by the first method) and rubella-GFP control detected by western blot of rubella proteins E1 and C. As illustrated in FIG. 5, two different epitopes of SIV gag were expressed (SGAG2L and $SGAG_0$). $SGAG_0$ has the same amino acid sequence as wild type SGAG; its RNA sequence is different, since it has been codon optimized. Besides giving better expression, the codon optimized insert appeared more like the GC rich rubella RNA surrounding it.

Figure 6:
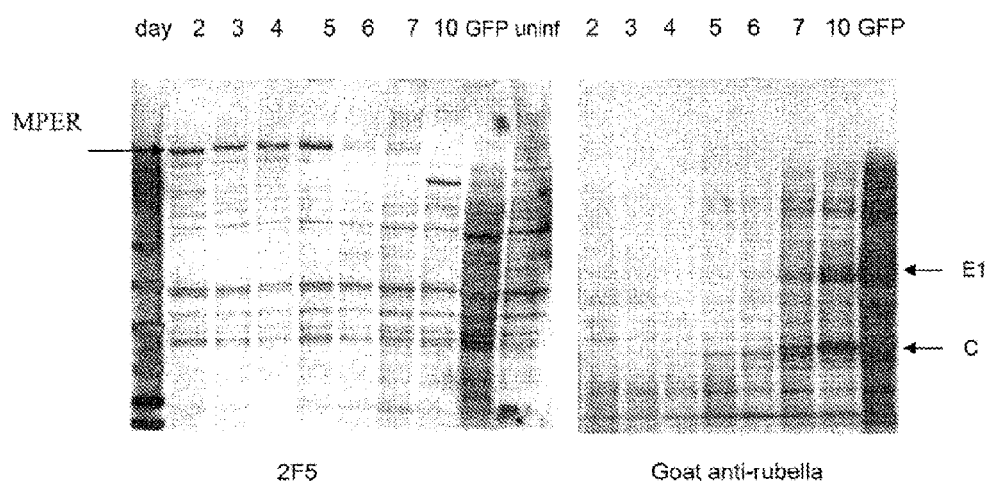
FIG. 6 is a digital image of a western blot illustrating a time course of MPER expression by rubella-$MPER_F$ vector as detected with anti-MPER monoclonal 2F5 or anti-rubella polyclonal antibodies.

Further, FIG. 6 shows the time course of MPER expression in which $MPER_f$ was expressed as part of an early gene of the rubella virus, from days 2 to 5 of infection.

FIG. 7 illustrates successful expression of seven rubella-sGag vectors at passage 2 (made by the second method) vs. a rubella-GFP control in second lane from the right and uninfected cells in last lane, as detected by western blot with antibodies to rubella capsid. Arrow indicates the capsid band (Lane 1, Molecular weight; Lane 2, SGAG2; Lane 3, SGAG2L; Lane 4, SGAG2L-A; Lane 5, SGAG2L-B; Lane 6, SGAG2L-C; Lane 7, BC-SGAG2; Lane 8, SGAG1-1; Lane 9, GFP insert; Lane 10, uninfected control).

These studies show stable expression of SIV and HIV epitopes in a rubella vector resulting in an infectious rubella hybrid that expresses the foreign protein for sufficient generations to allow expansion in a fermentor, followed by propagation and expression as a vaccine antigen in the immunized host.

Example 8

Materials and Methods

This example describes the materials and methods used in Example 9.

Analysis of Insert Stability.

To verify stability of the inserts in rubella, the rubella flanking regions, as well as the entire insert, was sequenced. Cells were infected with the vector for seven days and then treated with TRIzol (Invitrogen). RNA was purified from the aqueous phase with RNeasy Mini Kit, according to the manufacture's protocol (Qiagen GmbH, Germany). Reverse transcription was performed using a High Capacity RNA-to-cDNA Kit (Applied Biosystems), followed by PCR amplification using illustra puReTaq Ready-to-Go PCR beads (GE Healthcare). Oligonucleotide primers specific for rubella sequences flanking the Not I insertion site: Robo-seq67 (forward primer: 5'-gatgacgaggcgctcatcc, SEQ ID NO: 104) and Robo-seq6A (reverse primer: 5'-gagtgc-cgcgggcgtccgagtgc, SEQ ID NO: 105); or Robo-seq25 (forward primer: 5'-cgaactggtgagccccatgg, SEQ ID NO: 106) and Robo-seqSbfDn4 (reverse primer: 5'-gatctcgcaaatgcag-gctccagtg, SEQ ID NO: 107) for inserts in the structural region. The PCR products were analyzed by gel electrophoresis, purified from the gel using MinElute Gel Extraction Kit (Qiagen) and sequenced using the same primers.

Antibodies and Antigens.

Antibodies were obtained from the NIH AIDS Research and Reference Reagent Program, Division of AIDS, NIAID. Monoclonals 2F5 and 4E10 were obtained from Dr. Hermann Katinger. Polyclonal goat antibodies to rubella structural proteins were purchased from Fitzgerald Industries International, Inc. (Concord, Mass.). Rabbit antibodies to rubella nonstructural protein P150 were provided by Dr. Tero Ahola (University of Helsinki, Finland). Aldrithiol-2 inactivated SHIV virions with 89.6 envelope and SIV Gag proteins were a gift of Drs. Larry Arthur and Jeffrey Lifson at the AIDS Vaccine Program, NCI.

Construction of cDNA Plasmids Coding for Infectious RNA.

Plasmid p10RA coding for full-length infectious cDNA of the RA27/3 vaccine strain of rubella and plasmid pRobo302, coding for cDNA of the Therien strain of wild type rubella, were provided by Dr. T. Frey (Georgia State University, Atlanta). Wild type rubella cDNA was cloned into pBR322 to produce plasmid pBRobo3226. Infectious rubella virus RNA was generated by transcribing from the SP6 promoter, followed by RNA capping.

For cloning purposes, a sub-clone of p10RA (from Hind III to Bgl II), pBR322-Hind-Bgl-RA was created in pBR322. To create space for potential inserts, a deletion was made between the two Not I sites at positions 3661 and 4168 in the non-structural protein region, as reported for wild type rubella. Hind III-Cla I fragment from the sub-clone carrying the Not I deletion was cloned back to p10RA, giving pBRA3226-dNotI plasmid. The constructs were verified by sequencing.

Construction of Vectors with Insertions in the Nonstructural Gene Region.

Recognition sequences for Avr II and Nsi I restriction enzymes were cloned into the Not I deletion site. These unique restriction sites were then used for directional cloning of inserts into the Not I-deletion site. In the case of MPER$_F$, MPER$_E$, SGag2L-A, SGag2L-B, SGag2L-C, and BC-SGag2, cloning was done using SpeI and Nsi I sites. Spe I and Avr II have compatible sticky ends. Each insert was PCR amplified using primers listed in Table 4 and HIV-1 89.6 gp160 or SIV mac239 gag DNA as templates, cut with restriction enzymes, and ligated into the matching restriction sites. The amino acid sequences of these inserts are listed in FIG. 10.

Construction of Vectors with Insertions in the Structural Region.

For cloning purposes, a sub-clone of pBRobo3226 plasmid coding for wild type rubella was created. The new plasmid pBR322-NotI-BamHI contained rubella cDNA from the Not I site to BamH I in the structural protein region. DNA inserts coding for MPER$_F$-E2TM and MPER$_F$-E1TM, containing the 2F5 epitope, transmembrane domains of E2 and E1 rubella proteins, respectively, and E1 signal peptide sequence were synthesized by GeneArt (Regensburg, Germany). The inserts were flanked by Sbf I and Kpn I restriction sites, which were used to clone them into pBR322-NotI-BamHI. These plasmids were cut with Sbf I and BamH I restriction enzymes, and the products were cloned into plasmid pBRobo3226-dNotI, resulting in plasmids, which combined inserts in the structural genes with the deletion in the non-structural region at Not I. A similar construct on the RA27/3 background was made by inserting synthetic DNA coding for MPER, the transmembrane domain of HW-1 gp41 and the E1 signal peptide, flanked by Sbf I restriction sites, into the plasmid pBRA3226-dNotI coding for RA27/3 vaccine strain of rubella with the Not I deletion. All constructs were verified by sequencing. The amino acid sequences of these inserts are given in FIG. 10.

Generation of Rubella Virus.

The protocol for generation of capped, infectious rubella virus RNA from plasmid DNA and subsequent transfection of Vero cells was described previously. Virus was propagated on Vero cells maintained in DMEM containing L-glutamine, penicillin/streptomycin (MediaTech, Inc., Herndon, Va.) and 10% heat-inactivated fetal bovine serum at 37° C. in a humidified incubator with 5% CO2.

After 7-10 days of infection, culture supernatant ($P_0$) was centrifuged to produce cell-free supernatant and 0.1 mL of the supernatant was transferred onto fresh Vero cells to begin the next passage $P_1$. Alternatively, in early passages, it was found that passing infected cells from the previous culture along with virus, helped in propagating new viral vectors. Infected cells were continued to be passed for the first four passages, after that cell-free virus was just as efficient. Infected cells were tested for expression of rubella structural proteins, as a measure of vector replication, and insert expression was evaluated by Western blot, using specific antibodies. To expand a viral stock, virus from passage 4 or 5 was grown for 7 to 10 days on a Vero cell monolayer in a T75 flask, and multiple aliquots were frozen.

Detection of Rubella Proteins and MPER Inserts by Western Blot.

Infected Vero cells were lysed in RIPA buffer (Thermo Scientific, Rockford, Ill.) with addition of BD BaculoGold Protease inhibitor cocktail (BD Biosciences, San Jose, Calif.). Cell lysates were sonicated, run on a NuPAGE 4-12% polyacrylamide Bis-Tris gel (Invitrogen, Carlsbad, Calif.), transferred to nitrocellulose, and blocked with 2% BSA in TBS. Primary antibody was incubated in TBS with 0.2% Tween20, 0.2% BSA for 1½ hours at room temperature. Expression of rubella structural proteins was detected with goat anti-rubella polyclonal antibodies at 1:700 dilution, while rubella non-structural protein P150 was detected using rabbit polyclonal antibodies at a dilution of 1:1000 (30). Expression of MPER-derived inserts was detected with human monoclonal antibodies 2F5 or 4E10 at 1 µg/ml. Blots were washed three times with TBS/0.2% Tween20, followed by incubation with secondary antibody diluted in the same buffer for 60 min at room temperature on a rocking platform. The second antibody was either horseradish peroxidase-conjugated rabbit anti-goat IgG, goat anti-rabbit IgG or goat anti-human IgG at 1:5000 dilutions (Santa Cruz Biotechnology, CA). After the same washing procedure as above, blots were visualized with enhanced chemiluminescence (GE Healthcare).

TABLE 4

PCR primers used to generate inserts for rubella viral vectors. The inserts were generated using HIV-1 89.6 gp160 or SIV mac239 gag DNAs

| Insert | | PCR primers |
|---|---|---|
| MPER (89.6) | F: | 5'-gaagcacctaggtcagcccaagaaaagaatgaaaaagaattattggaattggataaatgg (SEQ ID NO: 108) |
| | R: | 5'-tgatctagatgcatctatgaatagtcttatataccacagccagtttgtta (SEQ ID NO: 109) |
| MPER$_F$ (89.6) | F: | 5'-gaacagactagtgcccaagaaaagaatgaaaaagaattattggaattggataaatgg (SEQ ID NO: 110) |
| | R: | 5'-ccagcagatgcatcattccacaaacttgcccatttatccaattccaataattcttttc (SEQ ID NO: 111) |
| MPER$_E$ (89.6) | F: | 5'-gaacagactagttggaattggtttgacataacaaactggctgtggtatat (SEQ ID NO: 112) |
| | R: | 5'-ccagcagatgcatctagtcttatataccacagccagtttgttatgtc (SEQ ID NO: 113) |
| sGag1 | F: | 5'-agatagcgcctagggaaggaagccaaaaaatactttcggtcttagctccattag (SEQ ID NO: 114) |
| | R: | 5'-tggcgatgatgcatcttctgcgtgaattgaccagatgaccgagacagtattataaaggct (SEQ ID NO: 115) |
| sGag2 | F: | 5'-agatagcgcctaggtttcaggcactgtcagaaggttgcac (SEQ ID NO: 116) |
| | R: | 5'-tgtaatgatgcatcagcctcctcgtttataatatctctgat (SEQ ID NO: 117) |
| sGag2L | F: | 5'-agatagcgcctaggctgccattaagcccgagaacattaaatg (SEQ ID NO: 118) |
| | R: | 5'-tggcgatgatgcatcactagtagcctcctcgtttataatatctctgat (SEQ ID NO: 119) |
| sGag2L-A | F: | 5'-gatagcgcctaggagccagaagatcctgagcgtgctggcccctctggt (SEQ ID NO: 120) |
| | R: | 5'-tgcgatgatgcatcactagtgggcaccagaggggccagcacgctcag (SEQ ID NO: 121) |
| sGag2L-B | F: | 5'-gatagcgcctaggaccggcagcgagaacctgaagagcctgtacaa (SEQ ID NO: 122) |
| | R: | 5'-tgcgatgatgcatcactagtgttgtacaggctcttcaggttctcgct (SEQ ID NO: 123) |
| sGag2L-C, BC-sGag2 | F: | 5'-gatagcgcctagggtgaagcacaccgaggaggccaagcagatcgtgcagcgccacctggtggtg (SEQ ID NO: 124) |
| | R: | 5'-tgcgatgatgcatcactagtggtgccggtctccaccaccaggtggcgctgcacgatct (SEQ ID NO: 125) |

TABLE 5

MPER$_F$ inserts expressed between structural proteins of rubella

| Inser name | Bp | Insert Amino acid sequence | SEQ ID NO. |
|---|---|---|---|
| MPER$_F$-E2TM | 219 | FEEPRQEKNEKELLELDKWASLWNWFDMHTLAAFVLLVPWVLIFM VCRRTCRRRGAAAALTAVVLQGYNPPAYG | 126 |
| MPER$_F$-E1TM | 231 | GEEPRQEKNEKELLELDKWASLWNWFDMHWWQLTGATCALPLAGL LACCARRTCRRRGAAAALTAVVLQGYNPPAYG | 127 |
| MPER-HIVTM | | GEEPRQEKNEKELLELDKWASLWNWFDITNWLWYIRLFIMIVGGL IGLRIVFAVLSIVCRRTCRRRGAAAALTAVVLQGYNPPAYG | 131 |

Example 9

Insertion of Foreign Genes into Rubella Viral Constructs

This example illustrates deletion/insertion strategies to construct rubella viral vectors carrying a foreign gene.

FIG. 9A illustrates a disclosed rubella viral construct which was created by a deletion and insertion at the same Not I site (FIG. 9A). FIG. 9B illustrates a construct including a deletion at the Not I site and insertion between the structural genes (FIG. 9B). As an example of the first strategy, a 507 bp deletion was made between two Not I restriction sites in the nonstructural region and then inserted a zGFP reporter gene (792 bp) into the same site. The product was a live vector that expressed zGFP (25 kDa) as a fusion protein with nonstructural protein P150. Viral replication kinetics and titer were nearly the same as for wild type rubella. The P150-zGFP fusion protein performed essential P150 functions during RNA replication and localized correctly to viral replication centers in the cytoplasm, as shown by fluorescence microscopy. Ten additional vectors of this type, bearing HIV and SIV inserts at the Not I site (FIGS. 9C and 9D) were created. Seven vectors expressed SIV Gag antigens (called sGag) and three vectors contained HIV MPER-derived inserts. The full length MPER insert coded for 33 amino acids and included epitopes recognized by human neutralizing monoclonal antibodies 2F5 and 4E10 (FIG. 9C, FIG. 10). An MPER insert containing 19 amino acids from the amino end was called MPER$_F$, corresponding to the epitope recognized by monoclonal 2F5. An insert coding for 15 amino acids from the carboxyl end of MPER was called MPER$_E$, corresponding to the 4E10 epitope. The MPER inserts were much shorter (60 to 111 bp) than the Not I deletion (507 bp), so the vector RNA should fit well within the size limits for rubella RNA packaging.

The sGag inserts were derived from SIV Gag amino acids 41-211 (FIG. 9D). This region codes for the carboxyl half of matrix protein p17 and the amino half of capsid protein p27. It is rich in epitopes (at least 5) targeted by T cells during the immune response to SIV infection in rhesus macaques (Table 6). Small inserts coding for two epitopes were first used, such as sGag1 and sGag2, and then added epitopes stepwise (FIG. 9D). Vector sGag1 contained T cell epitopes KP11 and GY9 within amino acids 54-91 of MA protein p17. Vectors sGag2 (amino acids 173-211) and sGag2L (amino acids 147-211) contained T cell epitopes CM9 and ME11 from CA protein p27. One epitope at a time was added to the carboxyl end of sGag2L to produce sGag2L-A (KP11), -B (GY9), or -C (TE15). Alternatively, two epitopes were added to the amino end of sGag2 to produce BC-sGag2. The sequences of these inserts are shown in FIG. 10. Together, these constructs code for a series of rubella vectors expressing sGag inserts of increasing size and antigenic complexity.

Each insert was ligated into the Not I site of the rubella vaccine strain RA27/3, as shown in FIG. 9A. Following transcription of plasmid DNA and capping, full length, infectious RNA was transfected into Vero cells to create passage zero ($P_o$). After 7 to 10 days in culture, the resulting virus was passed onto fresh Vero cells, either as clarified culture supernatant or as infected cells, for passage 1 ($P_1$). After each subsequent passage, vector replication was monitored by Western blot of the rubella structural proteins C and E1. For the largest vectors and those that were considered vaccine candidates, such as BC-sGag2 and MPER$_F$, stability of the inserts was verified by sequencing viral RNA after four to six passages in culture.

Figure 11A:
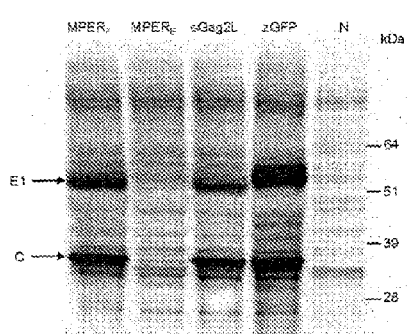
FIGS. 11A-11D are digital images of Western blot analyses illustrating replication of rubella vectors expressing HIV MPER and SIV Gag inserts at the Not I site. Replication of rubella vectors expressing HIV MPER and SIV Gag inserts at the Not I site. (A) Growth of rubella vectors expressing HIV MPER- or SW Gag-derived inserts at the Not I deletion site. Viral replication and protein expression were detected by Western blot with goat polyclonal antibodies specific for rubella structural proteins capsid C and envelope glycoprotein E1. Vectors expressing MPER$_F$ and SW Gag2L grew as well as a control vector expressing zGFP. Lane N represents uninfected cells. (B) Western blots showing a time course of HIV MPER$_F$ expression at the Not I site. MPER$_F$ (at passage P$_3$) was expressed as a high molecular-weight fusion protein with nonstructural protein P150 (arrow). It was detected with monoclonal antibody 2F5 (left panel). Maximal expression of P150-MPER$_F$ fusion protein was observed from day 2 to 5 after infection, showing that p150 is an early gene under control of the rubella genomic promoter. After 5 days, P150-MPER$_F$ expression became undetectable. Rubella structural proteins E1 and C (right panel) first appeared on day 5 or 6 and were strongly expressed on days 7-10. Lane zGFP represents a control infection with rubella expressing zGFP but no MPER antigens, and lane N shows uninfected cells. (C) Growth of rubella vectors expressing SIV Gag inserts at the Not I site. Vector replication at passage P$_2$ was detected by Western blot with anti-rubella antibodies. Vectors replicated strongly while expressing two, three or four Gag epitopes. Gag constructs and epitopes are labeled as in FIG. 1D. Lane N represents a mock infection. (D) Expression of the BC-sGag2 insert as a P150 fusion protein was detected by Western blot with antibodies to P150. The P150 band for each construct is indicated by arrowheads. Lane 1 shows the size of P150 with zGFP inserted at the Not I site. Lane 2 shows the size of P150 alone after Not I deletion. Lanes 3 and 4 show the size of the P150-BC-sGag2 fusion protein, which was expressed on days 6 and 7, respectively, and then declined by day 10 (lane 5). The shift of the P150-BC-sGag2 band, as compared to P150-NotI, indicates the presence of a BC-sGag-2 insert. The BC-sGag2 insert was confirmed by sequencing the viral genome at passage P$_6$.

Replication of rubella vectors expressing MPER$_F$, MPER$_E$ and sGag2L at passage $P_o$ was detected by Western blot (FIG. 11A), using goat polyclonal antibodies to the rubella structural proteins, capsid C and envelope protein E1. The vector expressing MPER$_F$ (FIG. 11A, lane 1) replicated strongly for at least seven passages, while the MPER$_E$ construct (lane 2) replicated poorly at first and then became undetectable. Similarly, rubella virus bearing full length MPER (with both 2F5 and 4E10 epitopes) at the Not I site did not replicate. At this site, MPER was expressed as a fusion protein with P150 (FIG. 9A). This placed constraints on the insert. P150 plays a role as a cofactor for both plus and minus strand RNA synthesis. The MPER-P150 fusion protein preserves P150 folding, stability, and function. Anything that reduced levels of functional P150 could be lethal for the virus. Similarly, a vector expressing SIV Gag antigens, sGag2L, replicated and expressed rubella structural proteins (FIG. 11A, lane 3) as well as the MPER$_F$ vector and nearly as well as a control vector expressing zGFP (lane 4). These estimates of viral replication, based on expression of rubella proteins, were generally borne out by measuring viral RNA titers (see below).

Figure 11B:
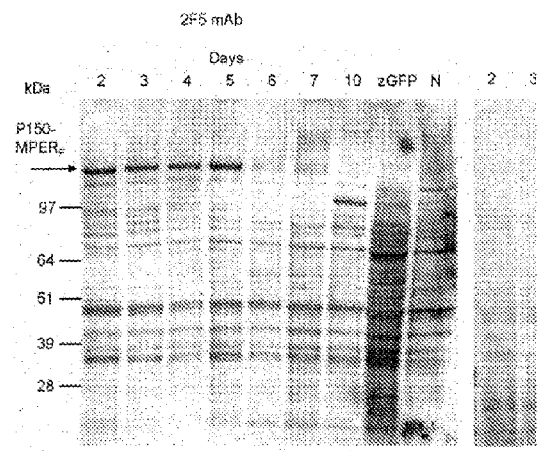

Expression of the MPER$_F$ insert was detected by Western blot with monoclonal antibody 2F5 (FIG. 11B). It was found in a high molecular weight band corresponding to a fusion protein with nonstructural protein P150 (P150-MPER$_F$ indicated by an arrow). A time course of MPER$_F$ expression showed that the P150-MPER$_F$ protein was expressed strongly by day 2 of infection, and expression continued at a high level until day 5. After that, MPER$_F$ expression quickly became undetectable. These results indicate that MPER$_F$ is expressed as an early antigen under control of the rubella genomic promoter. In contrast, rubella structural proteins C and E1, which are under control of the subgenomic promoter, appeared as late antigens on day 6 or 7 and increased steadily until day 10 post infection.

Figure 11C:
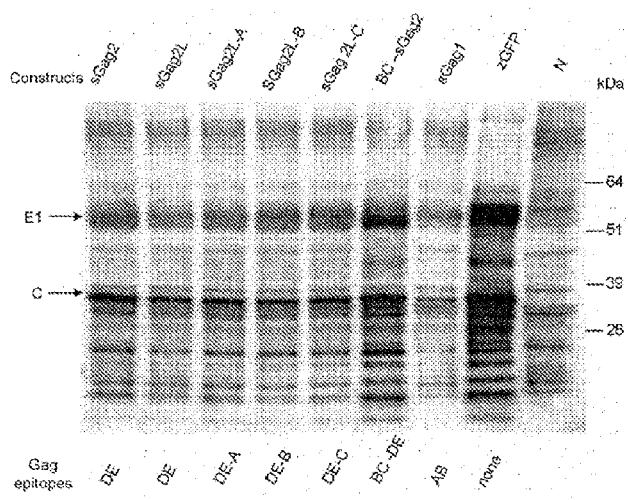

The seven vectors with sGag inserts included four of the five major epitopes from this region of Gag that are known targets of T cell immunity against SIV. Their replication was monitored by Western blot of rubella structural proteins (FIG. 11C). Each vector replicated strongly, as shown by expression of rubella proteins C and E1. The vector BC-sGag2 with four epitopes on the RA27/3 vaccine background, replicated nearly as well as a control vector expressing zGFP on a wild type rubella background (FIG. 11C, lanes BC-sGag2 and zGFP, respectively).

Figure 11D:
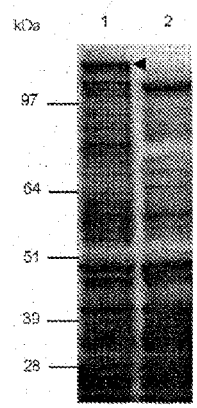

Due to lack of a monoclonal antibody specific for the T cell epitopes of SIV Gag, expression of BC-sGag2 at the Not I site was detected indirectly, by measuring a shift in the P150 band due to the size of the p150-BCs-Gag2 fusion protein (FIG. 11D). Polyclonal antibodies to P150 (30) showed the reduced size of P150 after Not I deletion (FIG. 11D, lane 2, arrowhead). Its size was shifted to a larger molecular weight by insertion of zGFP (lane 1, arrowhead) or BC-sGag2 (lanes 3 and 4, arrowheads). The size difference between P150 bands in lanes 3 and 4 vs. lane 2 was due to the BC-sGag2 insert. The P150-BC-sGag2 fusion protein was the major species of P150 in these cells. The P150-BC-sGag2 fusion protein showed a typical time course for the genomic promoter, since it was expressed early (lanes 3 and 4) and then was virtually undetectable by day 10 (FIG. 11D, lane 5). Viral RNA sequencing of the BC-sGag2 insert after six passages confirmed its stability: all four sGag epitopes were present and in the correct reading frame.

In some cases, vectors appeared to be replicating after the initial RNA transfection ($P_0$) but failed to propagate further by passing clarified culture supernatants. In these early passages, propagation efficiency was increased by transferring virus via infected cells, rather than culture supernatants. After passage $P_4$, cell-free passage was performed. This method helped to propagate vectors with inserts as large as BC-sGag2.

FIG. 9B shows the second strategy used to create rubella vectors with an insertion site in the structural region. To find a permissive site of insertion, the Not I deletion was kept constant and moved MPER$_F$ to different sites as a probe that could be readily expressed by rubella. Insertions were made between capsid C and envelope E2 genes, as well as between E2 and E1. The insertion site between C and E2 was not permissive for viral replication. However, MPER$_F$, combined with a membrane spanning domain and E1 signal peptide, was readily accepted between structural genes E2 and E1. The composition and sequence of each insert are given in FIG. 9C and FIG. 10. As before, vector replication and insert expression was monitored by Western blot.

Figure 12A:
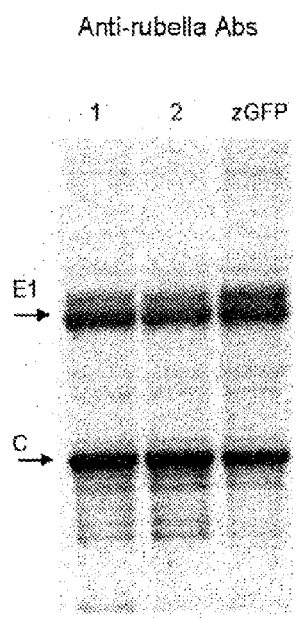
FIGS. 12A-12C are digital images of Western blot analyses illustrating replication of rubella vectors expressing HIV MPER antigens in the structural insertion site. Replication of rubella vectors expressing HIV MPER antigens in the structural insertion site. (A) Western blot showing replication of two rubella vectors with inserts between envelope glycoproteins E2 and E1, MPER$_F$-E2TM and MPER$_F$-E1TM (lanes 1 and 2) and a control vector expressing zGFP. (B) Western blot of the same samples with monoclonal antibody 2F5, showing high level expression of MPER$_F$ as an 8.5 kDa protein when inserted between E2 and E1 (lanes 1 and 2). Additional bands at higher molecular weight suggest incomplete cleavage of the structural polyprotein, leaving MPER$_F$ fused to either E2 or E1. These bands were not observed in uninfected cells (lane N). Lane SHIV represents a positive control with aldrithiol-2-inactivated SIV/HIV chimeric virions containing HIV-1 gp41. (C) Dual antigenicity of full length MPER expressed in the structural site. Vero cells were infected with a control rubella vector expressing zGFP (lanes 1, 3 and 5) or with a vector expressing MPER-HIVTM at the structural site at passage P$_8$ (lanes 2, 4 and 6). Cell lysates were sedimented on a 10-40% sucrose gradient for 16.5 hours at 39,000 rpm in an SW41Ti rotor to band the virus by density. Peak fractions of each gradient were probed with antibodies specific for rubella structural proteins (lanes 1 and 2) or MPER (monoclonal 2F5 in lanes 3 and 4 or monoclonal 4E10 in lanes 5 and 6). Expression of rubella proteins was slightly greater in lane 2 than in control lane 1. The 10 kDa band for MPER-HIVTM showed nearly equal staining with 2F5 or 4E10 (lanes 4 and 6), indicating that both epitopes were expressed equally. Neither monoclonal detected a band in vector control lanes 3 and 5, indicating specificity. A minor band above 62 kDa in lanes 4 and 6 may represent incomplete cleavage of the structural polyprotein, resulting in an MPER-HIVTM-E1 fusion protein.
Figure 12B:
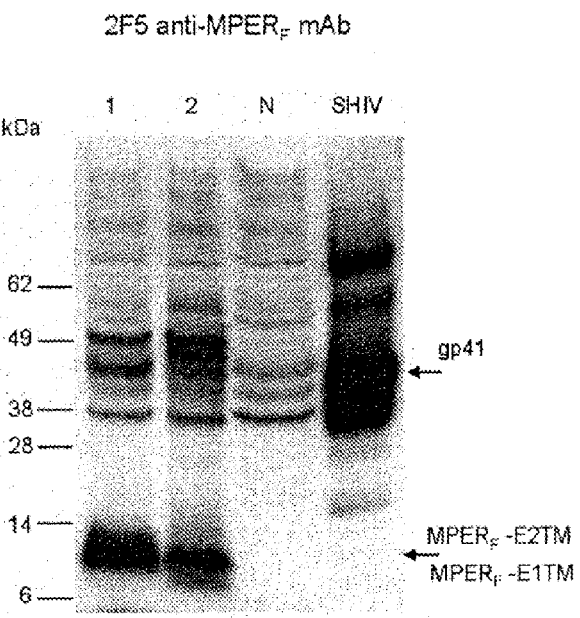

FIGS. 12A and 12B show replication of two rubella vectors bearing MPER$_F$ at the structural site and expression of the inserts, respectively. MPER$_F$ was fused with the membrane spanning domain of rubella E2 (lane 1) or E1 (lane 2) protein and inserted between envelope proteins E2 and E1. These vectors, based on wild type rubella, grew and expressed rubella proteins as well as the control vector carrying zGFP (lane zGFP). Both replicating vectors expressed MPER$_F$ fusion proteins (approximately 8.5 kDa), as detected by monoclonal 2F5 (FIG. 12B, lanes 1 and 2). MPER$_F$-E2TM gave consistently stronger MPER$_F$ expression than MPER$_F$-E1TM (lane 1 vs. lane 2). MPER$_F$ expression at the structural site (FIG. 12B) was stronger than at the Not I site (FIG. 11B). This is typical of rubella structural proteins, which are over-expressed by the strong subgenomic promoter as compared to the rubella genomic promoter. At the structural site, MPER$_F$ was expressed as part of the structural polyprotein, and its release from the polyprotein as a membrane-anchored 8.5 kDa protein depended on signal peptidase. Incomplete cleavage at either end of MPER$_F$ would produce MPER$_F$ linked to E2 or E1, and this could explain minor bands of MPER$_F$ found at higher molecular weight in FIG. 12B (lanes 1 and 2), which were not observed in uninfected cells (lane N).

Figure 12C:
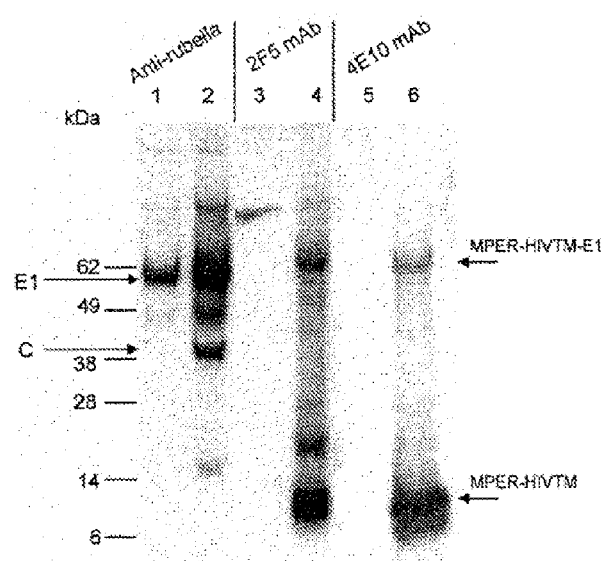

In addition, the insert was expanded to full length MPER, which included both the 2F5 and 4E10 epitopes, and anchored it to the membrane with the transmembrane domain of HIV gp41 linked to the E1 signal peptide (FIG. 9C and FIG. 10). The MPER-HIVTM vector replicated well and expressed MPER at about 10 kDa. To demonstrate its dual antigenicity for both monoclonals, the virus was purified by banding overnight in a 10-40% sucrose density gradient to remove cell proteins and reduce background binding. Monoclonal antibody binding was compared to the vector expressing MPER-HIVTM vs. a control vector expressing zGFP (FIG. 12C). Both MPER epitopes were detected equally as a 10 kDa band (FIG. 12C, lanes 4 and 6), indicating its dual antigenicity. These bands were not observed with a control vector expressing zGFP (lanes 3 and 5), indicating their specificity. A less prominent band above 62 kDa may represent partially unprocessed MPER-HIVTM linked to E1. The sequence of the MPER-HIVTM insert was confirmed by viral RNA sequencing.

Figure 13A:
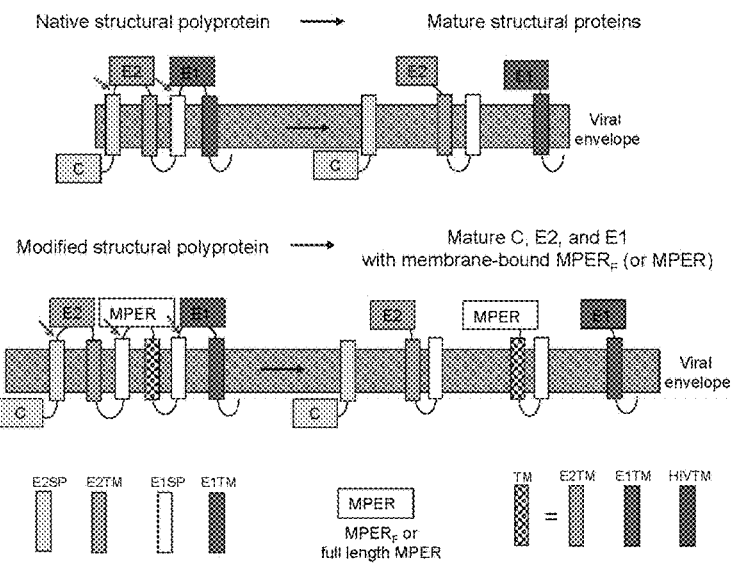
FIGS. 13A-13C.

A schematic of inserts at the structural site is shown in FIG. 13A. In the native structural polyprotein (FIG. 13A, upper panel), the transmembrane domains following capsid C and E2 protein include signal peptides (E2SP and E1SP) for the next protein. E2 and E1 proteins have additional transmembrane domains, E2TM and E1TM that anchor them to the membrane. Normally, the polyprotein is cleaved by signal peptidase at two sites (arrows), to release three mature proteins, capsid C, E2 and E1. In the MPER vectors (FIG. 13A, lower panel), to anchor the insert to a membrane, an additional transmembrane domain (E2TM, E1TM or the HIV-1 transmembrane domain, HIVTM) was added and a signal peptide (E1SP) after the MPER sequence. This polyprotein was cut three times to release three structural proteins plus the MPER insert. The mature 8.5 kDa to 10 kDa proteins containing MPER inserts were observed on Western blots (FIGS. 12B and C), as well as a minor band at about 68 kDa that may represent incomplete cleavage between MPER and E1.

Figure 13B:
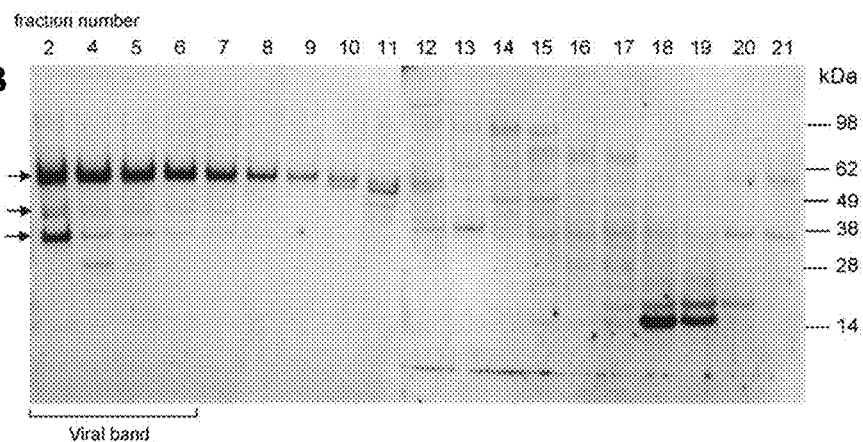
Figure 13C:
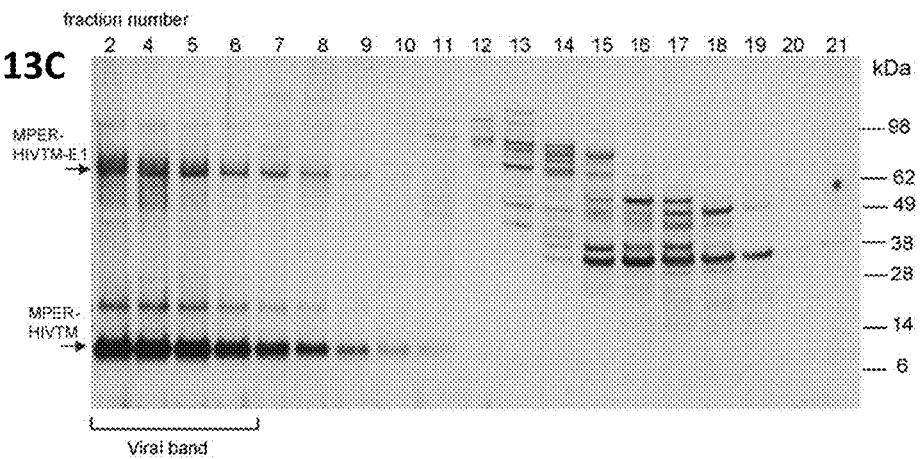

Since MPER was expressed with the rubella structural proteins, it was examined whether it could be incorporated into virions. After banding MPER-HIVTM virus (P$_8$) in sucrose density gradients, each fraction was analyzed for rubella viral proteins (FIG. 13B) and MPER antigen (FIG. 13C). As shown in FIG. 13B, the virus banded primarily in fractions 2 to 6, as shown by the presence of all three rubella structural proteins C (33 kDa), E2 (42-47 kDa), and E1 (58 kDa). The E1 band extended from fractions 2 to 8. Similarly, there was a strong MPER band in fractions 2 to 8 (FIG. 13C), and the relative intensity of each fraction followed that of E1. Little or no MPER was found at the top of the gradient, indicating the absence of free MPER. In addition to the expected MPER-HIVTM band at 10 kDa, a second MPER band was observed at about 68 kDa, corresponding to the combined size of an MPER-HIVTM-E1 fusion protein. This could be the product of incomplete cleavage by signal peptidase of the structural polyprotein between MPER-HIVTM and E1. The fact that nearly all MPER-HIVTM co-sedimented with the viral band, indicates a strong association with virions. Virion-associated MPER could contribute to immunogenicity by presenting an array of MPER antigens on the viral particle. A 38 kDa band reacting with 2F5 was observed in fractions 15 through 19 of the gradient. This band was also found in a Western blot of uninfected cells (FIG. 12B, lane N), and it may represent one of the self proteins recognized by monoclonal 2F5.

Rubella vectors would not be practical as a vaccine platform unless they could achieve high enough titers for vaccine production. Twenty ml stocks of rubella vectors were produced on the vaccine strain background (RA27/3). The vectors had MPER$_F$ or BC-sGag2 inserts at the Not I site, or an MPER-HIVTM insert in the structural site. Viral RNA content of the stocks were measured by real time RT-PCR, as described previously. As shown in Table 7, culture supernatants of MPER$_F$ contained $3.1 \times 10^7$ RNA copies/ml, BC-sGag2 grew to $2.5 \times 10^6$ RNA copies/ml, and MPER-HIVTM reached $1.3 \times 10^7$ RNA copies/ml. Comparing these vectors to a sample of rubella vaccine of known titer, titers were estimated of about $5.0 \times 10^6$ PFU/ml, $4.1 \times 10^5$ PFU/ml and $2.2 \times 10^6$ PFU/ml, respectively.

These studies identified two insertion sites where rubella can accommodate inserts into the viral genome: one is located between two Not I restriction sites in the nonstructural genes, while the other is located between the structural genes. When a protein antigen (zGFP, BC-sGag2 or MPER$_F$) is expressed at the Not I site, it forms a fusion protein with rubella nonstructural protein P150. It is expressed as an early viral antigen, under control of the rubella genomic promoter, with maximal expression between days 2 to 5 of infection. Based on the results with P150-zGFP and prior studies of P150, the P150 fusion protein localizes to the cytoplasm, where it participates in viral replicative centers. This location is near the entry point for proteasomal processing and could deliver SIV Gag antigen to the main processing pathway leading to antigen presentation with MHC class I for induction of T cell immunity. However, expression as a fusion protein with P150 also places constraints on the insert, as P150 function must be preserved. Within viral replication centers, P150 acts as an essential cofactor in RNA synthesis, both for plus and minus strand RNA. Loss of P150 function would be a lethal event for the virus. This could occur if an insert prevented normal P150 folding, interfered with its interaction with RNA polymerase, or caused instability through proteolytic degradation or aggregation.

The second insertion site is located in the structural region of rubella, between genes coding for envelope glycoproteins E2 and E1. An MPER insert at this site was expressed as a late viral protein, under control of the strong subgenomic promoter. The ability to express the full MPER determinant at this site, but not at the Not I site, suggested greater flexibility in protein expression at the structural site. MPER expression was maximal between days 5 and 10 after infection. It was expressed as part of the structural polyprotein and then processed to free MPER antigen. Sedimentation in sucrose gradients showed that most of the MPER was incorporated into virions, and almost none remained as a free protein. As shown in the schematic (FIG. 13A), MPER-HIVTM has a transmembrane domain and signal peptide similar to envelope glycoproteins E2 and E1, and its incorporation into virions may follow the same path as the structural proteins. Positioning MPER-derived antigens at the structural site contributes to immunogenicity by high level of expression, incorporation into viral particles, and by display on a membrane surface that resembles the natural milieu on HIV virions. In addition, some of the unprocessed MPER-HIVTM remains attached to envelope glycoprotein E1 (FIG. 13C). Such a fusion protein enhances MPER immunogenicity by linking it to a carrier protein E1.

The antigens expressed by recombinant rubella vectors include the MPER determinant of HW transmembrane protein gp41 and SIV Gag sequences, which are rich in T cell determinants. The MPER region is a target of broadly reactive neutralizing antibodies against HIV, such as monoclonal antibodies 2F5, 4E10, and Z13e. However, despite many attempts to elicit antibodies to MPER, there has been little success, presumably because MPER is a weak immunogen by itself, lacks the native conformation, or resembles self antigens. Its expression as part of a live, replicating viral vector may enhance the immune response to MPER by eliciting T cell help for MPER-specific B cells. Rubella vectors expressing MPER could also be combined with another vector in a prime and boost strategy or they could precede a boost with virus-like particles expressing MPER.

The SIV Gag determinants were derived from a region of Gag (aa 41-211) that is rich in targets of T cell immunity, including five T cell epitopes. Two epitopes, CM9 and GY9, are restricted by Mamu A01 and A02, respectively, and they have been identified as predominant targets of CTLs early after SIV infection. For these epitopes, virus escape occurs late, if at all. However, when it does occur, escape mutants at CM9 have been associated with loss of control of viremia and disease progression. These sites may be slow to mutate because they perform viral functions for SIV that require compensatory mutations before they can escape. By eliciting T cells specific for these epitopes prior to infection, the BC-sGag2 vector could potentially control a subsequent SIV infection.

Rubella's biological properties favor its use as a vaccine platform. Its safety has been demonstrated in millions of children around the world. The SIV Gag and HIV-1 MPER inserts at the Not I site were made with the RA27/3 vaccine strain, and our inserts at the structural site have been re-derived on this background. The vectors replicate to high titers during vaccine production, and the inserted genes are stably expressed for at least eight to ten passages in cell culture. The vaccine strain can be used safely in the host without further attenuation. Even if a vector loses its insert, it reverts to the vaccine strain. Rubella virus possesses little risk of viral persistence, has no DNA intermediates and does not integrate into host genomes as retroviral vectors do. Also, there is no interference with antigen processing and presentation, as with CMV and adenovirus vectors. While growing to high titers in cell culture, rubella vaccine immunizes at a low dose. Since the minimum recommended dose of the RA27/3 strain is $10^3$ PFU for humans, the titers obtained with rubella vectors (Table 7) correspond to between 410 and 5,000 human doses per milliliter. At this level, without further optimization, the entire US birth cohort of four million children could be immunized with the product of a 10 L fermentor.

Live attenuated rubella vaccine is immunogenic, and it elicits mucosal as well as systemic immunity. A live vector can immunize with a much lower dose than a non-replicating vector; through exponential growth, it exposes the host to more antigen over time. Rubella has low cytotoxicity, so infected cells can present antigen for 5 days at the Not I site and up to 10 days at the structural site. Persistent expression may help the induction of antigen specific T cells and B cells. Antigen presented in the context of an acute infection may combine innate and adaptive immunity to elicit a stronger immune response.

TABLE 6

T cell epitopes in SIV Gag (amino acids 41-211)

| sGag insert | Gag epitope | Sequence | Amino acids | Gag protein | MHC Class | MHC Type | SEQ ID NO. |
|---|---|---|---|---|---|---|---|
| A | KP11 | KILSVLAPLVP | 59-70 | p17 MA | II | $DP_{BI-06}$ | 94 |
| B | GY9 | GSENLKSLY | 71-79 | p17 MA | I | A02 | 93 |
| C | TE15/KT15 | TEEAKQIVQRHLVVE | 97-111 | p17 MA | II | $DR_{B-W606}$ | 95 |
| D | CM9 | CTPYDINQM | 181-189 | p27 CA | I | A01 | 92 |
| E | ME11 | MQIIRDIINEE | 200-210 | p27 CA | II | $DR_{B1-0306}$ | 96 |

TABLE 7

Titers of rubella vector stocks of potential vaccine candidates

| Viral vector | RNA copies/ml* | Estimated titer, PFU/ml |
|---|---|---|
| $MPER_F$ in NotI site ($P_6$) | $3.1 \times 10^7$ | $5.0 \times 10^6$ |
| BC-sGag2 in NotI site ($P_6$) | $2.5 \times 10^6$ | $4.1 \times 10^5$ |
| MPER-HIVTM in structural region ($P_5$) | $1.3 \times 10^7$ | $2.2 \times 10^6$ |

*The viral RNA content of each vector was determined by real time RT-PCR. The titer was estimated by comparison to a vaccine standard of known infectious titer. Sequences for inserts of the viral stocks were verified by viral genome sequencing.

Example 10

Characterization of Rubella Viral Constructs without a Deletion at the Not I Site within the Non-Structural Site This example characterizes rubella viral vector constructs carrying a foreign gene within the structural site without a deletion at the Not I site within the non-structural site.

Figure 14A:
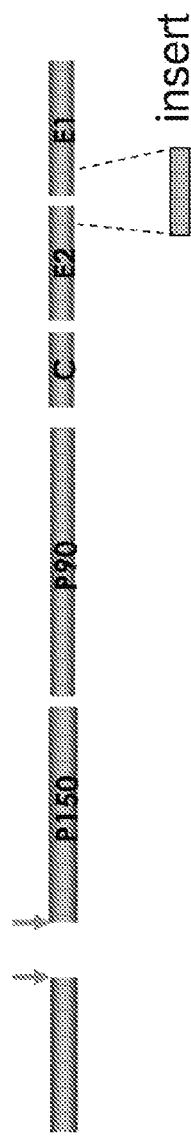
FIGS. 14A and 14B are schematics illustrating exemplary deletion/insertion strategies for producing rubella vectors.
Figure 14B:
Figure 15:
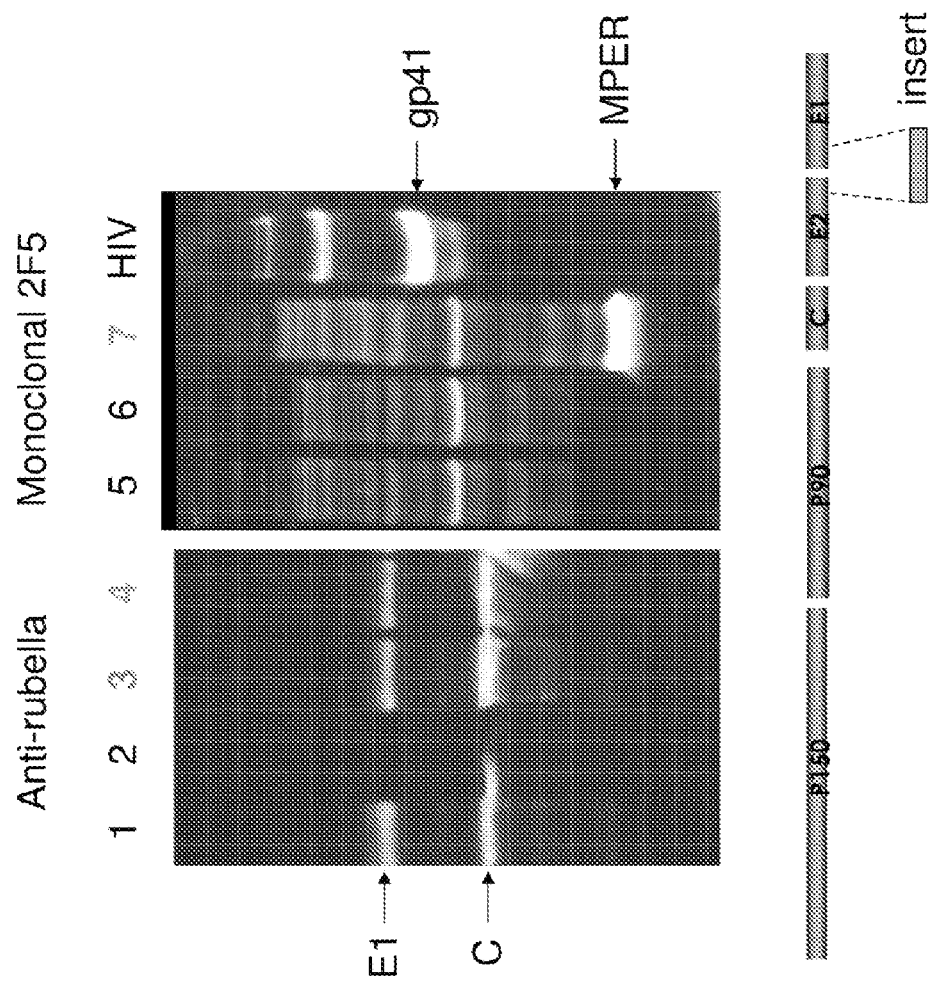
FIG. 15 shows digital images of Western blot analyses illustrating MPER antigen incorporation into rubella virions.

As shown in FIG. 14 rubella vectors were made with inserts at the structural site but without any deletion in the Not I site. These vectors were made initially with the same MPER-HIVTM and BC-sGag2 inserts as described above. The vectors grew well, as shown in FIG. 15, left panel. For example, as shown in FIG. 15, the first lane is the RA27/3 vaccine strain of rubella, and the second lane shows uninfected cells. Lanes 3 and 4 show rubella vectors with MPER-HIVTM or BC-sGag 2 inserts, respectively, which grew as well as the vaccine strain they were derived from (lane 1). The right panel in FIG. 15 shows strong expression of an MPER insert by the non-deleted vector (lane 7), but not by the empty vector (lane 5) or uninfected control (lane 6). Monoclonal antibody detected mature MPER protein as a 10 kDa protein, comparable in amount to the HIV gp41 control. These vectors were grown for at least 6 passages and stably expressed the MPER insert at each passage. These studies support the finding that vectors including inserts in the structural site without any deletion in the Not I site were viable.

Not only were the vector constructs viable, but such rubella vectors grew to high titers in vitro as illustrated in FIG. 16. FIG. 16 shows the titers obtained for rubella vectors bearing MPER and Gag inserts at the structural site. Titers were based on real time RT-PCR of rubella stocks, as compared to a rubella vaccine standard with a known plaque-forming titer. Comparison of sections B and C of the table shows that comparable titers were obtained when the same insert was expressed with or without a Not I deletion. Rubella immunization is highly efficient and requires only 1,000 PFU of virus. The titers of these vectors correspond to between 2300 and 5800 doses per ml. At this rate, the products of a 20 L fermentor could immunize the entire birth cohort of the US (4 million children) each year.

Subsequent studies were performed to determine if these rubella vector constructs were infectious in vivo and effective at immunizing subjects. FIG. 17 shows four attempted immunizations of a group of macaques with rubella vectors that have the same inserts but at different sites. The first two doses consisted of rubella vectors with inserts at the structural site and deletions at the Not I site. Despite giving 2 to 10 times the human dose, there was no virus replication or "take", as shown by the absence of antibodies to the vector (circles). The third dose consisted of vectors with inserts at the Not I site in place of a nonstructural protein deletion. One of three animals developed antibodies to the vector, suggesting an occasional take. The fourth dose, however, was a highly successful immunization, resulting in antibodies to the vector in 3 out of 3 animals tested (circle). The new vectors had inserts at the structural site but no deletions at the Not I site. The rate and titer of antibody formation was greater than or equal to the licensed rubella vaccine strain, given as a control.

The difference between vectors that did or did not grow in vivo was apparently due to the Not I deletion. The missing gene is probably required to deal with host defenses, most likely interferon. It was found that Not I deleted rubella viruses with a structural site insertion can only grow in cell lines, such as Vero cells, that are unable to make interferon. They do not grow in MRC-5 or WI-38 cells that are classic hosts for rubella and produce interferon. In contrast, vectors with the same structural insert but without a Not I deletion grow well in these cells. Thus, a vector's ability to grow in MRC-5 or WI-38 cells correlates well with successful immunization of monkeys and man. Thus, these studies demonstrate that rubella vectors lacking a Not I deletion are infectious in vivo and immunize macaques efficiently.

Figure 18:
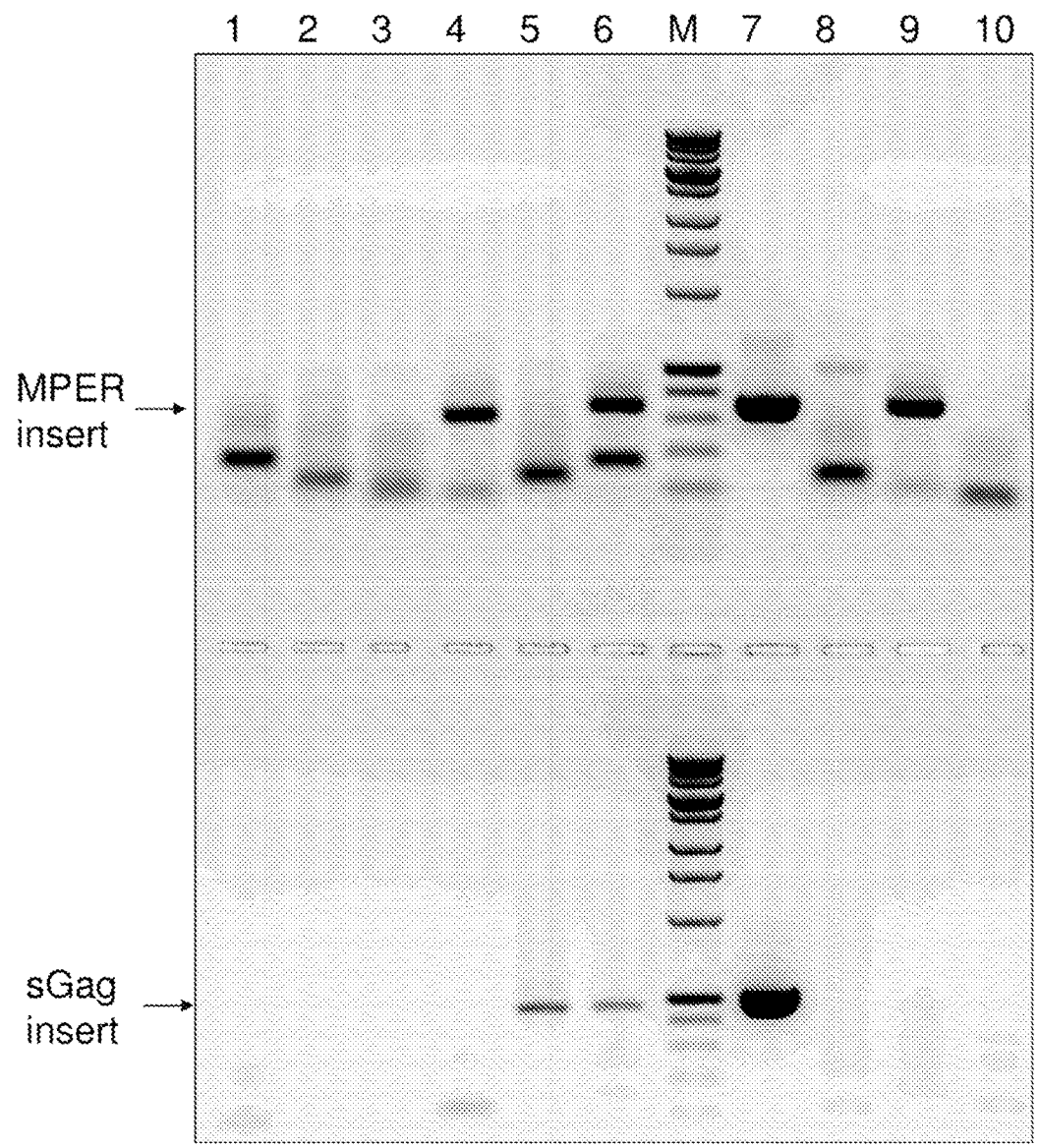
FIG. 18 is a digital image of PCR products separated by gel electrophoresis showing rubella vectors lacking a Not I deletion replicate efficiently in vivo.

Further studies were performed which also demonstrated rubella vectors lacking a Not I deletion replicate well in vivo, as detected by PCR of oral swabs. FIG. 18 shows a PCR study performed to detect rubella replication in macaques. Each monkey was vaccinated intramuscularly in the thigh with two rubella vectors: one containing MPER and the other containing BCsGag-2, but lacking deletions at Not I. The virus normally grows well in the mouth and pharynx and is spread by droplets. Oral samples were taken for detection of replicating virus on days 0, 7, and 14 after immunization. RT-PCR was used to detect virus in oral samples. The upper panel used primer pairs specific for the MPER insert, while the lower panel used primers specific for the BCsGag-2 insert. Lane 7 was a plasmid control, showing the expected band for each insert. As shown in lanes 1-3 of FIG. 18, all three monkeys were negative for rubella vectors on day 0. By day 7, (lanes 4-6) two macaques were positive of rubella-MPER and two were positive for rubella BCsGag-2. By day 14 (lanes 8-10), one animal was positive for rubella-MPER, and all were negative for rubella expressing BCsGag-2. In one animal (lane 5), BC-sGag2 appeared first, followed a week later by rubella-MPER. In another, (lane 6) both vectors appeared at the same time. In one animal (lane 4), rubella-MPER was detected, but no rubella-BCsGag-2. This result, combined with the results above, indicates that rubella vectors lacking a Not I deletion produced by the current method were infectious in 6 out of 6 animals and produced a vaccine take at a very low dose, comparable to conventional rubella vaccine.

Additional studies were performed to determine if the rubella vectors could elicit an immune response to the vaccine insert. FIG. 19 shows the antibody response to the BCsGag-2 insert. Antibodies were measured by ELISA, using plates coated with recombinant SIV Gag protein. Two controls were a pre-bleed of one macaque (J6L) and the serum of a macaque immunized with an empty rubella vector (CL6A). Both showed no antibodies to SW Gag. Subsequent studies demonstrated that all three macaques used in the experiment were negative for antibodies to the insert at the start of the study. As shown in FIG. 19, the vaccine elicited high titered antibodies to the insert in 3 out of 3 animals tested. In two animals, this was 7 weeks after the fourth dose of vaccine, but this was the first dose producing a vaccine take in these animals. In one case, DCVV was added to the group as a replacement for the animal that had a take from an earlier dose. Thus, for DCVV, this was the first dose of any rubella vector, and it elicited a strong antibody response to the BC-sGag-2 insert after a single dose. Importantly, the antibody response to rubella proteins was the same in the tested vectors as in a rubella control. Thus, the immune response to the insert does not detract from the response to rubella vector. This means that a rubella vector can be used to immunize against two viruses at the same time: the one in the insert and itself.

A set of studies was performed which determined that rubella constructs lacking a deletion at the Not I site were more robust and could accommodate much larger inserts at the structural site when compared to those including a deletion. As shown in FIG. 20, a series of large sGag inserts at the structural site in vectors lacking a Not I deletion were made. These grew well in culture, as shown by western blot of rubella proteins. They stably retained the insert, as shown by viral RNA sequencing. The maximum allowable insert size has grown dramatically from 255 bp in our largest previous vector (which included the Not I deletion) to 405 bp in sGag-E2TM (135-271), 510 bp in sGag-E2TM (41-211), 711 bp in full p28-sGag-E2TM, and 795 bp in full p28plus-sGag-E2TM. These new inserts are a significant improvement, both by increasing the number of sGag epitopes present and by allowing us to express complete native proteins such as Gag p27. Native proteins are more stable than fragments, and in the case of sGag, they have the well documented ability to assemble into virus like particles, which will further enhance immunogenicity. The larger insert size allows the expression of additional viral antigens. For example, native HIV gp120 can be expressed with selected deletions, ranging in size from 900 to 1100 base pairs. These are important immunogens, with the potential to elicit broadly crossreacting neutralizing antibodies that depend on the native conformation.

Example 11

Rubella Vectors Stably Express SIV Gag and HIV MPER Determinants at the Structural Site This example illustrates rubella vectors stably express SIV Gag and HIV MPER determinants at the structural site.

Figure 24A:
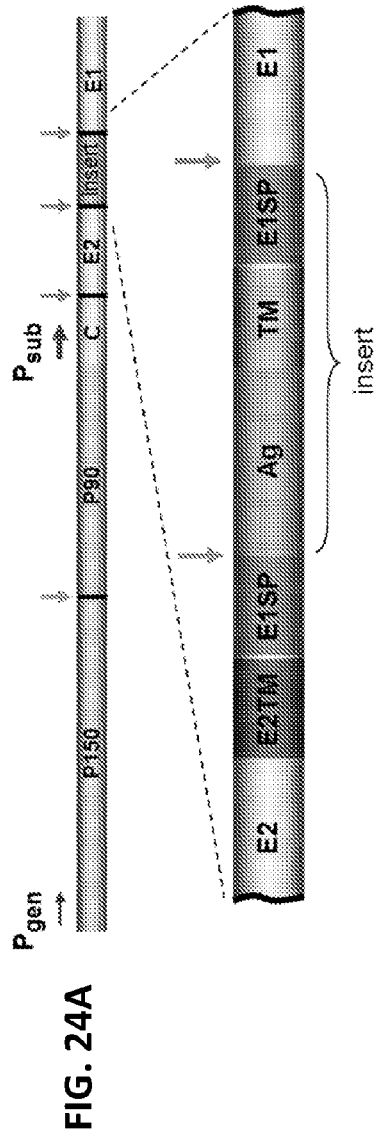
FIG. 24A is a schematic illustrating the general design of rubella vectors with an insert in the structural site, located between envelope glycoproteins E2 and E1. The detailed view shows antigen flanked by two signal peptidase cleavage sites (E1 SP) and followed by a transmembrane (TM) domain. This™ domain can vary from the TM domain of rubella E2 to the TM domain of HW or other viruses.

FIG. 24A shows the design of a typical rubella vector with an insert at the structural site. The structural insertion site is located between envelope glycoproteins E2 and E1 (FIG. 24A). The inserted sequences code for the membrane proximal external region (MPER) of HIV (18, 19, 27, 31) or for an SIV Gag construct containing four T cell epitopes linked together (called BC-sGag2) (18, 19, 32, 33). Each antigenic insert is preceded by the transmembrane domain of E2 (E2TM) and the signal peptidase site of E1 (E1SP), and it is followed by another transmembrane domain (TM) and E1SP peptidase site. Signal peptidase cleavage at three sites in the structural polyprotein (FIG. 24A, arrows) would release the three rubella structural proteins plus the vaccine insert. Unlike earlier constructs (18, 19), the type 3 vectors used in the example have no compensatory deletion at the Not I site.

Figure 24B:
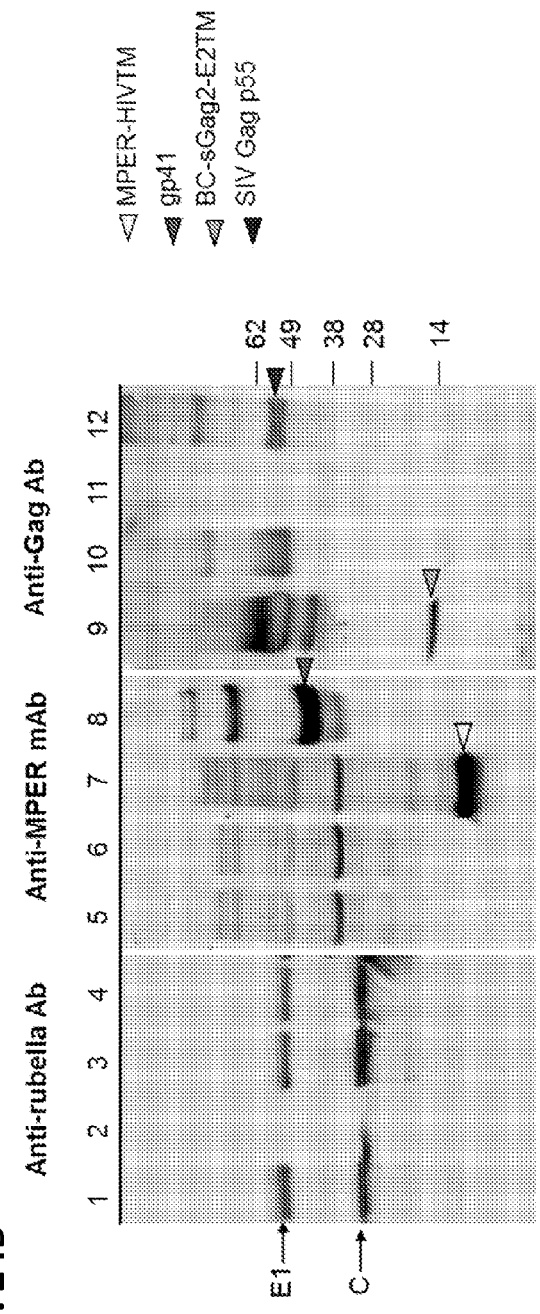
FIG. 24B is a digital image of replication of rubella vectors bearing foreign antigens demonstrated by western blot with antibodies to rubella structural proteins capsid and E1. Lanes 1, 3 and 4 show replicating virus, while lane 2 shows uninfected control cells. Lanes 5 to 8 were stained with monoclonal antibody specific for the MPER determinant of HIV. Only lane 7 generated a strong 10 kDa band for MPER, while rubella infected control lane 5 gave no band. Lanes 9 to 12 were stained with human polyclonal antibodies to HIV Gag. These antibodies detected SIV Gag antigen, called BCsGag2, in lane, as well as a positive control for SIV Gag in lane 12, but did not give a band for rubella infected cells in lane 10.

Vector replication in Vero cells was shown by Western blot with antibodies to the rubella structural proteins C and E1 (FIG. 24B, left panel). Rubella vectors expressing HIV MPER (lane 3) or SIV Gag antigen (lane 4) grew just as well as the vaccine strain without an insert (lane 1). Expression of the MPER-HIVTM insert was detected with monoclonal antibody 2F5 (FIG. 24B, middle panel). The MPER insert was strongly expressed as a 10 kDa band (lane 7, yellow arrowhead), which was absent in the empty rubella control (lane 5), and it was comparable to gp41 in the inactivated virus control (lane 8, red arrowhead). Expression of the SIV Gag insert was detected by cross-reaction with HIV immune globulin (FIG. 24B, right panel). The BC-sGag2 insert was expressed as a 14 kDa band (lane 9, green arrowhead), which was absent in the empty rubella control (lane 10) and was comparable to the control band for recombinant p57 Gag (lane 12). After 5 passages in cell culture, we expanded each vector to create viral stocks expressing MPER or SIV Gag inserts.

Rubella vector stocks for the monkey studies were produced and characterized rubella vector stocks for monkey studies. For each vector type, we made one vector with an MPER insert and the other with a Gag insert. The MPER insert at the structural site consisted of the complete membrane proximal external region, followed by the HIV transmembrane domain and an E1 SP signal sequence. The Gag insert consisted of four known T cell epitopes linked in tandem (called BC-sGag2), followed by the E2TM domain of rubella and the E1 SP signal peptide. For each vector stock, we demonstrated insert expression by Western blot.

Viral titers were determined by quantitative RT-PCR. The titers were estimated by comparison to a rubella reference sample of known PFU titer. Viral titers were $7.7 \times 10^6$ PFU/ml, or greater, which is equivalent to about 1500 human doses per ml. Viral sequencing showed that the insert was stable and in reading frame after at least five passages. The vector doses given to macaques, based on viral titer, were between two and ten times the typical human dose of rubella vaccine (about 5,000 PFU/dose).

FIG. 25 illustrates the time course of MPER expression by rubella-MPER vectors. The MPER antigen appeared at day 5 and persists at least until day 10. The right panel shows expression of the BCsGag2 antigen by rubella vectors, as detected with a polyclonal antibody from a vaccinated macaque (V584). The 14 kD band was not observed in control lanes from empty rubella infected cells (lane 2) or uninfected cells (lane 3). These studies indicate that illustrates rubella vectors stably express SIV Gag and HIV MPER determinants at the structural site.

Example 12

Rubella Vectors Bearing Gag and MPER Determinants are Highly Immunogenic

This example demonstrates that Rubella vectors bearing Gag and MPER determinants are highly immunogenic.

Monkeys were immunized according to a protocol. Group 1 macaques received three doses of DNA vaccine first, followed by a rubella vector boost at week 25. Group 3 macaques received three doses of non-replicating rubella vectors first, as we searched for a replication competent vector. They finally received replicating vectors at week 18, and this was followed by DNA vaccine given at weeks 25 and 31. A successful vaccine "take" was detected as the appearance of antibodies to the structural proteins of the rubella vector. All six macaques made antibodies to the replicating vector, as shown by ELISA assay on plates coated with rubella antigens. (These plates are used for diagnosis of human infections.)

Antibodies to the SIV Gag insert were shown. As shown in FIGS. 26A and 26B, all six macaques made high titered antibody responses to the Gag insert, regardless of whether they received DNA vaccine first. These antibodies were not found in prebleeds, nor were they found in control animals immunized with rubella vaccine lacking any inserts. Antibody titers elicited by vaccine in three macaques were compared with the anti-Gag titers elicited by natural SIV infection of five macaques (FIG. 26C). The anti-Gag antibodies elicited by rubella-Gag vaccination were greater than or equal to those elicited by natural SIV infection.

The kinetics of the response to SIV Gag are shown for individual macaques in FIGS. 27A and 27B. Two animals, DCVV (group 3) and V584 (group 1), demonstrate the sustained response elicited by a single dose of live rubella vectors. For DCVV, anti-Gag antibodies rose between 2 and 4 weeks and reached a peak 7 weeks post immunization (FIG. 27A). For macaque V584, which received three priming doses of DNA vaccine, a good anti-Gag titer was elicited by the DNA vaccine. This was followed by an even stronger anti-Gag response to the live vector that increased steadily between 2 and 4 weeks post immunization (FIG. 27B). The specificity of these antibodies for SIV Gag was shown by Western blot (FIG. 25).

Example 13

Antibodies Elicited by Rubella Vectors are Persistent and Boostable

This example demonstrates that antibodies elicited by rubella vectors are persistent and boostable.

The persistence of anti-Gag antibodies in Group 3 macaques for nine months after immunization was measured. This was compared to the persistence of anti-rubella antibodies in the same animals (FIGS. 28A-F). Anti-rubella titers in all three macaques (FIGS. 28A, 28C and 28E) peaked 4 to 7 weeks after immunization. They declined about 3-fold by 15 weeks for DCVV and CL67 and then remained constant until 38 weeks. The decline was greater for CL49, about 9-fold by 15 weeks and another 3-fold by 38 weeks.

Anti-Gag antibodies were measured in the same macaques at the same time points (FIGS. 28B, 28D, and 28F). Anti-Gag antibodies peaked 4 to 7 weeks post immunization and then declined 3-fold or less by 15 weeks. By 38 weeks, they declined another 3-fold or less in two macaques (DCVV and CL49) and 5-fold in the other (CL67). In two macaques, the durability of anti-Gag titers was greater than or equal to anti-rubella titers, and in one case, anti-Gag titers were less durable over a 9 month period. This indicates persistence of the anti-Gag antibodies, as anti-rubella immunity is long-lasting.

The inventors waited up to a year for rubella antibodies to decline to a level where they could boost with rubella vectors bearing new antigens. For group 4 macaques, which were primed with rubella vaccine without an insert, these antibodies declined about 2.5-fold after 6 months, and then remained constant or rose slightly by 1 year. After one year (group 4) or 6 months (group 1), we boosted the macaques with rubella vectors expressing MPER and SIV Gag antigens (week 57 of the study). All five animals showed a prompt rise in antibodies to rubella.

The anti-SIV Gag antibody response was measured four weeks after the boost (week 61 of the study, FIGS. 29A and 29B). For group 4 animals primed with empty rubella vaccine, the BC-sGag2 boost represented new antigens that were not seen previously. Neither macaque made anti-Gag antibodies (FIG. 29A), indicating that boosting could not elicit a new response in an unprimed animal. The group 1 animals were quite different: they still had antibody titers to SIV Gag that were primed six months earlier (FIG. 29B). In addition, they responded to the live vector boost with a strong increase in anti-Gag titers. In this group, the boost consisted of novel type 3 vectors expressing Gag as a combined MPER-BC-sGag2 antigen or as the complete Gag protein p27. The results indicate that the first dose of live rubella vectors elicited memory B cells specific for SIV Gag antigens, and these B cells were strongly boosted upon re-exposure to the vectors. In contrast, once the control animals failed to make anti-Gag memory B cells after the first rubella immunization, they could not be boosted by a subsequent exposure to the rubella Gag vector.

With other vaccines and vectors, the immune response to SIV and HIV antigens has been short-lived and lacked memory B cells. Transient antibody responses are considered one of the major obstacles to HIV vaccine development. Using live rubella vectors, it is shown herein that anti-Gag antibodies persist for over nine months and decline with nearly the same half-life as antibodies to rubella proteins. In general, persistent antibody titers are thought to depend on long-lived plasma cells, while boosting depends on memory B cells, and both of these are signs of germinal center function during immunization. The primary immune response to these vectors produced memory B cells, as shown by boosting 6 months later. The secondary response depended on successful priming, as control animals that were not primed to SIV Gag lacked memory B cells and could not respond to the boost. Potentially, two doses of live rubella vectors, given several years apart, could boost and update immunity to circulating strains of HIV. In addition, the ability to prime and boost memory B cells would allow us to combine rubella vectors with other viral vectors bearing similar HIV vaccine inserts.

Example 14

Immunization with Two Rubella Vectors at the Same Time Elicits Antibodies to Both Inserts This example demonstrates immunization with two rubella vectors at the same time elicits antibodies to both inserts.

Macaques of groups 1 and 3 were immunized with two rubella vectors concurrently. One vector expressed SIV Gag, and the other expressed HIV MPER with a transmembrane domain from HW. Antibodies to the MPER determinant were detected by ELISA assay on plates coated with gp140 trimers. As shown in FIG. 30, five out of six macaques from both groups made strong antibody responses to MPER. The antibodies appear to be specific for the trimeric form of gp140: they did not bind monomeric MPER peptides or to a peptide called T20 that has the complete sequence of our MPER insert. There was no binding to recombinant gp120 (right panel of FIG. 30).

When two rubella vectors were given simultaneously, they both replicated side by side, as shown by RT-PCR, and they elicited antibodies to both inserts. This means that rubella vectors can be used to immunize against two or more antigens at the same time.

Example 15

Immunization with MPER Determinants to Elicit Broadly Crossreactive Neutralizing Antibodies This example demonstrates that immunization with MPER determinants elicits broadly crossreactive neutralizing antibodies.

Additional MPER constructs are listed in the Table 8, part B. These are intended to improve signal peptidase cleavage, or to enhance immunogenicity by linkage to the SIV Gag sequence or by duplicating important epitopes recognized by neutralizing antibodies 2F5 and 10E8. The MPER determinants perform an essential viral function during membrane fusion and cell entry, and they are conserved sequences. They are also the target of broadly neutralizing antibodies. If MPER can be made more immunogenic, the resulting antibodies should have broadly crossreactive neutralizing activity.

TABLE 8

Inserts in the rubella structural site

A. Large Gag inserts
SGAG(41-363)-E2TM
(SEQ ID NO: 141)
LDRFGLAESLLENKEGCQKILSVLAPLVPTGSENLKSLYNTVCVIWCIHAEEKVKHTEEAKQIVQRHLVVE
TGTTETMPKTSRPTAPSSGRGGNYPVQQIGGNYVHLPLSPRTLNAWVKLIEEKKFGAEVVPGFQALSEGCT
PYDINQMLNCVGDHQAAMQIIRDIINEEAADWDLQHPQPAPQQGQLREPSGSDIAGTTSSVDEQIQWMYRQ
QNPIPVGNIYRRWIQLGLQKCVRMYNPTNILDVKQGPKEPFQSYVDRFYKSLRAEQTDAAVKNWMTQTLLI
QNANPDCKLVLKGLGVNPTLEEMLTACQGVGGPGQKARLMHTLAAFVLLVPWVLIFMVCRRTCRRR**GAAAA
LTAVVLQGYNPPAYG**

(E2TM, underlined; E1SP, bolded).

SGAG(41-391)-E2TM (SEQ ID NO: 142)

LDRFGLAESLLENKEGCQKILSVLAPLVPTGSENLKSLYNTVCVIWCIHAEEKVKHTEEAKQIVQRHLVVE
TGTTETMPKTSRPTAPSSGRGGNYPVQQIGGNYVHLPLSPRTLNAWVKLIEEKKFGAEVVPGFQALSEGCT
PYDINQMLNCVGDHQAAMQIIRDIINEEAADWDLQHPQPAPQQGQLREPSGSDIAGTTSSVDEQIQWMYRQ
QNPIPVGNIYRRWIQLGLQKCVRMYNPTNILDVKQGPKEPFQSYVDRFYKSLRAEQTDAAVKNWMTQTLLI
QNANPDCKLVLKGLGVNPTLEEMLTACQGVGGPGQKARLMAEALKEALAPVPIPFAAAQQRGPRKPIMHTL
AAFVLLVPWVLIFMVCRRTCRRRGAAAALTAVVLQGYNPPAYG

(E2TM, underlined; E1SP, bolded).

B. MPER inserts

MPER-E2TM (SEQ ID NO: 143)

EEPRQEKNEKELLELDKWASLWNWFDITNWLWYIRMHTLAAFVLLVPWVLIFMVCRRTCRRR**GAAAALTAV
VLQGYNPPAYG**

(E2TM, underlined; E1SP, bolded).

MPER-E1TM (SEQ ID NO: 144)

EEPRQEKNEKELLELDKWASLWNWFDITNWLWYIRMHWWQLTLGATCALPLAGLLACCARRTCRRR**GAAAA
LTAVVLQGYNPPAYG**

(E1TM, underlined; E1SP, bolded).

MPER-HIVTM-E2SP (SEQ ID NO: 145)

EEPRQEKNEKELLELDKWASLWNWFDITNWLWYIRLFIMIVGGLIGLRIVFAVLSIVCRRTCRRR**FGAPQA
FLAGLLLAAVAVGTARA**G (HIVTM, underlined; E2SP, bolded).

BC-SGAG2-MPER-HIVTM (SEQ ID NO: 146)

EEPRVPTGSENLKSLYNTVTRVKHTEEAKQIVQRHLVVETGTTSDAFQALSEGCTPYDINQMLNCVGDHQA
AMQIIRDIINEEAQEKNEKELLELDKWASLWNWFDITNWLWYIRLFIMIVGGLIGLRIVFAVLSIVCRRTC
RRRGAAAALTAVVLQGYNPPAYG

(HIVTM, underlined; E1SP, bolded).

MPER-BC-SGAG2-E2TM (SEQ ID NO: 147)

EEPRQEKNEKELLELDKWASLWNWFDITNWLVPTGSENLKSLYNTVTRVKHTEEAKQIVQRHLVVETGTTS
DAFQALSEGCTPYDINQMLNCVGDHQAAMQIIRDIINEEASLDLHTLAAFVLLVPWVLIFMVCRRTCRRR**G
AAAALTAVVLQGYNPPAYG**

(E2TM, underlined; E1SP, bolded).

10e8-MPER-HIVTM (SEQ ID NO: 148)

EEPSLWNWFDITNWLWYIRLNEKELLELDKWASLWNWFDITNWLWYIRLFIMIVGGLIGLRIVFAVLSIVC
RRTCRRRGAAAALTAVVLQGYNPPAYG

(HIVTM, underlined; E1SP, bolded).

10e8-MPER-E2TM (SEQ ID NO: 149)

EEPSLWNWFDITNWLWYIRLNEKELLELDKWASLWNWFDITNWLWYIRMHTLAAFVLLVPWVLIFMVCRRT
CRRRGAAAALTAVVLQGYNPPAYG

(E2TM, underlined; E1SP, bolded).

MPERF-MPER-HIVTM (SEQ ID NO: 150)

EEKELLELDKWASLWNEKELLELDKWASLWNWFDITNWLWYIRLFIMIVGGLIGLRIVFAVLSIVCRRTCR
RRGAAAALTAVVLQGYNPPAYG

(HIVTM, underlined; E1SP, bolded).

MPERF-MPER-E2TM (SEQ ID NO: 151)

EEKELLELDKWASLWNEKELLELDKWASLWNWFDITNWLWYIRMHTLAAFVLLVPWVLIFMVCRRTCRRR**G
AAAALTAVVLQGYNPPAYG**

(E2TM, underlined; E1SP, bolded).

TABLE 8-continued

Inserts in the rubella structural site

C. HIV gp120 inserts.
Outer domain of gp120 on a deleted inner domain scaffold
CC2(79-213-SIGG-252-506)dV1V2V3-G4S-E2TM (SEQ ID NO: 152)
EEPRNPQEVVLENVTENFNMWKNNMVDQMHEDIISLWDESLKPCVKLTPLSVQACPKVSFQPISIGGGIRP
VVSTQLLLNGSLAEEDIVIRSENFTDNAKTIIVQLNESVVINCTRPNNNTRGRRGDIRQAHCNISRAKWNN
TLQQIVIKLREKFRNKTIAFNQSSGGDPEIVMHSFNCGGEFFYCNTAQLFNSTWNVTGGTNGTEGNDIITL
QCRIKQLAMYAPPITGQIRCSSNITGLLLTRDGGNSTETETEIFRPGGGDMRDNWRSELYKYKVVRIEPIG
VAPTRAKRGGGGSM<u>HTLAAFVLLVPWVLIFMVC</u>RRTCRRRGAAAALTAVVLQGYNPPAYG
(E2TM, underlined; E1SP, bolded).

CC2(79-213-SIGG-252-506)dV1V2V3-G4S-SVE2TM (SEQ ID NO: 153)
EEPRNPQEVVLENVTENFNMWKNNMVDQMHEDIISLWDESLKPCVKLTPLSVQACPKVSFQPISIGGGIRP
VVSTQLLLNGSLAEEDIVIRSENFTDNAKTIIVQLNESVVINCTRPNNNTRGRRGDIRQAHCNISRAKWNN
TLQQIVIKLREKFRNKTIAFNQSSGGDPEIVMHSFNCGGEFFYCNTAQLFNSTWNVTGGTNGTEGNDIITL
QCRIKQLAMYAPPITGQIRCSSNITGLLLTRDGGNSTETETEIFRPGGGDMRDNWRSELYKYKVVRIEPIG
VAPTRAKRGGGGSM<u>HVYTILAVASATVAMMIGVTVAVLCAC</u>RRTCRRRGAAAALTAVVLQGYNPPAYG
(E1SP, bolded).

CC2(79-213-SIGG-252-506)dV1V2V3-G4S-HIVTM (SEQ ID NO: 154)
EEPRNPQEVVLENVTENFNMWKNNMVDQMHEDIISLWDESLKPCVKLTPLSVQACPKVSFQPISIGGGIRP
VVSTQLLLNGSLAEEDIVIRSENFTDNAKTIIVQLNESVVINCTRPNNNTRGRRGDIRQAHCNISRAKWNN
TLQQIVIKLREKFRNKTIAFNQSSGGDPEIVMHSFNCGGEFFYCNTAQLFNSTWNVTGGTNGTEGNDIITL
QCRIKQLAMYAPPITGQIRCSSNITGLLLTRDGGNSTETETEIFRPGGGDMRDNWRSELYKYKVVRIEPIG
VAPTRAKRGGGGSM<u>HLFIMIVGGLIGLRIVFAVLSIV</u>CRRTCRRRGAAAALTAVVLQGYNPPAYG
(HIVTM, underlined; E1SP, bolded).

CC2(79-213-SIGG-252-506)dV1V2V3-G4S-VSVGTM (SEQ ID NO: 155)
EEPRNPQEVVLENVTENFNMWKNNMVDQMHEDIISLWDESLKPCVKLTPLSVQACPKVSFQPISIGGGIRP
VVSTQLLLNGSLAEEDIVIRSENFTDNAKTIIVQLNESVVINCTRPNNNTRGRRGDIRQAHCNISRAKWNN
TLQQIVIKLREKFRNKTIAFNQSSGGDPEIVMHSFNCGGEFFYCNTAQLFNSTWNVTGGTNGTEGNDIITL
QCRIKQLAMYAPPITGQIRCSSNITGLLLTRDGGNSTETETEIFRPGGGDMRDNWRSELYKYKVVRIEPIG
VAPTRAKRGGGGSM<u>HSSIASFFFIIGLIIGLFLVL</u>CRRTCRRRGAAAALTAVVLQGYNPPAYG
(E1SP, bolded).

Outer domain on a Truncated inner domain scaffold
E2-CC2(79-506)dV1V2V3-G4S-E2TM (SEQ ID NO: 156)
EEPRNPQEVVLENVTENFNMWKNNMVDQMHEDIISLWDESLKPCVKLTPLTSVQACPKVSFQPIPIHYCVP
AGFAMLKCNDKKFNGSGPCKNVSTVQCTHGIRPVVSTQLLLNGSLAEEDIVIRSENFTDNAKTIIVQLNES
VVINCTRPNNNTRGRRGDIRQAHCNISRAKWNNTLQQIVIKLREKFRNKTIAFNQSSGGDPEIVMHSFNCG
GEFFYCNTAQLFNSTWNVTGGTNGTEGNDIITLQCRIKQLAMYAPPITGQIRCSSNITGLLLTRDGGNSTE
TETEIFRPGGGDMRDNWRSELYKYKVVRIEPIGVAPTRAKRGGGGSM<u>HTLAAFVLLVPWVLIFMVC</u>RRTCR
RRGAAAALTAVVLQGYNPPAYG
(E2TM, underlined; E1SP, bolded).

E2-CC2(79-506)dV1V2V3-G4S-E2TM (Nucleotide sequence, SEQ ID NO: 157)
gaagaacctagGAACCCACAAGAAGTAGTATTGGAGAATGTGACAGAAAATTTTAACATGTGGAAAAATAA
CATGGTAGATCAGATGCAcGAGGATATAATCAGTTTATGGGACGAAAGTCttaaGCCATGTGTAAAATTAA
CCCCGCTCACTAGTGTCCAGGCCTGTCCAAAGGTATCCTTTCAGCCAATTCCCATACATTATTGTGTCCCA
GCAGGGTTCGCGATGCTAAAGTGTAACGATAAGAAATTCAATGGATCAGGACCATGCAAGAATGTGAGCAC
AGTACAATGTACCCATGGAATTAGGCCAGTGGTGTCAACTCAGCTGCTGTTAAATGGCAGTCTAGCAGAAG
AAGACATAGTAATTAGATCTGAAAATTTCACAGACAATGCTAAAACCATAATAGTACAGCTAAATGAATCT
GTAGTAATTAATTgtacAAGACCCAACAACAATACAAGAGGAAGAAGGGGAGATATAAGACAAGCACATTG
TAACATTTCCCGGGCAAATGGAATAACACTTTACAACAGATAGTTATAAAATTAAGAGAAAAATTTAGGA
ATAAAACAATAGCCTTTAATCAATCCTCAGGAGGGGACCCAGAAATTGTAATGCACAGTTTTAATTGTGGA
GGGGAATTTTTCTACTGTAATACAGCCACAACTGTTTAATAGCACGTGGAATGTTACTGGAGGGACAAATGG
CACTGAAGGAAATGACATAATCACACTCCAATGCAGAATAAAACAGCTAGCAATGTATGCCCCTCCCATCA
CCGGTCAAATTAGATGTTCATCAAATATTACAGGGCTGCTACTAACGCGTGATGGAGGTAATAGTACTGAG
ACTGAGACTGAGATCTTCAGACCTGGAGGAGGAGATATGAGGGACAATTGGAGAAGTGAGCTCTATAAATA
TAAAGTAGTAAGAATTGAACCAATAGGAGTAGCACCCACCAGGGCAAAGAGAGGAGGCGGAGGAAGCAT<u>gc
atacccctggccgcgttcgtgctcctcgtgccatgggtgctcatctttatggtctgt</u>cggaggacctgcaga
cggagggggagctgccgctgcccttacagcagtggtcctgcaggggtacaacccccccgcctatggc
E2-CC2(88-506)dV1V2V3-G4S-E2TM (SEQ ID NO: 158)
EEPRVTENFNMWKNNMVDQMHEDIISLWDESLKPCVKLTPLTSVQACPKVSFQPIPIHYCVPAGFAMLKCN
DKKFNGSGPCKNVSTVQCTHGIRPVVSTQLLLNGSLAEEDIVIRSENFTDNAKTIIVQLNESVVINCTRPN
NNTRGRRGDIRQAHCNISRAKWNNTLQQIVIKLREKFRNKTIAFNQSSGGDPEIVMHSFNCGGEFFYCNTA
QLFNSTWNVTGGTNGTEGNDIITLQCRIKQLAMYAPPITGQIRCSSNITGLLLTRDGGNSTETETEIFRPG
GGDMRDNWRSELYKYKVVRIEPIGVAPTRAKRGGGGSM<u>HTLAAFVLLVPWVLIFMVC</u>RRTCRRR**GAAAALT
AVVLQGYNPPAYG**
(E2TM, underlined; E1P, bolded).

TABLE 8-continued

Inserts in the rubella structural site

E2-CC2(93-506)dV1V2V3-G4S-E2TM
(SEQ ID NO: 159)

EEPRNMWKNNMVDQMHEDIISLWDESLKPCVKLTPLTSVQACPKVSFQPIPIHYCVPAGFAMLKCNDKKFN
GSGPCKNVSTVQCTHGIRPVVSTQLLLNGSLAEEDIVIRSENFTDNAKTIIVQLNESVVINCTRPNNNTRG
RRGDIRQAHCNISRAKWNNTLQQIVIKLREKFRNKTIAFNQSSGGDPEIVMHSFNCGGEFFYCNTAQLFNS
TWNVTGGTNGTEGNDIITLQCRIKQLAMYAPPITGQIRCSSNITGLLLTRDGGNSTETETEIFRPGGGDMR
DNWRSELYKYKVVRIEPIGVAPTRAKRGGGGSMHTLAAFVLLVPWVLIFMVCRRTCRRRGAAAALTAVVLQ
GYNPPAYG
(E2TM, underlined; E1SP, bolded).

E2-CC2(93-484)dV1V2V3-G4S-E2TM (SEQ ID NO: 160)

EEPRNMWKNNMVDQMHEDIISLWDESLKPCVKLTPLTSVQACPKVSFQPIPIHYCVPAGFAMLKCNDKKFN
GSGPCKNVSTVQCTHGIRPVVSTQLLLNGSLAEEDIVIRSENFTDNAKTIIVQLNESVVINCTRPNNNTRG
RRGDIRQAHCNISRAKWNNTLQQIVIKLREKFRNKTIAFNQSSGGDPEIVMHSFNCGGEFFYCNTAQLFNS
TWNVTGGTNGTEGNDIITLQCRIKQLAMYAPPITGQIRCSSNITGLLLTRDGGNSTETETEIFRPGGGDMR
DNWRSELYGGGGSMHTLAAFVLLVPWVLIFMVCRRTCRRRGAAAALTAVVLQGYNPPAYG
(E2TM, underlined; E1SP, bolded).

Seamless E1 or E2 sequence at amino end of gp120
E1(1-20)-CC2(40-506)dV1V2V3C-G4S-E2TM (SEQ ID NO: 161)

EEAFTYLCTAPGCATQAPVPVWREATTTLFCASDAKAYDTEVHNVWATHACVPTDPNPQEVVLENVTENFN
MWKNNMVDQMHEDIISLWDESLKPCVKLTPLTSVQACPKVSFQPIPIHYCVPAGFAMLKCNDKKFNGSGPC
KNVSTVQCTHGIRPVVSTQLLLNGSLAEEDIVIRSENFTDNAKTIIVQLNESVVINCTRPNNNTRGRRGDI
RQAHCNISRAKWNNTLQQIVIKLREKFRNKTIAFNQSSGGDPEIVMHSFNCGGEFFYCNTAQLFNSTWNVT
GGTNGTEGNDIITLQCRIKQLAMYAPPITGQIRCSSNITGLLLTRDGGNSTETETEIFRPGGGDMRDNWRS
ELYKYKVVRIEPIGVAPTRAKRGGGGSMHTLAAFVLLVPWVLIFMVCRRTCRRRGAAAALTAVVLQGYNPP
AYG
(E2TM, underlined; E1SP, bolded).

Non-HIV envelope glycoproteins:
E2-WNVE(FVR)-TM1

(SEQ ID NO: 162)

EEPRFNCLGMSNRDFLEGVSGATWVDLVLEGDSCVTIMSKDKPTIDVKMMNMEAANLAEVRSYCYLATVSD
LSTKAACPTMGEAHNDKRADPAFVCRQGVVDRGWGNGCGFFGKGSIDTCAKFACSTKAIGRTILKENIKYE
VAIFVHGPTTVESHGNYSTQVGATQAGRLSITPAAPSYTLKLGEYGEVTVDCEPRSGIDTNAYYVMTVGTK
TFLVHREWFMDLNLPWSSAGSTVWRNRETLMEFEEPHATKQSVIALGSQEGALHQALAGAIPVEFSSNTVK
LTSGHLKCRVKMEKLQLKGTTYGVCSKAFKFLGTPVDTGHGTVVLELQYTGTDGPCKVPISSVASLNDLTP
VGRLVTVNPFVSVATANAKVLIELEPPFGDSYIVVGRGEQQINHHWHKSGSSIGKAFTTTLKGAQRLAALG
DTAWDFGSVGGVFTSVGRAVHQVFGGAFRSLFGGMSWITQGLLGALLLWMGINACRRTCRRRGAAAALTAV
VLQGYNPPAYG
(E1SP, bolded).

Example 16

Expression of Large Gag Inserts for Induction of CTLs

This example demonstrates expression of large Gag inserts for the induction of CTLs.

Rubella is a small RNA virus that replicates exclusively in the cytoplasm. This location is ideal for eliciting T cell immunity, since it delivers antigens directly into the proteasomal pathway leading to antigen presentation with MHC class I. The Gag proteins are important targets of CTLs during infection. The inventors have discovered that priming with DNA vaccine and boosting with the rubella-BCsGag2 vector gave high levels of Gag specific CD8+ T cells, ranging from 1 to 8% of all T cells. The inventors have also discovered that the structural insertion site can accommodate much larger Gag inserts than before. The large Gag inserts are shown schematically in FIG. 31, and their sequences are given in Table 8, part A. The known T cell epitopes are shown for MHC class I and MHC class II restricted epitopes. Each construct contains 7 to 9 epitopes for T cell induction.

Expression of two large Gag inserts was demonstrated by western blot in FIG. 32. Gag construct 41-363 combined part of Gag P17 and all of Gag protein P27. This antigen was stably expressed at passages P3 and P6 (lanes 1 to 3). The other construct, coding for amino acids 41-391, had all of the above plus P2, and it was stably expressed for at least six passages (lanes 4 to 6).

Example 17

Expression of the Outer Domain of Gp120 Scaffolded on Parts of the Inner Domain This example illustrates the expression of the outer domain of gp120 scaffolded on parts of the inner domain HIV envelope gp120 is an important target of neutralizing antibodies. These depend on the native conformation of gp120. Gp120 has inner and outer domains. The main target of neutralizing antibodies binding is located in the outer domain, but its folding depends on the inner domain. The inventors have developed a variety of gp120 constructs for use as vaccine inserts. In each of these, the outer domain is preserved, but the inner domain is deleted at either end. Deletion at the amino end produces a truncated gp120. A deletion at the carboxyl end of the inner domain would produce an internal deletion in gp120.

Four examples of internally deleted gp120 are shown in Table 8, part C. These all have amino acids 79-213, followed by an SIGG linker, followed by 252-506. In the examples given, they are followed by different transmembrane domains, from rubella E2 protein, HIV gp41, sindbis virus, or VSV. Expression of the first three of these inserts by rubella vectors are shown in FIG. 33, right panel, lanes 1 to 3. The fourth insert is also expressed well in rubella.

Four examples of truncated gp120 are also given: these are amino acids 79-506, 88-506, 93-506, and 93-484. The amino acid sequences are given in Table 8, part C. Expression of these truncated forms of gp120 by rubella vectors are shown in FIG. 34, lanes 1, 2, 4, and 5. These constructs are intended to be small enough for expression in rubella and yet large enough to fold correctly and form the native CD4 binding site. The inventors have also expressed gp120 with a short E1 sequence (20 amino acids) inserted seamlessly at the amino end of gp120. The sequence is given in Table 8. Expression of this seamless form of gp120 by a rubella vector is shown by western blot in FIG. 33, lane 5. This facilitates signal peptidase cleavage, and improves the release of mature rubella proteins. This may also reduce selective pressure against the insert, allowing stable expression for many passages. The envelope glycoprotein of West Nile virus has also been expressed at the structural site to make a novel rubella vector. The sequence is indicated in Table 8.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as my invention all that comes within the scope and spirit of these claims.

We claim:

1. An isolated rubella viral vector, comprising a rubella non-structural protein open reading frame (ORF) without an in-frame deletion, a rubella structural protein ORF, and a heterologous antigenic insert, wherein the heterologous antigenic insert is positioned within the rubella structural protein ORF in between a gene encoding structural protein E2 and a gene encoding structural protein E1.

2. The isolated rubella viral vector of claim 1, wherein the antigenic insert comprises an amino acid sequence set forth as SEQ ID NO: 126, 127, 131-156 or 158-162.

3. The isolated rubella viral vector of claim 1, wherein the antigenic insert consists of an amino acid sequence set forth as SEQ ID NO: 126, 127, 131-156 or 158-162.

4. The isolated rubella viral vector of claim 1, wherein the antigenic insert comprises an HIV antigenic insert.

5. The isolated rubella viral vector of claim 1, wherein the antigenic insert comprises a Gag antigenic insert, a gp41 antigenic insert, or a gp120 antigenic insert.

6. The isolated rubella viral vector of claim 5, wherein the Gag antigenic insert comprises at least one cytotoxic T-lymphocyte (CTL) Gag epitope with an amino acid sequence set forth by any one of SEQ ID NOs: 82-88, 90-103, 132-135 and 138-142.

7. The isolated rubella viral vector of claim 5, wherein the antigenic insert comprises a Gag antigenic insert comprising the amino acid sequence set forth as SEQ ID NO: 140.

8. The isolated rubella viral vector of claim 5, wherein the Gag antigenic insert comprises the amino acids FQALSEGCTPYDINQMLNCVGDHQAAMQIIRDIINEEA (SEQ ID NO: 83).

9. The isolated rubella viral vector of claim 8, wherein the antigenic insert further comprises the amino acids LPLSPRTLNAWVKLIEEKKFGAEVVPG (residues 1 to 27 of SEQ ID NO: 84).

10. The isolated rubella viral vector of claim 9, wherein the antigenic insert further comprises the amino acids SQKILSVLAPL (residues 4-14 of SEQ ID NO: 82).

11. The isolated rubella viral vector of claim 5, wherein the antigenic insert comprises a Gag antigenic insert, comprising the amino acids GSENLKSLYNT (residues 4-114 of SEQ ID NO: 88).

12. The isolated rubella viral vector of claim 5, wherein the antigenic insert comprises the amino acid sequence set forth as one of SEQ. ID NOs: 143-155; SEQ ID NO. 156; SEQ ID NOs: 158-162; or SEQ ID NOs: 84-91.

13. The isolated rubella viral vector of claim 5, wherein the antigenic insert consists of the amino acid sequence set forth as one of SEQ ID NOs: 143-155; SEQ ID NO. 156; SEQ ID NOs:158-162; or SEQ ID NOs: 84-91.

14. The isolated rubella viral vector of claim 1, wherein the antigenic insert comprises a gp41 antigenic insert, comprising:
  a) an antigenic polypeptide fragment of gp41 comprising the amino acid sequence of SEQ ID NO: 1 ($NEX_1X_2LLX_3LDKWASLWN$) wherein the polypeptide fragment of gp41 is between 16 and 150 amino acids in length; and
  b) a transmembrane membrane region of gp41 comprising the amino acid sequence set forth as SEQ ID NO: 25 ($X_4FIMIVGGLX_5GLRIVFTX_6LSIV$), wherein the transmembrane spanning region of gp41 is between 22 and 40 amino acids in length and wherein the transmembrane spanning region of gp41 is C-terminal to the antigenic polypeptide fragment of gp41, wherein $X_1$, $X_2$ and $X_3$ are any amino acid and $X_4$, $X_5$, and $X_6$ are any hydrophobic amino acid.

15. The isolated rubella viral vector of claim 1, wherein the antigenic polypeptide comprises the amino acid sequence set forth as one of:

| | | |
|---|---|---|
| a) | (PSAQEKNEKELLELDKWAS LWN); | SEQ ID NO: 30 |
| b) | (NEQELLALDKWASLWNWFDITNWLWYIK); | SEQ ID NO: 2 |
| c) | (NEQDLLALDKWASLWNWFDITNWLWYIK); | SEQ ID NO: 3 |
| d) | (NEQDLLALDKWANLWNWFDISNWLWYIK); | SEQ ID NO: 4 |
| e) | (NEQDLLALDKWANLWNWFNITNWLWYIR); | SEQ ID NO: 5 |
| f) | (NEQELLELDKWASLWNWFDITNWLWYIK); | SEQ ID NO: 6 |
| g) | (NEKDLLALDSWKNLWNWFDITNWLWYIK); | SEQ ID NO: 7 |
| h) | (NEQDLLALDSWENLWNWFDITNWLWYIK); | SEQ ID NO: 8 |

-continued i) (NEQELLELDKWASLWNWFSITQWLWYIK); SEQ ID NO: 9 j) (NEQELLALDKWASLWNWFDISNWLWYIK); SEQ ID NO: 10 k) (NEQDLLALDKWDNLWSWFTITNWLWYIK); SEQ ID NO: 11 l) (NEQDLLALDKWASLWNWFDITKWLWYIK); SEQ ID NO: 12 m) (NEQDLLALDKWASLWNWFSITNWLWYIK); SEQ ID NO: 13 n) (NEKDLLELDKWASLWNWFDITNWLWYIK); SEQ ID NO: 14 o) (NEQEILALDKWASLWNWFDISKWLWYIK); SEQ ID NO: 15 p) (NEQDLLALDKWANLWNWFNISNWLWYIK); SEQ ID NO: 16 q) (NEQDLLALDKWASLWSWFDISNWLWYIK); SEQ ID NO: 17 r) (NEKDLLALDSWKNLWSWFDITNWLWYIK); SEQ ID NO: 18 s) (NEQELLQLDKWASLWNWFSITNWLWYIK); SEQ ID NO: 19 t) (NEQDLLALDKWASLWNWFDISNWLWYIK); SEQ ID NO: 20 u) (NEQELLALDKWASLWNWFDISNWLWYIR); SEQ ID NO: 21 v) (NEQELLELDKWASLWNWFNITNWLWYIK); SEQ ID NO: 22 w) (QEKNEKELLELDKWASLWNWFDITNWLWYIRLFI); SEQ ID NO: 81
or x) (PSWNWFDITNWLWYIRLDA). SEQ ID NO: 89

16. The isolated rubella viral vector of claim 1, wherein the antigenic peptide consists of the amino acid sequence set forth as one of:

a) (AQEKNEKELLELDKWASLWN); SEQ ID NO: 30 b) (NEQELLALDKWASLWNWFDITNWLWYIK); SEQ ID NO: 2 c) (NEQDLLALDKWASLWNWFDITNWLWYIK); SEQ ID NO: 3 d) (NEQDLLALDKWANLWNWFDISNWLWYIK); SEQ ID NO: 4 e) (NEQDLLALDKWANLWNWFNITNWLWYIR); SEQ ID NO: 5 f) (NEQELLELDKWASLWNWFDITNWLWYIK); SEQ ID NO: 6 g) (NEKDLLALDSWKNLWNWFDITNWLWYIK); SEQ ID NO: 7

-continued h) (NEQDLLALDSWENLWNWFDITNWLWYIK); SEQ ID NO: 8 i) (NEQELLELDKWASLWNWFSITQWLWYIK); SEQ ID NO: 9 j) (NEQELLALDKWASLWNWFDISNWLWYIK); SEQ ID NO: 10 k) (NEQDLLALDKWDNLWSWFTITNWLWYIK); SEQ ID NO: 11 l) (NEQDLLALDKWASLWNWFDITKWLWYIK); SEQ ID NO: 12 m) (NEQDLLALDKWASLWNWFSITNWLWYIK); SEQ ID NO: 13 n) (NEKDLLELDKWASLWNWFDITNWLWYIK); SEQ ID NO: 14 o) (NEQEILALDKWASLWNWFDISKWLWYIK); SEQ ID NO: 15 p) (NEQDLLALDKWANLWNWFNISNWLWYIK); SEQ ID NO: 16 q) (NEQDLLALDKWASLWSWFDISNWLWYIK); SEQ ID NO: 17 r) (NEKDLLALDSWKNLWSWFDITNWLWYIK); SEQ ID NO: 18 s) (NEQELLQLDKWASLWNWFSITNWLWYIK); SEQ ID NO: 19 t) (NEQDLLALDKWASLWNWFDISNWLWYIK); SEQ ID NO: 20 u) (NEQELLALDKWASLWNWFDISNWLWYIR); SEQ ID NO: 21 v) (NEQELLELDKWASLWNWFNITNWLWYIK); SEQ ID NO: 22
or w) (QEKNEKELLELDKWASLWNWFDITNWLWYIRLFI). SEQ ID NO: 81

17. The isolated rubella viral vector of claim 1, wherein the heterologous antigenic insert comprises a transmembrane spanning region of gp41, and wherein the transmembrane spanning region of gp41 comprises the amino acid sequence set forth as one of:

a) (IFIMIVGGLIGLRIVFTVLSIV); SEQ ID NO: 26 b) (LFIMIVGGLIGLRIVFTALSIV); SEQ ID NO: 27
or c) (IFIMIVGGLVGLRIVFTALSIV). SEQ ID NO: 28

18. The isolated rubella viral vector of claim 17, wherein the membrane spanning region of gp41 consists of the amino acid sequence set forth as one of:

a) (IFIMIVGGLIGLRIVFTVLSIV); SEQ ID NO: 26 b) (LFIMIVGGLIGLRIVFTALSIV); SEQ ID NO: 27

```
                          -continued
                       or

SEQ ID NO: 28
               c)          (IFIMIVGGLVGLRIVFTALSIV).
```

19. The isolated rubella viral vector of claim 1, wherein the antigenic insert comprises a gp120 antigenic insert comprising amino acid sequence set forth by SEQ ID NOs: 63, 66, 67, 69, 71, 73, 74, 152, 153, 154, 155, 156, 158, 159 or 160.

20. The isolated rubella viral vector of claim 19, wherein the gp120 antigenic insert comprises a variant gp120 polypeptide comprising a deletion of at least 8 consecutive residues of the fourth conserved loop (C4) between residues 423 and 433 of SEQ ID NO: 63.

21. The isolated rubella viral vector of claim 20, wherein residues 424-432 of gp120 are deleted.

22. The isolated rubella viral vector of claim 20, wherein the sequence consisting of the amino acid sequence INMWQKVGK (residues 424 to 432 of SEQ ID NO: 63) is deleted.

23. The isolated rubella viral vector of claim 1, wherein the antigenic insert comprises the amino acid sequence of SEQ ID NO: 66.

24. The isolated rubella viral vector of claim 1, wherein the vector comprises the amino acid sequence of SEQ ID NO: 77, SEQ ID NO: 78, SEQ ID NO: 79 or SEQ ID NO: 80.

25. A host cell transformed with the isolated rubella viral vector of claim 1.

26. A viral-like particle produced by the isolated rubella viral vector of claim 1.

27. The viral-like particle of claim 26, further comprising at least one Toll-like receptor (TLR) ligand.

28. A composition comprising an effective amount of the viral-like particle of claim 26.

29. A method for inhibiting or treating an HIV infection in a subject, comprising administering an effective amount of a composition comprising a viral particle comprising the viral vector of claim 4 to the subject in need thereof, thereby inhibiting one or more signs or symptoms associated with HIV infection.

30. A method for inducing an immune response to HIV in a subject, comprising administering an effective amount of the composition of claim 28 to the subject, thereby inducing the immune response.

31. The method of claim 30, wherein the immune response comprises the induction of neutralizing antibodies to HIV or CTL.

32. A host cell transformed with the isolated rubella viral vector of claim 2.

33. A viral-like particle produced by the isolated rubella viral vector of claim 2.

34. The viral-like particle of claim 33, further comprising at least one TLR ligand.

35. A composition comprising an effective amount of the viral-like particle of claim 33.

36. A method for inhibiting or treating an HIV infection in a subject, comprising administering an effective amount of the composition of claim 35 to the subject in need thereof, thereby inhibiting one or more signs or symptoms associated with HIV infection.

37. A method for inducing an immune response to HIV in a subject, comprising administering an effective amount of the composition of claim 35 to the subject, thereby inducing the immune response.

* * * * *

SEQUENCE LISTING

```
<160> NUMBER OF SEQ ID NOS: 162

<210> SEQ ID NO 1
<211> LENGTH: 16
<212> TYPE: PRT
<213> ORGANISM: Human immunodeficiency virus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Asn Glu Xaa Xaa Leu Leu Xaa Leu Asp Lys Trp Ala Ser Leu Trp Asn
1               5                   10                  15

<210> SEQ ID NO 2
<211> LENGTH: 28
<212> TYPE: PRT
<213> ORGANISM: Human immunodeficiency virus

<400> SEQUENCE: 2

Asn Glu Gln Glu Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 3
<211> LENGTH: 28
<212> TYPE: PRT
<213> ORGANISM: Human immunodeficiency virus

<400> SEQUENCE: 3

Asn Glu Gln Asp Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 4
<211> LENGTH: 28
<212> TYPE: PRT
<213> ORGANISM: Human immunodeficiency virus

<400> SEQUENCE: 4

Asn Glu Gln Asp Leu Leu Ala Leu Asp Lys Trp Ala Asn Leu Trp Asn
```

```
1               5                   10                  15

Trp Phe Asp Ile Ser Asn Trp Leu Trp Tyr Ile Lys
            20                  25

<210> SEQ ID NO 5
<211> LENGTH: 28
<212> TYPE: PRT
<213> ORGANISM: Human immunodeficiency virus

<400> SEQUENCE: 5

Asn Glu Gln Asp Leu Leu Ala Leu Asp Lys Trp Ala Asn Leu Trp Asn
1               5                   10                  15

Trp Phe Asn Ile Thr Asn Trp Leu Trp Tyr Ile Arg
            20                  25

<210> SEQ ID NO 6
<211> LENGTH: 28
<212> TYPE: PRT
<213> ORGANISM: Human immunodeficiency virus

<400> SEQUENCE: 6

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 7
<211> LENGTH: 28
<212> TYPE: PRT
<213> ORGANISM: Human immunodeficiency virus

<400> SEQUENCE: 7

Asn Glu Lys Asp Leu Leu Ala Leu Asp Ser Trp Lys Asn Leu Trp Asn
1               5                   10                  15

Trp Phe Asp Ile Thr Asn Trp Leu Trp Tyr Ile Lys
            20                  25

<210> SEQ ID NO 8
<211> LENGTH: 28
<212> TYPE: PRT
<213> ORGANISM: Human immunodeficiency virus

<400> SEQUENCE: 8

Asn Glu Gln Asp Leu Leu Ala Leu Asp Ser Trp Glu Asn Leu Trp Asn
1               5                   10                  15

Trp Phe Asp Ile Thr Asn Trp Leu Trp Tyr Ile Lys
            20                  25

<210> SEQ ID NO 9
<211> LENGTH: 28
<212> TYPE: PRT
<213> ORGANISM: Human immunodeficiency virus

<400> SEQUENCE: 9

Asn Glu Gln Glu Leu Leu Glu Leu Asp Lys Trp Ala Ser Leu Trp Asn
1               5                   10                  15

Trp Phe Ser Ile Thr Gln Trp Leu Trp Tyr Ile Lys
            20                  25

<210> SEQ ID NO 10
<211> LENGTH: 28
<212> TYPE: PRT
```

```
<213> ORGANISM: Human immunodeficiency virus

<400> SEQUENCE: 10

Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 11
<211> LENGTH: 28
<212> TYPE: PRT
<213> ORGANISM: Human immunodeficiency virus

<400> SEQUENCE: 11

Asn Glu Gln Asp Leu Leu Ala Leu Asp Lys Trp Asp Asn Leu Trp Ser
1               5                   10                  15

Trp Phe Thr Ile Thr Asn Trp Leu Trp Tyr Ile Lys
            20                  25

<210> SEQ ID NO 12
<211> LENGTH: 28
<212> TYPE: PRT
<213> ORGANISM: Human immunodeficiency virus

<400> SEQUENCE: 12

Asn Glu Gln Asp Leu Leu Ala Leu Asp Lys Trp Ala Ser Leu Trp Asn
1               5                   10                  15

Trp Phe Asp Ile Thr Lys Trp Leu Trp Tyr Ile Lys
            20                  25

<210> SEQ ID NO 13
<211> LENGTH: 28
<212> TYPE: PRT
<213> ORGANISM: Human immunodeficiency virus

<400> SEQUENCE: 13

Asn Glu Gln Asp Leu Leu Ala Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 14
<211> LENGTH: 28
<212> TYPE: PRT
<213> ORGANISM: Human immunodeficiency virus

<400> SEQUENCE: 14

Asn Glu Lys Asp Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 15
<211> LENGTH: 28
<212> TYPE: PRT
<213> ORGANISM: Human immunodeficiency virus

<400> SEQUENCE: 15

Asn Glu Gln Glu Ile Leu Ala Leu Asp Lys Trp Ala Ser Leu Trp Asn
1               5                   10                  15

Trp Phe Asp Ile Ser Lys Trp Leu Trp Tyr Ile Lys
            20                  25
```

<210> SEQ ID NO 16
<211> LENGTH: 28
<212> TYPE: PRT
<213> ORGANISM: Human immunodeficiency virus

<400> SEQUENCE: 16

Asn Glu Gln Asp Leu Leu Ala Leu Asp Lys Trp Ala Asn Leu Trp Asn
1               5                   10                  15

Trp Phe Asn Ile Ser Asn Trp Leu Trp Tyr Ile Lys
            20                  25

<210> SEQ ID NO 17
<211> LENGTH: 28
<212> TYPE: PRT
<213> ORGANISM: Human immunodeficiency virus

<400> SEQUENCE: 17

Asn Glu Gln Asp Leu Leu Ala Leu Asp Lys Trp Ala Ser Leu Trp Ser
1               5                   10                  15

Trp Phe Asp Ile Ser Asn Trp Leu Trp Tyr Ile Lys
            20                  25

<210> SEQ ID NO 18
<211> LENGTH: 28
<212> TYPE: PRT
<213> ORGANISM: Human immunodeficiency virus

<400> SEQUENCE: 18

Asn Glu Lys Asp Leu Leu Ala Leu Asp Ser Trp Lys Asn Leu Trp Ser
1               5                   10                  15

Trp Phe Asp Ile Thr Asn Trp Leu Trp Tyr Ile Lys
            20                  25

<210> SEQ ID NO 19
<211> LENGTH: 28
<212> TYPE: PRT
<213> ORGANISM: Human immunodeficiency virus

<400> SEQUENCE: 19

Asn Glu Gln Glu Leu Leu Gln Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 20
<211> LENGTH: 28
<212> TYPE: PRT
<213> ORGANISM: Human immunodeficiency virus

<400> SEQUENCE: 20

Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 21
<211> LENGTH: 28
<212> TYPE: PRT
<213> ORGANISM: Human immunodeficiency virus

<400> SEQUENCE: 21

-continued

```
Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Arg
            20                  25

<210> SEQ ID NO 22
<211> LENGTH: 28
<212> TYPE: PRT
<213> ORGANISM: Human immunodeficiency virus

<400> SEQUENCE: 22

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25

<210> SEQ ID NO 23
<211> LENGTH: 23
<212> TYPE: PRT
<213> ORGANISM: Human immunodeficiency virus

<400> SEQUENCE: 23

Cys Cys Ala Thr Thr Ala Ala Gly Cys Gly Gly Thr Thr Cys Cys Thr
1               5                   10                  15

Cys Gly Gly Thr Ala Gly Cys
            20

<210> SEQ ID NO 24
<211> LENGTH: 23
<212> TYPE: PRT
<213> ORGANISM: Human immunodeficiency virus

<400> SEQUENCE: 24

Gly Ala Gly Thr Gly Cys Cys Gly Cys Gly Ala Gly Cys Gly Thr Cys
1               5                   10                  15

Cys Gly Ala Gly Thr Gly Cys
            20

<210> SEQ ID NO 25
<211> LENGTH: 22
<212> TYPE: PRT
<213> ORGANISM: Human immunodeficiency virus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be any hydrophobic amino acid.
<220> FEATURE:
<221> NAME/KEY: MISC_FEATURE
<222> LOCATION: (10)..(10)
<223> OTHER INFORMATION: Xaa can be any hydrophobic amino acid.
<220> FEATURE:
<221> NAME/KEY: MISC_FEATURE
<222> LOCATION: (18)..(18)
<223> OTHER INFORMATION: Xaa can be any hydrophobic amino acid.

<400> SEQUENCE: 25

Xaa Phe Ile Met Ile Val Gly Gly Leu Xaa Gly Leu Arg Ile Val Phe
1               5                   10                  15

Thr Xaa Leu Ser Ile Val
            20
```

-continued

```
<210> SEQ ID NO 26
<211> LENGTH: 22
<212> TYPE: PRT
<213> ORGANISM: Human immunodeficiency virus

<400> SEQUENCE: 26

Ile Phe Ile Met Ile Val Gly Gly Leu Ile Gly Leu Arg Ile Val Phe
1               5                   10                  15

Thr Val Leu Ser Ile Val
            20

<210> SEQ ID NO 27
<211> LENGTH: 22
<212> TYPE: PRT
<213> ORGANISM: Human immunodeficiency virus

<400> SEQUENCE: 27

Leu Phe Ile Met Ile Val Gly Gly Leu Ile Gly Leu Arg Ile Val Phe
1               5                   10                  15

Thr Ala Leu Ser Ile Val
            20

<210> SEQ ID NO 28
<211> LENGTH: 22
<212> TYPE: PRT
<213> ORGANISM: Human immunodeficiency virus

<400> SEQUENCE: 28

Ile Phe Ile Met Ile Val Gly Gly Leu Val Gly Leu Arg Ile Val Phe
1               5                   10                  15

Thr Ala Leu Ser Ile Val
            20

<210> SEQ ID NO 29
<211> LENGTH: 276
<212> TYPE: PRT
<213> ORGANISM: Human immunodeficiency virus

<400> SEQUENCE: 29

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160
```

```
Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Pro Ser Ser Trp Ala Phe Ala
            195                 200                 205

Lys Tyr Leu Trp Glu Trp Ala Ser Val Arg Phe Ser Trp Leu Ser Leu
        210                 215                 220

Leu Val Pro Phe Val Gln Trp Phe Val Gly Leu Ser Pro Thr Val Trp
225                 230                 235                 240

Leu Ser Ala Ile Trp Met Met Trp Tyr Trp Gly Pro Ser Leu Tyr Ser
                245                 250                 255

Ile Val Ser Pro Phe Ile Pro Leu Leu Pro Ile Phe Phe Cys Leu Trp
            260                 265                 270

Val Tyr Ile Gly
        275

<210> SEQ ID NO 30
<211> LENGTH: 22
<212> TYPE: PRT
<213> ORGANISM: Human immunodeficiency virus

<400> SEQUENCE: 30

Pro Ser Ala Gln Glu Lys Asn Glu Lys Glu Leu Leu Glu Leu Asp Lys
1               5                   10                  15

Trp Ala Ser Leu Trp Asn
            20

<210> SEQ ID NO 31
<211> LENGTH: 226
<212> TYPE: PRT
<213> ORGANISM: Human immunodeficiency virus

<400> SEQUENCE: 31

Glu Phe Ile Thr Ser Gly Phe Leu Gly Pro Leu Leu Val Leu Gln Ala
1               5                   10                  15

Gly Phe Phe Leu Leu Thr Arg Ile Leu Thr Ile Pro Gln Ser Leu Asp
            20                  25                  30

Ser Trp Trp Thr Ser Leu Asn Phe Leu Gly Gly Ser Pro Val Cys Leu
        35                  40                  45

Gly Gln Asn Ser Gln Ser Pro Thr Ser Asn His Ser Pro Thr Ser Cys
    50                  55                  60

Pro Pro Ile Cys Pro Gly Tyr Arg Trp Met Cys Leu Arg Arg Phe Ile
65                  70                  75                  80

Ile Phe Leu Phe Ile Leu Leu Leu Cys Leu Ile Phe Leu Leu Val Leu
                85                  90                  95

Leu Asp Tyr Gln Gly Met Leu Pro Val Cys Pro Leu Ile Pro Gly Ser
            100                 105                 110

Thr Thr Thr Ser Thr Gly Pro Cys Lys Thr Cys Thr Thr Pro Ala Gln
        115                 120                 125

Gly Asn Ser Lys Phe Pro Ser Cys Cys Cys Thr Lys Pro Thr Asp Gly
    130                 135                 140

Asn Cys Thr Cys Ile Ser Ile Pro Ser Ser Trp Ala Phe Ala Lys Tyr
145                 150                 155                 160

Leu Trp Glu Trp Ala Ser Val Arg Phe Ser Trp Leu Ser Leu Leu Val
                165                 170                 175
```

```
Pro Phe Val Gln Trp Phe Val Gly Leu Ser Pro Thr Val Trp Leu Ser
            180                 185                 190

Ala Ile Trp Met Met Trp Tyr Trp Gly Pro Ser Leu Tyr Ser Ile Val
        195                 200                 205

Ser Pro Phe Ile Pro Leu Leu Pro Ile Phe Phe Cys Leu Trp Val Tyr
    210                 215                 220

Ile Gly
225

<210> SEQ ID NO 32
<211> LENGTH: 15
<212> TYPE: PRT
<213> ORGANISM: Human immunodeficiency virus

<400> SEQUENCE: 32

Ala Ser Leu Trp Asn Trp Phe Asn Ile Thr Asn Trp Leu Trp Tyr
1               5                   10                  15

<210> SEQ ID NO 33
<211> LENGTH: 15
<212> TYPE: PRT
<213> ORGANISM: Human immunodeficiency virus

<400> SEQUENCE: 33

Ile Lys Leu Phe Ile Met Ile Val Gly Gly Leu Val Gly Leu Arg
1               5                   10                  15

<210> SEQ ID NO 34
<211> LENGTH: 4
<212> TYPE: PRT
<213> ORGANISM: Human immunodeficiency virus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Cys Ala Ala Xaa
1

<210> SEQ ID NO 35
<211> LENGTH: 7
<212> TYPE: PRT
<213> ORGANISM: Human immunodeficiency virus

<400> SEQUENCE: 35

Glu Leu Asp Lys Trp Ala Ser
1               5

<210> SEQ ID NO 36
<211> LENGTH: 6
<212> TYPE: PRT
<213> ORGANISM: Human immunodeficiency virus

<400> SEQUENCE: 36

Asn Trp Phe Asp Ile Thr
1               5

<210> SEQ ID NO 37
<211> LENGTH: 4
<212> TYPE: PRT
<213> ORGANISM: Human immunodeficiency virus

<400> SEQUENCE: 37
```

Gly Pro Gly Pro
1

<210> SEQ ID NO 38
<211> LENGTH: 18
<212> TYPE: DNA
<213> ORGANISM: Artificial sequence
<220> FEATURE:
<223> OTHER INFORMATION: Synthetic neucleic acid primer.

<400> SEQUENCE: 38
ggagctcgtc gacagcaa                                             18

<210> SEQ ID NO 39
<211> LENGTH: 23
<212> TYPE: DNA
<213> ORGANISM: Artificial sequence
<220> FEATURE:
<223> OTHER INFORMATION: Synthetic neucleic acid primer.

<400> SEQUENCE: 39
gctctagacc cgatgtacac cca                                       23

<210> SEQ ID NO 40
<211> LENGTH: 26
<212> TYPE: DNA
<213> ORGANISM: Artificial sequence
<220> FEATURE:
<223> OTHER INFORMATION: Synthetic neucleic acid primer.

<400> SEQUENCE: 40
gctctagaaa cgagcaggag ctgctg                                    26

<210> SEQ ID NO 41
<211> LENGTH: 36
<212> TYPE: DNA
<213> ORGANISM: Artificial sequence
<220> FEATURE:
<223> OTHER INFORMATION: Synthetic neucleic acid primer.

<400> SEQUENCE: 41
cgcggatcct caccccttga tgtaccacag ccactt                         36

<210> SEQ ID NO 42
<211> LENGTH: 33
<212> TYPE: DNA
<213> ORGANISM: Artificial sequence
<220> FEATURE:
<223> OTHER INFORMATION: Synthetic neucleic acid primer.

<400> SEQUENCE: 42
cgcggatcct caatggtgat ggtgatggtg ggg                            33

<210> SEQ ID NO 43
<211> LENGTH: 26
<212> TYPE: DNA
<213> ORGANISM: Artificial sequence
<220> FEATURE:
<223> OTHER INFORMATION: Synthetic neucleic acid primer.

<400> SEQUENCE: 43
gctctagagc cgtggagcgg tacctg                                    26

<210> SEQ ID NO 44
<211> LENGTH: 33
<212> TYPE: DNA

<213> ORGANISM: Artificial sequence
<220> FEATURE:
<223> OTHER INFORMATION: Synthetic neucleic acid primer.

<400> SEQUENCE: 44
ctcggatcct caaatcatga tgaaaatctt gat                                    33

<210> SEQ ID NO 45
<211> LENGTH: 30
<212> TYPE: DNA
<213> ORGANISM: Artificial sequence
<220> FEATURE:
<223> OTHER INFORMATION: Synthetic neucleic acid primer.

<400> SEQUENCE: 45
ctcggatcct cacaccaggc caccaacaat                                        30

<210> SEQ ID NO 46
<211> LENGTH: 30
<212> TYPE: DNA
<213> ORGANISM: Artificial sequence
<220> FEATURE:
<223> OTHER INFORMATION: Synthetic neucleic acid primer.

<400> SEQUENCE: 46
ctcggatcct cacaccagcc tcaggcccac                                        30

<210> SEQ ID NO 47
<211> LENGTH: 21
<212> TYPE: DNA
<213> ORGANISM: Artificial sequence
<220> FEATURE:
<223> OTHER INFORMATION: Synthetic neucleic acid primer.

<400> SEQUENCE: 47
ctcggatcct caggcgggcg c                                                 21

<210> SEQ ID NO 48
<211> LENGTH: 48
<212> TYPE: DNA
<213> ORGANISM: Artificial sequence
<220> FEATURE:
<223> OTHER INFORMATION: Synthetic neucleic acid primer.

<400> SEQUENCE: 48
ccctgcaaga cctgcaccac caccggtcag ggcaactcca agttcccc                    48

<210> SEQ ID NO 49
<211> LENGTH: 48
<212> TYPE: DNA
<213> ORGANISM: Artificial sequence
<220> FEATURE:
<223> OTHER INFORMATION: Synthetic neucleic acid primer.

<400> SEQUENCE: 49
ggggaacttg gagttgccct gaccggtggt ggtgcaggtc ttgcaggg                    48

<210> SEQ ID NO 50
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 50
ggcaccggta acgagcagga gctgctg                                           27

<210> SEQ ID NO 51
<211> LENGTH: 33
<212> TYPE: DNA
<213> ORGANISM: Artificial sequence
<220> FEATURE:
<223> OTHER INFORMATION: Synthetic neucleic acid primer.

<400> SEQUENCE: 51
ggcaccggtc cccttgatgt accacagcca ctt                              33

<210> SEQ ID NO 52
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 52
agcgaattca acgagcagga gctgctg                                     27

<210> SEQ ID NO 53
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 53
cgcggatcct cacccgatgt acaccca                                     27

<210> SEQ ID NO 54
<211> LENGTH: 45
<212> TYPE: DNA
<213> ORGANISM: Artificial sequence
<220> FEATURE:
<223> OTHER INFORMATION: Synthetic neucleic acid primer.

<400> SEQUENCE: 54
caggaagccg gaggtgatga acccctttgat gtaccacagc cactt                45

<210> SEQ ID NO 55
<211> LENGTH: 45
<212> TYPE: DNA
<213> ORGANISM: Artificial sequence
<220> FEATURE:
<223> OTHER INFORMATION: Synthetic neucleic acid primer.

<400> SEQUENCE: 55
aagtggctgt ggtacatcaa ggggttcatc acctccggct tcctg                 45

<210> SEQ ID NO 56
<211> LENGTH: 515
<212> TYPE: DNA
<213> ORGANISM: Artificial sequence
<220> FEATURE:
<223> OTHER INFORMATION: Neucleic acid sequence for recombinant
     antigenic insert peptide.

<400> SEQUENCE: 56
attagataga tttggattag cagaaagcct gttggagaac aaagaaggat gtcaaaaaat     60
actttcggtc ttagctccat tagtgccaac aggctcagaa aatttaaaaa gcctttataa   120
tactgtctgc gtcatctggt gcattcacgc agaagagaaa gtgaaacaca ctgaggaagc   180
aaaacagata gtgcagagac acctagtggt ggaaacagga acaacagaaa ctatgccaaa   240

```
aacaagtaga ccaacagcac catctagcgg cagaggagga aattacccag tacaacaaat    300
aggtggtaac tatgtccacc tgccattaag cccgagaaca ttaaatgcct gggtaaaatt    360
gatagaggaa agaaatttg gagcagaagt agtgccagga tttcaggcac tgtcagaagg    420
ttgcaccccc tatgacatta atcagatgtt aaattgtgtg ggagaccatc aagcggctat    480
gcagattatc agagatatta taaacgagga ggctg                              515
```

<210> SEQ ID NO 57
<211> LENGTH: 295
<212> TYPE: PRT
<213> ORGANISM: Artificial sequence
<220> FEATURE:
<223> OTHER INFORMATION: Recombinant antigenic insert peptide construct.

<400> SEQUENCE: 57

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Asn Glu Lys Glu Leu Leu Glu
        195                 200                 205

Leu Asp Lys Trp Ala Ser Leu Trp Asn Trp Phe Asp Ile Thr Asn Trp
    210                 215                 220

Leu Trp Tyr Ile Arg Leu Phe Ile Met Ile Val Gly Gly Leu Ile Gly
225                 230                 235                 240

Leu Arg Ile Val Phe Ala Val Leu Ser Ile Val Val Gly Leu Ser Pro
                245                 250                 255

Thr Val Trp Leu Ser Ala Ile Trp Met Met Trp Tyr Trp Gly Pro Ser
            260                 265                 270

Leu Tyr Ser Ile Val Ser Pro Phe Ile Pro Leu Leu Pro Ile Phe Phe
        275                 280                 285

Cys Leu Trp Val Tyr Ile Gly
    290                 295
```

<210> SEQ ID NO 58
<211> LENGTH: 1730
<212> TYPE: DNA
<213> ORGANISM: Artificial sequence
<220> FEATURE:
<223> OTHER INFORMATION: Recombinant antigenic insert peptide.

<400> SEQUENCE: 58

```
ggtaccgtcg acagcaaaag caggggataa ttctattaac catgaagact atcattgctt      60
ccatggcagc tgtcgttttc gtcccctatt aagataattg gtacttctga tagtaacgaa     120
tgagctacat tttctgtctg gttttcgccc aagaccttcc aggaaatgac aacaacagcg     180
actcgatgta aaagacagac caaaagcggg ttctggaagg tcctttactg ttgttgtcgc     240
aattcatcac ctccggcttc ctgggccccc tgctggtcct gcaggccggg ttcttcctgc     300
ttaagtagtg gaggccgaag gacccggggg acgaccagga cgtccggccc aagaaggacg     360
tgacccgcat cctcaccatc ccccagtccc tggactcgtg gtggacctcc ctcaactttc     420
actgggcgta ggagtggtag ggggtcaggg acctgagcac cacctggagg gagttgaaag     480
tgggggggctc ccccgtgtgt ctgggccaga actcccagtc cccacctcc aaccactccc     540
accccccgag ggggcacaca gacccggtct tgagggtcag gggtggagg ttggtgaggg     600
ccacctcctg ccccccatc tgccccggct accgctggat gtgcctgcgc cgcttcatca     660
ggtggaggac gggggggtag acggggccga tggcgaccta cacggacgcg gcgaagtagt     720
tcttcctgtt catcctgctg ctgtgcctga tcttcctgct ggtgctgctg gactaccagg     780
agaaggacaa gtaggacgac gacacggact agaaggacga ccacgacgac ctgatggtcc     840
gcatgctgcc cgtgtgcccc ctgatccccg gctccaccac cacctccacc ggcccctgca     900
cgtacgacgg gcacacgggg gactagggggc cgaggtggtg gtggaggtgg ccggggacgt     960
agacctgcac caccccgcc cagggcaact ccaagttccc ctcctgctgc tgcaccaagc    1020
tctggacgtg gtgggggcgg gtcccgttga ggttcaaggg gaggacgacg acgtggttcg    1080
ccaccgacgg caactgcacc tgcatcaata ttaatgaaaa agaattattg gaattggata    1140
ggtggctgcc gttgacgtgg acgtagttat aattactttt tcttaataac cttaacctat    1200
aatgggcaag tttgtggaat tggtttgaca taacaaactg gctgtggtat ataagattat    1260
ttacccgttc aaacaccta accaaactgt attgtttgac cgacaccata tattctaata    1320
tcataatgat agtaggaggc ttgataggtt taagaatagt ttttgctgta ctttctatag    1380
agtattacta tcatcctccg aactatccaa attcttatca aaaacgacat gaaagatatc    1440
tagtgggcct gtcccccacc gtgtggctgt ccgccatctg gatgatgtgg tactggggcc    1500
atcacccgga caggggggtgg cacaccgaca ggcggtagac ctactacacc atgaccccgg    1560
cctccctgta ctccatcgtg tccccccttca tccccctgct gcccatcttc ttctgcctgt    1620
ggagggacat gaggtagcac aggggggaagt aggggggacga cgggtagaag aagacggaca    1680
gggtgtacat ctgactagtg agctccccac atgtagactg atcactcgag                1730
```

<210> SEQ ID NO 59
<211> LENGTH: 271
<212> TYPE: PRT
<213> ORGANISM: Artificial sequence
<220> FEATURE:
<223> OTHER INFORMATION: Recombinant antigenic insert peptide construct.

<400> SEQUENCE: 59

```
Met Lys Thr Ile Ile Ala Leu Ser Tyr Ile Phe Cys Leu Val Phe Ala
1               5                   10                  15
```

Gln Asp Leu Pro Gly Asn Asp Asn Asn Ser Glu Phe Ile Thr Ser Gly
            20                  25                  30

Phe Leu Gly Pro Leu Val Leu Gln Ala Gly Phe Phe Leu Leu Thr
        35                  40                  45

Arg Ile Leu Thr Ile Pro Gln Ser Leu Asp Ser Trp Trp Thr Ser Leu
50                  55                  60

Asn Phe Leu Gly Gly Ser Pro Val Cys Leu Gly Gln Asn Ser Gln Ser
65                  70                  75                  80

Pro Thr Ser Asn His Ser Pro Thr Ser Cys Pro Pro Ile Cys Pro Gly
                85                  90                  95

Tyr Arg Trp Met Cys Leu Arg Arg Phe Ile Ile Phe Leu Phe Ile Leu
            100                 105                 110

Leu Leu Cys Leu Ile Phe Leu Leu Val Leu Leu Asp Tyr Gln Gly Met
        115                 120                 125

Leu Pro Val Cys Pro Leu Ile Pro Gly Ser Thr Thr Thr Ser Thr Gly
130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Asn
                165                 170                 175

Ile Asn Glu Lys Glu Leu Leu Glu Leu Asp Lys Trp Ala Ser Leu Trp
            180                 185                 190

Asn Trp Phe Asp Ile Thr Asn Trp Leu Trp Tyr Ile Arg Leu Phe Ile
        195                 200                 205

Met Ile Val Gly Gly Leu Ile Gly Leu Arg Ile Val Phe Ala Val Leu
210                 215                 220

Ser Ile Val Val Gly Leu Ser Pro Thr Val Trp Leu Ser Ala Ile Trp
225                 230                 235                 240

Met Met Trp Tyr Trp Gly Pro Ser Leu Tyr Ser Ile Val Ser Pro Phe
                245                 250                 255

Ile Pro Leu Leu Pro Ile Phe Phe Cys Leu Trp Val Tyr Ile Gly
            260                 265                 270

<210> SEQ ID NO 60
<211> LENGTH: 15
<212> TYPE: PRT
<213> ORGANISM: Human immunodeficiency virus

<400> SEQUENCE: 60

Asn Glu Lys Glu Leu Leu Glu Leu Asp Lys Trp Ala Ser Leu Trp
1               5                   10                  15

<210> SEQ ID NO 61
<211> LENGTH: 25
<212> TYPE: PRT
<213> ORGANISM: Human immunodeficiency virus

<400> SEQUENCE: 61

Asn Glu Lys Glu Leu Leu Glu Leu Asp Lys Trp Ala Ser Leu Trp Asn
1               5                   10                  15

Trp Phe Asp Ile Thr Asn Trp Leu Trp
            20                  25

<210> SEQ ID NO 62
<211> LENGTH: 300
<212> TYPE: PRT
<213> ORGANISM: Artificial sequence

```
<220> FEATURE:
<223> OTHER INFORMATION: Recombinant antigenic insert peptide construct.

<400> SEQUENCE: 62

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Ser Ile Asn Glu Lys Glu Leu Leu Glu
        195                 200                 205

Leu Asp Lys Trp Ala Ser Leu Trp Asn Trp Phe Asp Ile Thr Asn Trp
    210                 215                 220

Leu Trp Ser Ser Leu Trp Ala Ile Lys Tyr Leu Trp Glu Trp Ala Ser
225                 230                 235                 240

Val Arg Phe Ser Trp Leu Ser Leu Leu Val Pro Phe Val Gln Trp Phe
                245                 250                 255

Val Gly Leu Ser Pro Thr Val Trp Leu Ser Ala Ile Trp Met Met Trp
            260                 265                 270

Tyr Trp Gly Pro Ser Leu Tyr Ser Ile Val Ser Pro Phe Ile Pro Leu
        275                 280                 285

Leu Pro Ile Phe Phe Cys Leu Trp Val Tyr Ile Gly
    290                 295                 300

<210> SEQ ID NO 63
<211> LENGTH: 382
<212> TYPE: PRT
<213> ORGANISM: Artificial sequence
<220> FEATURE:
<223> OTHER INFORMATION: Recombinant antigenic insert peptide construct.

<400> SEQUENCE: 63

Val Pro Val Trp Arg Glu Ala Thr Thr Thr Leu Phe Cys Ala Ser Asp
1               5                   10                  15

Ala Lys Ala Tyr Asp Thr Glu Val His Asn Val Trp Ala Thr His Ala
            20                  25                  30

Cys Val Pro Thr Asp Pro Asn Pro Gln Glu Val Val Leu Gly Asn Val
```

```
                35                  40                  45
Thr Glu Asn Phe Asn Met Trp Lys Asn Met Val Asp Gln Met His
 50                  55                  60

Glu Asp Ile Ile Ser Leu Trp Asp Glu Ser Leu Lys Pro Cys Val Lys
 65                  70                  75                  80

Leu Thr Pro Leu Ser Val Gln Ala Cys Pro Lys Val Ser Phe Gln Pro
                 85                  90                  95

Ile Pro Ile His Tyr Cys Val Pro Ala Gly Phe Ala Met Leu Lys Cys
                100                 105                 110

Asn Asn Lys Thr Phe Asn Gly Ser Gly Pro Cys Thr Asn Val Ser Thr
                115                 120                 125

Val Gln Cys Thr His Gly Ile Arg Pro Val Val Ser Thr Gln Leu Leu
                130                 135                 140

Leu Asn Gly Ser Leu Ala Glu Glu Asp Ile Val Ile Arg Ser Glu Asn
145                 150                 155                 160

Phe Thr Asp Asn Ala Lys Thr Ile Ile Val Gln Leu Asn Glu Ser Val
                165                 170                 175

Val Ile Asn Cys Thr Arg Pro Asn Asn Asn Thr Arg Arg Arg Leu Ser
                180                 185                 190

Ile Gly Pro Gly Arg Ala Phe Tyr Ala Arg Arg Asn Ile Ile Gly Asp
                195                 200                 205

Ile Arg Gln Ala His Cys Asn Ile Ser Arg Ala Lys Trp Asn Asn Thr
                210                 215                 220

Leu Gln Gln Ile Val Ile Lys Leu Arg Glu Lys Phe Arg Asn Lys Thr
225                 230                 235                 240

Ile Ala Phe Asn Gln Ser Ser Gly Gly Asp Pro Glu Ile Val Met His
                245                 250                 255

Ser Phe Asn Cys Gly Gly Glu Phe Phe Tyr Cys Asn Thr Ala Gln Leu
                260                 265                 270

Phe Asn Ser Thr Trp Asn Val Thr Gly Thr Asn Gly Thr Glu Gly
                275                 280                 285

Asn Asp Ile Ile Thr Leu Gln Cys Arg Ile Lys Gln Ile Ile Asn Met
290                 295                 300

Trp Gln Lys Val Gly Lys Ala Met Tyr Ala Pro Pro Ile Thr Gly Gln
305                 310                 315                 320

Ile Arg Cys Ser Ser Asn Ile Thr Gly Leu Leu Leu Thr Arg Asp Gly
                325                 330                 335

Gly Asn Ser Thr Glu Thr Glu Thr Glu Ile Phe Arg Pro Gly Gly Gly
                340                 345                 350

Asp Met Arg Asp Asn Trp Arg Ser Glu Leu Tyr Lys Tyr Lys Val Val
                355                 360                 365

Arg Ile Glu Pro Ile Gly Val Ala Pro Thr Arg Ala Lys Arg
                370                 375                 380

<210> SEQ ID NO 64
<211> LENGTH: 337
<212> TYPE: PRT
<213> ORGANISM: Artificial sequence
<220> FEATURE:
<223> OTHER INFORMATION: Recombinant antigenic insert peptide construct.

<400> SEQUENCE: 64

Met Lys Thr Ile Ile Ala Leu Ser Tyr Ile Phe Cys Leu Val Phe Ala
 1               5                  10                  15

Gln Asp Leu Pro Gly Asn Asp Asn Asn Ser Glu Phe Asn Glu Lys Glu
```

```
                20                  25                  30
Leu Leu Glu Leu Asp Lys Trp Ala Ser Leu Trp Asn Trp Phe Asp Ile
            35                  40                  45

Thr Asn Trp Leu Trp Tyr Ile Arg Leu Phe Ile Met Ile Val Gly Gly
        50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
        130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Ser Ile Asn Glu Lys Glu Leu Leu Glu
        195                 200                 205

Leu Asp Lys Trp Ala Ser Leu Trp Ala Ile Asn Glu Lys Glu Leu Leu
    210                 215                 220

Glu Leu Asp Lys Trp Ala Ser Leu Trp Ala Ile Asn Glu Lys Glu Leu
225                 230                 235                 240

Leu Glu Leu Asp Lys Trp Ala Ser Leu Trp Ala Ile Asn Glu Lys Glu
                245                 250                 255

Leu Leu Glu Leu Asp Lys Trp Ala Ser Leu Trp Ala Ile Lys Tyr Leu
            260                 265                 270

Trp Glu Trp Ala Ser Val Arg Phe Ser Trp Leu Ser Leu Leu Val Pro
        275                 280                 285

Phe Val Gln Trp Phe Val Gly Leu Ser Pro Thr Val Trp Leu Ser Ala
    290                 295                 300

Ile Trp Met Met Trp Tyr Trp Gly Pro Ser Leu Tyr Ser Ile Val Ser
305                 310                 315                 320

Pro Phe Ile Pro Leu Leu Pro Ile Phe Phe Cys Leu Trp Val Tyr Ile
                325                 330                 335

Gly

<210> SEQ ID NO 65
<211> LENGTH: 313
<212> TYPE: PRT
<213> ORGANISM: Human immunodeficiency virus

<400> SEQUENCE: 65

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Ile Thr Ser Gly
            20                  25                  30

Phe Leu Gly Pro Leu Leu Val Leu Gln Ala Gly Phe Phe Leu Leu Thr
        35                  40                  45

Arg Ile Leu Thr Ile Pro Gln Ser Leu Asp Ser Trp Trp Thr Ser Leu
```

```
                    50                  55                  60
Asn Phe Leu Gly Gly Ser Pro Val Cys Leu Gly Gln Asn Ser Gln Ser
 65                  70                  75                  80

Pro Thr Ser Asn His Ser Pro Thr Ser Cys Pro Pro Ile Cys Pro Gly
                 85                  90                  95

Tyr Arg Trp Met Cys Leu Arg Arg Phe Ile Ile Phe Leu Phe Ile Leu
            100                 105                 110

Leu Leu Cys Leu Ile Phe Leu Leu Val Leu Leu Asp Tyr Gln Gly Met
        115                 120                 125

Leu Pro Val Cys Pro Leu Ile Pro Gly Ser Thr Thr Thr Ser Thr Gly
    130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Ser
                165                 170                 175

Ile Asn Glu Lys Glu Leu Leu Glu Leu Asp Lys Trp Ala Ser Leu Trp
            180                 185                 190

Ala Ile Asn Glu Lys Glu Leu Leu Glu Leu Asp Lys Trp Ala Ser Leu
        195                 200                 205

Trp Ala Ile Asn Glu Lys Glu Leu Leu Glu Leu Asp Lys Trp Ala Ser
    210                 215                 220

Leu Trp Ala Ile Asn Glu Lys Glu Leu Leu Glu Leu Asp Lys Trp Ala
225                 230                 235                 240

Ser Leu Trp Ala Ile Lys Tyr Leu Trp Glu Trp Ala Ser Val Arg Phe
                245                 250                 255

Ser Trp Leu Ser Leu Leu Val Pro Phe Val Gln Trp Phe Val Gly Leu
            260                 265                 270

Ser Pro Thr Val Trp Leu Ser Ala Ile Trp Met Met Trp Tyr Trp Gly
        275                 280                 285

Pro Ser Leu Tyr Ser Ile Val Ser Pro Phe Ile Pro Leu Leu Pro Ile
    290                 295                 300

Phe Phe Cys Leu Trp Val Tyr Ile Gly
305                 310

<210> SEQ ID NO 66
<211> LENGTH: 373
<212> TYPE: PRT
<213> ORGANISM: Human immunodeficiency virus

<400> SEQUENCE: 66

Val Pro Val Trp Arg Glu Ala Thr Thr Thr Leu Phe Cys Ala Ser Asp
 1               5                  10                  15

Ala Lys Ala Tyr Asp Thr Glu Val His Asn Val Trp Ala Thr His Ala
            20                  25                  30

Cys Val Pro Thr Asp Pro Asn Pro Gln Glu Val Val Leu Gly Asn Val
        35                  40                  45

Thr Glu Asn Phe Asn Met Trp Lys Asn Asn Met Val Asp Gln Met His
    50                  55                  60

Glu Asp Ile Ile Ser Leu Trp Asp Glu Ser Leu Lys Pro Cys Val Lys
 65                  70                  75                  80

Leu Thr Pro Leu Ser Val Gln Ala Cys Pro Lys Val Ser Phe Gln Pro
                 85                  90                  95

Ile Pro Ile His Tyr Cys Val Pro Ala Gly Phe Ala Met Leu Lys Cys
            100                 105                 110
```

-continued

```
Asn Asn Lys Thr Phe Asn Gly Ser Gly Pro Cys Thr Asn Val Ser Thr
            115                 120                 125

Val Gln Cys Thr His Gly Ile Arg Pro Val Val Ser Thr Gln Leu Leu
130                 135                 140

Leu Asn Gly Ser Leu Ala Glu Glu Asp Ile Val Ile Arg Ser Glu Asn
145                 150                 155                 160

Phe Thr Asp Asn Ala Lys Thr Ile Ile Val Gln Leu Asn Glu Ser Val
                165                 170                 175

Val Ile Asn Cys Thr Arg Pro Asn Asn Thr Arg Arg Leu Ser
            180                 185                 190

Ile Gly Pro Gly Arg Ala Phe Tyr Ala Arg Asn Ile Ile Gly Asp
            195                 200                 205

Ile Arg Gln Ala His Cys Asn Ile Ser Arg Ala Lys Trp Asn Asn Thr
            210                 215                 220

Leu Gln Gln Ile Val Ile Lys Leu Arg Glu Lys Phe Arg Asn Lys Thr
225                 230                 235                 240

Ile Ala Phe Asn Gln Ser Ser Gly Gly Asp Pro Glu Ile Val Met His
                245                 250                 255

Ser Phe Asn Cys Gly Gly Glu Phe Phe Tyr Cys Asn Thr Ala Gln Leu
            260                 265                 270

Phe Asn Ser Thr Trp Asn Val Thr Gly Gly Thr Asn Gly Thr Glu Gly
            275                 280                 285

Asn Asp Ile Ile Thr Leu Gln Cys Arg Ile Lys Gln Leu Ala Met Tyr
290                 295                 300

Ala Pro Pro Ile Thr Gly Gln Ile Arg Cys Ser Ser Asn Ile Thr Gly
305                 310                 315                 320

Leu Leu Leu Thr Arg Asp Gly Gly Asn Ser Thr Glu Thr Glu Thr Glu
                325                 330                 335

Ile Phe Arg Pro Gly Gly Gly Asp Met Arg Asp Asn Trp Arg Ser Glu
            340                 345                 350

Leu Tyr Lys Tyr Lys Val Val Arg Ile Glu Pro Ile Gly Val Ala Pro
            355                 360                 365

Thr Arg Ala Lys Arg
    370
```

<210> SEQ ID NO 67
<211> LENGTH: 664
<212> TYPE: PRT
<213> ORGANISM: Human immunodeficiency virus

<400> SEQUENCE: 67

```
Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
                20                  25                  30

Leu Thr Met Lys Thr Ile Ile Ala Leu Ser Tyr Ile Leu Cys Leu Val
            35                  40                  45

Leu Ala Gln Lys Leu Pro Gly Asn Asp Asn Asn Ser Glu Phe Ile Thr
50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110
```

-continued

```
Gln Ser Pro Thr Ser Asn His Ser Pro Thr Ser Cys Pro Ile Cys
        115                 120                 125
Pro Gly Tyr Arg Met Cys Leu Arg Arg Phe Ile Ile Phe Leu Phe Ile
130                 135                 140
Leu Leu Leu Cys Leu Ile Phe Leu Leu Val Leu Leu Asp Tyr Gln Gly
145                 150                 155                 160
Met Leu Pro Val Cys Pro Leu Ile Pro Gly Ser Thr Thr Ser Thr
                165                 170                 175
Gly Pro Cys Lys Thr Cys Thr Thr Pro Ala Gln Gly Asn Ser Lys Phe
            180                 185                 190
Pro Ser Cys Cys Cys Thr Lys Pro Thr Asp Gly Asn Cys Thr Cys Ile
            195                 200                 205
Pro Ile Pro Ser Ser Trp Ala Phe Ala Lys Tyr Leu Trp Glu Trp Ala
        210                 215                 220
Ser Val Arg Phe Ser Trp Leu Ser Leu Leu Val Pro Phe Val Gln Trp
225                 230                 235                 240
Phe Val Gly Leu Ser Pro Thr Val Trp Leu Ser Ala Ile Trp Met Met
                245                 250                 255
Trp Tyr Trp Gly Pro Ser Leu Tyr Ser Ile Val Ser Pro Phe Ile Pro
            260                 265                 270
Leu Leu Pro Ile Phe Phe Cys Leu Trp Val Tyr Ile Gly Val Pro Val
        275                 280                 285
Trp Lys Glu Ala Thr Thr Thr Leu Phe Cys Ala Ser Asp Ala Lys Ala
290                 295                 300
Tyr Asp Thr Glu Val His Asn Val Trp Ala Thr His Ala Cys Val Pro
305                 310                 315                 320
Thr Asp Pro Asn Pro Gln Glu Val Val Leu Glu Asn Val Thr Glu His
                325                 330                 335
Phe Asn Met Trp Lys Asn Asn Met Val Glu Gln Met Gln Glu Asp Ile
            340                 345                 350
Ile Ser Leu Trp Asp Gln Ser Leu Lys Pro Cys Val Lys Leu Thr Pro
        355                 360                 365
Leu Gln Ala Cys Pro Lys Ile Ser Phe Glu Pro Ile Pro Ile His Tyr
370                 375                 380
Cys Ala Pro Ala Gly Phe Ala Ile Leu Lys Cys Asn Asp Lys Thr Phe
385                 390                 395                 400
Asn Gly Lys Gly Pro Cys Lys Asn Val Ser Thr Val Gln Cys Thr His
                405                 410                 415
Gly Ile Arg Pro Val Val Ser Thr Gln Leu Leu Leu Asn Gly Ser Leu
            420                 425                 430
Ala Glu Glu Glu Val Val Ile Arg Ser Asp Asn Phe Thr Asn Asn Ala
        435                 440                 445
Lys Thr Ile Ile Val Gln Leu Lys Glu Ser Val Glu Ile Asn Cys Thr
450                 455                 460
Arg Pro Asn Asn Asn Thr Arg Lys Ser Ile His Ile Gly Pro Gly Arg
465                 470                 475                 480
Ala Phe Tyr Thr Thr Gly Glu Ile Ile Gly Asp Ile Arg Gln Ala His
                485                 490                 495
Cys Asn Ile Ser Arg Ala Lys Trp Asn Asp Thr Leu Lys Gln Ile Val
            500                 505                 510
Ile Lys Leu Arg Glu Gln Phe Glu Asn Lys Thr Ile Val Phe Asn His
        515                 520                 525
```

Ser Ser Gly Gly Asp Pro Glu Ile Val Met His Ser Phe Asn Cys Gly
530                 535                 540

Gly Glu Phe Phe Tyr Cys Asn Ser Thr Gln Leu Phe Asn Ser Thr Trp
545                 550                 555                 560

Asn Asn Asn Thr Glu Gly Ser Asn Asn Thr Glu Gly Asn Thr Ile Thr
                565                 570                 575

Leu Pro Cys Arg Ile Lys Gln Leu Ala Met Tyr Ala Pro Pro Ile Arg
            580                 585                 590

Gly Gln Ile Arg Cys Ser Ser Asn Ile Thr Gly Leu Leu Leu Thr Arg
        595                 600                 605

Asp Gly Gly Ile Asn Glu Asn Gly Thr Glu Ile Phe Arg Pro Gly Gly
    610                 615                 620

Gly Asp Met Arg Asp Asn Trp Arg Ser Glu Leu Tyr Lys Tyr Lys Val
625                 630                 635                 640

Val Lys Ile Glu Pro Leu Gly Val Ala Pro Thr Lys Ala Lys Arg Leu
                645                 650                 655

Val Ala Ala Ala Phe Glu Ser Arg
            660

<210> SEQ ID NO 68
<211> LENGTH: 2000
<212> TYPE: DNA
<213> ORGANISM: Human immunodeficiency virus

<400> SEQUENCE: 68

```
ggattattca taccgtccca ccatcgggcg cggatcccgg tccgaagcgc gcggaattca      60
aaggcctacg tcgacagcaa agcagggga taattctatt aaccatgaag actatcattg     120
ctttgagcta cattttatgt ctggttctcg ctcaaaaact tcccggaaat gacaacaaca     180
gcgaattcat cacctccggc ttcctgggcc cctgctggt gctgcaggcc ggcttcttcc     240
tgctgacccg catcctgacc atccccagt ccctggactc ctggtggacc tccctgaact     300
tcctgggcgg ctcccccgtg tgcctgggcc agaactccca gtcccccacc tccaaccact     360
ccccaccctc ctgcccccccc atctgccccg gctaccgctg gatgtgcctg cgccgcttca     420
tcatcttcct gttcatcctg ctgctgtgcc tgatcttcct gctggtgctg ctggactacc     480
agggcatgct gcccgtgtgc ccctgatcc ccggctccac caccacctcc accggccccct     540
gcaagacctg caccacccc gcccagggca actccaagtt ccccctcctgc tgctgcacca     600
agcccaccga cggcaactgc acctgcatcc ccatccccctc ctcctgggcc ttcgccaagt     660
acctgtggga gtgggcctcc gtgcgcttct cctggctgtc cctgctggtg cccttcgtgc     720
agtggttcgt gggcctgtcc cccaccgtgt ggctgtccgc catctggatg atgtggtact     780
ggggccccctc cctgtactcc atcgtgtccc ccttcatccc cctgctgccc atcttcttct     840
gcctgtgggt gtacatcggg gtacctgtgt ggaaagaagc aaccaccact ctattttgtg     900
catcagatgc taaagcatat gatacagagg tacataatgt ttgggccaca catgcctgtg     960
tacccacaga ccccaaccca caagaagtag tattggaaaa tgtaacagaa cattttaaca    1020
tgtggaaaaa taacatggta gaacagatgc aggaggatat aatcagttta tgggatcaaa    1080
gcctaaagcc atgtgtaaaa ttaaccccac tccaggcctg tccaaagata cctttgagc    1140
caattcccat acattattgt gccccggctg gttttgcgat tctaaagtgt aatgataaga    1200
cgttcaatgg aaaaggacca tgtaaaaatg tcagcacagt acaatgtaca catggaatta    1260
ggccagtagt atcaactcaa ctgctgctaa atggcagtct agcagaagaa gaggtagtaa    1320
```

```
ttagatctga caatttcacg aacaatgcta aaaccataat agtacagctg aaagaatctg    1380
tagaaattaa ttgtacaaga cccaacaaca atacaagaaa aagtatacat ataggaccag    1440
ggagagcatt ttatactaca ggagaaataa taggagatat aagacaagca cattgtaaca    1500
ttagtagagc aaaatggaat gacactttaa aacagatagt tataaaatta agagaacaat    1560
ttgagaataa aacaatagtc tttaatcact cctcaggagg ggacccagaa attgtaatgc    1620
acagttttaa ttgtggagga gaattttttct actgtaattc aacacaactg tttaatagta    1680
cttggaataa taatactgaa gggtcaaata acactgaagg aaatactatc acactcccat    1740
gcagaataaa acagctagca atgtatgccc ctcccatcag aggacaaatt agatgttcat    1800
caaatattac agggctgcta ttaacaagag atggtggtat taatgagaat gggaccgaga    1860
tcttcagacc tggaggagga gatatgaggg acaattggag aagtgaatta tataaatata    1920
aagtagtaaa aattgaacca ttaggagtag caccccaccaa ggcaaagaga tgactagtcg    1980
cggccgcttt cgaatctaga                                                 2000
```

<210> SEQ ID NO 69
<211> LENGTH: 665
<212> TYPE: PRT
<213> ORGANISM: Human immunodeficiency virus

<400> SEQUENCE: 69

```
Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
    130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
            180                 185                 190

Phe Pro Ser Cys Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
    210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255
```

```
Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
            275                 280                 285

Val Trp Lys Glu Ala Thr Thr Thr Leu Phe Cys Ala Ser Asp Ala Lys
            290                 295                 300

Ala Tyr Asp Thr Glu Val His Asn Val Trp Ala Thr His Ala Cys Val
305                 310                 315                 320

Pro Thr Asp Pro Asn Pro Gln Glu Val Leu Glu Asn Val Thr Glu
                    325                 330                 335

Asn Phe Asn Met Trp Lys Asn Asn Met Val Glu Gln Met His Glu Asp
            340                 345                 350

Ile Ile Ser Leu Trp Asp Gln Ser Leu Lys Pro Cys Val Lys Leu Thr
            355                 360                 365

Pro Leu Gln Ala Cys Pro Lys Val Ser Phe Glu Pro Ile Pro Ile His
            370                 375                 380

Tyr Cys Thr Pro Ala Gly Phe Ala Ile Leu Lys Cys Lys Asp Lys Lys
385                 390                 395                 400

Phe Asn Gly Thr Gly Pro Cys Lys Asn Val Ser Thr Val Gln Cys Thr
                    405                 410                 415

His Gly Ile Arg Pro Val Val Ser Thr Gln Leu Leu Leu Asn Gly Ser
            420                 425                 430

Leu Ala Glu Glu Glu Val Val Ile Arg Ser Ser Asn Phe Thr Asp Asn
            435                 440                 445

Ala Lys Asn Ile Ile Val Gln Leu Lys Glu Ser Val Glu Ile Asn Cys
            450                 455                 460

Thr Arg Pro Asn Asn Asn Thr Arg Lys Ser Ile His Ile Gly Pro Gly
465                 470                 475                 480

Arg Ala Phe Tyr Thr Thr Gly Glu Ile Ile Gly Asp Ile Arg Gln Ala
                    485                 490                 495

His Cys Asn Ile Ser Arg Thr Lys Trp Asn Asn Thr Leu Asn Gln Ile
            500                 505                 510

Ala Thr Lys Leu Lys Glu Gln Phe Gly Asn Asn Lys Thr Ile Val Phe
            515                 520                 525

Asn Gln Ser Ser Gly Gly Asp Pro Glu Ile Val Met His Ser Phe Asn
530                 535                 540

Cys Gly Gly Glu Phe Phe Tyr Cys Asn Ser Thr Gln Leu Phe Asn Ser
545                 550                 555                 560

Thr Trp Asn Phe Asn Gly Thr Trp Asn Leu Thr Gln Ser Asn Gly Thr
                    565                 570                 575

Glu Gly Asn Asp Thr Ile Thr Leu Pro Cys Arg Ile Lys Gln Leu Ala
            580                 585                 590

Met Tyr Ala Pro Pro Ile Arg Gly Gln Ile Arg Cys Ser Ser Asn Ile
            595                 600                 605

Thr Gly Leu Ile Leu Thr Arg Asp Gly Gly Asn His Asn Asn Asp
            610                 615                 620

Thr Glu Thr Phe Arg Pro Gly Gly Gly Asp Met Arg Asp Asn Trp Arg
625                 630                 635                 640

Ser Glu Leu Tyr Lys Tyr Lys Val Val Lys Ile Glu Pro Leu Gly Val
                    645                 650                 655

Ala Pro Thr Lys Ala Lys Arg Leu Val
            660                 665
```

<210> SEQ ID NO 70
<211> LENGTH: 2000
<212> TYPE: DNA
<213> ORGANISM: Human immunodeficiency virus

<400> SEQUENCE: 70

```
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta cattttatgt ctggttctcg ctcaaaaact tcccggaaat gacaacaaca     180
gcgaattcat cacctccggc ttcctgggcc cctgctggt gctgcaggcc ggcttcttcc      240
tgctgacccg catcctgacc atccccagt ccctggactc ctggtggacc tccctgaact     300
tcctgggcgg ctccccgtg tgcctgggcc agaactccca gtcccccacc tccaaccact     360
cccccacctc ctgcccccc atctgccccg ctaccgctg gatgtgcctg cgccgcttca     420
tcatcttcct gttcatcctg ctgctgtgcc tgatcttcct gctggtgctg ctggactacc     480
agggcatgct gcccgtgtgc ccctgatcc ccggctccac caccacctcc accggcccct     540
gcaagacctg caccacccc gcccagggca actccaagtt ccctcctgc tgctgcacca     600
agcccaccga cggcaactgc acctgcatcc ccatcccctc ctcctgggcc ttcgccaagt     660
acctgtggga gtgggcctcc gtgcgcttct cctggctgtc cctgctggtg cccttcgtgc     720
agtggttcgt gggcctgtcc ccaccgtgt ggctgtccgc catctggatg atgtggtact     780
ggggcccctc cctgtactcc atcgtgtccc ccttcatccc cctgctgccc atcttcttct     840
gcctgtgggt gtacatcggg gtacctgtgt ggaaagaagc aaccaccact ctattttgtg     900
catcagatgc taaagcatat gatacagagg tacataatgt ttgggccaca catgcctgtg     960
tacccacaga ccccaaccca caagaagtag tattggaaaa tgtgacagaa aattttaaca    1020
tgtggaaaaa taacatggta gaacagatgc atgaggatat aatcagttta tgggatcaaa    1080
gcctaaagcc atgtgtaaaa ttaaccccac tccaggcctg tccaaaggta tcctttgagc    1140
caattcccat acattattgt accccggctg gttttgcgat tctaaagtgt aaagacaaga    1200
agttcaatgg aacagggcca tgtaaaaatg tcagcacagt acaatgtaca catggaatta    1260
ggccagtagt gtcaactcaa ctgctgttaa atggcagtct agcagaagaa gaggtagtaa    1320
ttagatctag taatttcaca gacaatgcaa aaaacataat agtacagttg aaagaatctg    1380
tagaaattaa ttgtacaaga cccaacaaca atacaaggaa aagtatacat ataggaccag    1440
gaagagcatt ttatacaaca ggagaaataa taggagatat aagacaagca cattgcaaca    1500
ttagtagaac aaaatggaat aacactttaa atcaaatagc tacaaaatta aagaacaat    1560
ttgggaataa taaacaata gtctttaatc aatcctcagg aggggaccca gaaattgtaa    1620
tgcacagttt taattgtgga ggggaatttt tctactgtaa ttcaacacaa ctgtttaata    1680
gtacttggaa ttttaatggt acttggaatt taacacaatc gaatggtact gaaggaaatg    1740
acactatcac actcccatgt agaataaaac agctagcaat gtatgcccct cccatcagag    1800
gacaaattag atgctcatca aatattacag ggctaatatt aacaagagat ggtggaaata    1860
accacaataa tgataccgag acctttagac ctggaggagg agatatgagg gacaattgga    1920
gaagtgaatt atataaatat aaagtagtaa aaattgaacc attaggagta gcacccacca    1980
aggcaaaaag atgactagtc                                                2000
```

<210> SEQ ID NO 71
<211> LENGTH: 665

<212> TYPE: PRT
<213> ORGANISM: Human immunodeficiency virus

<400> SEQUENCE: 71

```
Ile Ile His Thr Val Pro Pro Ser Gly Ala Asp Pro Gly Pro Lys Arg
1               5                   10                  15

Ala Glu Phe Lys Gly Leu Arg Arg Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
            180                 185                 190

Phe Pro Ser Cys Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
        275                 280                 285

Val Trp Lys Glu Ala Thr Thr Thr Leu Phe Cys Ala Ser Asp Ala Lys
290                 295                 300

Ala Tyr Asp Thr Glu Val His Asn Val Trp Ala Thr His Ala Cys Val
305                 310                 315                 320

Pro Thr Asp Pro Asn Pro Gln Glu Val Glu Leu Glu Asn Val Thr Glu
                325                 330                 335

Asn Phe Asn Met Trp Lys Asn Asn Met Val Glu Gln Met His Glu Asp
            340                 345                 350

Ile Ile Ser Leu Trp Asp Gln Ser Leu Lys Pro Cys Val Lys Leu Thr
        355                 360                 365

Pro Leu Gln Ala Cys Pro Lys Ile Ser Phe Glu Pro Ile Pro Ile His
370                 375                 380

Tyr Cys Ala Pro Ala Gly Phe Ala Ile Leu Lys Cys Lys Asp Lys Lys
385                 390                 395                 400
```

```
Phe Asn Gly Lys Gly Pro Cys Ser Asn Val Ser Thr Val Gln Cys Thr
                405                 410                 415

His Gly Ile Arg Pro Val Ser Thr Gln Leu Leu Leu Asn Gly Ser
            420                 425                 430

Leu Ala Glu Glu Val Val Ile Arg Ser Glu Asn Phe Ala Asp Asn
        435                 440                 445

Ala Lys Thr Ile Ile Val Gln Leu Asn Glu Ser Val Glu Ile Asn Cys
    450                 455                 460

Thr Arg Pro Asn Asn Asn Thr Arg Lys Ser Ile His Ile Gly Pro Gly
465                 470                 475                 480

Arg Ala Leu Tyr Thr Thr Gly Glu Ile Ile Gly Asp Ile Arg Gln Ala
                485                 490                 495

His Cys Asn Leu Ser Arg Ala Lys Trp Asn Asp Thr Leu Asn Lys Ile
            500                 505                 510

Val Ile Lys Leu Arg Glu Gln Phe Gly Asn Lys Thr Ile Val Phe Lys
        515                 520                 525

His Ser Ser Gly Gly Asp Pro Glu Ile Val Thr His Ser Phe Asn Cys
    530                 535                 540

Gly Gly Glu Phe Phe Tyr Cys Asn Ser Thr Gln Leu Phe Asn Ser Thr
545                 550                 555                 560

Trp Asn Val Thr Glu Glu Ser Asn Asn Thr Val Glu Asn Asn Thr Ile
                565                 570                 575

Thr Leu Pro Cys Arg Ile Lys Gln Leu Ala Met Tyr Ala Pro Pro Ile
            580                 585                 590

Arg Gly Gln Ile Arg Cys Ser Ser Asn Ile Thr Gly Leu Leu Leu Thr
        595                 600                 605

Arg Asp Gly Gly Pro Glu Asp Asn Lys Thr Glu Val Phe Arg Pro Gly
    610                 615                 620

Gly Gly Asp Met Arg Asp Asn Trp Arg Ser Glu Leu Tyr Lys Tyr Lys
625                 630                 635                 640

Val Val Lys Ile Glu Pro Leu Gly Val Ala Pro Thr Lys Ala Lys Arg
                645                 650                 655

Leu Val Ala Ala Ala Phe Glu Ser Arg
            660                 665

<210> SEQ ID NO 72
<211> LENGTH: 2000
<212> TYPE: PRT
<213> ORGANISM: Human immunodeficiency virus

<400> SEQUENCE: 72

Gly Gly Ala Thr Thr Ala Thr Thr Cys Ala Thr Ala Cys Cys Gly Thr
1               5                   10                  15

Cys Cys Cys Ala Cys Cys Ala Thr Cys Gly Gly Gly Cys Gly Cys Gly
                20                  25                  30

Gly Ala Thr Cys Cys Cys Gly Gly Thr Cys Cys Gly Ala Ala Gly Cys
            35                  40                  45

Gly Cys Gly Cys Gly Gly Ala Ala Thr Cys Ala Ala Ala Gly Gly Gly
        50                  55                  60

Cys Cys Thr Ala Cys Gly Thr Cys Gly Ala Cys Ala Gly Cys Ala Ala
65                  70                  75                  80

Ala Ala Gly Cys Ala Gly Gly Gly Ala Thr Ala Ala Thr Thr Cys
                85                  90                  95

Thr Ala Thr Thr Ala Ala Cys Cys Ala Thr Gly Ala Ala Gly Ala Cys
```

-continued 100 105 110

Thr Ala Thr Cys Ala Thr Thr Gly Cys Thr Thr Thr Gly Ala Gly Cys
115 120 125

Thr Ala Cys Ala Thr Thr Thr Thr Ala Thr Gly Thr Cys Thr Gly Gly
130 135 140

Thr Thr Cys Thr Cys Gly Cys Thr Cys Ala Ala Ala Ala Ala Cys Thr
145 150 155 160

Thr Cys Cys Cys Gly Gly Ala Ala Ala Thr Gly Ala Cys Ala Ala Cys
165 170 175

Ala Ala Cys Ala Gly Cys Gly Ala Ala Thr Thr Cys Ala Thr Cys Ala
180 185 190

Cys Cys Thr Cys Cys Gly Gly Cys Thr Thr Cys Cys Thr Gly Gly Gly
195 200 205

Cys Cys Cys Cys Cys Thr Gly Cys Thr Gly Gly Thr Gly Cys Thr Gly
210 215 220

Cys Ala Gly Gly Cys Cys Gly Gly Cys Thr Thr Cys Thr Thr Cys Cys
225 230 235 240

Thr Gly Cys Thr Gly Ala Cys Cys Cys Gly Cys Ala Thr Cys Cys Thr
245 250 255

Gly Ala Cys Cys Ala Thr Cys Cys Cys Cys Cys Ala Gly Thr Cys Cys
260 265 270

Cys Thr Gly Gly Ala Cys Thr Cys Cys Thr Gly Gly Thr Gly Gly Ala
275 280 285

Cys Cys Thr Cys Cys Cys Thr Gly Ala Ala Cys Thr Thr Cys Cys Thr
290 295 300

Gly Gly Gly Cys Gly Gly Cys Thr Cys Cys Cys Cys Cys Gly Thr Gly
305 310 315 320

Thr Gly Cys Cys Thr Gly Gly Gly Cys Cys Ala Gly Ala Ala Cys Thr
325 330 335

Cys Cys Cys Ala Gly Thr Cys Cys Cys Cys Cys Ala Cys Cys Thr Cys
340 345 350

Cys Ala Ala Cys Cys Ala Cys Thr Cys Cys Cys Cys Cys Ala Cys Cys
355 360 365

Thr Cys Cys Thr Gly Cys Cys Cys Cys Cys Cys Cys Ala Thr Cys Thr
370 375 380

Gly Cys Cys Cys Cys Gly Gly Cys Thr Ala Cys Cys Gly Cys Thr Gly
385 390 395 400

Gly Ala Thr Gly Thr Gly Cys Cys Thr Gly Cys Gly Cys Cys Gly Cys
405 410 415

Thr Thr Cys Ala Thr Cys Ala Thr Cys Thr Thr Cys Cys Thr Gly Thr
420 425 430

Thr Cys Ala Thr Cys Cys Thr Gly Cys Thr Gly Cys Thr Gly Thr Gly
435 440 445

Cys Cys Thr Gly Ala Thr Cys Thr Thr Cys Cys Thr Gly Cys Thr Gly
450 455 460

Gly Thr Gly Cys Thr Gly Cys Thr Gly Gly Ala Cys Thr Ala Cys Cys
465 470 475 480

Ala Gly Gly Gly Cys Ala Thr Gly Cys Thr Gly Cys Cys Cys Gly Thr
485 490 495

Gly Thr Gly Cys Cys Cys Cys Cys Thr Gly Ala Thr Cys Cys Cys Cys
500 505 510

Gly Gly Cys Thr Cys Cys Ala Cys Cys Ala Cys Cys Ala Cys Cys Thr
515 520 525

-continued

```
Cys Cys Ala Cys Cys Gly Gly Cys Cys Cys Thr Gly Cys Ala Ala
        530                 535                 540
Gly Ala Cys Cys Thr Gly Cys Ala Cys Cys Ala Cys Cys Cys Cys
545                 550                 555                 560
Gly Cys Cys Cys Ala Gly Gly Cys Ala Ala Cys Thr Cys Cys Ala
                565                 570                 575
Ala Gly Thr Thr Cys Cys Cys Thr Cys Cys Thr Gly Cys Thr Gly
                580                 585                 590
Cys Thr Gly Cys Ala Cys Cys Ala Ala Gly Cys Cys Ala Cys Cys
            595                 600                 605
Gly Ala Cys Gly Gly Cys Ala Ala Cys Thr Gly Cys Ala Cys Cys Thr
        610                 615                 620
Gly Cys Ala Thr Cys Cys Cys Ala Thr Cys Cys Cys Thr Cys
625                 630                 635                 640
Cys Thr Cys Cys Thr Gly Gly Cys Cys Thr Thr Cys Gly Cys Cys
                645                 650                 655
Ala Ala Gly Thr Ala Cys Cys Thr Gly Thr Gly Gly Ala Gly Thr
        660                 665                 670
Gly Gly Gly Cys Cys Thr Cys Cys Gly Thr Gly Cys Gly Cys Thr Thr
        675                 680                 685
Cys Thr Cys Cys Thr Gly Gly Cys Thr Gly Thr Cys Cys Cys Thr Gly
            690                 695                 700
Cys Thr Gly Gly Thr Gly Cys Cys Cys Thr Thr Cys Gly Thr Gly Cys
705                 710                 715                 720
Ala Gly Thr Gly Gly Thr Thr Cys Gly Thr Gly Gly Cys Cys Thr
                725                 730                 735
Gly Thr Cys Cys Cys Cys Cys Ala Cys Cys Gly Thr Gly Thr Gly Gly
        740                 745                 750
Cys Thr Gly Thr Cys Cys Gly Cys Cys Ala Thr Cys Thr Gly Gly Ala
            755                 760                 765
Thr Gly Ala Thr Gly Thr Gly Gly Thr Ala Cys Thr Gly Gly Gly Gly
        770                 775                 780
Cys Cys Cys Cys Thr Cys Cys Cys Thr Gly Thr Ala Cys Thr Cys Cys
785                 790                 795                 800
Ala Thr Cys Gly Thr Gly Thr Cys Cys Cys Cys Thr Thr Cys Ala
                805                 810                 815
Thr Cys Cys Cys Cys Cys Thr Gly Cys Thr Gly Cys Cys Ala Thr
            820                 825                 830
Cys Thr Thr Cys Thr Thr Cys Thr Gly Cys Cys Thr Gly Thr Gly Gly
        835                 840                 845
Gly Thr Gly Thr Ala Cys Ala Thr Cys Gly Gly Gly Thr Ala Cys
        850                 855                 860
Cys Thr Gly Thr Gly Thr Gly Gly Ala Ala Gly Ala Ala Gly Cys
865                 870                 875                 880
Ala Ala Cys Cys Ala Cys Cys Ala Cys Thr Cys Thr Ala Thr Thr Thr
                885                 890                 895
Thr Gly Thr Gly Cys Ala Thr Cys Ala Gly Ala Thr Gly Cys Thr Ala
            900                 905                 910
Ala Ala Gly Cys Ala Thr Ala Thr Gly Ala Thr Ala Cys Ala Gly Ala
        915                 920                 925
Gly Gly Thr Ala Cys Ala Thr Ala Ala Thr Gly Thr Thr Thr Gly Gly
        930                 935                 940
```

```
Gly Cys Cys Ala Cys Ala Cys Ala Thr Gly Cys Cys Thr Gly Thr Gly
945                 950                 955                 960

Thr Ala Cys Cys Ala Cys Ala Gly Ala Cys Cys Cys Ala Ala
            965                 970                 975

Cys Cys Cys Ala Cys Ala Ala Gly Ala Ala Gly Thr Ala Gly Ala Ala
                980                 985                 990

Thr Thr Gly Gly Ala Ala Ala Ala Thr Gly Thr Gly Ala Cys Ala Gly
            995                 1000                1005

Ala Ala Ala Ala Thr Thr Thr Thr Ala Ala Cys Ala Thr Gly Thr
        1010                1015                1020

Gly Gly Ala Ala Ala Ala Ala Thr Ala Cys Ala Thr Gly Gly
        1025                1030                1035

Thr Ala Gly Ala Ala Cys Ala Gly Ala Thr Gly Cys Ala Thr Gly
        1040                1045                1050

Ala Gly Gly Ala Thr Ala Thr Ala Ala Thr Cys Ala Gly Thr Thr
        1055                1060                1065

Thr Ala Thr Gly Gly Gly Ala Thr Cys Ala Ala Gly Cys Cys
        1070                1075                1080

Thr Ala Ala Ala Gly Cys Cys Ala Thr Gly Thr Gly Thr Ala Ala
        1085                1090                1095

Ala Ala Thr Thr Ala Ala Cys Thr Cys Cys Ala Cys Thr Cys Cys
        1100                1105                1110

Ala Gly Gly Cys Cys Thr Gly Thr Cys Cys Ala Ala Ala Gly Ala
        1115                1120                1125

Thr Ala Thr Cys Cys Thr Thr Thr Gly Ala Gly Cys Cys Ala Ala
        1130                1135                1140

Thr Thr Cys Cys Cys Ala Thr Ala Cys Ala Thr Thr Ala Thr Thr
        1145                1150                1155

Gly Thr Gly Cys Cys Cys Cys Gly Gly Cys Thr Gly Gly Thr Thr
        1160                1165                1170

Thr Thr Gly Cys Gly Ala Thr Thr Cys Thr Ala Ala Ala Gly Thr
        1175                1180                1185

Gly Thr Ala Ala Ala Gly Ala Thr Ala Ala Gly Ala Ala Gly Thr
        1190                1195                1200

Thr Cys Ala Ala Thr Gly Gly Ala Ala Ala Ala Gly Gly Ala Cys
        1205                1210                1215

Cys Ala Thr Gly Thr Thr Cys Ala Ala Ala Thr Gly Thr Cys Ala
        1220                1225                1230

Gly Cys Ala Cys Ala Gly Thr Ala Cys Ala Ala Thr Gly Thr Ala
        1235                1240                1245

Cys Ala Cys Ala Thr Gly Gly Gly Ala Thr Thr Ala Gly Gly Cys
        1250                1255                1260

Cys Ala Gly Thr Ala Gly Thr Ala Thr Cys Ala Ala Cys Thr Cys
        1265                1270                1275

Ala Ala Cys Thr Gly Cys Thr Gly Thr Thr Ala Ala Ala Thr Gly
        1280                1285                1290

Gly Cys Ala Gly Thr Cys Thr Ala Gly Cys Ala Gly Ala Ala Gly
        1295                1300                1305

Ala Ala Gly Ala Gly Gly Thr Ala Gly Thr Ala Ala Thr Thr Ala
        1310                1315                1320

Gly Ala Thr Cys Cys Gly Ala Ala Ala Ala Thr Thr Thr Cys Gly
        1325                1330                1335

Cys Gly Gly Ala Cys Ala Ala Thr Gly Cys Thr Ala Ala Ala Ala
```

-continued

Cys Cys Ala Thr Ala Ala Thr Ala Gly Thr Ala Cys Ala Gly Cys
        1355                1360                1365

Thr Gly Ala Ala Thr Gly Ala Ala Thr Cys Thr Gly Thr Ala Gly
    1370                1375                1380

Ala Ala Ala Thr Thr Ala Ala Thr Thr Gly Thr Ala Cys Ala Ala
    1385                1390                1395

Gly Ala Cys Cys Cys Ala Ala Cys Ala Ala Cys Ala Ala Thr Ala
    1400                1405                1410

Cys Ala Ala Gly Ala Ala Ala Ala Ala Gly Thr Ala Thr Ala Cys
    1415                1420                1425

Ala Thr Ala Thr Ala Gly Gly Ala Cys Cys Ala Gly Gly Cys Ala
    1430                1435                1440

Gly Ala Gly Cys Ala Thr Thr Ala Thr Ala Thr Ala Cys Ala Ala
    1445                1450                1455

Cys Ala Gly Gly Ala Gly Ala Ala Ala Thr Ala Ala Thr Ala Gly
    1460                1465                1470

Gly Ala Gly Ala Thr Ala Thr Ala Ala Gly Ala Cys Ala Ala Gly
    1475                1480                1485

Cys Ala Cys Ala Thr Thr Gly Thr Ala Ala Cys Cys Thr Thr Ala
    1490                1495                1500

Gly Thr Ala Gly Ala Gly Cys Ala Ala Ala Thr Gly Gly Ala
    1505                1510                1515

Ala Thr Gly Ala Cys Ala Cys Thr Thr Ala Ala Ala Thr Ala
    1520                1525                1530

Ala Gly Ala Thr Ala Gly Thr Thr Ala Thr Ala Ala Ala Ala Thr
    1535                1540                1545

Thr Ala Ala Gly Ala Gly Ala Ala Cys Ala Ala Thr Thr Thr Gly
    1550                1555                1560

Gly Gly Ala Ala Thr Ala Ala Ala Ala Cys Ala Ala Thr Ala Gly
    1565                1570                1575

Thr Cys Thr Thr Thr Ala Ala Gly Cys Ala Thr Thr Cys Cys Thr
    1580                1585                1590

Cys Ala Gly Gly Ala Gly Gly Gly Ala Cys Cys Cys Ala Gly
    1595                1600                1605

Ala Ala Ala Thr Thr Gly Thr Gly Ala Cys Gly Cys Ala Cys Ala
    1610                1615                1620

Gly Thr Thr Thr Thr Ala Ala Thr Thr Gly Thr Gly Gly Ala Gly
    1625                1630                1635

Gly Gly Gly Ala Ala Thr Thr Thr Thr Cys Thr Ala Cys Thr
    1640                1645                1650

Gly Thr Ala Ala Thr Thr Cys Ala Ala Cys Ala Cys Ala Ala Cys
    1655                1660                1665

Thr Gly Thr Thr Thr Ala Ala Thr Ala Gly Thr Ala Cys Thr Thr
    1670                1675                1680

Gly Gly Ala Ala Thr Gly Thr Thr Ala Cys Thr Gly Ala Ala Gly
    1685                1690                1695

Ala Gly Thr Cys Ala Ala Ala Thr Ala Ala Cys Ala Cys Thr Gly
    1700                1705                1710

Thr Ala Gly Ala Ala Ala Ala Thr Ala Ala Cys Ala Cys Ala Ala
    1715                1720                1725

Thr Cys Ala Cys Ala Cys Thr Cys Cys Cys Ala Thr Gly Cys Ala
    1730                1735                1740

```
Gly Ala  Ala Thr Ala Ala Ala  Ala Cys Ala Gly Cys  Thr Ala Gly
    1745                 1750                 1755

Cys Ala  Ala Thr Gly Thr Ala  Thr Gly Cys Cys Cys  Cys Thr Cys
    1760                 1765                 1770

Cys Cys  Ala Thr Cys Ala Gly  Ala Gly Gly Ala Cys  Ala Ala Ala
    1775                 1780                 1785

Thr Thr  Ala Gly Ala Thr Gly  Thr Thr Cys Ala Thr  Cys Ala Ala
    1790                 1795                 1800

Ala Thr  Ala Thr Thr Ala Cys  Ala Gly Gly Gly Cys  Thr Gly Cys
    1805                 1810                 1815

Thr Ala  Thr Thr Ala Ala Cys  Ala Ala Gly Ala Gly  Ala Thr Gly
    1820                 1825                 1830

Gly Thr  Gly Gly Thr Cys Cys  Ala Gly Ala Gly Gly  Ala Cys Ala
    1835                 1840                 1845

Ala Cys  Ala Ala Gly Ala Cys  Cys Gly Ala Gly Gly  Thr Cys Thr
    1850                 1855                 1860

Thr Cys  Ala Gly Ala Cys Cys  Thr Gly Gly Ala Gly  Gly Ala Gly
    1865                 1870                 1875

Gly Ala  Gly Ala Thr Ala Thr  Gly Ala Gly Gly Gly  Ala Cys Ala
    1880                 1885                 1890

Ala Thr  Thr Gly Gly Ala Gly  Ala Ala Gly Thr Gly  Ala Ala Thr
    1895                 1900                 1905

Thr Ala  Thr Ala Thr Ala Ala  Ala Thr Ala Thr Ala  Ala Ala Gly
    1910                 1915                 1920

Thr Ala  Gly Thr Ala Ala Ala  Ala Ala Thr Thr Gly  Ala Ala Cys
    1925                 1930                 1935

Cys Ala  Thr Thr Ala Gly Gly  Ala Gly Thr Ala Gly  Cys Ala Cys
    1940                 1945                 1950

Cys Cys  Ala Cys Cys Ala Ala  Gly Gly Cys Ala Ala  Ala Gly Ala
    1955                 1960                 1965

Gly Ala  Thr Gly Ala Cys Thr  Ala Gly Thr Cys Gly  Cys Gly Gly
    1970                 1975                 1980

Cys Cys  Gly Cys Thr Thr Thr  Cys Gly Ala Ala Thr  Cys Thr Ala
    1985                 1990                 1995

Gly Ala
    2000
```

<210> SEQ ID NO 73
<211> LENGTH: 665
<212> TYPE: PRT
<213> ORGANISM: Human immunodeficiency virus

<400> SEQUENCE: 73

```
Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
```

```
                    85                  90                  95
Ser Leu Asn Phe Leu Gly Gly Ser Pro Val Cys Leu Gly Gln Asn Ser
                100                 105                 110

Gln Ser Pro Thr Ser Asn His Ser Pro Thr Ser Cys Pro Pro Ile Cys
                115                 120                 125

Pro Gly Tyr Arg Trp Met Cys Leu Arg Arg Phe Ile Ile Phe Leu Phe
                130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
                180                 185                 190

Phe Pro Ser Cys Cys Cys Thr Lys Pro Thr Asp Gly Asn Cys Thr Cys
                195                 200                 205

Ile Pro Ile Pro Ser Ser Trp Ala Phe Ala Lys Tyr Leu Trp Glu Trp
210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
                260                 265                 270

Pro Leu Leu Pro Ile Phe Phe Cys Leu Trp Val Tyr Ile Gly Val Pro
                275                 280                 285

Val Trp Lys Glu Ala Thr Thr Thr Leu Phe Cys Ala Ser Asp Ala Lys
290                 295                 300

Ala Tyr Asp Thr Glu Val His Asn Val Trp Ala Thr His Ala Cys Val
305                 310                 315                 320

Pro Thr Asp Pro Asn Pro Gln Glu Val Val Leu Val Asn Val Thr Glu
                325                 330                 335

Asn Phe Asn Met Trp Lys Asn Asp Met Val Glu Gln Met His Glu Asp
                340                 345                 350

Ile Ile Ser Leu Trp Asp Gln Ser Leu Lys Pro Cys Val Lys Leu Thr
                355                 360                 365

Pro Leu Ser Val Gln Ala Cys Pro Lys Val Ser Phe Glu Pro Ile Pro
                370                 375                 380

Ile His Tyr Cys Ala Pro Ala Gly Phe Ala Ile Leu Lys Cys Asn Asn
385                 390                 395                 400

Lys Thr Phe Asn Gly Thr Gly Pro Cys Thr Asn Val Ser Thr Val Gln
                405                 410                 415

Cys Thr His Gly Ile Arg Pro Val Val Ser Thr Gln Leu Leu Leu Asn
                420                 425                 430

Gly Ser Leu Ala Glu Glu Val Val Ile Arg Ser Val Asn Phe Thr
                435                 440                 445

Asp Asn Ala Lys Thr Ile Ile Val Gln Leu Asn Thr Ser Val Glu Ile
                450                 455                 460

Asn Cys Thr Arg Pro Ser Val Asn Phe Thr Asp Asn Ala Lys Thr Ile
465                 470                 475                 480

Ile Val Gln Leu Asn Thr Ser Val Glu Ile Asn Cys Thr Arg Pro Met
                485                 490                 495

Arg Gln Ala His Cys Asn Ile Ser Arg Ala Lys Trp Asn Asn Thr Leu
                500                 505                 510
```

```
Lys Gln Ile Ala Ser Lys Leu Arg Glu Gln Phe Gly Asn Asn Lys Thr
            515                 520                 525

Ile Ile Phe Lys Gln Ser Ser Gly Gly Asp Pro Glu Ile Val Thr His
        530                 535                 540

Ser Phe Asn Cys Gly Gly Glu Phe Phe Tyr Cys Asn Ser Thr Gln Leu
545                 550                 555                 560

Phe Asn Ser Thr Trp Phe Asn Ser Thr Trp Ser Thr Glu Gly Ser Asn
                565                 570                 575

Asn Thr Glu Gly Ser Asp Thr Ile Thr Leu Pro Cys Arg Ile Lys Gln
            580                 585                 590

Ser Ile Ala Met Tyr Ala Pro Pro Ile Ser Gly Gln Ile Arg Cys Ser
        595                 600                 605

Ser Asn Ile Thr Gly Leu Leu Leu Thr Arg Asp Gly Gly Asn Ser Asn
    610                 615                 620

Asn Glu Ser Glu Ile Phe Arg Pro Gly Gly Gly Asp Met Arg Asp Asn
625                 630                 635                 640

Trp Arg Ser Glu Leu Tyr Lys Tyr Lys Val Val Lys Ile Glu Pro Leu
                645                 650                 655

Gly Val Ala Pro Thr Lys Ala Lys Arg
            660                 665

<210> SEQ ID NO 74
<211> LENGTH: 2000
<212> TYPE: DNA
<213> ORGANISM: Human immunodeficiency virus

<400> SEQUENCE: 74
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta catttatgt ctggttctcg ctcaaaaact tcccggaaat gacaacaaca      180
gcgaattcat cacctccggc ttcctgggcc cctgctggt gctgcaggcc ggcttcttcc      240
tgctgacccg catcctgacc atcccccagt ccctggactc ctggtggacc tccctgaact     300
tcctgggcgg ctcccccgtg tgcctggccc agaactccca gtcccccacc tccaaccact     360
ccccaccctc ctgccccccc atctgccccg gctaccgctg gatgtgcctg cgccgcttca     420
tcatcttcct gttcatcctg ctgctgtgcc tgatcttcct gctggtgctg ctggactacc     480
agggcatgct gcccgtgtgc cccctgatcc ccggctccac caccacctcc accggcccct     540
gcaagacctg caccacccc gcccagggca actccaagtt cccctcctgc tgctgcacca     600
agcccaccga cggcaactgc acctgcatcc ccatcccctc ctcctgggcc ttcgccaagt     660
acctgtggga gtgggcctcc gtgcgcttct cctggctgtc cctgctggtg cccttcgtgc     720
agtggttcgt gggcctgtcc cccaccgtgt ggctgtccgc catctggatg atgtggtact     780
ggggcccctc cctgtactcc atcgtgtccc cttcatccc cctgctgccc atcttcttct     840
gcctgtgggt gtacatcggg gtacctgtgt ggaaggaagc aaccaccact ctatttgtg     900 catcagatgc taaagcatat gatacagagg tacataatgt ttgggccaca catgcctgtg     960
tacccacaga ccccaacca caagaagtag tattggtaaa tgtgacagaa aattttaaca    1020
tgtggaaaaa tgacatggta gaacagatgc atgaggatat aatcagttta tgggatcaaa    1080
gcctaaagcc atgtgtaaaa ttaacccac tctcggtcca ggcctgtcca aaggtatcct    1140
ttgagccaat tcccatacat tattgtgccc cggctggttt tgcgattcta aaatgtaata    1200
```

-continued

```
ataagacgtt caatggaaca ggaccatgta caaatgtcag cacagtacaa tgtacacatg    1260
gaattaggcc agtagtatca actcaactgc tgttaaatgg cagtctagca gaagaagagg    1320
tagtaattag atctgtcaat ttcacggaca atgctaaaac cataatagta cagctgaaca    1380
catctgtaga aattaattgt acaagaccct ctgtcaattt cacggacaat gctaaaacca    1440
taatagtaca gctgaacaca tctgtagaaa ttaattgtac aagacccatg agacaagcac    1500
attgtaacat tagtagagca aaatggaata acactttaaa acagatagct agcaaattaa    1560
gagaacaatt tggaaataat aaaacaataa tctttaagca atcctcagga ggggacccag    1620
aaattgtaac gcacagtttt aattgtggag gggaattttt ctactgtaat tcaacacaac    1680
tgtttaatag tacttggttt aatagtactt ggagtactga agggtcaaat aacactgaag    1740
gaagtgacac aatcaccctc ccatgcagaa taaaacaatc gatagcaatg tatgcccctc    1800
ccatcagtgg acaaattaga tgttcatcaa atattacagg gctgctatta acaagagatg    1860
gtggtaatag caacaatgag tccgagatct tcagacctgg aggaggagat atgagggaca    1920
attggagaag tgaattatat aaatataaag tagtaaaaat tgaaccatta ggagtagcac    1980
ccaccaaggc aaagagataa                                                2000
```

```
<210> SEQ ID NO 75
<211> LENGTH: 50
<212> TYPE: DNA
<213> ORGANISM: Artificial sequence
<220> FEATURE:
<223> OTHER INFORMATION: Synthetic neucleic acid primer.

<400> SEQUENCE: 75
cggcggccgc accggtcgcc accatggccc agtccaagca cggcctgacc             50
```

```
<210> SEQ ID NO 76
<211> LENGTH: 47
<212> TYPE: DNA
<213> ORGANISM: Artificial sequence
<220> FEATURE:
<223> OTHER INFORMATION: Synthetic neucleic acid primer.

<400> SEQUENCE: 76
tggcggccgc tctagatccg gtggatcccg ggcccgcggt accgtcg                47
```

```
<210> SEQ ID NO 77
<211> LENGTH: 366
<212> TYPE: PRT
<213> ORGANISM: Artificial sequence
<220> FEATURE:
<223> OTHER INFORMATION: Recombinant antigenic insert peptide construct.

<400> SEQUENCE: 77
```

Pro Gln Gly Ala Arg Met Ala Ser Thr Thr Pro Ile Thr Met Glu Asp
1               5                   10                  15

Leu Gln Lys Ala Leu Glu Ala Gln Ser Arg Ala Leu Arg Ala Asp Leu
            20                  25                  30

Ala Ala Gly Ala Ser Gln Ser Arg Arg Pro Arg Pro Pro Arg Gln Arg
        35                  40                  45

Asp Ser Ser Thr Ser Gly Asp Asp Ser Gly Arg Asp Ser Gly Gly Pro
    50                  55                  60

Arg Arg Arg Arg Gly Asn Arg Gly Arg Gly Gln Arg Arg Asp Trp Ser
65                  70                  75                  80

Arg Ala Pro Pro Pro Pro Glu Glu Arg Gln Glu Ser Arg Ser Gln Thr
                85                  90                  95

Pro Ala Pro Lys Pro Ser Arg Ala Pro Pro Gln Gln Pro Gln Pro Pro
            100                 105                 110

Arg Met Gln Thr Gly Arg Gly Gly Ser Ala Pro Arg Pro Glu Leu Gly
            115                 120                 125

Pro Pro Thr Asn Pro Phe Gln Ala Ala Val Ala Arg Gly Leu Arg Pro
            130                 135                 140

Pro Leu His Asp Pro Asp Thr Glu Ala Pro Thr Glu Ala Cys Val Thr
145                 150                 155                 160

Ser Trp Leu Trp Ser Glu Gly Glu Gly Ala Val Phe Tyr Arg Val Asp
                165                 170                 175

Leu His Phe Thr Asn Leu Gly Thr Pro Leu Asp Glu Asp Gly Arg
            180                 185                 190

Trp Asp Pro Ala Leu Met Tyr Asn Pro Cys Gly Pro Glu Pro Pro Ala
            195                 200                 205

His Val Val Arg Ala Tyr Asn Gln Pro Ala Gly Asp Val Arg Gly Val
            210                 215                 220

Trp Gly Lys Gly Glu Arg Thr Tyr Ala Glu Gln Asp Phe Arg Val Gly
225                 230                 235                 240

Gly Thr Arg Trp His Arg Leu Leu Arg Met Pro Val Arg Gly Leu Asp
                245                 250                 255

Gly Asp Ser Ala Pro Leu Pro Pro Tyr Thr Thr Glu Arg Ile Glu Thr
            260                 265                 270

Arg Ser Ala Arg His Pro Trp Arg Ile Arg Phe Gly Ala Pro Gln Ala
            275                 280                 285

Phe Leu Ala Gly Leu Leu Leu Ala Thr Val Ala Val Gly Thr Ala Arg
            290                 295                 300

Ala Gly Leu Gln Pro Arg Ala Asp Met Ala Ala Pro Pro Thr Leu Pro
305                 310                 315                 320

Arg Ser Ala Gln Glu Lys Asn Glu Lys Glu Leu Leu Glu Leu Asp Lys
                325                 330                 335

Trp Ala Ser Leu Trp Asn Trp Phe Asp Ile Thr Asn Trp Leu Trp Tyr
            340                 345                 350

Ile Arg Leu Phe Ile Asp Ala Ser Thr Arg Ser Ala Arg His
            355                 360                 365

<210> SEQ ID NO 78
<211> LENGTH: 367
<212> TYPE: PRT
<213> ORGANISM: Artificial sequence
<220> FEATURE:
<223> OTHER INFORMATION: Recombinant antigenic insert peptide construct.

<400> SEQUENCE: 78

Asp Ser Ala Pro Leu Pro Pro His Thr Thr Glu Arg Ile Glu Thr Arg
1               5                   10                  15

Ser Ala Arg His Pro Trp Arg Ile Arg Phe Gly Ala Pro Gln Ala Phe
            20                  25                  30

Leu Ala Gly Leu Leu Leu Ala Thr Val Ala Val Gly Thr Ala Arg Ala
            35                  40                  45

Gly Pro Arg Ser Ala Gln Glu Lys Asn Glu Lys Glu Leu Leu Glu Leu
        50                  55                  60

Asp Lys Trp Ala Ser Leu Trp Asn Trp Phe Asp Ile Thr Asn Trp Leu
65                  70                  75                  80

Trp Tyr Ile Arg Leu Phe Ile Asp Ala Ser Ala Gly Leu Gln Pro Arg
                85                  90                  95

Ala Asp Met Ala Ala Pro Pro Thr Leu Pro Gln Pro Cys Ala His
                100                 105                 110

Gly Gln His Tyr Gly His His His Gln Leu Pro Phe Leu Gly His
        115                 120                 125

Asp Gly His His Gly Gly Thr Leu Arg Val Gly Gln His Tyr Arg Asn
130                 135                 140

Ala Ser Asp Val Leu Pro Gly His Trp Leu Gln Gly Gly Trp Gly Cys
145                 150                 155                 160

Tyr Asn Leu Ser Asp Trp His Gln Gly Thr His Val Cys His Thr Lys
                165                 170                 175

His Met Asp Phe Trp Cys Val Glu His Asp Arg Pro Pro Ala Thr
            180                 185                 190

Pro Thr Pro Leu Thr Thr Ala Ala Asn Ser Thr Thr Ala Ala Thr Pro
                195                 200                 205

Ala Thr Ala Pro Ala Pro Cys His Ala Gly Leu Asn Asp Ser Cys Gly
        210                 215                 220

Gly Phe Leu Ser Gly Cys Gly Pro Met Arg Leu Arg His Gly Ala Asp
225                 230                 235                 240

Thr Arg Cys Gly Arg Leu Ile Cys Gly Leu Ser Thr Thr Ala Gln Tyr
                245                 250                 255

Pro Pro Thr Arg Phe Gly Cys Ala Met Arg Trp Gly Leu Pro Pro Trp
            260                 265                 270

Glu Leu Val Val Leu Thr Ala Arg Pro Glu Asp Gly Trp Thr Cys Arg
        275                 280                 285

Gly Val Pro Ala His Pro Gly Ala Arg Cys Pro Glu Leu Val Ser Pro
        290                 295                 300

Met Gly Arg Ala Thr Cys Ser Pro Ala Ser Ala Leu Trp Leu Ala Thr
305                 310                 315                 320

Ala Asn Ala Leu Ser Leu Asp His Ala Leu Ala Phe Val Leu Leu
                325                 330                 335

Val Pro Trp Val Leu Ile Phe Met Val Cys Arg Arg Ala Cys Arg Arg
            340                 345                 350

Arg Gly Ala Ala Ala Ala Leu Thr Ala Val Val Leu Gln Gly Tyr
            355                 360                 365

<210> SEQ ID NO 79
<211> LENGTH: 367
<212> TYPE: PRT
<213> ORGANISM: Artificial sequence
<220> FEATURE:
<223> OTHER INFORMATION: Recombinant antigenic insert peptide construct.

<400> SEQUENCE: 79

Ala Gly Leu Leu Leu Ala Thr Val Ala Val Gly Thr Ala Arg Ala Gly
1               5                   10                  15

Leu Gln Pro Arg Ala Asp Met Ala Ala Pro Thr Leu Pro Gln Pro
            20                  25                  30

Pro Cys Ala His Gly Gln His Tyr Gly His His His Gln Leu Pro
        35                  40                  45

Phe Leu Gly His Asp Gly His His Gly Gly Thr Leu Arg Val Gly Gln
    50                  55                  60

His Tyr Arg Asn Ala Ser Asp Val Leu Pro Gly His Trp Leu Gln Gly
65                  70                  75                  80

Gly Trp Gly Cys Tyr Asn Leu Ser Asp Trp His Gln Gly Thr His Val
                85                  90                  95

-continued

```
Cys His Thr Lys His Met Asp Phe Trp Cys Val Glu His Asp Arg Pro
            100                 105                 110

Pro Pro Ala Thr Pro Thr Pro Leu Thr Thr Ala Ala Asn Ser Thr Thr
        115                 120                 125

Ala Ala Thr Pro Ala Thr Ala Pro Ala Pro Cys His Ala Gly Leu Asn
130                 135                 140

Asp Ser Cys Gly Gly Phe Leu Ser Gly Cys Gly Pro Met Arg Leu Arg
145                 150                 155                 160

His Gly Ala Asp Thr Arg Cys Gly Arg Leu Ile Cys Gly Leu Ser Thr
                165                 170                 175

Thr Ala Gln Tyr Pro Pro Thr Arg Phe Gly Cys Ala Met Arg Trp Gly
            180                 185                 190

Leu Pro Pro Trp Glu Leu Val Val Leu Thr Ala Arg Pro Glu Asp Gly
        195                 200                 205

Trp Thr Cys Arg Gly Val Pro Ala His Pro Gly Ala Arg Cys Pro Glu
210                 215                 220

Leu Val Ser Pro Met Gly Arg Ala Thr Cys Ser Pro Ala Ser Ala Leu
225                 230                 235                 240

Trp Leu Ala Thr Ala Asn Ala Leu Ser Leu Asp His Ala Leu Ala Ala
                245                 250                 255

Phe Val Leu Leu Val Pro Trp Val Leu Ile Phe Met Val Cys Arg Arg
            260                 265                 270

Ala Cys Arg Arg Arg Gly Ala Ala Ala Leu Thr Ala Val Val Leu
        275                 280                 285

Gln Gly Pro Arg Ser Ala Gln Glu Lys Asn Glu Lys Glu Leu Leu Glu
290                 295                 300

Leu Asp Lys Trp Ala Ser Leu Trp Asn Trp Phe Asp Ile Thr Asn Trp
305                 310                 315                 320

Leu Trp Tyr Ile Arg Leu Phe Ile Asp Ala Ser Arg Arg Gly Ala
                325                 330                 335

Ala Ala Ala Leu Thr Ala Val Val Leu Gln Gly Tyr Asn Pro Pro Ala
            340                 345                 350

Tyr Gly Glu Glu Ala Phe Thr Tyr Leu Cys Thr Ala Pro Gly Cys
        355                 360                 365

<210> SEQ ID NO 80
<211> LENGTH: 566
<212> TYPE: PRT
<213> ORGANISM: Artificial sequence
<220> FEATURE:
<223> OTHER INFORMATION: Recombinant antigenic insert peptide construct.

<400> SEQUENCE: 80

Met Val Cys Arg Arg Ala Cys Arg Arg Gly Ala Ala Ala Ala Leu
1               5                   10                  15

Thr Ala Val Val Leu Gln Gly Tyr Asn Pro Pro Ala Tyr Gly Glu Ala
            20                  25                  30

Pro Arg Ser Ala Gln Glu Lys Asn Glu Lys Glu Leu Leu Glu Leu Asp
        35                  40                  45

Lys Trp Ala Ser Leu Trp Asn Trp Phe Asp Ile Thr Asn Trp Leu Trp
    50                  55                  60

Tyr Ile Arg Leu Phe Ile Asp Ala Ser Leu Gln Gly Tyr Asn Pro Pro
65                  70                  75                  80

Ala Tyr Gly Glu Glu Ala Phe Thr Tyr Leu Cys Thr Ala Pro Gly Cys
                85                  90                  95
```

```
Ala Thr Gln Ala Pro Val Pro Val Arg Leu Ala Gly Val Arg Phe Glu
            100                 105                 110

Ser Lys Ile Val Asp Gly Gly Cys Phe Ala Pro Trp Asp Leu Glu Ala
            115                 120                 125

Thr Gly Ala Cys Ile Cys Glu Ile Pro Thr Asp Val Ser Cys Glu Gly
            130                 135                 140

Leu Gly Ala Trp Val Pro Ala Ala Pro Cys Ala Arg Ile Trp Asn Gly
145                 150                 155                 160

Thr Gln Arg Ala Cys Thr Phe Trp Ala Val Asn Ala Tyr Ser Ser Gly
                165                 170                 175

Gly Tyr Ala Gln Leu Ala Ser Tyr Phe Asn Pro Gly Gly Ser Tyr Tyr
            180                 185                 190

Lys Gln Tyr His Pro Thr Ala Cys Glu Val Glu Pro Ala Phe Gly His
            195                 200                 205

Ser Asp Ala Ala Cys Trp Gly Phe Pro Thr Asp Thr Val Met Ser Val
            210                 215                 220

Phe Ala Leu Ala Ser Tyr Val Gln His Pro His Lys Thr Val Arg Val
225                 230                 235                 240

Lys Phe His Thr Glu Thr Arg Thr Val Trp Gln Leu Ser Val Ala Gly
                245                 250                 255

Val Ser Cys Asn Val Thr Thr Glu His Pro Phe Cys Asn Thr Pro His
            260                 265                 270

Gly Gln Leu Glu Val Gln Val Pro Pro Asp Pro Gly Asp Leu Val Glu
            275                 280                 285

Tyr Ile Met Asn Tyr Thr Gly Asn Gln Gln Ser Arg Trp Gly Leu Gly
            290                 295                 300

Ser Pro Asn Cys His Gly Pro Asp Trp Ala Ser Pro Val Cys Gln Arg
305                 310                 315                 320

His Ser Pro Asp Cys Ser Arg Leu Val Gly Ala Thr Pro Glu Arg Pro
                325                 330                 335

Arg Leu Arg Leu Val Asp Ala Asp Pro Leu Leu Arg Thr Ala Pro
            340                 345                 350

Gly Pro Gly Glu Val Trp Val Thr Pro Val Ile Gly Ser Gln Ala Arg
            355                 360                 365

Lys Cys Gly Leu His Ile Arg Ala Gly Pro Tyr Gly His Ala Thr Val
370                 375                 380

Glu Met Pro Glu Trp Ile His Ala His Thr Thr Ser Asp Pro Trp His
385                 390                 395                 400

Pro Pro Gly Pro Leu Gly Leu Lys Phe Lys Thr Val Arg Pro Val Ala
                405                 410                 415

Leu Pro Arg Thr Leu Ala Pro Pro Arg Asn Val Arg Val Thr Gly Cys
            420                 425                 430

Tyr Gln Cys Gly Thr Pro Ala Leu Val Glu Gly Leu Ala Pro Gly Gly
            435                 440                 445

Gly Asn Cys His Leu Thr Val Asn Gly Glu Asp Leu Gly Ala Val Pro
            450                 455                 460

Pro Gly Lys Phe Val Thr Ala Ala Leu Leu Asn Thr Pro Pro Tyr
465                 470                 475                 480

Gln Val Ser Cys Gly Gly Glu Ser Asp Arg Ala Thr Ala Arg Val Ile
                485                 490                 495

Asp Pro Ala Ala Gln Ser Phe Thr Gly Val Val Tyr Gly Thr His Thr
            500                 505                 510
```

-continued

```
Thr Ala Val Ser Glu Thr Arg Gln Thr Trp Ala Glu Trp Ala Ala Ala
            515                 520                 525

His Trp Trp Gln Leu Thr Leu Gly Ala Ile Cys Ala Leu Pro Leu Ala
530                 535                 540

Gly Leu Leu Ala Cys Cys Ala Lys Cys Leu Tyr Tyr Leu Arg Gly Ala
545                 550                 555                 560

Ile Ala Pro Arg Trp Ala
                565

<210> SEQ ID NO 81
<211> LENGTH: 34
<212> TYPE: PRT
<213> ORGANISM: Artificial sequence
<220> FEATURE:
<223> OTHER INFORMATION: Recombinant antigenic insert peptide.

<400> SEQUENCE: 81

Gln Glu Lys Asn Glu Lys Glu Leu Leu Glu Leu Asp Lys Trp Ala Ser
1               5                  10                  15

Leu Trp Asn Trp Phe Asp Ile Thr Asn Trp Leu Trp Tyr Ile Arg Leu
            20                  25                  30

Phe Ile

<210> SEQ ID NO 82
<211> LENGTH: 39
<212> TYPE: PRT
<213> ORGANISM: Artificial sequence
<220> FEATURE:
<223> OTHER INFORMATION: Recombinant antigenic insert peptide.

<400> SEQUENCE: 82

Arg Glu Gly Ser Gln Lys Ile Leu Ser Val Leu Ala Pro Leu Val Pro
1               5                  10                  15

Thr Gly Ser Glu Asn Leu Lys Ser Leu Tyr Asn Thr Val Ser Val Ile
            20                  25                  30

Trp Ser Ile His Ala Glu Asp
        35

<210> SEQ ID NO 83
<211> LENGTH: 38
<212> TYPE: PRT
<213> ORGANISM: Artificial sequence
<220> FEATURE:
<223> OTHER INFORMATION: Recombinant antigenic insert peptide.

<400> SEQUENCE: 83

Phe Gln Ala Leu Ser Glu Gly Cys Thr Pro Tyr Asp Ile Asn Gln Met
1               5                  10                  15

Leu Asn Cys Val Gly Asp His Gln Ala Ala Met Gln Ile Ile Arg Asp
            20                  25                  30

Ile Ile Asn Glu Glu Ala
        35

<210> SEQ ID NO 84
<211> LENGTH: 65
<212> TYPE: PRT
<213> ORGANISM: Artificial sequence
<220> FEATURE:
<223> OTHER INFORMATION: Recombinant antigenic insert peptide.

<400> SEQUENCE: 84

Leu Pro Leu Ser Pro Arg Thr Leu Asn Ala Trp Val Lys Leu Ile Glu
```

-continued

```
                1               5                  10                  15
Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala
65

<210> SEQ ID NO 85
<211> LENGTH: 81
<212> TYPE: PRT
<213> ORGANISM: Artificial sequence
<220> FEATURE:
<223> OTHER INFORMATION: Recombinant antigenic insert peptide.

<400> SEQUENCE: 85

Leu Pro Leu Ser Pro Arg Thr Leu Asn Ala Trp Val Lys Leu Ile Glu
1               5                  10                  15

Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala Thr Arg Ser Gln Lys Ile Leu Ser Val Leu Ala Pro Leu Val Pro
65                  70                  75                  80

Thr

<210> SEQ ID NO 86
<211> LENGTH: 79
<212> TYPE: PRT
<213> ORGANISM: Artificial sequence
<220> FEATURE:
<223> OTHER INFORMATION: Recombinant antigenic insert peptide.

<400> SEQUENCE: 86

Leu Pro Leu Ser Pro Arg Thr Leu Asn Ala Trp Val Lys Leu Ile Glu
1               5                  10                  15

Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala Thr Arg Thr Gly Ser Glu Asn Leu Lys Ser Leu Tyr Asn Thr
65                  70                  75

<210> SEQ ID NO 87
<211> LENGTH: 87
<212> TYPE: PRT
<213> ORGANISM: Artificial sequence
<220> FEATURE:
<223> OTHER INFORMATION: Recombinant antigenic insert peptide.

<400> SEQUENCE: 87

Leu Pro Leu Ser Pro Arg Thr Leu Asn Ala Trp Val Lys Leu Ile Glu
1               5                  10                  15
```

```
Glu Lys Lys Phe Gly Ala Glu Val Val Pro Gly Phe Gln Ala Leu Ser
            20                  25                  30

Glu Gly Cys Thr Pro Tyr Asp Ile Asn Gln Met Leu Asn Cys Val Gly
        35                  40                  45

Asp His Gln Ala Ala Met Gln Ile Ile Arg Asp Ile Ile Asn Glu Glu
    50                  55                  60

Ala Thr Arg His Thr Glu Ala Lys Gln Ile Val Gln Arg His Leu
65                  70                  75                  80

Val Val Glu Thr Gly Thr Thr
                85

<210> SEQ ID NO 88
<211> LENGTH: 80
<212> TYPE: PRT
<213> ORGANISM: Artificial sequence
<220> FEATURE:
<223> OTHER INFORMATION: Recombinant antigenic insert peptide.

<400> SEQUENCE: 88

Val Pro Thr Gly Ser Glu Asn Leu Lys Ser Leu Tyr Asn Thr Val Thr
1               5                   10                  15

Arg Val Lys His Thr Glu Glu Ala Lys Gln Ile Val Gln Arg His Leu
            20                  25                  30

Val Val Glu Thr Gly Thr Thr Ser Asp Ala Phe Gln Ala Leu Ser Glu
        35                  40                  45

Gly Cys Thr Pro Tyr Asp Ile Asn Gln Met Leu Asn Cys Val Gly Asp
    50                  55                  60

His Gln Ala Ala Met Gln Ile Ile Arg Asp Ile Ile Asn Glu Glu Ala
65                  70                  75                  80

<210> SEQ ID NO 89
<211> LENGTH: 19
<212> TYPE: PRT
<213> ORGANISM: Human immunodeficiency virus

<400> SEQUENCE: 89

Pro Ser Trp Asn Trp Phe Asp Ile Thr Asn Trp Leu Trp Tyr Ile Arg
1               5                   10                  15

Leu Asp Ala

<210> SEQ ID NO 90
<211> LENGTH: 109
<212> TYPE: PRT
<213> ORGANISM: Artificial sequence
<220> FEATURE:
<223> OTHER INFORMATION: Recombinant antigenic insert peptide.

<400> SEQUENCE: 90

Leu Asp Arg Phe Gly Leu Ala Glu Ser Leu Leu Glu Asn Lys Glu Gly
1               5                   10                  15

Ser Gln Lys Ile Leu Ser Val Leu Ala Pro Leu Val Pro Thr Gly Ser
            20                  25                  30

Glu Asn Leu Lys Ser Leu Tyr Asn Thr Val Thr Arg Val Lys His Thr
        35                  40                  45

Glu Glu Ala Lys Gln Ile Val Gln Arg His Leu Val Val Glu Thr Gly
    50                  55                  60

Thr Thr Glu Thr Ser Asp Ala Phe Gln Ala Leu Ser Glu Gly Cys Thr
65                  70                  75                  80

Pro Tyr Asp Ile Asn Gln Met Leu Asn Cys Val Gly Asp His Gln Ala
```

-continued

```
                85                  90                  95

Ala Met Gln Ile Ile Arg Asp Ile Ile Asn Glu Glu Ala
            100                 105

<210> SEQ ID NO 91
<211> LENGTH: 134
<212> TYPE: PRT
<213> ORGANISM: Artificial sequence
<220> FEATURE:
<223> OTHER INFORMATION: Recombinant antigenic insert peptide.

<400> SEQUENCE: 91

Leu Asp Arg Phe Gly Leu Ala Glu Ser Leu Glu Asn Lys Glu Gly
1               5                   10                  15

Ser Gln Lys Ile Leu Ser Val Leu Ala Pro Leu Val Pro Thr Gly Ser
            20                  25                  30

Glu Asn Leu Lys Ser Leu Tyr Asn Thr Val Thr Arg Val Lys His Thr
        35                  40                  45

Glu Glu Ala Lys Gln Ile Val Gln Arg His Leu Val Glu Thr Gly
    50                  55                  60

Thr Thr Glu Thr Arg Leu Pro Leu Ser Pro Arg Thr Leu Asn Ala Trp
65                  70                  75                  80

Val Lys Leu Ile Glu Glu Lys Lys Phe Gly Ala Glu Val Val Pro Gly
                85                  90                  95

Phe Gln Ala Leu Ser Glu Gly Cys Thr Pro Tyr Asp Ile Asn Gln Met
            100                 105                 110

Leu Asn Cys Val Gly Asp His Gln Ala Ala Met Gln Ile Ile Arg Asp
        115                 120                 125

Ile Ile Asn Glu Glu Ala
    130

<210> SEQ ID NO 92
<211> LENGTH: 9
<212> TYPE: PRT
<213> ORGANISM: Human immunodeficiency virus

<400> SEQUENCE: 92

Cys Thr Pro Tyr Asp Ile Asn Gln Met
1               5

<210> SEQ ID NO 93
<211> LENGTH: 9
<212> TYPE: PRT
<213> ORGANISM: Human immunodeficiency virus

<400> SEQUENCE: 93

Gly Ser Glu Asn Leu Lys Ser Leu Tyr
1               5

<210> SEQ ID NO 94
<211> LENGTH: 11
<212> TYPE: PRT
<213> ORGANISM: Human immunodeficiency virus

<400> SEQUENCE: 94

Lys Ile Leu Ser Val Leu Ala Pro Leu Val Pro
1               5                   10

<210> SEQ ID NO 95
<211> LENGTH: 16
<212> TYPE: PRT
```

<213> ORGANISM: Human immunodeficiency virus

<400> SEQUENCE: 95

Thr Glu Glu Ala Lys Gln Ile Val Gln Arg His Leu Val Val Glu Thr
1               5                   10                  15

<210> SEQ ID NO 96
<211> LENGTH: 11
<212> TYPE: PRT
<213> ORGANISM: Human immunodeficiency virus

<400> SEQUENCE: 96

Met Gln Ile Ile Arg Asp Ile Ile Asn Glu Glu
1               5                   10

<210> SEQ ID NO 97
<211> LENGTH: 9
<212> TYPE: PRT
<213> ORGANISM: Human immunodeficiency virus

<400> SEQUENCE: 97

Thr Arg Ala Asn Ser Pro Thr Arg Arg
1               5

<210> SEQ ID NO 98
<211> LENGTH: 8
<212> TYPE: PRT
<213> ORGANISM: Human immunodeficiency virus

<400> SEQUENCE: 98

Asn Ser Pro Thr Arg Arg Glu Leu
1               5

<210> SEQ ID NO 99
<211> LENGTH: 9
<212> TYPE: PRT
<213> ORGANISM: Human immunodeficiency virus

<400> SEQUENCE: 99

Pro Thr Arg Arg Glu Leu Gln Val Trp
1               5

<210> SEQ ID NO 100
<211> LENGTH: 9
<212> TYPE: PRT
<213> ORGANISM: Human immunodeficiency virus

<400> SEQUENCE: 100

Pro Thr Ser Arg Glu Leu Gln Val Trp
1               5

<210> SEQ ID NO 101
<211> LENGTH: 9
<212> TYPE: PRT
<213> ORGANISM: Human immunodeficiency virus

<400> SEQUENCE: 101

Ala Gly Ala Glu Arg Gln Gly Thr Leu
1               5

<210> SEQ ID NO 102
<211> LENGTH: 9
<212> TYPE: PRT
<213> ORGANISM: Human immunodeficiency virus

<400> SEQUENCE: 102

Phe Ser Phe Pro Gln Ile Thr Leu Trp
1               5

<210> SEQ ID NO 103
<211> LENGTH: 171
<212> TYPE: PRT
<213> ORGANISM: Human immunodeficiency virus

<400> SEQUENCE: 103

Leu Asp Arg Phe Gly Leu Ala Glu Ser Leu Leu Glu Asn Lys Glu Gly
1               5                   10                  15

Cys Gln Lys Ile Leu Ser Val Leu Ala Pro Leu Val Pro Thr Gly Ser
            20                  25                  30

Glu Asn Leu Lys Ser Leu Tyr Asn Thr Val Cys Val Ile Trp Cys Ile
        35                  40                  45

His Ala Glu Glu Lys Val Lys His Thr Glu Glu Ala Lys Gln Ile Val
    50                  55                  60

Gln Arg His Leu Val Val Glu Thr Gly Thr Thr Glu Thr Met Pro Lys
65                  70                  75                  80

Thr Ser Arg Pro Thr Ala Pro Ser Ser Gly Arg Gly Gly Asn Tyr Pro
                85                  90                  95

Val Gln Gln Ile Gly Gly Asn Tyr Val His Leu Pro Leu Ser Pro Arg
            100                 105                 110

Thr Leu Asn Ala Trp Val Lys Leu Ile Glu Glu Lys Lys Phe Gly Ala
        115                 120                 125

Glu Val Val Pro Gly Phe Gln Ala Leu Ser Glu Gly Cys Thr Pro Tyr
    130                 135                 140

Asp Ile Asn Gln Met Leu Asn Cys Val Gly Asp His Gln Ala Ala Met
145                 150                 155                 160

Gln Ile Ile Arg Asp Ile Ile Asn Glu Glu Ala
                165                 170

<210> SEQ ID NO 104
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 104
gatgacgagg cgctcatcc                                              19

<210> SEQ ID NO 105
<211> LENGTH: 23
<212> TYPE: DNA
<213> ORGANISM: Artificial Sequence
<220> FEATURE:
<223> OTHER INFORMATION: synthetic oligonucleotide primer

<400> SEQUENCE: 105
gagtgccgcg ggcgtccgag tgc                                         23

<210> SEQ ID NO 106
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 106
cgaactggtg agccccatgg                                               20

<210> SEQ ID NO 107
<211> LENGTH: 25
<212> TYPE: DNA
<213> ORGANISM: Artificial Sequence
<220> FEATURE:
<223> OTHER INFORMATION: synthetic oligonucleotide primer

<400> SEQUENCE: 107
gatctcgcaa atgcaggctc cagtg                                         25

<210> SEQ ID NO 108
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 108
gaagcaccta ggtcagccca agaaaagaat gaaaagaat tattggaatt ggataaatgg    60

<210> SEQ ID NO 109
<211> LENGTH: 50
<212> TYPE: DNA
<213> ORGANISM: Artificial Sequence
<220> FEATURE:
<223> OTHER INFORMATION: synthetic oligonucleotide primer

<400> SEQUENCE: 109
tgatctagat gcatctatga atagtcttat ataccacagc cagtttgtta              50

<210> SEQ ID NO 110
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 110
gaacagacta gtgcccaaga aagaatgaa aagaattat tggaattgga taaatgg        57

<210> SEQ ID NO 111
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 111
ccagcagatg catcattcca caaacttgcc catttatcca attccaataa ttcttttc     59

<210> SEQ ID NO 112
<211> LENGTH: 50
<212> TYPE: DNA
<213> ORGANISM: Artificial Sequence
<220> FEATURE:
<223> OTHER INFORMATION: synthetic oligonucleotide primer

<400> SEQUENCE: 112
gaacagacta gttggaattg gtttgacata acaaactggc tgtggtatat              50

<210> SEQ ID NO 113
<211> LENGTH: 47
<212> TYPE: DNA

```
<213> ORGANISM: Artificial Sequence
<220> FEATURE:
<223> OTHER INFORMATION: synthetic oligonucleotide primer

<400> SEQUENCE: 113
ccagcagatg catctagtct tataccac agccagtttg ttatgtc                            47

<210> SEQ ID NO 114
<211> LENGTH: 54
<212> TYPE: DNA
<213> ORGANISM: Artificial Sequence
<220> FEATURE:
<223> OTHER INFORMATION: synthetic oligonucleotide primer

<400> SEQUENCE: 114
agatagcgcc tagggaagga agccaaaaaa tactttcggt cttagctcca ttag                  54

<210> SEQ ID NO 115
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 115
tggcgatgat gcatcttctg cgtgaattga ccagatgacc gagacagtat tataaaggct            60

<210> SEQ ID NO 116
<211> LENGTH: 40
<212> TYPE: DNA
<213> ORGANISM: Artificial Sequence
<220> FEATURE:
<223> OTHER INFORMATION: synthetic oligonucleotide primer

<400> SEQUENCE: 116
agatagcgcc taggtttcag gcactgtcag aaggttgcac                                  40

<210> SEQ ID NO 117
<211> LENGTH: 41
<212> TYPE: DNA
<213> ORGANISM: Artificial Sequence
<220> FEATURE:
<223> OTHER INFORMATION: synthetic oligonucleotide primer

<400> SEQUENCE: 117
tgtaatgatg catcagcctc ctcgtttata atatctctga t                                41

<210> SEQ ID NO 118
<211> LENGTH: 42
<212> TYPE: DNA
<213> ORGANISM: Artificial Sequence
<220> FEATURE:
<223> OTHER INFORMATION: synthetic oligonucleotide primer

<400> SEQUENCE: 118
agatagcgcc taggctgcca ttaagcccga gaacattaaa tg                               42

<210> SEQ ID NO 119
<211> LENGTH: 48
<212> TYPE: DNA
<213> ORGANISM: Artificial Sequence
<220> FEATURE:
<223> OTHER INFORMATION: synthetic oligonucleotide primer

<400> SEQUENCE: 119
tggcgatgat gcatcactag tagcctcctc gtttataata tctctgat                         48
```

<210> SEQ ID NO 120
<211> LENGTH: 48
<212> TYPE: DNA
<213> ORGANISM: Artificial Sequence
<220> FEATURE:
<223> OTHER INFORMATION: synthetic oligonucleotide primer

<400> SEQUENCE: 120
gatagcgcct aggagccaga agatcctgag cgtgctggcc cctctggt            48

<210> SEQ ID NO 121
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 121
tgcgatgatg catcactagt gggcaccaga ggggccagca cgctcag             47

<210> SEQ ID NO 122
<211> LENGTH: 45
<212> TYPE: DNA
<213> ORGANISM: Artificial Sequence
<220> FEATURE:
<223> OTHER INFORMATION: synthetic oligonucleotide primer

<400> SEQUENCE: 122
gatagcgcct aggaccggca gcgagaacct gaagagcctg tacaa               45

<210> SEQ ID NO 123
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 123
tgcgatgatg catcactagt gttgtacagg ctcttcaggt tctcgct             47

<210> SEQ ID NO 124
<211> LENGTH: 64
<212> TYPE: DNA
<213> ORGANISM: Artificial Sequence
<220> FEATURE:
<223> OTHER INFORMATION: synthetic oligonucleotide primer

<400> SEQUENCE: 124
gatagcgcct agggtgaagc acaccgagga ggccaagcag atcgtgcagc gccacctggt    60
ggtg                                                                64

<210> SEQ ID NO 125
<211> LENGTH: 58
<212> TYPE: DNA
<213> ORGANISM: Artificial Sequence
<220> FEATURE:
<223> OTHER INFORMATION: synthetic oligonucleotide primer

<400> SEQUENCE: 125
tgcgatgatg catcactagt ggtgccggtc tccaccacca ggtggcgctg cacgatct      58

<210> SEQ ID NO 126
<211> LENGTH: 74
<212> TYPE: PRT

```
<213> ORGANISM: Artificial Sequence
<220> FEATURE:
<223> OTHER INFORMATION: MPERF insert

<400> SEQUENCE: 126

Phe Glu Glu Pro Arg Gln Glu Lys Asn Glu Lys Glu Leu Leu Glu Leu
1               5                   10                  15

Asp Lys Trp Ala Ser Leu Trp Asn Trp Phe Asp Met His Thr Leu Ala
            20                  25                  30

Ala Phe Val Leu Leu Val Pro Trp Val Leu Ile Phe Met Val Cys Arg
        35                  40                  45

Arg Thr Cys Arg Arg Arg Gly Ala Ala Ala Leu Thr Ala Val Val
    50                  55                  60

Leu Gln Gly Tyr Asn Pro Pro Ala Tyr Gly
65                  70

<210> SEQ ID NO 127
<211> LENGTH: 77
<212> TYPE: PRT
<213> ORGANISM: Artificial Sequence
<220> FEATURE:
<223> OTHER INFORMATION: MPERF insert

<400> SEQUENCE: 127

Gly Glu Glu Pro Arg Gln Glu Lys Asn Glu Lys Glu Leu Leu Glu Leu
1               5                   10                  15

Asp Lys Trp Ala Ser Leu Trp Asn Trp Phe Asp Met His Trp Trp Gln
            20                  25                  30

Leu Thr Gly Ala Thr Cys Ala Leu Pro Leu Ala Gly Leu Ala Cys
        35                  40                  45

Cys Ala Arg Arg Thr Cys Arg Arg Arg Gly Ala Ala Ala Leu Thr
    50                  55                  60

Ala Val Val Leu Gln Gly Tyr Asn Pro Pro Ala Tyr Gly
65                  70                  75

<210> SEQ ID NO 128
<211> LENGTH: 19
<212> TYPE: PRT
<213> ORGANISM: Artificial Sequence
<220> FEATURE:
<223> OTHER INFORMATION: MPERF insert

<400> SEQUENCE: 128

Gln Glu Lys Asn Glu Lys Glu Leu Leu Glu Leu Asp Lys Trp Ala Ser
1               5                   10                  15

Leu Trp Asn

<210> SEQ ID NO 129
<211> LENGTH: 15
<212> TYPE: PRT
<213> ORGANISM: Artificial Sequence
<220> FEATURE:
<223> OTHER INFORMATION: MPERE insert

<400> SEQUENCE: 129

Trp Asn Trp Phe Asp Ile Thr Asn Trp Leu Trp Tyr Ile Arg Leu
1               5                   10                  15

<210> SEQ ID NO 130
<211> LENGTH: 33
<212> TYPE: PRT
<213> ORGANISM: Artificial Sequence
```

```
<220> FEATURE:
<223> OTHER INFORMATION: MPER insert

<400> SEQUENCE: 130

Gln Glu Asn Glu Lys Glu Leu Leu Glu Leu Asp Lys Trp Ala Ser Leu
1               5                   10                  15

Trp Asn Trp Phe Asp Ile Thr Asn Trp Leu Trp Tyr Ile Arg Leu Phe
            20                  25                  30

Ile

<210> SEQ ID NO 131
<211> LENGTH: 86
<212> TYPE: PRT
<213> ORGANISM: Artificial Sequence
<220> FEATURE:
<223> OTHER INFORMATION: MPER-HIVTM  insert

<400> SEQUENCE: 131

Gly Glu Glu Pro Arg Gln Glu Lys Asn Glu Lys Glu Leu Leu Glu Leu
1               5                   10                  15

Asp Lys Trp Ala Ser Leu Trp Asn Trp Phe Asp Ile Thr Asn Trp Leu
            20                  25                  30

Trp Tyr Ile Arg Leu Phe Ile Met Ile Val Gly Gly Leu Ile Gly Leu
        35                  40                  45

Arg Ile Val Phe Ala Val Leu Ser Ile Val Cys Arg Arg Thr Cys Arg
    50                  55                  60

Arg Arg Gly Ala Ala Ala Ala Leu Thr Ala Val Val Leu Gln Gly Tyr
65                  70                  75                  80

Asn Pro Pro Ala Tyr Gly
                85

<210> SEQ ID NO 132
<211> LENGTH: 221
<212> TYPE: PRT
<213> ORGANISM: Artificial Sequence
<220> FEATURE:
<223> OTHER INFORMATION: SIV Gag insert (sGag-E2TM amino acids 41-211)

<400> SEQUENCE: 132

Leu Asp Arg Phe Gly Leu Ala Glu Ser Leu Leu Glu Asn Lys Glu Gly
1               5                   10                  15

Cys Gln Lys Ile Leu Ser Val Leu Ala Pro Leu Val Pro Thr Gly Ser
            20                  25                  30

Glu Asn Leu Lys Ser Leu Tyr Asn Thr Val Cys Val Ile Trp Cys Ile
        35                  40                  45

His Ala Glu Glu Lys Val Lys His Thr Glu Glu Ala Lys Gln Ile Val
    50                  55                  60

Gln Arg His Leu Val Val Glu Thr Gly Thr Thr Glu Thr Met Pro Lys
65                  70                  75                  80

Thr Ser Arg Pro Thr Ala Pro Ser Ser Gly Arg Gly Gly Asn Tyr Pro
                85                  90                  95

Val Gln Gln Ile Gly Gly Asn Tyr Val His Leu Pro Leu Ser Pro Arg
            100                 105                 110

Thr Leu Asn Ala Trp Val Lys Leu Ile Glu Glu Lys Lys Phe Gly Ala
        115                 120                 125

Glu Val Val Pro Gly Phe Gln Ala Leu Ser Glu Gly Cys Thr Pro Tyr
    130                 135                 140

Asp Ile Asn Gln Met Leu Asn Cys Val Gly Asp His Gln Ala Ala Met
```

```
                145                 150                 155                 160
Gln Ile Ile Arg Asp Ile Ile Asn Glu Glu Ala Ser Leu Asp Met His
                    165                 170                 175

Thr Leu Ala Ala Phe Val Leu Leu Val Pro Trp Val Leu Ile Phe Met
                    180                 185                 190

Val Cys Arg Arg Thr Cys Arg Arg Gly Ala Ala Ala Ala Leu Thr
                    195                 200                 205

Ala Val Val Leu Gln Gly Tyr Asn Pro Pro Ala Tyr Gly
                    210                 215                 220

<210> SEQ ID NO 133
<211> LENGTH: 184
<212> TYPE: PRT
<213> ORGANISM: Artificial Sequence
<220> FEATURE:
<223> OTHER INFORMATION: SIV Gag insert (SGag-E2TM, amino acids 135-271)

<400> SEQUENCE: 133

Tyr Pro Val Gln Gln Ile Gly Gly Asn Tyr Val His Leu Pro Leu Ser
1               5                   10                  15

Pro Arg Thr Leu Asn Ala Trp Val Lys Leu Ile Glu Glu Lys Lys Phe
                20                  25                  30

Gly Ala Glu Val Val Pro Gly Phe Gln Ala Leu Ser Glu Gly Cys Thr
            35                  40                  45

Pro Tyr Asp Ile Asn Gln Met Leu Asn Cys Val Gly Asp His Gln Ala
        50                  55                  60

Ala Met Gln Ile Ile Arg Asp Ile Ile Asn Glu Glu Ala Ala Asp Trp
65                  70                  75                  80

Asp Leu Gln His Pro Gln Pro Ala Pro Gln Gln Gly Gln Leu Arg Glu
                85                  90                  95

Pro Ser Gly Ser Asp Ile Ala Gly Thr Thr Ser Ser Val Asp Glu Gln
            100                 105                 110

Ile Gln Trp Met Tyr Arg Gln Gln Asn Pro Ile Pro Val Gly Asn Ile
        115                 120                 125

Tyr Arg Arg Trp Ile Gln Leu Gly Leu Met His Thr Leu Ala Ala Phe
    130                 135                 140

Val Leu Leu Val Pro Trp Val Leu Ile Phe Met Val Cys Arg Arg Thr
145                 150                 155                 160

Cys Arg Arg Gly Ala Ala Ala Ala Leu Thr Ala Val Val Leu Gln
                165                 170                 175

Gly Tyr Asn Pro Pro Ala Tyr Gly
            180

<210> SEQ ID NO 134
<211> LENGTH: 276
<212> TYPE: PRT
<213> ORGANISM: Artificial Sequence
<220> FEATURE:
<223> OTHER INFORMATION: SIV Gag insert (full p28-sGag-E2TM)

<400> SEQUENCE: 134

Tyr Pro Val Gln Gln Ile Gly Gly Asn Tyr Val His Leu Pro Leu Ser
1               5                   10                  15

Pro Arg Thr Leu Asn Ala Trp Val Lys Leu Ile Glu Glu Lys Lys Phe
                20                  25                  30

Gly Ala Glu Val Val Pro Gly Phe Gln Ala Leu Ser Glu Gly Cys Thr
            35                  40                  45
```

```
Pro Tyr Asp Ile Asn Gln Met Leu Asn Cys Val Gly Asp His Gln Ala
    50                  55                  60

Ala Met Gln Ile Ile Arg Asp Ile Ile Asn Glu Glu Ala Ala Asp Trp
65                  70                  75                  80

Asp Leu Gln His Pro Gln Pro Ala Pro Gln Gln Gly Gln Leu Arg Glu
                85                  90                  95

Pro Ser Gly Ser Asp Ile Ala Gly Thr Thr Ser Ser Val Asp Glu Gln
            100                 105                 110

Ile Gln Trp Met Tyr Arg Gln Gln Asn Pro Ile Pro Val Gly Asn Ile
            115                 120                 125

Tyr Arg Arg Trp Ile Gln Leu Gly Leu Gln Lys Cys Val Arg Met Tyr
    130                 135                 140

Asn Pro Thr Asn Ile Leu Asp Val Lys Gln Gly Pro Lys Glu Pro Phe
145                 150                 155                 160

Gln Ser Tyr Val Asp Arg Phe Tyr Lys Ser Leu Arg Ala Glu Gln Thr
                165                 170                 175

Asp Ala Ala Val Lys Asn Trp Met Thr Gln Thr Leu Leu Ile Gln Asn
            180                 185                 190

Ala Asn Pro Asp Cys Lys Leu Val Leu Lys Gly Leu Gly Val Asn Pro
            195                 200                 205

Thr Leu Glu Glu Met Leu Thr Ala Cys Gln Gly Val Gly Gly Pro Gly
    210                 215                 220

Gln Lys Ala Arg Leu Met His Thr Leu Ala Ala Phe Val Leu Leu Val
225                 230                 235                 240

Pro Trp Val Leu Ile Phe Met Val Cys Arg Arg Thr Cys Arg Arg Arg
                245                 250                 255

Gly Ala Ala Ala Ala Leu Thr Ala Val Val Leu Gln Gly Tyr Asn Pro
            260                 265                 270

Pro Ala Tyr Gly
        275

<210> SEQ ID NO 135
<211> LENGTH: 304
<212> TYPE: PRT
<213> ORGANISM: Artificial Sequence
<220> FEATURE:
<223> OTHER INFORMATION: SIV Gag insert (fullp28 plus-sGag-E2TM)

<400> SEQUENCE: 135

Tyr Pro Val Gln Gln Ile Gly Gly Asn Tyr Val His Leu Pro Leu Ser
1               5                   10                  15

Pro Arg Thr Leu Asn Ala Trp Val Lys Leu Ile Glu Glu Lys Lys Phe
            20                  25                  30

Gly Ala Glu Val Val Pro Gly Phe Gln Ala Leu Ser Glu Gly Cys Thr
        35                  40                  45

Pro Tyr Asp Ile Asn Gln Met Leu Asn Cys Val Gly Asp His Gln Ala
    50                  55                  60

Ala Met Gln Ile Ile Arg Asp Ile Ile Asn Glu Glu Ala Ala Asp Trp
65                  70                  75                  80

Asp Leu Gln His Pro Gln Pro Ala Pro Gln Gln Gly Gln Leu Arg Glu
                85                  90                  95

Pro Ser Gly Ser Asp Ile Ala Gly Thr Thr Ser Ser Val Asp Glu Gln
            100                 105                 110

Ile Gln Trp Met Tyr Arg Gln Gln Asn Pro Ile Pro Val Gly Asn Ile
            115                 120                 125
```

```
Tyr Arg Arg Trp Ile Gln Leu Gly Leu Gln Lys Cys Val Arg Met Tyr
    130                 135                 140

Asn Pro Thr Asn Ile Leu Asp Val Lys Gln Gly Pro Lys Glu Pro Phe
145                 150                 155                 160

Gln Ser Tyr Val Asp Arg Phe Tyr Lys Ser Leu Arg Ala Glu Gln Thr
                165                 170                 175

Asp Ala Ala Val Lys Asn Trp Met Thr Gln Thr Leu Leu Ile Gln Asn
            180                 185                 190

Ala Asn Pro Asp Cys Lys Leu Val Leu Lys Gly Leu Gly Val Asn Pro
        195                 200                 205

Thr Leu Glu Glu Met Leu Thr Ala Cys Gln Gly Val Gly Gly Pro Gly
    210                 215                 220

Gln Lys Ala Arg Leu Met Ala Glu Ala Leu Lys Glu Ala Leu Ala Pro
225                 230                 235                 240

Val Pro Ile Pro Phe Ala Ala Ala Gln Gln Arg Gly Pro Arg Lys Pro
                245                 250                 255

Ile Met His Thr Leu Ala Ala Phe Val Leu Leu Val Pro Trp Val Leu
            260                 265                 270

Ile Phe Met Val Cys Arg Arg Thr Cys Arg Arg Arg Gly Ala Ala Ala
        275                 280                 285

Ala Leu Thr Ala Val Val Leu Gln Gly Tyr Asn Pro Pro Ala Tyr Gly
    290                 295                 300
```

<210> SEQ ID NO 136
<211> LENGTH: 367
<212> TYPE: PRT
<213> ORGANISM: Artificial Sequence
<220> FEATURE:
<223> OTHER INFORMATION: variant rubella construct

<400> SEQUENCE: 136

```
Gly Leu Gln Pro Arg Ala Asp Met Ala Ala Pro Pro Thr Leu Pro Gln
1               5                   10                  15

Pro Pro Arg Ala His Gly Gln His Tyr Gly His His His His Gln Leu
            20                  25                  30

Pro Phe Leu Gly His Asp Gly His His Gly Gly Thr Leu Arg Val Gly
        35                  40                  45

Gln His Tyr Arg Asn Ala Ser Asp Val Leu Pro Gly His Trp Leu Gln
    50                  55                  60

Gly Gly Trp Gly Cys Tyr Asn Leu Ser Asp Trp His Gln Gly Thr His
65                  70                  75                  80

Val Cys His Thr Lys His Met Asp Phe Trp Cys Val Glu His Ala Arg
                85                  90                  95

Pro Pro Pro Ala Thr Pro Thr Pro Leu Thr Thr Ala Ala Asn Ser Thr
            100                 105                 110

Thr Ala Ala Thr Pro Ala Thr Ala Pro Ala Pro Cys His Ala Gly Leu
        115                 120                 125

Asn Asp Ser Cys Gly Gly Phe Leu Ser Gly Cys Gly Pro Met Arg Leu
    130                 135                 140

Arg His Gly Ala Asp Thr Arg Cys Gly Arg Leu Ile Cys Gly Leu Ser
145                 150                 155                 160

Thr Thr Ala Gln Tyr Pro Pro Thr Arg Phe Gly Cys Ala Met Arg Trp
                165                 170                 175

Gly Leu Pro Pro Trp Glu Leu Val Val Leu Thr Ala Arg Pro Glu Asp
            180                 185                 190
```

```
Gly Trp Thr Cys Arg Gly Val Pro Ala His Pro Gly Ala Arg Cys Pro
            195                 200                 205

Glu Leu Val Ser Pro Met Gly Arg Ala Thr Cys Ser Pro Ala Ser Ala
    210                 215                 220

Leu Trp Leu Ala Thr Ala Asn Ala Leu Ser Leu Asp His Ala Leu Ala
225                 230                 235                 240

Ala Phe Val Leu Leu Val Pro Trp Val Leu Ile Phe Met Val Cys Arg
                245                 250                 255

Arg Ala Cys Arg Arg Gly Ala Ala Ala Leu Thr Ala Val Val
            260                 265                 270

Leu Gln Gly Tyr Asn Pro Pro Ala Tyr Gly Glu Glu Pro Arg Gln Glu
            275                 280                 285

Lys Asn Glu Lys Glu Leu Leu Glu Leu Asp Lys Trp Ala Ser Leu Trp
    290                 295                 300

Asn Trp Phe Asp Ile Thr Asn Trp Leu Trp Tyr Ile Arg Leu Phe Ile
305                 310                 315                 320

Met Ile Val Gly Gly Leu Ile Gly Leu Arg Ile Val Phe Ala Val Leu
                325                 330                 335

Ser Ile Val Cys Arg Arg Thr Cys Arg Arg Gly Ala Ala Ala
            340                 345                 350

Leu Thr Ala Val Val Leu Gln Gly Tyr Asn Pro Pro Ala Tyr Gly
            355                 360                 365

<210> SEQ ID NO 137
<211> LENGTH: 142
<212> TYPE: PRT
<213> ORGANISM: Artificial Sequence
<220> FEATURE:
<223> OTHER INFORMATION: MPER construct

<400> SEQUENCE: 137

Pro Arg Asn Asn Leu Leu Arg Ala Ile Glu Ala Gln Gln His Met Leu
1               5                   10                  15

Gln Leu Thr Val Trp Gly Ile Lys Gln Leu Gln Ala Arg Gly Gly
            20                  25                  30

Gly Ser Gly Gly Gly Ser Gly Gly Gly Ser Trp Met Glu Trp
        35                  40                  45

Glu Arg Glu Ile Asp Asn Tyr Thr Asp Tyr Ile Tyr Asp Leu Leu Glu
    50                  55                  60

Lys Ser Gln Thr Gln Gln Glu Lys Asn Glu Lys Glu Leu Leu Glu Leu
65                  70                  75                  80

Asp Lys Trp Ala Ser Leu Trp Asn Trp Phe Asp Ile Thr Asn Trp Leu
                85                  90                  95

Trp Tyr Ile Arg Leu Phe Ile Met Ile Val Gly Gly Leu Ile Gly Leu
            100                 105                 110

Arg Ile Val Phe Ala Val Leu Ser Ile Val Cys Arg Arg Thr Cys Arg
            115                 120                 125

Arg Arg Gly Ala Ala Ala Ala Leu Thr Ala Val Val Leu Gln
        130                 135                 140

<210> SEQ ID NO 138
<211> LENGTH: 220
<212> TYPE: PRT
<213> ORGANISM: Artificial Sequence
<220> FEATURE:
<223> OTHER INFORMATION: HIV Gag insert

<400> SEQUENCE: 138
```

```
Leu Glu Arg Phe Ala Val Asn Pro Ser Leu Leu Thr Ser Glu Gly
1               5                   10                  15

Cys Arg Gln Ile Leu Gly Gln Leu Gln Ser Ser Leu Gln Thr Gly Ser
                20                  25                  30

Glu Glu Leu Lys Ser Leu Tyr Asn Thr Val Ala Thr Leu Tyr Cys Val
            35                  40                  45

His Gln Arg Ile Glu Val Lys Asp Thr Lys Glu Ala Leu Asp Lys Ile
    50                  55                  60

Glu Glu Gln Asn Lys Ser Lys Lys Ala Gln Gln Ala Ala Ala
65                  70                  75                  80

Asp Thr Gly Asn Ser Ser Gln Val Ser Gln Asn Tyr Pro Ile Val Gln
                85                  90                  95

Asn Ile Gln Gly Gln Met Val His Gln Ala Ile Ser Pro Arg Thr Leu
            100                 105                 110

Asn Ala Trp Val Lys Val Val Glu Glu Lys Ala Phe Ser Pro Glu Val
        115                 120                 125

Ile Pro Met Phe Ser Ala Leu Ser Glu Gly Ala Thr Pro Gln Asp Leu
    130                 135                 140

Asn Thr Met Leu Asn Thr Val Gly Gly His Gln Ala Ala Met Gln Met
145                 150                 155                 160

Leu Lys Glu Thr Ile Asn Glu Glu Ala Ala Glu Trp Asp Met His Thr
                165                 170                 175

Leu Ala Ala Phe Val Leu Leu Val Pro Trp Val Leu Ile Phe Met Val
            180                 185                 190

Cys Arg Arg Thr Cys Arg Arg Arg Gly Ala Ala Ala Leu Thr Ala
        195                 200                 205

Val Val Leu Gln Gly Tyr Asn Pro Pro Ala Tyr Gly
    210                 215                 220

<210> SEQ ID NO 139
<211> LENGTH: 186
<212> TYPE: PRT
<213> ORGANISM: Artificial Sequence
<220> FEATURE:
<223> OTHER INFORMATION: HIV Gag insert

<400> SEQUENCE: 139

Tyr Pro Ile Val Gln Asn Ile Gln Gly Gln Met Val His Gln Ala Ile
1               5                   10                  15

Ser Pro Arg Thr Leu Asn Ala Trp Val Lys Val Val Glu Glu Lys Ala
                20                  25                  30

Phe Ser Pro Glu Val Ile Pro Met Phe Ser Ala Leu Ser Glu Gly Ala
            35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Leu His Pro Val Gln Ala Gly Pro Val Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
    115                 120                 125

Glu Ile Tyr Lys Arg Trp Ile Ile Leu Gly Leu Met His Thr Leu Ala
    130                 135                 140
```

```
Ala Phe Val Leu Leu Val Pro Trp Val Leu Ile Phe Met Val Cys Arg
145                 150                 155                 160

Arg Thr Cys Arg Arg Arg Gly Ala Ala Ala Ala Leu Thr Ala Val Val
                165                 170                 175

Leu Gln Gly Tyr Asn Pro Pro Ala Tyr Gly
            180                 185
```

<210> SEQ ID NO 140
<211> LENGTH: 278
<212> TYPE: PRT
<213> ORGANISM: Artificial Sequence
<220> FEATURE:
<223> OTHER INFORMATION: HIV Gag insert

<400> SEQUENCE: 140

```
Tyr Pro Ile Val Gln Asn Ile Gln Gly Gln Met Val His Gln Ala Ile
1               5                   10                  15

Ser Pro Arg Thr Leu Asn Ala Trp Val Lys Val Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Leu His Pro Val Gln Ala Gly Pro Val Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Gln Lys Cys Val Arg
    130                 135                 140

Met Tyr Asn Pro Thr Asn Ile Leu Asp Val Lys Gln Gly Pro Lys Glu
145                 150                 155                 160

Pro Phe Gln Ser Tyr Val Asp Arg Phe Tyr Lys Ser Leu Arg Ala Glu
                165                 170                 175

Gln Thr Asp Ala Ala Val Lys Asn Trp Met Thr Gln Thr Leu Leu Ile
            180                 185                 190

Gln Asn Ala Asn Pro Asp Cys Lys Leu Val Leu Lys Gly Leu Gly Val
        195                 200                 205

Asn Pro Thr Leu Glu Glu Met Leu Thr Ala Cys Gln Gly Val Gly Gly
    210                 215                 220

Pro Gly Gln Lys Ala Arg Leu Met His Thr Leu Ala Ala Phe Val Leu
225                 230                 235                 240

Leu Val Pro Trp Val Leu Ile Phe Met Val Cys Arg Arg Thr Cys Arg
                245                 250                 255

Arg Arg Gly Ala Ala Ala Ala Leu Thr Ala Val Val Leu Gln Gly Tyr
            260                 265                 270

Asn Pro Pro Ala Tyr Gly
        275
```

<210> SEQ ID NO 141
<211> LENGTH: 370
<212> TYPE: PRT
<213> ORGANISM: Artificial Sequence
<220> FEATURE:
<223> OTHER INFORMATION: SGAG(41-363)-E2TM Gag insert

<400> SEQUENCE: 141

```
Leu Asp Arg Phe Gly Leu Ala Glu Ser Leu Leu Glu Asn Lys Glu Gly
1               5                   10                  15

Cys Gln Lys Ile Leu Ser Val Leu Ala Pro Leu Val Pro Thr Gly Ser
                20                  25                  30

Glu Asn Leu Lys Ser Leu Tyr Asn Thr Val Cys Val Ile Trp Cys Ile
            35                  40                  45

His Ala Glu Glu Lys Val Lys His Thr Glu Glu Ala Lys Gln Ile Val
        50                  55                  60

Gln Arg His Leu Val Val Glu Thr Gly Thr Thr Glu Thr Met Pro Lys
65                  70                  75                  80

Thr Ser Arg Pro Thr Ala Pro Ser Ser Gly Arg Gly Gly Asn Tyr Pro
                85                  90                  95

Val Gln Gln Ile Gly Gly Asn Tyr Val His Leu Pro Leu Ser Pro Arg
                100                 105                 110

Thr Leu Asn Ala Trp Val Lys Leu Ile Glu Glu Lys Lys Phe Gly Ala
            115                 120                 125

Glu Val Val Pro Gly Phe Gln Ala Leu Ser Glu Gly Cys Thr Pro Tyr
        130                 135                 140

Asp Ile Asn Gln Met Leu Asn Cys Val Gly Asp His Gln Ala Ala Met
145                 150                 155                 160

Gln Ile Ile Arg Asp Ile Ile Asn Glu Glu Ala Ala Asp Trp Asp Leu
                165                 170                 175

Gln His Pro Gln Pro Ala Pro Gln Gln Gly Gln Leu Arg Glu Pro Ser
                180                 185                 190

Gly Ser Asp Ile Ala Gly Thr Thr Ser Ser Val Asp Glu Gln Ile Gln
            195                 200                 205

Trp Met Tyr Arg Gln Gln Asn Pro Ile Pro Val Gly Asn Ile Tyr Arg
        210                 215                 220

Arg Trp Ile Gln Leu Gly Leu Gln Lys Cys Val Arg Met Tyr Asn Pro
225                 230                 235                 240

Thr Asn Ile Leu Asp Val Lys Gln Gly Pro Lys Glu Pro Phe Gln Ser
                245                 250                 255

Tyr Val Asp Arg Phe Tyr Lys Ser Leu Arg Ala Glu Gln Thr Asp Ala
                260                 265                 270

Ala Val Lys Asn Trp Met Thr Gln Thr Leu Leu Ile Gln Asn Ala Asn
            275                 280                 285

Pro Asp Cys Lys Leu Val Leu Lys Gly Leu Gly Val Asn Pro Thr Leu
        290                 295                 300

Glu Glu Met Leu Thr Ala Cys Gln Gly Val Gly Gly Pro Gly Gln Lys
305                 310                 315                 320

Ala Arg Leu Met His Thr Leu Ala Ala Phe Val Leu Leu Val Pro Trp
                325                 330                 335

Val Leu Ile Phe Met Val Cys Arg Arg Thr Cys Arg Arg Arg Gly Ala
                340                 345                 350

Ala Ala Ala Leu Thr Ala Val Val Leu Gln Gly Tyr Asn Pro Pro Ala
            355                 360                 365

Tyr Gly
    370
```

<210> SEQ ID NO 142

```
<211> LENGTH: 398
<212> TYPE: PRT
<213> ORGANISM: Artificial Sequence
<220> FEATURE:
<223> OTHER INFORMATION: SGAG(41-391)-E2TM Gag insert

<400> SEQUENCE: 142
```

| | | | | | | | | | | | | | | |
|---|---|---|---|---|---|---|---|---|---|---|---|---|---|---|
| Leu | Asp | Arg | Phe | Gly | Leu | Ala | Glu | Ser | Leu | Leu | Glu | Asn | Lys | Gly |
| 1 | | | | 5 | | | | | 10 | | | | | 15 |
| Cys | Gln | Lys | Ile | Leu | Ser | Val | Leu | Ala | Pro | Leu | Val | Pro | Thr | Gly | Ser |
| | | | 20 | | | | | 25 | | | | | 30 | | |
| Glu | Asn | Leu | Lys | Ser | Leu | Tyr | Asn | Thr | Val | Cys | Val | Ile | Trp | Cys | Ile |
| | | | 35 | | | | 40 | | | | | 45 | | | |
| His | Ala | Glu | Glu | Lys | Val | Lys | His | Thr | Glu | Glu | Ala | Lys | Gln | Ile | Val |
| | 50 | | | | | 55 | | | | | 60 | | | | |
| Gln | Arg | His | Leu | Val | Val | Glu | Thr | Gly | Thr | Thr | Glu | Thr | Met | Pro | Lys |
| 65 | | | | | 70 | | | | | 75 | | | | | 80 |
| Thr | Ser | Arg | Pro | Thr | Ala | Pro | Ser | Ser | Gly | Arg | Gly | Gly | Asn | Tyr | Pro |
| | | | | 85 | | | | | 90 | | | | | 95 | |
| Val | Gln | Gln | Ile | Gly | Gly | Asn | Tyr | Val | His | Leu | Pro | Leu | Ser | Pro | Arg |
| | | | 100 | | | | | 105 | | | | | 110 | | |
| Thr | Leu | Asn | Ala | Trp | Val | Lys | Leu | Ile | Glu | Glu | Lys | Lys | Phe | Gly | Ala |
| | | | 115 | | | | | 120 | | | | | 125 | | |
| Glu | Val | Val | Pro | Gly | Phe | Gln | Ala | Leu | Ser | Glu | Gly | Cys | Thr | Pro | Tyr |
| | 130 | | | | | 135 | | | | | 140 | | | | |
| Asp | Ile | Asn | Gln | Met | Leu | Asn | Cys | Val | Gly | Asp | His | Gln | Ala | Ala | Met |
| 145 | | | | | 150 | | | | | 155 | | | | | 160 |
| Gln | Ile | Ile | Arg | Asp | Ile | Ile | Asn | Glu | Glu | Ala | Ala | Asp | Trp | Asp | Leu |
| | | | | 165 | | | | | 170 | | | | | 175 | |
| Gln | His | Pro | Gln | Pro | Ala | Pro | Gln | Gln | Gly | Gln | Leu | Arg | Glu | Pro | Ser |
| | | | 180 | | | | | 185 | | | | | 190 | | |
| Gly | Ser | Asp | Ile | Ala | Gly | Thr | Thr | Ser | Ser | Val | Asp | Glu | Gln | Ile | Gln |
| | | | 195 | | | | | 200 | | | | | 205 | | |
| Trp | Met | Tyr | Arg | Gln | Gln | Asn | Pro | Ile | Pro | Val | Gly | Asn | Ile | Tyr | Arg |
| | 210 | | | | | 215 | | | | | 220 | | | | |
| Arg | Trp | Ile | Gln | Leu | Gly | Leu | Gln | Lys | Cys | Val | Arg | Met | Tyr | Asn | Pro |
| 225 | | | | | 230 | | | | | 235 | | | | | 240 |
| Thr | Asn | Ile | Leu | Asp | Val | Lys | Gln | Gly | Pro | Lys | Glu | Pro | Phe | Gln | Ser |
| | | | | 245 | | | | | 250 | | | | | 255 | |
| Tyr | Val | Asp | Arg | Phe | Tyr | Lys | Ser | Leu | Arg | Ala | Glu | Gln | Thr | Asp | Ala |
| | | | 260 | | | | | 265 | | | | | 270 | | |
| Ala | Val | Lys | Asn | Trp | Met | Thr | Gln | Thr | Leu | Leu | Ile | Gln | Asn | Ala | Asn |
| | | | 275 | | | | | 280 | | | | | 285 | | |
| Pro | Asp | Cys | Lys | Leu | Val | Leu | Lys | Gly | Leu | Gly | Val | Asn | Pro | Thr | Leu |
| | 290 | | | | | 295 | | | | | 300 | | | | |
| Glu | Glu | Met | Leu | Thr | Ala | Cys | Gln | Gly | Val | Gly | Gly | Pro | Gly | Gln | Lys |
| 305 | | | | | 310 | | | | | 315 | | | | | 320 |
| Ala | Arg | Leu | Met | Ala | Glu | Ala | Leu | Lys | Glu | Ala | Leu | Ala | Pro | Val | Pro |
| | | | | 325 | | | | | 330 | | | | | 335 | |
| Ile | Pro | Phe | Ala | Ala | Ala | Gln | Gln | Arg | Gly | Pro | Arg | Lys | Pro | Ile | Met |
| | | | 340 | | | | | 345 | | | | | 350 | | |
| His | Thr | Leu | Ala | Ala | Phe | Val | Leu | Leu | Val | Pro | Trp | Val | Leu | Ile | Phe |
| | | | 355 | | | | | 360 | | | | | 365 | | |
| Met | Val | Cys | Arg | Arg | Thr | Cys | Arg | Arg | Gly | Ala | Ala | Ala | Ala | Leu |
| | 370 | | | | | 375 | | | | | 380 | | | | |

```
Thr Ala Val Val Leu Gln Gly Tyr Asn Pro Pro Ala Tyr Gly
385                 390                 395
```

<210> SEQ ID NO 143
<211> LENGTH: 82
<212> TYPE: PRT
<213> ORGANISM: Artificial Sequence
<220> FEATURE:
<223> OTHER INFORMATION: MPER-E2TM

<400> SEQUENCE: 143

```
Glu Glu Pro Arg Gln Glu Lys Asn Glu Lys Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Arg Met His Thr Leu Ala Ala Phe Val Leu Val Pro Trp
        35                  40                  45

Val Leu Ile Phe Met Val Cys Arg Arg Thr Cys Arg Arg Gly Ala
    50                  55                  60

Ala Ala Ala Leu Thr Ala Val Val Leu Gln Gly Tyr Asn Pro Pro Ala
65                  70                  75                  80

Tyr Gly
```

<210> SEQ ID NO 144
<211> LENGTH: 86
<212> TYPE: PRT
<213> ORGANISM: Artificial Sequence
<220> FEATURE:
<223> OTHER INFORMATION: MPER-E1TM insert

<400> SEQUENCE: 144

```
Glu Glu Pro Arg Gln Glu Lys Asn Glu Lys Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Arg Met His Trp Trp Gln Leu Thr Leu Gly Ala Thr Cys Ala
        35                  40                  45

Leu Pro Leu Ala Gly Leu Leu Ala Cys Cys Ala Arg Arg Thr Cys Arg
    50                  55                  60

Arg Arg Gly Ala Ala Ala Ala Leu Thr Ala Val Val Leu Gln Gly Tyr
65                  70                  75                  80

Asn Pro Pro Ala Tyr Gly
                85
```

<210> SEQ ID NO 145
<211> LENGTH: 89
<212> TYPE: PRT
<213> ORGANISM: Artificial Sequence
<220> FEATURE:
<223> OTHER INFORMATION: MPER-HIVTM-E2SP

<400> SEQUENCE: 145

```
Glu Glu Pro Arg Gln Glu Lys Asn Glu Lys Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Arg Leu Phe Ile Met Ile Val Gly Gly Leu Ile Gly Leu Arg
        35                  40                  45

Ile Val Phe Ala Val Leu Ser Ile Val Cys Arg Arg Thr Cys Arg Arg
```

```
                50                  55                  60
Arg Phe Gly Ala Pro Gln Ala Phe Leu Ala Gly Leu Leu Ala Ala
 65                  70                  75                  80

Val Ala Val Gly Thr Ala Arg Ala Gly
                 85

<210> SEQ ID NO 146
<211> LENGTH: 165
<212> TYPE: PRT
<213> ORGANISM: Artificial Sequence
<220> FEATURE:
<223> OTHER INFORMATION: BC-SGAG2-MPER-HIVTM insert

<400> SEQUENCE: 146

Glu Glu Pro Arg Val Pro Thr Gly Ser Glu Asn Leu Lys Ser Leu Tyr
 1               5                  10                  15

Asn Thr Val Thr Arg Val Lys His Thr Glu Ala Lys Gln Ile Val
                 20                  25                  30

Gln Arg His Leu Val Val Glu Thr Gly Thr Thr Ser Asp Ala Phe Gln
             35                  40                  45

Ala Leu Ser Glu Gly Cys Thr Pro Tyr Asp Ile Asn Gln Met Leu Asn
 50                  55                  60

Cys Val Gly Asp His Gln Ala Ala Met Gln Ile Ile Arg Asp Ile Ile
 65                  70                  75                  80

Asn Glu Glu Ala Gln Glu Lys Asn Glu Lys Glu Leu Leu Glu Leu Asp
                 85                  90                  95

Lys Trp Ala Ser Leu Trp Asn Trp Phe Asp Ile Thr Asn Trp Leu Trp
               100                 105                 110

Tyr Ile Arg Leu Phe Ile Met Ile Val Gly Gly Leu Ile Gly Leu Arg
           115                 120                 125

Ile Val Phe Ala Val Leu Ser Ile Val Cys Arg Arg Thr Cys Arg Arg
       130                 135                 140

Arg Gly Ala Ala Ala Ala Leu Thr Ala Val Val Leu Gln Gly Tyr Asn
145                 150                 155                 160

Pro Pro Ala Tyr Gly
                165

<210> SEQ ID NO 147
<211> LENGTH: 161
<212> TYPE: PRT
<213> ORGANISM: Artificial Sequence
<220> FEATURE:
<223> OTHER INFORMATION: MPER-BC-SGAG2-E2TM insert

<400> SEQUENCE: 147

Glu Glu Pro Arg Gln Glu Lys Asn Glu Lys Glu Leu Leu Glu Leu Asp
 1               5                  10                  15

Lys Trp Ala Ser Leu Trp Asn Trp Phe Asp Ile Thr Asn Trp Leu Val
                 20                  25                  30

Pro Thr Gly Ser Glu Asn Leu Lys Ser Leu Tyr Asn Thr Val Thr Arg
             35                  40                  45

Val Lys His Thr Glu Glu Ala Lys Gln Ile Val Gln Arg His Leu Val
 50                  55                  60

Val Glu Thr Gly Thr Thr Ser Asp Ala Phe Gln Ala Leu Ser Glu Gly
 65                  70                  75                  80

Cys Thr Pro Tyr Asp Ile Asn Gln Met Leu Asn Cys Val Gly Asp His
                 85                  90                  95
```

Gln Ala Ala Met Gln Ile Ile Arg Asp Ile Ile Asn Glu Glu Ala Ser
                100                 105                 110
Leu Asp Leu His Thr Leu Ala Ala Phe Val Leu Leu Val Pro Trp Val
            115                 120                 125
Leu Ile Phe Met Val Cys Arg Arg Thr Cys Arg Arg Arg Gly Ala Ala
        130                 135                 140
Ala Ala Leu Thr Ala Val Val Leu Gln Gly Tyr Asn Pro Pro Ala Tyr
145                 150                 155                 160
Gly

<210> SEQ ID NO 148
<211> LENGTH: 98
<212> TYPE: PRT
<213> ORGANISM: Artificial Sequence
<220> FEATURE:
<223> OTHER INFORMATION: 10e8-MPER-HIVTM insert

<400> SEQUENCE: 148

Glu Glu Pro Ser Leu Trp Asn Trp Phe Asp Ile Thr Asn Trp Leu Trp
1               5                   10                  15
Tyr Ile Arg Leu Asn Glu Lys Glu Leu Leu Glu Leu Asp Lys Trp Ala
            20                  25                  30
Ser Leu Trp Asn Trp Phe Asp Ile Thr Asn Trp Leu Trp Tyr Ile Arg
        35                  40                  45
Leu Phe Ile Met Ile Val Gly Gly Leu Ile Gly Leu Arg Ile Val Phe
    50                  55                  60
Ala Val Leu Ser Ile Val Cys Arg Arg Thr Cys Arg Arg Arg Gly Ala
65                  70                  75                  80
Ala Ala Ala Leu Thr Ala Val Val Leu Gln Gly Tyr Asn Pro Pro Ala
                85                  90                  95
Tyr Gly

<210> SEQ ID NO 149
<211> LENGTH: 95
<212> TYPE: PRT
<213> ORGANISM: Artificial Sequence
<220> FEATURE:
<223> OTHER INFORMATION: 10e8-MPER-E2TM insert

<400> SEQUENCE: 149

Glu Glu Pro Ser Leu Trp Asn Trp Phe Asp Ile Thr Asn Trp Leu Trp
1               5                   10                  15
Tyr Ile Arg Leu Asn Glu Lys Glu Leu Leu Glu Leu Asp Lys Trp Ala
            20                  25                  30
Ser Leu Trp Asn Trp Phe Asp Ile Thr Asn Trp Leu Trp Tyr Ile Arg
        35                  40                  45
Met His Thr Leu Ala Ala Phe Val Leu Leu Val Pro Trp Val Leu Ile
    50                  55                  60
Phe Met Val Cys Arg Arg Thr Cys Arg Arg Arg Gly Ala Ala Ala Ala
65                  70                  75                  80
Leu Thr Ala Val Val Leu Gln Gly Tyr Asn Pro Pro Ala Tyr Gly
                85                  90                  95

<210> SEQ ID NO 150
<211> LENGTH: 93
<212> TYPE: PRT
<213> ORGANISM: Artificial Sequence
<220> FEATURE:
<223> OTHER INFORMATION: MPERF-MPER-HIVTM

<400> SEQUENCE: 150

Glu Glu Lys Glu Leu Leu Glu Leu Asp Lys Trp Ala Ser Leu Trp Asn
1 5 10 15

Glu Lys Glu Leu Leu Glu Leu Asp Lys Trp Ala Ser Leu Trp Asn Trp
20 25 30

Phe Asp Ile Thr Asn Trp Leu Trp Tyr Ile Arg Leu Phe Ile Met Ile
35 40 45

Val Gly Gly Leu Ile Gly Leu Arg Ile Val Phe Ala Val Leu Ser Ile
50 55 60

Val Cys Arg Arg Thr Cys Arg Arg Arg Gly Ala Ala Ala Ala Leu Thr
65 70 75 80

Ala Val Val Leu Gln Gly Tyr Asn Pro Pro Ala Tyr Gly
85 90

<210> SEQ ID NO 151
<211> LENGTH: 90
<212> TYPE: PRT
<213> ORGANISM: Artificial Sequence
<220> FEATURE:
<223> OTHER INFORMATION: MPERF-MPER-E2TM

<400> SEQUENCE: 151

Glu Glu Lys Glu Leu Leu Glu Leu Asp Lys Trp Ala Ser Leu Trp Asn
1 5 10 15

Glu Lys Glu Leu Leu Glu Leu Asp Lys Trp Ala Ser Leu Trp Asn Trp
20 25 30

Phe Asp Ile Thr Asn Trp Leu Trp Tyr Ile Arg Met His Thr Leu Ala
35 40 45

Ala Phe Val Leu Leu Val Pro Trp Val Leu Ile Phe Met Val Cys Arg
50 55 60

Arg Thr Cys Arg Arg Arg Gly Ala Ala Ala Ala Leu Thr Ala Val Val
65 70 75 80

Leu Gln Gly Tyr Asn Pro Pro Ala Tyr Gly
85 90

<210> SEQ ID NO 152
<211> LENGTH: 344
<212> TYPE: PRT
<213> ORGANISM: Artificial Sequence
<220> FEATURE:
<223> OTHER INFORMATION: HIV gp120 insert

<400> SEQUENCE: 152

Glu Glu Pro Arg Asn Pro Gln Glu Val Val Leu Glu Asn Val Thr Glu
1 5 10 15

Asn Phe Asn Met Trp Lys Asn Asn Met Val Asp Gln Met His Glu Asp
20 25 30

Ile Ile Ser Leu Trp Asp Glu Ser Leu Lys Pro Cys Val Lys Leu Thr
35 40 45

Pro Leu Ser Val Gln Ala Cys Pro Lys Val Ser Phe Gln Pro Ile Ser
50 55 60

Ile Gly Gly Gly Ile Arg Pro Val Val Ser Thr Gln Leu Leu Leu Asn
65 70 75 80

Gly Ser Leu Ala Glu Glu Asp Ile Val Ile Arg Ser Glu Asn Phe Thr
85 90 95

Asp Asn Ala Lys Thr Ile Ile Val Gln Leu Asn Glu Ser Val Val Ile
100 105 110

```
Asn Cys Thr Arg Pro Asn Asn Thr Arg Gly Arg Arg Gly Asp Ile
            115                 120                 125

Arg Gln Ala His Cys Asn Ile Ser Arg Ala Lys Trp Asn Asn Thr Leu
130                 135                 140

Gln Gln Ile Val Ile Lys Leu Arg Glu Lys Phe Arg Asn Lys Thr Ile
145                 150                 155                 160

Ala Phe Asn Gln Ser Ser Gly Gly Asp Pro Glu Ile Val Met His Ser
                165                 170                 175

Phe Asn Cys Gly Gly Glu Phe Phe Tyr Cys Asn Thr Ala Gln Leu Phe
            180                 185                 190

Asn Ser Thr Trp Asn Val Thr Gly Gly Thr Asn Gly Thr Glu Gly Asn
            195                 200                 205

Asp Ile Ile Thr Leu Gln Cys Arg Ile Lys Gln Leu Ala Met Tyr Ala
            210                 215                 220

Pro Pro Ile Thr Gly Gln Ile Arg Cys Ser Ser Asn Ile Thr Gly Leu
225                 230                 235                 240

Leu Leu Thr Arg Asp Gly Gly Asn Ser Thr Glu Thr Glu Thr Glu Ile
                245                 250                 255

Phe Arg Pro Gly Gly Gly Asp Met Arg Asp Asn Trp Arg Ser Glu Leu
            260                 265                 270

Tyr Lys Tyr Lys Val Val Arg Ile Glu Pro Ile Gly Val Ala Pro Thr
            275                 280                 285

Arg Ala Lys Arg Gly Gly Gly Ser Met His Thr Leu Ala Ala Phe
            290                 295                 300

Val Leu Leu Val Pro Trp Val Leu Ile Phe Met Val Cys Arg Arg Thr
305                 310                 315                 320

Cys Arg Arg Arg Gly Ala Ala Ala Leu Thr Ala Val Val Leu Gln
                325                 330                 335

Gly Tyr Asn Pro Pro Ala Tyr Gly
                340

<210> SEQ ID NO 153
<211> LENGTH: 352
<212> TYPE: PRT
<213> ORGANISM: Artificial Sequence
<220> FEATURE:
<223> OTHER INFORMATION: HIV gp120 insert

<400> SEQUENCE: 153

Glu Glu Pro Arg Asn Pro Gln Glu Val Val Leu Glu Asn Val Thr Glu
1               5                   10                  15

Asn

```
Arg Gln Ala His Cys Asn Ile Ser Arg Ala Lys Trp Asn Asn Thr Leu
            130                 135                 140

Gln Gln Ile Val Ile Lys Leu Arg Glu Lys Phe Arg Asn Lys Thr Ile
145                 150                 155                 160

Ala Phe Asn Gln Ser Ser Gly Gly Asp Pro Glu Ile Val Met His Ser
                165                 170                 175

Phe Asn Cys Gly Gly Glu Phe Phe Tyr Cys Asn Thr Ala Gln Leu Phe
                180                 185                 190

Asn Ser Thr Trp Asn Val Thr Gly Thr Asn Gly Thr Glu Gly Asn
            195                 200                 205

Asp Ile Ile Thr Leu Gln Cys Arg Ile Lys Gln Leu Ala Met Tyr Ala
            210                 215                 220

Pro Pro Ile Thr Gly Gln Ile Arg Cys Ser Ser Asn Ile Thr Gly Leu
225                 230                 235                 240

Leu Leu Thr Arg Asp Gly Gly Asn Ser Thr Glu Thr Glu Thr Glu Ile
                245                 250                 255

Phe Arg Pro Gly Gly Asp Met Arg Asp Asn Trp Arg Ser Glu Leu
                260                 265                 270

Tyr Lys Tyr Lys Val Val Arg Ile Glu Pro Ile Gly Val Ala Pro Thr
            275                 280                 285

Arg Ala Lys Arg Gly Gly Gly Ser Met His Val Tyr Thr Ile Leu
290                 295                 300

Ala Val Ala Ser Ala Thr Val Ala Met Met Ile Gly Val Thr Val Ala
305                 310                 315                 320

Val Leu Cys Ala Cys Arg Arg Thr Cys Arg Arg Gly Ala Ala Ala
                325                 330                 335

Ala Leu Thr Ala Val Val Leu Gln Gly Tyr Asn Pro Pro Ala Tyr Gly
                340                 345                 350
```

<210> SEQ ID NO 154
<211> LENGTH: 349
<212> TYPE: PRT
<213> ORGANISM: Artificial Sequence
<220> FEATURE:
<223> OTHER INFORMATION: HIV gp120 insert

<400> SEQUENCE: 154

```
Glu Glu Pro Arg Asn Pro Gln Glu Val Val Leu Glu Asn Val Thr Glu
1               5                   10                  15

Asn Phe Asn Met Trp Lys Asn Asn Met Val Asp Gln Met His Glu Asp
            20                  25                  30

Ile Ile Ser Leu Trp Asp Glu Ser Leu Lys Pro Cys Val Lys Leu Thr
        35                  40                  45

Pro Leu Ser Val Gln Ala Cys Pro Lys Val Ser Phe Gln Pro Ile Ser
    50                  55                  60

Ile Gly Gly Gly Ile Arg Pro Val Val Ser Thr Gln Leu Leu Leu Asn
65                  70                  75                  80

Gly Ser Leu Ala Glu Glu Asp Ile Val Ile Arg Ser Glu Asn Phe Thr
                85                  90                  95

Asp Asn Ala Lys Thr Ile Ile Val Gln Leu Asn Glu Ser Val Val Ile
            100                 105                 110

Asn Cys Thr Arg Pro Asn Asn Asn Thr Arg Gly Arg Arg Gly Asp Ile
        115                 120                 125

Arg Gln Ala His Cys Asn Ile Ser Arg Ala Lys Trp Asn Asn Thr Leu
    130                 135                 140
```

```
Gln Gln Ile Val Ile Lys Leu Arg Glu Lys Phe Arg Asn Lys Thr Ile
145                 150                 155                 160

Ala Phe Asn Gln Ser Ser Gly Gly Asp Pro Glu Ile Val Met His Ser
                165                 170                 175

Phe Asn Cys Gly Gly Glu Phe Phe Tyr Cys Asn Thr Ala Gln Leu Phe
            180                 185                 190

Asn Ser Thr Trp Asn Val Thr Gly Gly Thr Asn Gly Thr Glu Gly Asn
        195                 200                 205

Asp Ile Ile Thr Leu Gln Cys Arg Ile Lys Gln Leu Ala Met Tyr Ala
            210                 215                 220

Pro Pro Ile Thr Gly Gln Ile Arg Cys Ser Ser Asn Ile Thr Gly Leu
225                 230                 235                 240

Leu Leu Thr Arg Asp Gly Gly Asn Ser Thr Glu Thr Glu Thr Glu Ile
                245                 250                 255

Phe Arg Pro Gly Gly Gly Asp Met Arg Asp Asn Trp Arg Ser Glu Leu
            260                 265                 270

Tyr Lys Tyr Lys Val Val Arg Ile Glu Pro Ile Gly Val Ala Pro Thr
        275                 280                 285

Arg Ala Lys Arg Gly Gly Gly Ser Met His Leu Phe Ile Met Ile
290                 295                 300

Val Gly Gly Leu Ile Gly Leu Arg Ile Val Phe Ala Val Leu Ser Ile
305                 310                 315                 320

Val Cys Arg Arg Thr Cys Arg Arg Gly Ala Ala Ala Leu Thr
                325                 330                 335

Ala Val Val Leu Gln Gly Tyr Asn Pro Pro Ala Tyr Gly
            340                 345

<210> SEQ ID NO 155
<211> LENGTH: 347
<212> TYPE: PRT
<213> ORGANISM: Artificial Sequence
<220> FEATURE:
<223> OTHER INFORMATION: HIV gp120 insert

<400> SEQUENCE: 155

Glu Glu Pro Arg Asn Pro G

Ala Phe Asn Gln Ser Ser Gly Asp Pro Glu Ile Val Met His Ser
            165                 170                 175

Phe Asn Cys Gly Gly Glu Phe Phe Tyr Cys Asn Thr Ala Gln Leu Phe
            180                 185                 190

Asn Ser Thr Trp Asn Val Thr Gly Gly Thr Asn Gly Thr Glu Gly Asn
            195                 200                 205

Asp Ile Ile Thr Leu Gln Cys Arg Ile Lys Gln Leu Ala Met Tyr Ala
            210                 215                 220

Pro Pro Ile Thr Gly Gln Ile Arg Cys Ser Ser Asn Ile Thr Gly Leu
225                 230                 235                 240

Leu Leu Thr Arg Asp Gly Gly Asn Ser Thr Glu Thr Glu Thr Glu Ile
            245                 250                 255

Phe Arg Pro Gly Gly Gly Asp Met Arg Asp Asn Trp Arg Ser Glu Leu
            260                 265                 270

Tyr Lys Tyr Lys Val Val Arg Ile Glu Pro Ile Gly Val Ala Pro Thr
            275                 280                 285

Arg Ala Lys Arg Gly Gly Gly Ser Met His Ser Ser Ile Ala Ser
            290                 295                 300

Phe Phe Phe Ile Ile Gly Leu Ile Ile Gly Leu Phe Leu Val Leu Cys
305                 310                 315                 320

Arg Arg Thr Cys Arg Arg Gly Ala Ala Ala Leu Thr Ala Val
            325                 330                 335

Val Leu Gln Gly Tyr Asn Pro Pro Ala Tyr Gly
            340                 345

<210> SEQ ID NO 156
<211> LENGTH: 377
<212> TYPE: PRT
<213> ORGANISM: Artificial Sequence
<220> FEATURE:
<223> OTHER INFORMATION: HIV gp120 insert

<400> SEQUENCE: 156

Glu Glu Pro Arg Asn Pro Gln Glu Val Val Leu Glu Asn Val Thr Glu
1               5                   10                  15

Asn Phe Asn Met Trp Lys Asn Asn Met Val Asp Gln Met His Glu Asp
            20                  25                  30

Ile Ile Ser Leu Trp Asp Glu Ser Leu Lys Pro Cys Val Lys Leu Thr
            35                  40                  45

Pro Leu Thr Ser Val Gln Ala Cys Pro Lys Val Ser Phe Gln Pro Ile
            50                  55                  60

Pro Ile His Tyr Cys Val Pro Ala Gly Phe Ala Met Leu Lys Cys Asn
65                  70                  75                  80

Asp Lys Lys Phe Asn Gly Ser Gly Pro Cys Lys Asn Val Ser Thr Val
            85                  90                  95

Gln Cys Thr His Gly Ile Arg Pro Val Val Ser Thr Gln Leu Leu Leu
            100                 105                 110

Asn Gly Ser Leu Ala Glu Glu Asp Ile Val Ile Arg Ser Glu Asn Phe
            115                 120                 125

Thr Asp Asn Ala Lys Thr Ile Ile Val Gln Leu Asn Glu Ser Val Val
            130                 135                 140

Ile Asn Cys Thr Arg Pro Asn Asn Asn Thr Arg Gly Arg Arg Gly Asp
145                 150                 155                 160

Ile Arg Gln Ala His Cys Asn Ile Ser Arg Ala Lys Trp Asn Asn Thr
            165                 170                 175

Leu Gln Gln Ile Val Ile Lys Leu Arg Glu Lys Phe Arg Asn Lys Thr
                180                 185                 190

Ile Ala Phe Asn Gln Ser Ser Gly Gly Asp Pro Glu Ile Val Met His
            195                 200                 205

Ser Phe Asn Cys Gly Gly Glu Phe Phe Tyr Cys Asn Thr Ala Gln Leu
    210                 215                 220

Phe Asn Ser Thr Trp Asn Val Thr Gly Thr Asn Gly Thr Glu Gly
225                 230                 235                 240

Asn Asp Ile Ile Thr Leu Gln Cys Arg Ile Lys Gln Leu Ala Met Tyr
                245                 250                 255

Ala Pro Pro Ile Thr Gly Gln Ile Arg Cys Ser Ser Asn Ile Thr Gly
                260                 265                 270

Leu Leu Leu Thr Arg Asp Gly Gly Asn Ser Thr Glu Thr Glu Thr Glu
            275                 280                 285

Ile Phe Arg Pro Gly Gly Gly Asp Met Arg Asp Asn Trp Arg Ser Glu
            290                 295                 300

Leu Tyr Lys Tyr Lys Val Val Arg Ile Glu Pro Ile Gly Val Ala Pro
305                 310                 315                 320

Thr Arg Ala Lys Arg Gly Gly Gly Gly Ser Met His Thr Leu Ala Ala
                325                 330                 335

Phe Val Leu Leu Val Pro Trp Val Leu Ile Phe Met Val Cys Arg Arg
                340                 345                 350

Thr Cys Arg Arg Arg Gly Ala Ala Ala Ala Leu Thr Ala Val Val Leu
            355                 360                 365

Gln Gly Tyr Asn Pro Pro Ala Tyr Gly
            370                 375

<210> SEQ ID NO 157
<211> LENGTH: 1131
<212> TYPE: DNA
<213> ORGANISM: Artificial Sequence
<220> FEATURE:
<223> OTHER INFORMATION: nucleotide sequence for Seq_156 HIV gp120
      insert

<400> SEQUENCE: 157
gaagaaccta ggaacccaca agaagtagta ttggagaatg tgacagaaaa ttttaacatg      60
tggaaaaata acatggtaga tcagatgcac gaggatataa tcagtttatg ggacgaaagt     120
cttaagccat gtgtaaaatt aaccccgctc actagtgtcc aggcctgtcc aaaggtatcc     180
tttcagccaa ttcccataca ttattgtgtc ccagcagggt tcgcgatgct aaagtgtaac     240
gataagaaat tcaatggatc aggaccatgc aagaatgtga gcacagtaca atgtacccat     300
ggaattaggc cagtggtgtc aactcagctg ctgttaaatg gcagtctagc agaagaagac     360
atagtaatta gatctgaaaa tttcacagac aatgctaaaa ccataatagt acagctaaat     420
gaatctgtag taattaattg tacaagaccc aacaacaata agaggaag aaggggagat       480 ataagacaag cacattgtaa catttcccgg gcaaaatgga taacactttt acaacagata     540
gttataaaat taagagaaaa atttaggaat aaaacaatag cctttaatca atcctcagga     600
ggggacccag aaattgtaat gcacagtttt aattgtggag gggaattttt ctactgtaat     660
acagcacaac tgtttaatag cacgtggaat gttactggag ggacaaatgg cactgaagga     720
aatgacataa tcacactcca atgcagaata aaacagctag caatgtatgc ccctcccatc     780
accggtcaaa ttagatgttc atcaaatatt acagggctgc tactaacgcg tgatggaggt     840

```
aatagtactg agactgagac tgagatcttc agacctggag gaggagatat gagggacaat    900
tggagaagtg agctctataa atataaagta gtaagaattg aaccaatagg agtagcaccc    960
accagggcaa agagaggagg cggaggaagc atgcataccc tggccgcgtt cgtgctcctc   1020
gtgccatggg tgctcatctt tatggtctgt cggaggacct gcagacggag gggagctgcc   1080
gctgccctta cagcagtggt cctgcagggg tacaaccccc ccgcctatgg c            1131
```

<210> SEQ ID NO 158
<211> LENGTH: 368
<212> TYPE: PRT
<213> ORGANISM: Artificial Sequence
<220> FEATURE:
<223> OTHER INFORMATION: HIV gp120 insert

<400> SEQUENCE: 158

```
Glu Glu Pro Arg Val Thr Glu Asn Phe Asn Met Trp Lys Asn Asn Met
1               5                   10                  15

Val Asp Gln Met His Glu Asp Ile Ile Ser Leu Trp Asp Glu Ser Leu
            20                  25                  30

Lys Pro Cys Val Lys Leu Thr Pro Leu Thr Ser Val Gln Ala Cys Pro
        35                  40                  45

Lys Val Ser Phe Gln Pro Ile Pro His Tyr Cys Val Pro Ala Gly
    50                  55                  60

Phe Ala Met Leu Lys Cys Asn Asp Lys Lys Phe Asn Gly Ser Gly Pro
65                  70                  75                  80

Cys Lys Asn Val Ser Thr Val Gln Cys Thr His Gly Ile Arg Pro Val
                85                  90                  95

Val Ser Thr Gln Leu Leu Leu Asn Gly Ser Leu Ala Glu Glu Asp Ile
            100                 105                 110

Val Ile Arg Ser Glu Asn Phe Thr Asp Asn Ala Lys Thr Ile Ile Val
        115                 120                 125

Gln Leu Asn Glu Ser Val Val Ile Asn Cys Thr Arg Pro Asn Asn Asn
    130                 135                 140

Thr Arg Gly Arg Arg Gly Asp Ile Arg Gln Ala His Cys Asn Ile Ser
145                 150                 155                 160

Arg Ala Lys Trp Asn Asn Thr Leu Gln Gln Ile Val Ile Lys Leu Arg
                165                 170                 175

Glu Lys Phe Arg Asn Lys Thr Ile Ala Phe Asn Gln Ser Ser Gly Gly
            180                 185                 190

Asp Pro Glu Ile Val Met His Ser Phe Asn Cys Gly Gly Glu Phe Phe
        195                 200                 205

Tyr Cys Asn Thr Ala Gln Leu Phe Asn Ser Thr Trp Asn Val Thr Gly
    210                 215                 220

Gly Thr Asn Gly Thr Glu Gly Asn Asp Ile Ile Thr Leu Gln Cys Arg
225                 230                 235                 240

Ile Lys Gln Leu Ala Met Tyr Ala Pro Pro Ile Thr Gly Gln Ile Arg
                245                 250                 255

Cys Ser Ser Asn Ile Thr Gly Leu Leu Leu Thr Arg Asp Gly Gly Asn
            260                 265                 270

Ser Thr Glu Thr Glu Thr Glu Ile Phe Arg Pro Gly Gly Gly Asp Met
        275                 280                 285

Arg Asp Asn Trp Arg Ser Glu Leu Tyr Lys Tyr Lys Val Val Arg Ile
    290                 295                 300

Glu Pro Ile Gly Val Ala Pro Thr Arg Ala Lys Arg Gly Gly Gly Gly
305                 310                 315                 320
```

```
Ser Met His Thr Leu Ala Ala Phe Val Leu Leu Val Pro Trp Val Leu
                325                 330                 335

Ile Phe Met Val Cys Arg Arg Thr Cys Arg Arg Arg Gly Ala Ala Ala
            340                 345                 350

Ala Leu Thr Ala Val Val Leu Gln Gly Tyr Asn Pro Pro Ala Tyr Gly
        355                 360                 365

<210> SEQ ID NO 159
<211> LENGTH: 363
<212> TYPE: PRT
<213> ORGANISM: Artificial Sequence
<220> FEATURE:
<223> OTHER INFORMATION: HIV gp120 insert

<400> SEQUENCE: 159

Glu Glu Pro Arg Asn Met Trp Lys Asn Asn Met Val Asp Gln Met His
1               5                   10                  15

Glu Asp Ile Ile Ser Leu Trp Asp Glu Ser Leu Lys Pro Cys Val Lys
            20                  25                  30

Leu Thr Pro Leu Thr Ser Val Gln Ala Cys Pro Lys Val Ser Phe Gln
        35                  40                  45

Pro Ile Pro Ile His Tyr Cys Val Pro Ala Gly Phe Ala Met Leu Lys
    50                  55                  60

Cys Asn Asp Lys Lys Phe Asn Gly Ser Gly Pro Cys Lys Asn Val Ser
65                  70                  75                  80

Thr Val Gln Cys Thr His Gly Ile Arg Pro Val Val Ser Thr Gln Leu
                85                  90                  95

Leu Leu Asn Gly Ser Leu Ala Glu Glu Asp Ile Val Ile Arg Ser Glu
            100                 105                 110

Asn Phe Thr Asp Asn Ala Lys Thr Ile Ile Val Gln Leu Asn Glu Ser
        115                 120                 125

Val Val Ile Asn Cys Thr Arg Pro Asn Asn Asn Thr Arg Gly Arg Arg
    130                 135                 140

Gly Asp Ile Arg Gln Ala His Cys Asn Ile Ser Arg Ala Lys Trp Asn
145                 150                 155                 160

Asn Thr Leu Gln Gln Ile Val Ile Lys Leu Arg Glu Lys Phe Arg Asn
                165                 170                 175

Lys Thr Ile Ala Phe Asn Gln Ser Ser Gly Gly Asp Pro Glu Ile Val
            180                 185                 190

Met His Ser Phe Asn Cys Gly Gly Glu Phe Phe Tyr Cys Asn Thr Ala
        195                 200                 205

Gln Leu Phe Asn Ser Thr Trp Asn Val Thr Gly Gly Thr Asn Gly Thr
    210                 215                 220

Glu Gly Asn Asp Ile Ile Thr Leu Gln Cys Arg Ile Lys Gln Leu Ala
225                 230                 235                 240

Met Tyr Ala Pro Pro Ile Thr Gly Gln Ile Arg Cys Ser Ser Asn Ile
                245                 250                 255

Thr Gly Leu Leu Leu Thr Arg Asp Gly Gly Asn Ser Thr Glu Thr Glu
            260                 265                 270

Thr Glu Ile Phe Arg Pro Gly Gly Gly Asp Met Arg Asp Asn Trp Arg
        275                 280                 285

Ser Glu Leu Tyr Lys Tyr Lys Val Val Arg Ile Glu Pro Ile Gly Val
    290                 295                 300

Ala Pro Thr Arg Ala Lys Arg Gly Gly Gly Gly Ser Met His Thr Leu
305                 310                 315                 320
```

```
Ala Ala Phe Val Leu Leu Val Pro Trp Val Leu Ile Phe Met Val Cys
                325                 330                 335

Arg Arg Thr Cys Arg Arg Arg Gly Ala Ala Ala Ala Leu Thr Ala Val
            340                 345                 350

Val Leu Gln Gly Tyr Asn Pro Pro Ala Tyr Gly
        355                 360

<210> SEQ ID NO 160
<211> LENGTH: 344
<212> TYPE: PRT
<213> ORGANISM: Artificial Sequence
<220> FEATURE:
<223> OTHER INFORMATION: HIV gp120 insert

<400> SEQUENCE: 160

Glu Glu Pro Arg Asn Met Trp Lys Asn Asn Met Val Asp Gln Met His
1               5                   10                  15

Glu Asp Ile Ile Ser Leu Trp Asp Glu Ser Leu Lys Pro Cys Val Lys
            20                  25                  30

Leu Thr Pro Leu Thr Ser Val Gln Ala Cys Pro Lys Val Ser Phe Gln
        35                  40                  45

Pro Ile Pro Ile His Tyr Cys Val Pro Ala Gly Phe Ala Met Leu Lys
    50                  55                  60

Cys Asn Asp Lys Lys Phe Asn Gly Ser Gly Pro Cys Lys Asn Val Ser
65                  70                  75                  80

Thr Val Gln Cys Thr His Gly Ile Arg Pro Val Val Ser Thr Gln Leu
                85                  90                  95

Leu Leu Asn Gly Ser Leu Ala Glu Glu Asp Ile Val Ile Arg Ser Glu
            100                 105                 110

Asn Phe Thr Asp Asn Ala Lys Thr Ile Ile Val Gln Leu Asn Glu Ser
        115                 120                 125

Val Val Ile Asn Cys Thr Arg Pro Asn Asn Asn Thr Arg Gly Arg Arg
    130                 135                 140

Gly Asp Ile Arg Gln Ala His Cys Asn Ile Ser Arg Ala Lys Trp Asn
145                 150                 155                 160

Asn Thr Leu Gln Gln Ile Val Ile Lys Leu Arg Glu Lys Phe Arg Asn
                165                 170                 175

Lys Thr Ile Ala Phe Asn Gln Ser Ser Gly Gly Asp Pro Glu Ile Val
            180                 185                 190

Met His Ser Phe Asn Cys Gly Gly Glu Phe Phe Tyr Cys Asn Thr Ala
        195                 200                 205

Gln Leu Phe Asn Ser Thr Trp Asn Val Thr Gly Gly Thr Asn Gly Thr
    210                 215                 220

Glu Gly Asn Asp Ile Ile Thr Leu Gln Cys Arg Ile Lys Gln Leu Ala
225                 230                 235                 240

Met Tyr Ala Pro Pro Ile Thr Gly Gln Ile Arg Cys Ser Ser Asn Ile
                245                 250                 255

Thr Gly Leu Leu Leu Thr Arg Asp Gly Gly Asn Ser Thr Glu Thr Glu
            260                 265                 270

Thr Glu Ile Phe Arg Pro Gly Gly Gly Asp Met Arg Asp Asn Trp Arg
        275                 280                 285

Ser Glu Leu Tyr Gly Gly Gly Gly Ser Met His Thr Leu Ala Ala Phe
    290                 295                 300

Val Leu Leu Val Pro Trp Val Leu Ile Phe Met Val Cys Arg Arg Thr
305                 310                 315                 320
```

Cys Arg Arg Arg Gly Ala Ala Ala Leu Thr Ala Val Val Leu Gln
            325                 330                 335

Gly Tyr Asn Pro Pro Ala Tyr Gly
            340

<210> SEQ ID NO 161
<211> LENGTH: 429
<212> TYPE: PRT
<213> ORGANISM: Artificial Sequence
<220> FEATURE:
<223> OTHER INFORMATION: antigenic insert Seamless E1 or E2 sequence
      at amino end of gp120

<400> SEQUENCE: 161

Glu Glu Ala Phe Thr Tyr Leu Cys Thr Ala Pro Gly Cys Ala Thr Gln
1               5                   10                  15

Ala Pro Val Pro Val Trp Arg Glu Ala Thr Thr Thr Leu Phe Cys Ala
            20                  25                  30

Ser Asp Ala Lys Ala Tyr Asp Thr Glu Val His Asn Val Trp Ala Thr
        35                  40                  45

His Ala Cys Val Pro Thr Asp Pro Asn Pro Gln Glu Val Val Leu Glu
    50                  55                  60

Asn Val Thr Glu Asn Phe Asn Met Trp Lys Asn Asn Met Val Asp Gln
65                  70                  75                  80

Met His Glu Asp Ile Ile Ser Leu Trp Asp Glu Ser Leu Lys Pro Cys
                85                  90                  95

Val Lys Leu Thr Pro Leu Thr Ser Val Gln Ala Cys Pro Lys Val Ser
            100                 105                 110

Phe Gln Pro Ile Pro Ile His Tyr Cys Val Pro Ala Gly Phe Ala Met
        115                 120                 125

Leu Lys Cys Asn Asp Lys Lys Phe Asn Gly Ser Gly Pro Cys Lys Asn
    130                 135                 140

Val Ser Thr Val Gln Cys Thr His Gly Ile Arg Pro Val Val Ser Thr
145                 150                 155                 160

Gln Leu Leu Leu Asn Gly Ser Leu Ala Glu Glu Asp Ile Val Ile Arg
                165                 170                 175

Ser Glu Asn Phe Thr Asp Asn Ala Lys Thr Ile Ile Val Gln Leu Asn
            180                 185                 190

Glu Ser Val Val Ile Asn Cys Thr Arg Pro Asn Asn Asn Thr Arg Gly
        195                 200                 205

Arg Arg Gly Asp Ile Arg Gln Ala His Cys Asn Ile Ser Arg Ala Lys
    210                 215                 220

Trp Asn Asn Thr Leu Gln Gln Ile Val Ile Lys Leu Arg Glu Lys Phe
225                 230                 235                 240

Arg Asn Lys Thr Ile Ala Phe Asn Gln Ser Ser Gly Gly Asp Pro Glu
                245                 250                 255

Ile Val Met His Ser Phe Asn Cys Gly Gly Glu Phe Phe Tyr Cys Asn
            260                 265                 270

Thr Ala Gln Leu Phe Asn Ser Thr Trp Asn Val Thr Gly Gly Thr Asn
        275                 280                 285

Gly Thr Glu Gly Asn Asp Ile Ile Thr Leu Gln Cys Arg Ile Lys Gln
    290                 295                 300

Leu Ala Met Tyr Ala Pro Pro Ile Thr Gly Gln Ile Arg Cys Ser Ser
305                 310                 315                 320

Asn Ile Thr Gly Leu Leu Leu Thr Arg Asp Gly Gly Asn Ser Thr Glu

```
                       325                 330                 335
Thr Glu Thr Glu Ile Phe Arg Pro Gly Gly Asp Met Arg Asp Asn
            340                 345                 350

Trp Arg Ser Glu Leu Tyr Lys Tyr Lys Val Val Arg Ile Glu Pro Ile
            355                 360                 365

Gly Val Ala Pro Thr Arg Ala Lys Arg Gly Gly Gly Ser Met His
            370                 375                 380

Thr Leu Ala Ala Phe Val Leu Leu Val Pro Trp Val Leu Ile Phe Met
385                 390                 395                 400

Val Cys Arg Arg Thr Cys Arg Arg Gly Ala Ala Ala Leu Thr
                405                 410                 415

Ala Val Val Leu Gln Gly Tyr Asn Pro Pro Ala Tyr Gly
            420                 425

<210> SEQ ID NO 162
<211> LENGTH: 383
<212> TYPE: PRT
<213> ORGANISM: Artificial Sequence
<220> FEATURE:
<223> OTHER INFORMATION: Non-HIV envelope glycoprotein

<400> SEQUENCE: 162

Glu Glu Pro Arg Phe Asn Cys Leu Gly Met Ser Asn Arg Asp Phe Leu
1               5                   10                  15

Glu Gly Val Ser Gly Ala Thr Trp Val Asp Leu Val Leu Glu Gly Asp
            20                  25                  30

Ser Cys Val Thr Ile Met Ser Lys Asp Lys Pro Thr Ile Asp Val Lys
            35                  40                  45

Met Met Asn Met Glu Ala Ala Asn Leu Ala Glu Val Arg Ser Tyr Cys
        50                  55                  60

Tyr Leu Ala Thr Val Ser Asp Leu Ser Thr Lys Ala Ala Cys Pro Thr
65                  70                  75                  80

Met Gly Glu Ala His Asn Asp Lys Arg Ala Asp Pro Ala Phe Val Cys
                85                  90                  95

Arg Gln Gly Val Val Asp Arg Gly Trp Gly Asn Gly Cys Gly Phe Phe
            100                 105                 110

Gly Lys Gly Ser Ile Asp Thr Cys Ala Lys Phe Ala Cys Ser Thr Lys
        115                 120                 125

Ala Ile Gly Arg Thr Ile Leu Lys Glu Asn Ile Lys Tyr Glu Val Ala
            130                 135                 140

Ile Phe Val His Gly Pro Thr Thr Val Glu Ser His Gly Asn Tyr Ser
145                 150                 155                 160

Thr Gln Val Gly Ala Thr Gln Ala Gly Arg Leu Ser Ile Thr Pro Ala
                165                 170                 175

Ala Pro Ser Tyr Thr Leu Lys Leu Gly Glu Tyr Gly Glu Val Thr Val
            180                 185                 190

Asp Cys Glu Pro Arg Ser Gly Ile Asp Thr Asn Ala Tyr Tyr Val Met
        195                 200                 205

Thr Val Gly Thr Lys Thr Phe Leu Val His Arg Glu Trp Phe Met Asp
    210                 215                 220

Leu Asn Leu Pro Trp Ser Ser Ala Gly Ser Thr Val Trp Arg Asn Arg
225                 230                 235                 240

Glu Thr Leu Met Glu Phe Glu Glu Pro His Ala Thr Lys Gln Ser Val
                245                 250                 255

Ile Ala Leu Gly Ser Gln Glu Gly Ala Leu His Gln Ala Leu Ala Gly
```

-continued

```
                   260                 265                 270
Ala Ile Pro Val Glu Phe Ser Ser Asn Thr Val Lys Leu Thr Ser Gly
            275                 280                 285

His Leu Lys Cys Arg Val Lys Met Glu Lys Leu Gln Leu Lys Gly Thr
            290                 295                 300

Thr Tyr Gly Val Cys Ser Lys Ala Phe Lys Phe Leu Gly Thr Pro Val
305                 310                 315                 320

Asp Thr Gly His Gly Thr Val Val Leu Glu Leu Gln Tyr Thr Gly Thr
                325                 330                 335

Asp Gly Pro Cys Lys Val Pro Ile Ser Ser Val Ala Ser Leu Asn Asp
            340                 345                 350

Leu Thr Pro Val Gly Arg Leu Val Thr Val Asn Pro Phe Val Ser Val
            355                 360                 365

Ala Thr Ala Asn Ala Lys Val Leu Ile Glu Leu Glu Pro Pro Phe
            370                 375                 380
```